(12) United States Patent
Fujita et al.

(10) Patent No.: US 6,875,718 B2
(45) Date of Patent: Apr. 5, 2005

(54) OLEFIN POLYMERIZATION CATALYSTS, TRANSITION METAL COMPOUNDS, PROCESSES FOR OLEFIN POLYMERIZATION, AND α-OLEFIN/ CONJUGATED DIENE COPOLYMERS

(75) Inventors: Terunori Fujita, Yamaguchi (JP); Yasushi Tohi, Yamaguchi (JP); Makoto Mitani, Yamaguchi (JP); Shigekazu Matsui, Yamaguchi (JP); Junji Saito, Yamaguchi (JP); Masatoshi Nitabaru, Yamaguchi (JP); Kiyoaki Sugi, Yamaguchi (JP); Haruyuki Makio, Yamaguchi (JP); Toshiyuki Tsutsui, Yamaguchi (JP)

(73) Assignee: Mitsui Chemicals, Inc., Tokyo (JP)

(*) Notice: Subject to any disclaimer, the term of this patent is extended or adjusted under 35 U.S.C. 154(b) by 267 days.

(21) Appl. No.: 09/942,706

(22) Filed: Aug. 31, 2001

(65) Prior Publication Data

US 2002/0115557 A1 Aug. 22, 2002

Related U.S. Application Data

(62) Division of application No. 09/065,593, filed on Apr. 24, 1998, now Pat. No. 6,309,997.

(30) Foreign Application Priority Data

Apr. 25, 1997 (JP) ............................................. 9-109922
Apr. 28, 1997 (JP) ............................................. 9-111439
May 22, 1997 (JP) ............................................. 9-132333
Mar. 3, 1998 (JP) ............................................ 10-050541

(51) Int. Cl.$^7$ .......................... B01J 31/00; B01J 37/00; C08F 4/02; C08F 4/60; C08F 4/44
(52) U.S. Cl. .................. 502/103; 502/117; 502/155; 502/171; 502/167; 526/161; 526/172
(58) Field of Search ......................... 502/103, 117, 502/167, 155, 171, 152, 156, 157, 172; 526/161, 172

(56) References Cited

U.S. PATENT DOCUMENTS

| 3,931,127 | A | | 1/1976 | Halasa et al. |
| 3,965,078 | A | | 6/1976 | Priola et al. |
| 4,990,640 | A | | 2/1991 | Tsutsui et al. |
| 5,155,080 | A | | 10/1992 | Elder et al. |
| 5,191,052 | A | | 3/1993 | Welborn, Jr. |
| 5,225,500 | A | | 7/1993 | Ewen et al. |
| 5,321,106 | A | | 6/1994 | LaPointe |
| 5,387,568 | A | | 2/1995 | Ewen et al. |
| 5,502,125 | A | | 3/1996 | Bordeianu et al. |
| 5,637,660 | A | * | 6/1997 | Nagy et al. ............ 502/103 |
| 5,714,556 | A | | 2/1998 | Johnson et al. |
| 5,811,379 | A | | 9/1998 | Rossi et al. |
| 6,309,997 | B1 | * | 10/2001 | Fujita et al. ........... 502/167 |
| 6,333,389 | B2 | * | 12/2001 | Whiteker et al. ...... 526/161 |
| 6,747,105 | B2 | * | 6/2004 | Chen et al. ............ 526/160 |
| 6,747,106 | B2 | * | 6/2004 | Wang et al. ........... 526/172 |
| 2002/0082366 | A1 | * | 6/2002 | Johnson et al. ........ 502/117 |

FOREIGN PATENT DOCUMENTS

| EP | 426638 A2 | | 5/1991 |
| EP | 427697 A2 | | 5/1991 |
| EP | 667357 A1 | | 8/1995 |
| EP | 680976 A1 | | 11/1995 |
| GB | 1 390 530 | * | 4/1975 |
| JP | 58 019309 A | | 2/1983 |
| JP | 61 130314 A | | 6/1986 |
| JP | 01 501633 W | | 6/1989 |
| JP | 1501950 A | | 7/1989 |
| JP | 1502036 A | | 7/1989 |
| JP | 278687 A | | 3/1990 |
| JP | 3207704 A | | 2/1991 |
| JP | 3179005 A | | 8/1991 |
| JP | 3179006 A | | 8/1991 |
| JP | 3207703 A | | 9/1991 |
| WO | WO88 05792 | | 8/1988 |
| WO | WO88 05793 | | 8/1988 |
| WO | WO 93/03838 | * | 4/1993 |
| WO | WO 94/03271 | * | 2/1994 |
| WO | WO96 23010 | | 8/1996 |
| WO | WO 96/28402 | * | 9/1996 |
| WO | WO97 02298 A1 | | 1/1997 |

| WO | WO98 30609 | 7/1998 |
| WO | WO98 42664 | 10/1998 |

OTHER PUBLICATIONS

W. Herrmann et al., J. Organomet. Chem., vol. 511, pp. 299–302 (1996).*
T. Repo et al., Macromolecules, vol. 30, no. 2, pp. 171–175 (1997).*
A. de Blas et al., Synth. React. Inorg. Met.–Org. Chem., vol. 21, no. 8, pp. 1273–1298 (1991).*
C. Parrado et al., Synth. React. Inorg. Met.–Org. Chem., vol. 24, no. 9, pp. 1613–1629 (1994).*
D. Owiny et al., J. Organomet. Chem., vol. 678 (2003), pp. 134–141.*
Maurizio Galimberti, Enrico Albizzati, Luigi Abis, Giancarlo Bacchilega, "Die Makromolekulare Chemie" *Makramol. Chem.*, vol. 192, p. 2591–2601 (1991).
Chemical Abstracts, vol. 124, No. 5 (Jan. 1996).
Milani et al. "Catalytic Activity of Vanadium (III) and Oxovanadium (IV). ." Inorganica Chimica Acta, 103, (1985), Sep. 15–18.
M. Galimberti et al. "Die Makromolekulare Chemie", vol. 192, p. 2591, (1991).

* cited by examiner

*Primary Examiner*—Mark L. Bell
*Assistant Examiner*—J. Pasterczyk
(74) *Attorney, Agent, or Firm*—Birch, Stewart, Kolasch & Birch, LLP

(57) ABSTRACT

The invention provides olefin polymerization catalysts exhibiting excellent polymerization activities, a process for olefin polymerization using the catalysts, a novel transition metal compound useful for the catalysts, and α-olefin/conjugated diene copolymers having specific properties. The olefin polymerization catalysts of the invention contain (A) a transition metal compound of formula (I), and (B) an organometallic compound, an organoaluminum oxy-compound or an ionizing ionic compound. The novel transition metal compounds of the invention are compounds of formula (I) wherein M is a transition metal atom of Group 3 or 4 of the periodic table; $R^1$ is a hydrocarbon group, etc.; $R^2$ to $R^5$ are each H, a halogen, a hydrocarbon group, etc.; $R^6$ is a halogen, a hydrocarbon group, etc.; n is a number satisfying a valence of M; and X is a halogen, a hydrocarbon group, etc 15 Claims, 4 Drawing Sheets (A) Transition metal compound M : Transition metal atom of Groups 3–11
$R^1 - R^6$ : H, hydrocarbon group, etc.
m : 1–6
n : Number satisfying valence of M
X : Hal, hydrocarbon group, etc.

(B)

(A) Transition metal compound

M : Transition metal atom of Groups 3–11
$R^1 - R^{10}$ : Hal, hydrocarbon group, etc.
n : Number satisfying valence of M
X : Hal, etc.
Q : Hydrocarbon group of $C_3$ or more, etc.

(B)

Structure of Compound A-1 from X-ray crystal structure analysis

Structure of Compound B-1 from X-ray crystal structure analysis

OLEFIN POLYMERIZATION CATALYSTS, TRANSITION METAL COMPOUNDS, PROCESSES FOR OLEFIN POLYMERIZATION, AND α-OLEFIN/CONJUGATED DIENE COPOLYMERS

This application is a divisional of application Ser. No. 09/065,593, filed on Apr. 24, 1998 now U.S. Pat. No. 6,309,997, the entire contents of which are hereby incorporated by reference and for which priority is claimed under 35 U.S.C. § 120; and this application claims priority of Application No. 109922; 111439; 132333; 50541 filed in JAPAN on Apr. 25, 1997; Apr. 28 , 1997; May 22, 1997 and Mar. 3, 1998, respectively under 35 U.S.C. § 119.

FIELD OF THE INVENTION

The present invention relates to novel olefin polymerization catalysts, transition metal compounds and processes for olefin polymerization using the olefin polymerization catalysts.

The present invention also relates to α-olefin/conjugated diene copolymers which have narrow molecular weight distribution and are favorably used as rubbers.

BACKGROUND OF THE INVENTION

As olefin polymerization catalysts, "Kaminsky catalysts" are well known. The Kaminsky catalysts have extremely high polymerization activities, and by the use of them, polymers of narrow molecular weight distribution can be obtained. Transition metal compounds which are known as those employable for the Kaminsky catalysts are, for example, bis(cyclopentadienyl)zirconium dichloride (see: Japanese Patent Laid-Open Publication No. 19309/1083) and ethylenebis(4,5,6,7-tetrahydroindenyl)zirconium dichloride (see: Japanese Patent Laid-Open Publication No. 130314/1086). It is also known that the olefin polymerization activities or the properties of the resulting polyolefins greatly vary when different transition metal compounds are used in the polymerization. Further, transition metal compounds having a ligand of diimine structure have been recently proposed as novel olefin polymerization catalysts (see: International Patent Publication No. 9623010).

By the way, polyolefins generally have excellent mechanical properties, and therefore they are used in many fields such as fields of various molded products. However, with variation of requirements for the polyolefins, polyolefins of various properties have been desired in recent years. Moreover, increase of productivity has been also desired.

Under such circumstances as mentioned above, there has been desired development of olefin polymerization catalysts having excellent olefin polymerization activities and capable of producing polyolefins of excellent properties.

It is well known that copolymerization of several kinds of (α-olefins and non-conjugated dienes proceeds when Ziegler-Natta polymerization catalysts are used. Since the copolymers thus obtained are useful as rubbers, copolymers of various types have been produced. However, the non-conjugated dienes used in the copolymerization are generally expensive and have low reactivity. Therefore, diene components which are inexpensive and have high reactivity are desired.

Examples of such diene components include conjugated dienes such as 1,3-butadiene and isoprene. Though these conjugated dienes are more inexpensive and have higher reactivity as compared with the conventional non-conjugated dienes, they have problem such that the activities are markedly lowered or only ununiform copolymers of wide composition distribution or wide molecular weight distribution are obtained if the copolymerization is conducted by the use of the conventional Ziegler-Natta polymerization catalysts. In case of a Ziegler-Natta catalyst system using a vanadium compound, the polymerization activities are extremely low, though relatively uniform copolymers are obtainable. In the circumstances, copolymerization of ethylene and butadiene using metallocene catalysts which have been studied extensively and thus known to exhibit high polymerization activities has been investigated (National Publication of International Patent No. 501633/1989).

In the above case, however, it has been reported that from the diene unit and ethylene incorporated into the polymer form together cyclopentane skeleton in the polymer chain, and that the proportion of the cyclopentane skeleton becomes not less than 50% of all the diene units. The conversion of double bonds of the diene unit into the cyclopentane skeleton is very disadvantageous in the procedure of "vulcanization" required to use the copolymers as rubbers. Further, the cyclopentane skeleton is an unfavorable skeleton because it functions to increase glass transition temperature of the copolymers and is detrimental to the low-temperature properties of the rubbers.

Under these circumstances, as mentioned above, there has been eagerly desired development of copolymers of a α-olefins and conjugated dienes, which have narrow molecular weight distribution and uniform composition and contain almost no cyclopentane skeleton in their polymer chains.

OBJECT OF THE INVENTION

It is an object of the present invention to provide an olefin polymerization catalyst having excellent olefin polymerization activities.

It is another object of the invention to provide a novel transition metal compound useful for such catalyst.

It is a further object of the invention to provide a process for olefin polymerization using the catalyst.

It is a still further object of the invention to provide an α-olefin/conjugated diene copolymer having a narrow molecular weight distribution and containing almost no cyclopentane skeleton in its polymer chain.

SUMMARY OF THE INVENTION

The first olefin polymerization catalyst according to the present invention comprises:

(A) a transition metal compound represented by the following formula (I), and
(B) at least one compound selected from:
   (B-1) an organometallic compound,
   (B-2) an organoaluminum oxy-compound, and
   (B-3) a compound which reacts with the transition metal compound (A) to form an ion pair:

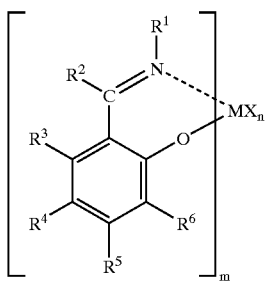

(I)

wherein M is a transition metal atom of Group 3 to Group 11 of the periodic table, m is an integer of 1 to 6, $R^1$ to $R^6$ may be the same or different, and are each a hydrogen atom, a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group, and two or more of them may be bonded to each other to form a ring, when m is 2 or greater, two of the groups $R^1$ to $R^6$ may be bonded to each other, with the proviso that the groups $R^1$ are not bonded to each other, n is a number satisfying a valence of M, and X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, and when n is 2 or greater, plural groups X may be the same or different and may be bonded to each other to form a ring.

In the present invention, $R^6$ in the formula (I) is preferably a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group.

In the present invention, the transition metal compound represented by the formula (I) is preferably a transition metal compound represented by the following formula (I-a):

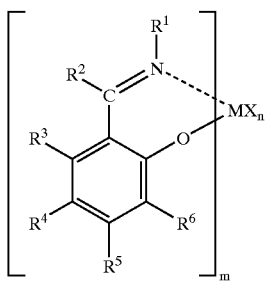

(I-a)

wherein M is a transition metal atom of Group 3 to Group 11 of the periodic table, m is an integer of 1 to 3, $R^1$ to $R^6$ may be the same or different, and are each a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group, a carboxyl group, a sulfo group, a mercapto group or a hydroxyl group, and two or more of them may be bonded to each other to form a ring, when m is 2 or greater, two of the groups $R^1$ to $R^6$ may be bonded to each other, with the proviso that the groups $R^1$ are not bonded to each other, n is a number satisfying a valence of M, and X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, and when n is 2 or greater, plural groups X may be the same or different and may be bonded to each other to form a ring.

In the above formula (I-a), $R^6$ is preferably a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group, a carboxyl group, a sulfo group, a mercapto group or a hydroxyl group.

Further, the transition metal compound represented by the formula (I) is preferably a transition metal compound represented by the following formula (I-a-1):

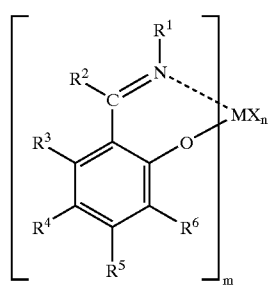

(I-a-1)

wherein M is a transition metal atom of Group 3 to Group 11 of the periodic table, m is an integer of 1 to 3, $R^1$ to $R^6$ may be the same or different, and are each a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group or a hydroxyl group, and two or more of them may be bonded to each other to form a ring, when m is 2 or greater, two of the groups $R^1$ to $R^6$ may be bonded to each other, with the proviso that the groups $R^1$ are not bonded to each other, n is a member satisfying a valence of M, and X is a hydrogen atom, a halogen atom, a hydrocarbon group of 1 to 20 carbon atoms, a halogenated hydrocarbon group of 1 to 20 carbon atoms, an oxygen-containing group, a sulfur-containing group or a silicon-containing group, and when n is 2 or greater, plural groups X may be the same or different and may be bonded to each other to form a ring.

In the formula (I-a-1), $R^6$ is preferably a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group or a hydroxyl group.

In the present invention, further, the transition metal compound represented by the formula (I) is preferably a transition metal compound represented by the following formula (I-b):

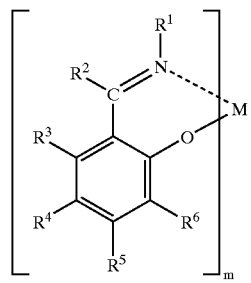

(I-b)

wherein M is a transition metal atom of Group 3 to Group 11 of the periodic table, m is an integer of 1 to 6, $R^1$ to $R^6$ may be the same or different, and are each a hydrogen atom, a halogen atom, a hydrocarbon group, a hydrocarbon-substituted silyl group, an alkoxy group, an aryloxy group, an ester group, an amido group, an amino group, a sulfonamido group, a cyano group or a nitro group, and two or more of them may be bonded to each other to form a ring, and when m is 2 or greater, two of the groups $R^1$ to $R^6$ may be bonded to each other, with the proviso that the groups $R^1$ are not bonded to each other.

In the formula (I-b), $R^6$ is preferably a halogen atom, a hydrocarbon group, a hydrocarbon-substituted silyl group, an alkoxy group, an aryloxy group, an ester group, an amido group, an amino group, a sulfonamido group, a cyano group or a nitro group.

It is preferred that M in the transition metal compound (A) is at least one transition metal atom selected from Groups 3 to 5 and Group 9 of the periodic table.

The first olefin polymerization catalyst according to the invention may further comprise a carrier (C), in addition to the transition metal compound (A) and at least one compound (B) selected from the organometallic compound (B-1), the organoaluminum oxy-compound (B-2) and the compound (B-3) which reacts with the transition metal compound (A) to form an ion pair.

The first process for olefin polymerization according to the present invention comprises polymerizing or copolymerizing an olefin in the presence of the above-mentioned olefin polymerization catalyst.

The second olefin polymerization catalyst according to the present invention comprises:

(A') a transition metal compound represented by the following formula (II), and (B) at least one compound selected from:

(B-1) an organometallic compound, (B-2) an organoaluminum oxy-compound, and (B-3) a compound which reacts with the transition metal compound (A') to form an ion pair.

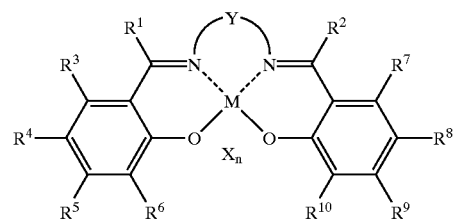

(II)

wherein M is a transition metal atom of Group 3 to Group 11 of the periodic table, $R^1$ to $R^{10}$ may be the same or different, and are each a hydrogen atom, a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group, and two car more of them may be bonded to each other to form a ring, n is a number satisfying a valence of M, X is; a hydrogen atom, a halogen atom, a hydrocarbon group, an, oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, arid when n is 2 or greater, plural groups X may be the same or different and may be bonded to each other to form a ring, and Y is a divalent bonding group containing at least one element selected from the group consisting of oxygen, sulfur, carbon, nitrogen, phosphorus, silicon, selenium tin and boron, and when it is a hydrocarbon group, the hydrocarbon group has 3 or more carbon atoms.

In the above formula (II), at least one of $R^6$ and $R^{10}$ is preferably a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group.

The transition metal compound represented by the formula (II) is preferably a transition metal compound represented by the following formula (II-a).

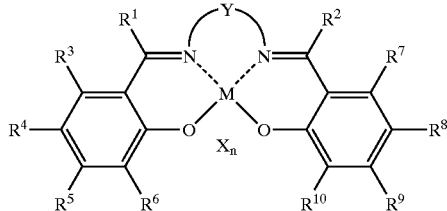

(II-a)

wherein M is a transition metal atom of group 3 to Group 11 of the periodic table, $R^1$ to $R^{10}$ may be the same or different, they are each a hydrogen atom, a halogen atom, a hydrocarbon group, a hydrocarbon-substituted silyl group, an alkoxy group, an aryloxy group, an ester group, an amido group, an amino group, a sulfonamido group, a cyano group or a nitro group, and two or more of them may be bonded to each ocher to form a ring, n is a number satisfying a valence of M, X is a hydrogen atom, a halogen atom, a hydrocarbon group of 1 to 20 carbon atoms, a halogenated hydrocarbon group of 1 to 20 carbon atoms, an oxygen-containing group, a sulfur-containing group or a silicon-containing group, and when n is 2 or greater, plural groups X may be the same or different and may be bonded to each other to form a ring, and Y is a divalent bonding group containing at least one element selected from the group consisting of oxygen, sulfur, carbon, nitrogen, phosphorus, silicon, selenium, tin and boron, and when it is a hydrocarbon group, the hydrocarbon group has 3 or more carbon atoms.

In the above formula (II-a), at least one of $R^6$ and $R^{10}$ is preferably a halogen atom, a hydrocarbon group, a hydrocarbon-substituted silyl group, an alkoxy group, an aryloxy group, an ester group, an amido group, an amino group, a sulfonamido group, a cyano group or a nitro group.

It is preferred that M in the transition metal compound (A') is at least one transition metal atom from Groups 4 and 5 of the periodic table.

The second olefin polymerization catalyst according to the invention may further comprise a carrier (C), in addition to the transition metal compound (A') and at least one compound (B) selected from the organometallic compound (B-1), the organoaluminum oxy-compound (B-2) and the compound (B-3) which reacts with the transition metal compound (A') to form an ion pair.

The second process for olefin polymerization comprises polymerizing or copolymerizing an olefin in the presence of the above-mentioned olefin polymerization catalyst.

The novel transition metal compound according to the present invention is represented by the following formula (III):

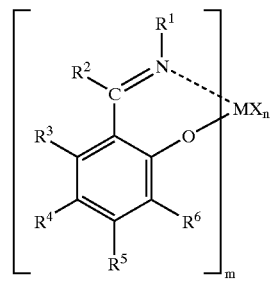

(III)

wherein M is a transition metal atom of Group 4 or Group 5 of the periodic table, m is an integer of 1 to 3, $R^1$ is a hydrocarbon group, a hydrocarbon-substituted silyl group, a hydrocarbon-substituted siloxy group, an alkoxy group, an alkylthio group, an aryloxy group, an arylthio group, an ester group, a thioester group, a sulfonester group or a hydroxyl group, $R^2$ to $R^5$ may be the same or different, and are each a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an ester group, a thioester group, an amido group, an imido group, an amino group, an imino group, a sulfonester group, a sulfonamido group, a cyano group, a nitro group, a carboxyl group, a sulfo group, a mercapto group or a hydroxyl group, $R^6$ is a halogen atom, a hydrocarbon group, a hydrocarbon-substituted silyl group, a hydrocarbon-substituted siloxy group, an alkoxy group, an alkylthio group, an aryloxy group, an arylthio group, an ester group, a thioester group, an amido group, an imido group, an imino group, a sulfonester group, a sulfonamido group or a cyano group, two or more of $R^1$ to $R^6$ may be bonded to each other to form a ring, when m is 2 or greater, two of the groups $R^1$ to $R^6$ may be bonded to each other, with the proviso that the groups $R^1$ are not bonded to each other, n is a number satisfying a valence of M, and X is a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, and when n is 2 or greater, plural groups X may be the same or different and may be bonded to each other to form a ring.

The above-mentioned transition metal compound is preferably a compound represented by the following formula (III-a):

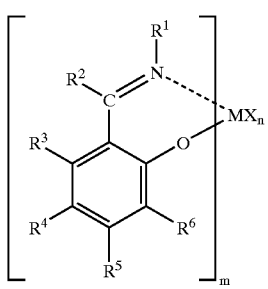

(III-a)

wherein M is a transition metal atom of Group 4 or Group 5 of the periodic table, m is an integer of 1 to 3, $R^1$ to $R^5$ may be the same or different, and are each a hydrocarbon group, an alkoxy group or a hydrocarbon-substituted silyl group, $R^6$ is a halogen atom, a hydrocarbon group, a hydrocarbon-substituted silyl group, an alkoxy group, a alkylthio group or a cyano group, two or more of $R^1$ to $R^6$ may be bonded to each other to form a ring, when m is 2 or greater, two groups of the groups $R^1$ to $R^6$ may be bonded to each other, with the proviso that the groups $R^1$ are not bonded to each other, n is a number satisfying a valence of M, and X is a halogen atom, a hydrocarbon group, an oxygen-containing group, a sulfur-containing group, a nitrogen-containing group, a halogen-containing group or a silicon-containing group, and when n is 2 or greater, plural groups X may be the same or different and may be bonded to each other to form a ring.

In the formula (III-a), m is preferably 2.

The third olefin polymerization catalyst according to the present invention comprises:

(A'') a novel transition metal compound as described above, and (B) at least one compound selected from:
(B-1) an organometallic compound,
(B-2) an organoaluminum oxy-compound, and
(B-3) a compound which reacts with the transition metal compound (A) to form an ion pair.

The third olefin polymerization catalyst according to the present invention may further comprise a carrier (C) in addition to the transition metal compound (A'') and at least one compound (B) selected from the organometallic compound (B-1), the organoaluminum oxy-compound (B-2) and the compound (B-3) which reacts with the transition metal compound (A'') to form an ion pair.

The third process for olefin polymerization comprises polymerizing or copolymerizing an olefin in the presence of the above-mentioned olefin polymerization catalyst.

The α-olefin/conjugated diene copolymer according to the present invention is an α-olefin/conjugated diene copolymer having a molecular weight distribution (Mw/Mn) of not more than 3.5, a content of constituent units derived from an α-olefin in the range of 1 to 99.9% by mol and a content of constituent units derived from a conjugated diene in the range of 99 to 0.1% by mol, in which the polymer chain contains 1,2-cyclopentane skeleton derived from the conjugated diene in an amount of not more than 1% by mol, and preferably the polymer chain does not substantially contain the 1,2-cyclopentane skeleton.

In the α-olefin/conjugated diene copolymer according to the invention, it is preferred that the content of the constituent units derived from the α-olefin is in the range of 50 to 99.9% by mol and the content of the constituent units derived from the conjugated diene is in the range of 50 to 0.1% by mol.

In the α-olefin/conjugated diene copolymer according to the invention, it is preferred that the α-olefin is ethylene and/or propylene and the conjugated diene is butadiene and/or isoprene.

DETAILED DESCRIPTION OF THE INVENTION

Figure 1:
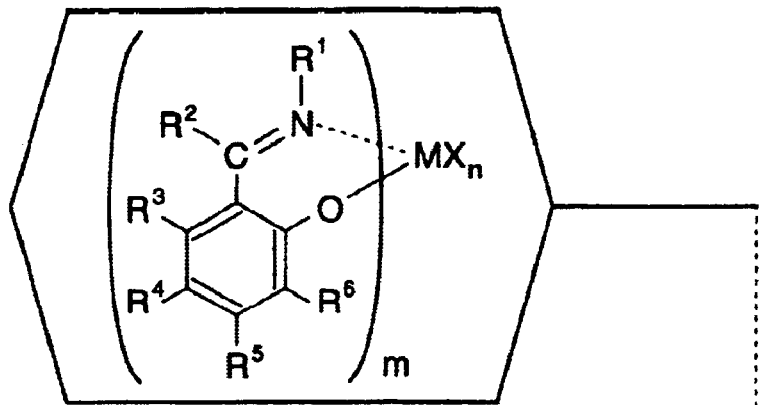
FIG. 1 shows steps for preparing the first olefin polymerization catalyst according to the invention.
Figure 1:
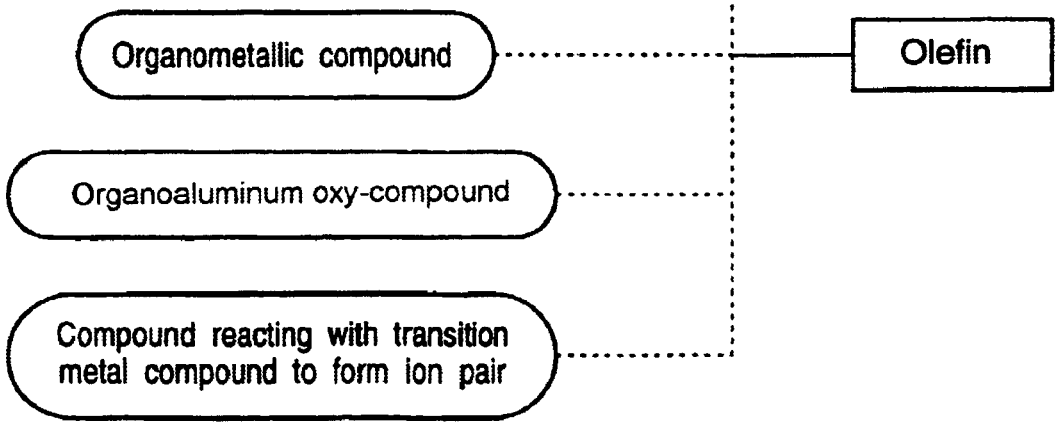

The olefin polymerization catalyst of the present invention and the process for olefin polymerization using the catalyst are described in detail hereinafter.

The meaning of the term "polymerization" used herein is not limited to "homopolymerization" but may comprehend "copolymerization". Also, the meaning of the term "polymer" used herein is not limited to "homopolymer" but may comprehend "copolymer".

First Olefin Polymerization Catalyst

The first olefin polymerization catalyst of the invention is formed from:

(A) a transition metal compound represented by the below-described formula (I), and (B) at least one compound selected from:
(B-1) an organometallic compound,
(B-2) an organoaluminum oxy-compound, and
(B-3) a compound which reacts with the transition metal compound (A) to form an ion pair.

First, the catalyst components for forming the olefin polymerization catalyst of the invention are described.

(A) Transition Metal Compound

The transition metal compound (A) for use in the invention is a compound represented by the following formula (I).

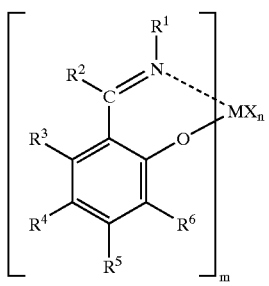

(I)

In the formula (I), M is a transition metal atom of Group 3 to Group 11 of the periodic table (Group 3 includes lantanoids), preferably Groups 3 to 9 (Group 3 includes lantanoids), more preferably Group 3 to Group 5 and Group 9, and particularly preferably Groups 4 or 5. Specific Examples of transition metal atoms M include scandium, titanium, zirconium, hafnium, vanadium, niobium, tanthalum, cobalt, rhodium, yttriumn, chromium, molybdenum, tungsten, mangafese, rhenium, iron and ruthenium. Of these, preferred are scandium, titanium, zirconium, hafnium, vanadium, niobium, tanthalum, cobalt and rhodium; more preferred are titanium, zirconium, hafnium, vanadium, niobium, tanthalum, cobalt and rhodium; and particularly preferred are titanium, zirconium and hafnium.

m is an integer of 1 to 6, preferably 1 to 4.

$R^1$ to $R^6$ may be the same or different, and are each a hydrogen atom, a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group, and two or more of them may be bonded to each other to form a ring, The halogen atom is fluorine, chlorine, bromine or iodine.

Examples of the hydrocarbon groups include straight-chain or branched alkyl groups of 1 to 30, preferably 1 to 20 carbon atoms, such as methyl, ethyl, n-propyl, isopropyl, n-butyl, isobutyl, sec-butyl, tert-butyl, neopentyl and n-hexyl;

straight-chain or branched alkenyl groups of 2 to 30, preferably 2 to 20 carbon atoms, such as vinyl, allyl and isopropenyl;

straight-chain or branched alkynyl groups of 2 to 30, preferably 2 to 20 carbon atoms, such as ethynyl and propargyl;

cyclic saturated hydrocarbon groups of 3 to 30, preferably 3 to 20 carbon atoms, such as cyclopropyl, cyclobutyl, cyclopentyl, cyclohexyl and adamantyl;

cyclic unsaturated hydrocarbon groups of 5 to 30, preferably 5 to 20 carbon atoms, such as cyclopentadienyl, indenyl and fluorenyl; and aryl groups of 6 to 30, preferably 6 to 20 carbon atoms, such as phenyl, benzyl, naphthyl, biphenyl and terphenyl.

The hydrocarbon groups may be substituted with halogen atoms and for such examples halogenated hydrocarbon groups of 1 to 30, preferably 1 to 20 carbon atoms, such as trifluoromethyl, pentafluorophenyl and cholophenyl may be mentioned.

The hydrocarbon groups may also be substituted with other hydrocarbon groups and for such examples aryl-substituted alkyl groups such as benzyl and cumyl may be mentioned.

Further, the hydrocarbon groups may have heterocyclic compound residues; oxygen-containing groups such as alkoxy, aryl, ester, ether, acyl, carboxyl, carbonate, hydroxy, peroxy and carboxylic acid anhydride groups; nitrogen-containing groups such as ammonium salts of amino, imino, amide, imide, hydrazino, hydrazono, nitro, nitroso, cyano, isocyano, cyanic acid ester, amidino and diazo groups; boron-containing groups such as borandiyl, borantriyl and diboranyl groups; sulfur-containing groups such as mercapto, thioester, dithioester, alkylthio, arylthio, thioacyl, thioether, thiocyanic acid ester, isothiocyanic acid ester, sulfon ester, sulfon amide, thiocarboxyl, dithiocarboxyl, sulfo, sulfonyl, sulfinyl and sulfenyl groups; phosphorus-containing groups such as phosphido, phosphoryl, thiophosphoryl and phosphate groups; silicon-containing groups; germanium-containing groups; and tin-containing groups.

Of these, particularly preferable are straight-chain or branched alkyl groups of 1 to 30, preferably 1 to 20 carbon atoms, such as methyl, ethyl, n-propyl, isopropyl, n-butyl, isobutyl, sec-butyl, tert-butyl, neopentyl and n-hexyl; aryl groups of 6 to 30, preferably 6 to 20 carbon atoms, such as phenyl, naphthyl, biphenyl, terphenyl, phenanthryl and antracenyl; and these aryl groups which are substituted with 1 to 5 substituents such as alkyl or arkoxy groups of 1 to 30, preferably 1 to 20 carbon atoms, aryl or aryloxy groups of 6 to 30, preferably 6 to 20 carbon atoms.

Examples of nitrogen-containing groups, boron-containing groups, sulfur-containing groups and phosphorus-containing groups are those exemplified above.

Examples of the heterocyclic residues include those of nitrogen-containing compounds (e.g., pyrrole, pyridine, pyrimidine, quinoline and triazine), oxygen-containing compounds (e.g., furan and pyran) and sulfur-containing compounds (e.g., thiophene), and these heterocyclic residues, which are substituted with substituents such as alkyl or alkoxy groups of 1 to 20 carbon atoms.

Examples of the silicon-containing groups include silyl, siloxy, hydrocarbon-substituted silyl groups such as methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl and dimethyl(pentafluorophenyl)silyl, preferably methylsilyl, dimethylsilyl, trimethylsilyl, ethylsilyl, diethylsilyl, triethylsilyl and triphenylsilyl, particularly preferably trimethylsilyl, triethylsilyl, triphenylsilyl and dimethylphenylsilyl, and hydrocarbon-substituted siloxy groups such as trimethylsiloxy.

The germanium-containing groups and the tin-containing groups include the above-mentioned silicon-containing groups in which silicon is replaced by germanium and tin, respectively.

The more specific illustration on the above $R^1$ to $R^6$ is given below.

Examples of the alkoxy groups include methoxy, ethoxy, n-propoxy, isopropoxy, n-butoxy, isobutoxy and tert-butoxy.

Examples of the alkylthio groups include methylthio and ethylthio.

Examples of the aryloxy groups include phenoxy, 2,6-dimethylphenoxy and 2,4,6-trimethylphenoxy.

Examples of the arylthio groups include phenylthio, methylphenylthio and naphthylthio.

Examples of the acyl groups include formyl, acyl, benzoyl, p-chlorobenzoyl and p-methoxybenzoyl.

Examples of the ester groups include acetyloxy, benzoyloxy, methoxycarbonyl, phenoxycarbonyl and p-chlorophenoxycarbonyl.

Examples of the thioester groups include acetylthio, benzoylthio, methylthiocarbonyl and phenylthiocarbonyl.

Examples of the amido groups include acetamido, N-methylacetamido and N-methylbenzamido.

Examples of the imido groups include acetimido and benzimido.

Examples of the amino groups include dimethylamino, ethylmethylamino and diphenylamino.

Examples of the imino groups include methylimino, ethylimino, propylimino, butylimino and phenylimino.

Examples of the sulfonester groups include methylsulfonato, ethylsulfonato and phenylsulfonato.

Examples of the sulfonamido groups include phenylsulfonamido, N-methylsulfonamido and N-methyl-p-toluenesulfonamido.

$R^6$ is preferably a substituent other than hydrogen. That is, a hydrogen atom, a halogen atom, a hydrocarbon group, a heterocyclic compound residue, an oxygen-containing group, a nitrogen-containing group, a boron-containing group, a sulfur-containing group, a phosphorous-containing group, a silicon-containing group, a germanium-containing group or a tin-containing group, and two or more of them may be bonded to each other to form a ring. $R^6$ is particularly preferably a halogen atom, a hydrocarbon group, a heterocyclic compound residual group, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group or a hydroxyl group.

Preferred examples of the hydrocarbon groups available as $R^6$ include straight-chain or branched alkyl groups of 1 to 30, preferably 1 to 20 carbon atoms, such as methyl, ethyl, n-propyl, isopropyl, n-butyl, isobutyl, sec-butyl, tert-butyl, neopentyl and n-hexyl; cyclic Saturated hydrocarbon groups of 3 to 30, preferably 3 to 20 carbon atoms, such as cyclopropanyl, cyclobutanyl, cyclopentanyl, cyclohexyl and adamantyl; aryl groups of 6 to 30, preferably 6 to 20 carbon atoms, such as phenyl, benzyl, naphthyl, biphenyl and terphenyl; and these groups which are substituted with substituents such as alkyl or alkoxy groups of 1 to 30, preferably 1 to 20 carbon atoms, halogenated alkyl groups of 1 to 30, preferably 1 to 20 carbon atoms, aryl or alkoxy groups of 6 to 30, preferably 6 to 20 carbon atoms, halogen, cyano, nitro and hydroxyl.

Preferred examples of the hydrocarbon-substituted silyl groups as $R^6$ include methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl and dimethyl(pentafluorophenyl)silyl. Particularly preferable are trimethylsilyl, triphenylsilyl, diphenylmethylsilyl, isophenylsilyl, dimethylphenylsilyl, dimethyl-t-butylsilyl and dimethyl(pentafluorophenyl)silyl.

In the present invention, $R^6$ is a preferably selected from branched alkyl groups of 3 to 30, preferably 3 to 20 carbon atoms (e.g., isopropyl, isobutyl, sec-butyl and tert-butyl neopentyl), these alkyl groups which are substituted with aryl groups of 6 to 30, preferably 6 to 20 carbon atoms (e.g., cumyl), and cyclic saturated hydrocarbon groups of 3 to 30, preferably 3 to 20 carbon atoms (e.g., adamantyl, cyclopropyl, cyclobutyl, cyclopentyl and cyclohexyl).

Also, preferable $R^6$ is an aryl group of 6 to 30, preferably 6 to 20 carbon atoms (e.g., phenyl, naphthyl, fluorenyl, anthranyl or phenanthryl) or a hydrocarbon-substituted silyl group.

Two or more of the groups $R^1$ to $R^6$, preferably adjacent groups, may be bonded to each other to form an aliphatic ring, an aromatic ring or a hydrocarbon ring containing a hetero atom such as a nitrogen atom, and these rings may further have a substituent.

When m is 2 or greaser, two of the groups $R^1$ to $R^6$ may be bonded to each other, with the proviso that the groups $R^1$ are not bonded to each other. $R^1$s, $R^2$s, $R^3$s, $R^4$s, $R^5$s, or $R^6$s may be the same as or different from each other.

n is a number satisfying a valence of M, specifically an integer of 0 to 5, preferably 1 to 4, more preferably 1 to 3.

X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, and when n is 2 or greater, plural groups X may be the same or different and may be bonded to each other to form a ring.

Examples of the halogen atom include fluorine, chlorine, bromine and iodine.

Examples of the hydrocarbon groups include those exemplified for $R^1$ to $R^6$. Specifically, there can be mentioned, but not limited to, alkyl groups, such as methyl, ethyl, propyl, butyl, hexyl, octyl, nonyl, dodecyl and eicosyl; cycloalkyl groups of 3 to 30 carbon atoms, such as cyclopentyl, cyclohexyl, norbornyl and adamantyl; alkenyl groups, such as vinyl, propenyl and cyclohexenyl; arylalkyl groups, such as benzyl, phenylethyl and phenylpropyl; and aryl groups, such as phenyl, tolyl, dimethylphenyl, trimethylphenyl, ethylphenyl, propylphenyl, biphenyl, naphthyl, methylnaphthyl, anthryl and phenanthryl.

These hydrocarbon groups include halogenated hydrocarbon groups, and more specifically at least one hydrogen of the hydrocarbon groups of 1 to 30 carbon atoms may be substituted with a halogen atom.

Of these, preferable are chose of 1 to 20 carbon atoms.

Examples of the heterocyclic compound residues include those exemplified for $R^1$ to $R^6$ Examples of the oxygen-containing groups include those exemplified for $R^1$ to $R^6$. Specifically, there can be mentioned, but not limited to, hydroxyl; alkoxy groups, such as methoxy, ethoxy, propoxy and butoxy; aryloxy groups, such as phenoxy, methylphenoxy, dimethylphenoxy and naphthoxy; arylalkoxy groups, such as phenylmethoxy and phenylethoxy; acetoxy groups; and carbonyl group.

Examples of the sulfur-containing groups include those exemplified for $R^1$ to $R^6$. Specifically, there can be mentioned, but not limited to, sulfonato groups, such as methylsulfonato, trifluoromethanesulfonato, phenylsulfonato, benzylsulfonato, p-toluenesulfonato, trimethylbenzenesulfonato, triisobutylbenzenesulfonato, p-chlorobenzenesulfonato and pentafluorobenzene-sulfonato; sulfinato groups, such as methylsulfinato, phenylsulfinato, benzylsulfinato, p-toluenesulfonato, trimethylbenzenesulfinato and pentafluorobenzenesulfinato; alkylthio groups; and arylthio groups.

Examples of the nitrogen-containing groups include those exemplified for $R^1$ to $R^6$. Specifically, there can be mentioned, but not limited to, amino group; alkylamino groups, such as methyl amino, dimethylamino; diethylamino; dipropylamino, dibutylamino and dicyclohexylamino; arylamino groups and alkylarylamino groups, such as phenylamino, diphenylamino, ditolylamino, dinaphthylamino and methylphenylamino.

Examples of the boron-containing groups include $BR_4$ groups (where R is a hydrogen, an aryl group which may have a substituent, a halogen, etc.).

Examples of the silicon-containing groups include those exemplified for $R^1$ to $R^6$. Specifically, there can be mentioned, but not limited to, hydrocarbon-substituted silyl groups, such as phenylsilyl, diphenylsilyl, trimethylsilyl, triethylsilyl, tripropylsilyl, tricyclohexylsilyl, triphenylsilyl, methyldiphenylsilyl, tritolylsilyl and trinaphthylsilyl; hydrocarbon-substituted silylether groups, such as trimethylsilylether; silicon-substituted alkyl groups, such as trimethylsilylmethyl; and silicon-substituted aryl groups, such as trimethylsilylphenyl.

Examples of the germanium-containing groups include those exemplified for $R^1$ to $R^6$. Specifically, there can be mentioned the above-mentioned silicon-containing groups in which silicon is replaced by germanium.

Examples of the tin-containing groups include those exemplified for $R^1$ to $R^6$. Specifically, there can be mentioned the above-mentioned silicon-containing groups in which silicon is replaced by tin.

Examples of the halogen-containing groups include fluorine-containing groups, such as $PF_6$ and $BF_4$; chlorine-containing groups, such as $ClO_4$ and $SbCl_6$; and iodine-containing groups, such as $IO_4$, but not limited thereto.

Examples of the aluminium-containing groups include $AR_4$ groups (where R is a hydrogen, an alkyl group, an aryl group which may have a substituent, a halogen atom, etc.), but not limited thereto.

When n is 2 or greater, plural groups X may be the same or different and may be bonded to each other to form a ring.

Transition Metal Compound (I-a)

The transition compound represented by the formula (I) is preferably a compound represented by the formula (I-a).

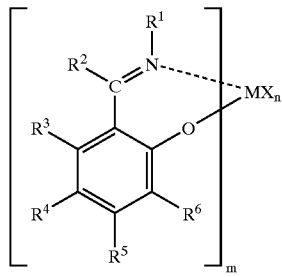

(I-a)

In the formula (I-a), M is a transition metal atom of Group 3 to Group 11 of the periodic table. Examples of M include the above-mentioned transition metal atoms.

m is an integer of 1 to 3, preferably 2.

$R^1$ to $R^6$ may be the same or different, and are each a hydrogen atom, a halogen atom, a hydrocarbon group, a heterocyclic compound residues, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group, a carboxyl group, a sulfo group, a mercapto group or a hydroxyl group, and two or more of them may be bonded to each other to form a ring.

Examples of $R^1$ to $R^6$ include those described above.

When m is 2 or greater, two of the groups $R^1$ to $R^6$ may be bonded to each other, with the proviso that the groups $R^1$ are not bonded to each other.

n is a number satisfying a valence of M, specifically an integer of 0 to 5, preferably 1 to 4, more preferably 1 to 3.

X is a hydrogen atom, a halogen atom, a hydrocarbon group, an oxygen-containing group, a nitrogen-containing group, a boron-containing group, a sulfur-containing group, a phosphorus-containing group, a silicon-containing group, a germanium-containing group or a tin-containing group. Examples of X include those described above.

When n is 2 or greater, plural groups X may be the same or different and may be bonded to each other to form a ring.

The transition metal compound represented by the formula (I) is preferably a compound represented by the following formula (I-a-1).

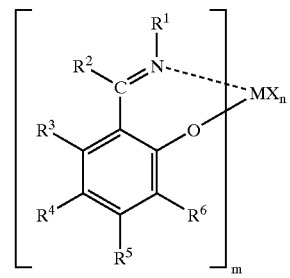

(I-a-1)

In the formula (I-a-1), $R^1$ to $R^6$, M and X have the same meanings as mentioned above, and are preferably those described below.

M is a transition metal atom of Group 3 to Group 11 of the periodic table, preferably of Group 3 to Group 5 and Group 9, e.g., scandium, titanium, zirconium, hafnium, vanadium, niobium, tantalum, cobalt or rhodium, more preferably titanium, zirconium, hafnium, cobalt or rhodium, particularly preferably titanium, zirconium or hafnium.

m is an integer of 1 to 3.

$R^1$ to $R^6$ may be the same or different, and are each a hydrogen atom, a halogen atom, a hydrocarbon group, a heterocyclic compound residues, a hydrocarbon-substituted silyl group, a hydrocarbon-substituted siloxy group, an alkoxy group, an alkylthio group, an aryloxy group, an arylthio group, a thioester group, an ester group, an acyl group, an amido group, an imido group, an amino group, an imino group, a sulfonester group, a sulfonamido group, a cyano group, a nitro group or a hydroxyl group. Of these, particularly preferable is a hydrogen atom, a halogen atom, a hydrocarbon-substituted silyl group, an alkoxy group, an aryloxy group, an ester group, an amido group, an amino group, a sulfonamido group, a cyano group or a nitro group.

Examples of the halogen atom include fluorine, chlorine, bromine and iodine.

Examples of the hydrocarbon groups include straight-chain or branched alkyl groups of 1 to 20 carbon atoms, such as methyl, ethyl, n-propyl, isopropyl, n-butyl, isobutyl, sec-butyl, tert-butyl, pentyl and hexyl; straight-chain or branched alkenyl groups of 2 to 20 carbon atoms, such as vinyl, allyl and isopropenyl; straight-chain or branched alkynyl groups of 2 to 20 carbon atoms, such as ethynyl and propargyl; cyclic saturated hydrocarbon groups of 3 to 20 carbon atoms, such as cyclopropyl, cyclobutyl, cyclopentyl, cyclohexyl and adamantyl; aryl groups of 6 to 20 carbon atoms, such as phenyl, benzyl, naphthyl, biphenylyl and triphenylyl; cyclic unsaturated hydrocarbon groups of 5 to 20 carbon atoms, such as cyclopentadienyl, indenyl and fluorenyl; and these groups which are substituted with substituents such as alkyl groups of 1 to 20 carbon atoms, halogenated alkyl groups of 1 to 20 carbon atoms, aryl groups of 6 to 20 carbon atoms, alkoxy groups of 1 to 20 carbon atoms, aryloxy groups of 6 to 20 carbon atoms, halogen, cyano, nitro and hydroxyl. Of these, particularly preferable are straight-chain or branched alkyl groups of 1 to 20 carbon atoms, such as methyl, ethyl, n-propyl, isopropyl, n-butyl, isobutyl, sec-butyl, tert-butyl, pentyl and hexyl; aryl groups of 6 to 20 carbon atoms, such as phenyl and naphthyl; and these aryl groups which are substituted with 1 to 5 substituents such as alkyl groups of 1 to 20 carbon atoms, aryl groups of 6 to 20 carbon atoms, alkoxy groups of 1 to 20 carbon atoms and aryloxy groups of 6 to 20 carbon atoms.

Examples of the heterocyclic residues include residues of nitrogen-containing compounds (e.g., pyrrole, pyridine, pyrimidine, quinoline and triazine), oxygen-containing compounds (e.g., furan and pyran) and sulfur-containing compounds (e.g., thiophene), and these heterocyclic residues which are substituted with substituents such as alkyl groups and alkoxy groups from 1 to 20 carbon atoms.

Examples of the hydrocarbon-substituted silyl groups include methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl and dimethyl(pentafluorophenyl)silyl. Of these, particularly preferable are methylsilyl, dimethylsilyl, trimethylsilyl, ethylsilyl, diethylsilyl, triethylsilyl and triphenylsilyl.

Examples of the hydrocarbon-substituted siloxy groups include trimethylsiloxy.

Examples of the alkoxy groups include methoxy, ethoxy, n-propoxy, isopropoxy, n-butoxy, isobutoxy and tert-butoxy.

Examples of the alkylthio groups include methylthio and ethylthio.

Examples of the aryloxy groups include phenoxy, 2,6-dimethylphenoxy and 2,4,6-trimethylphenoxy.

Examples of the arylthio groups include phenylthio, methylphenylthio and naphthylthio.

Examples of the acyl groups include formyl, acetyl, benzoyl, p-chlorobenzoyl and p-methoxybenzoyl.

Examples of the ester groups include acetyloxy, benzoyloxy, methoxycarbonyl, phenoxycarbonyl and p-chlorophenoxycarbonyl.

Examples of the thioester groups include acetylthio, benzoylthio, methylthiocarbonyl and phenylthiocarbonyl.

Examples of the amido groups include acetamido, N-methylacetamido and N-methylbenzamido.

Examples of the imido groups include acetimido and benzimido.

Examples of the amino groups include dimethylamino, ethylmethylamino and diphenylamino.

Examples of the imino groups include methylimino, ethylimino, propylimino, butylimino and phenylimino.

Examples of the sulfonester groups include methylsulfonato, ethylsulfonato and phenylsulfonato.

Examples of the sulfonamido groups include phenylsulfonamido, N-methylsulfonamido and N-methyl-p-toluenesulfonamido.

$R^6$ is preferably a substituent other than hydrogen. That is, $R^6$ is preferably a halogen atom, a hydrocarbon group, a heterocyclic compound residues, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group or a hydroxyl group.

Preferred examples of the hydrocarbon groups as $R^6$ include straight-chain or branched alkyl groups of 1 to 20 carbon atoms, such as methyl, ethyl, n-propyl, isopropyl, n-butyl, isobutyl, sec-butyl, tert-butyl, pentyl and hexyl; cyclic saturated hydrocarbon groups of 3 to 20 carbon atoms, such as cyclopropyl, cyclobutnyl, cyclopentyl, cyclohexyl and adamantyl; aryl groups of 6 to 20 carbon atoms, such as phenyl, benzyl, naphthyl, biphenylyl and triphenylyl; and these groups which are substituted with substituents such as alkyl groups of 1 to 20 carbon atoms, halogenated alkyl groups of 1 to 20 carbon atoms, aryl groups of 6 to 20 carbon atoms, alkoxy groups of 1 to 20 carbon atoms, aryloxy groups of 6 to 20 carbon atoms, halogen, cyano, nitro and hydroxyl.

Preferred examples of the hydrocarbon-substituted silyl groups as $R^6$ include methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl and dimethyl(pentafluorophenyl)silyl.

In the present invention, $R^6$ is preferably selected from branched alkyl groups of 3 to 20 carbon atoms (e.g., isopropyl, isobutyl, sec-butyl and tert-butyl), these alkyl groups which are substituted with aryl groups of 6 to 20 carbon atoms (e.g., cumyl), and cyclic saturated hydrocarbon groups of 3 to 20 carbon atoms (e.g., adamantyl, cyclopropyl, cyclobutyl, cyclopentyl and cyclohexyl). Also, preferable $R^6$ is a hydrocarbon-substituted silyl group.

Two or more groups $R^1$ to $R^6$, preferably adjacent groups, may be bonded to each other to form an aliphatic ring, an aromatic ring or a hydrocarbon ring containing a hetero atom such as a nitrogen atom, and these rings may further have a substituent.

When m is 2 or greater, two of the groups $R^1$ to $R^6$ may be bonded to each other, with the proviso that the groups $R^1$ are not bonded to each other. $R^1$s, $R^2$s, $R^3$s, $R^4$s, $R^5$s, or $R^6$s may be the same as or different from each other.

n is a number satisfying a valence of M, specifically an integer of 1 to 3.

X is a hydrogen atom, a halogen atom, a hydrocarbon group of 1 to 20 carbon atoms, a halogenated hydrocarbon group of 1 to 20 carbon atoms, an oxygen-containing group, a sulfur-containing group or a silicon-containing group, and when n is 2 or greater, plural groups X may be the same or different.

Examples of the he halogen atoms include fluorine, chlorine, bromine and iodine.

Examples of the hydrocarbon groups of 1 to 20 carbon atoms include alkyl groups, cycloalkyl groups, alkenyl groups, arylalkyl groups and aryl groups. Specifically, there can be mentioned alkyl groups, such as methyl, ethyl, propyl, butyl, hexyl, octyl, nonyl, dodecyl and eicosyl; cycloalkyl groups, such as cyclopentyl, cyclohexyl, norbornyl and adamantyl; alkenyl groups, such as vinyl, propenyl and cyclohexenyl; arylalkyl groups, such as benzyl, phenylethyl and phenylpropyl; and aryl groups, such as phenyl, tolyl, dimethylphenyl, trimethylphenyl, ethylphenyl, propylphenyl, biphenyl, naphthyl, methylnaphthyl, anthryl and phenanthryl.

Examples of the halogenated hydrocarbon groups of 1 to 20 carbon atoms include the above-mentioned hydrocarbon groups of 1 to 20 carbon atoms which are substituted with halogens.

Examples of the oxygen-containing groups include hydroxyl; alkoxy groups, such as methoxy, ethoxy, propoxy and butoxy; aryloxy groups, such as phenoxy, methylphenoxy, dimethylphenoxy and naphthoxy; and arylalkoxy groups, such as phenylmethoxy and phenylethoxy.

Examples of the sulfur-containing groups include the above-exemplified oxygen-containing groups in which oxygen is replaced with sulfur; sulfonato groups, such as methylsulfonato, trifluoromethanesulfonato, phenylsulfonato, benzylsulfonato, p-toluenesulfonato, trimethylbenzenesulfonato, triisobutylbenzenesulfonato, p-chlorobenzenesulfonato and pentafluorobenzene-sulfonato; and sulfinato groups, such as methylsulfinato, phenylsulfinato, benzylsulfinato, p-toluenesulfinato, trimethylbenzenesulfinato and pentafluorobenzenesulfinato.

Examples of the silicon-containing groups include monohydrocarbon-substituted silyl groups, such as methylsilyl and phenylsilyl; dihydrocarbon-substituted silyl groups, such as dimethylsilyl and diphenylsilyl; trihydrocarbon-substituted silyl groups, such as trimethylsilyl, triethylsilyl, tripropylsilyl, tricyclohexylsilyl, triphenylsilyl, dimethylphenylsilyl, methyldiphenylsilyl, tritolylsilyl and trinaphthylsilyl; silyl ether groups of hydrocarbon-substituted silyl, such as trimethylsilyl ether; silicon-substituted alkyl groups, such as trimethylsilylmethyl; and silicon-substituted aryl groups, such as trimethylsilylphenyl.

Of these, preferable groups X are halogen atoms, hydrocarbon atoms of 1 to 20 carbon atoms and sulfonato groups.

When n is 2 or greater, groups X may be bonded to each other to form a ring.

Of the transition metal compounds represented by the formula (I-a-1), the compound wherein m is 2 and two of the groups $R^1$ to $R^6$ (except for the groups $R^1$) are bonded to each other is, for example, a compound represented by the following formula (I-a-2).

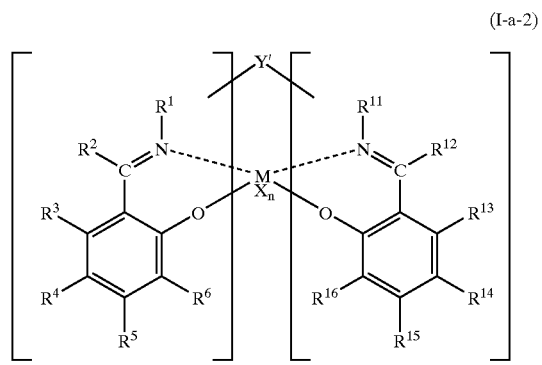

(I-a-2)

In the formula (I-a-2), M, $R^1$ to $R^6$, and X are identical with M, $R^1$ to $R^6$, and X in the formula (I).

$R^1$ to $R^{16}$ may be the same or different, and are each a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group or a nitro group, specifically, the same atom or group as described for $R^1$ to $R^6$. Two or more of groups $R^1$ to $R^{16}$, preferably adjacent groups, may be bonded to each other to form an aliphatic ring, an aromatic ring or a hydrocarbon ring containing a hetero atom such as a nitrogen atom.

Y' is a bonding group or a single bond for bonding at least one group selected from $R^1$ to $R^6$ to at least one group selected from $R^{11}$ to $R^{16}$ (except a case of bonding $R^1$ and $R^{11}$ to each other).

The bonding group Y' is a group containing at least one element selected from among oxygen, sulfur, carbon, nitrogen, phosphorus, silicon, selenium, tin, boron and the like. Examples of such groups include groups containing halogen atoms such as —O—, —S— and —Se—; nitrogen- or phosphorus-containing groups, such as —NH—, —N(CH$_3$)$_2$, —PH— and —P(CH$_3$)$_2$—; hydrocarbon groups of 1 to 20 carbon atoms, such as —CH$_2$—, —CH$_2$—CH$_2$— and —C(CH$_3$)$_2$—; residues of cyclic unsaturated hydrocarbons of 6 to 20 carbon atoms, such as benzene, naphthalene and anthracene; residues of heterocyclic compounds having 3 to 20 carbon atoms and containing hetero atoms, such as pyridine, quinoline, thiophene and furan; silicon atom-containing groups, such as —SiH$_2$— and —Si(CH$_3$)$_2$; tin atom-containing groups, such as —SiH$_2$— and —Sn(CH$_3$)$_2$; and boron atom-containing groups, such as —BH—, —B(CH$_3$)— and —BF—.

Examples of the transition metal compounds represented by the formula (I-a-1) are given below, but are not limited thereto.

In the following examples, M is a transition metallic element, and specifically represents, but not limited to, Sc(III), Ti(III), Ti(IV), Zr(III), Zr(IV), Hf(IV), V(IV), Nb(V), Ta(V), Co(II), Co(III), Rh(II), Ph(III), Ph(IV). Of these, particularly preferable is Ti(IV), Zr(IV) or Hf(IV).

X is halogen such as Cl or Br, or an alkyl group such as methyl, but not limited thereto. When plural X are present, they may be the same or different.

n depends on a valence of the metal M. For example, when two monoanion species are bonded to the metal, n=0 in case of a divalent metal, n=1 in case of a trivalent metal, n=2 in case of a tetravalent metal, and n=3 in case of a pentavalent metal. More specifically, there can be mentioned n=2 in case of Ti(IV), n=2 in case of Zr(IV), and n=2 in case of Hf(IV).

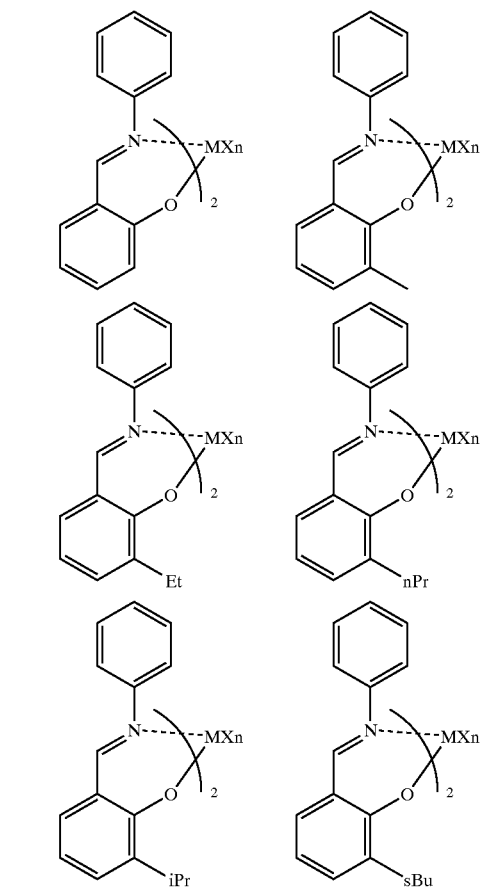

-continued
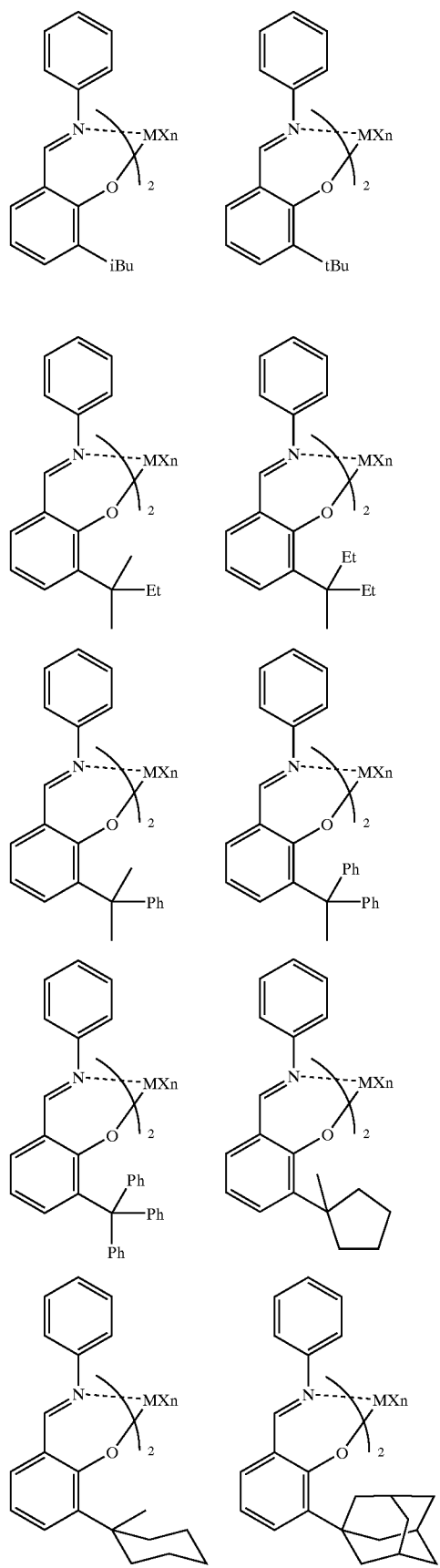
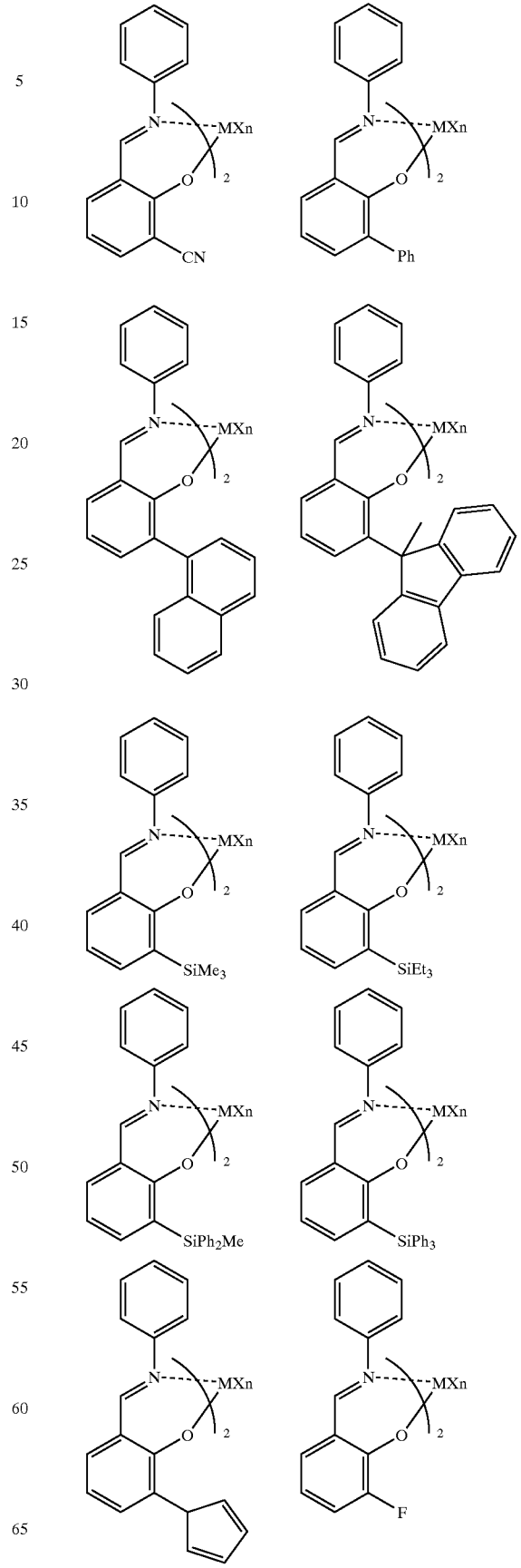

-continued
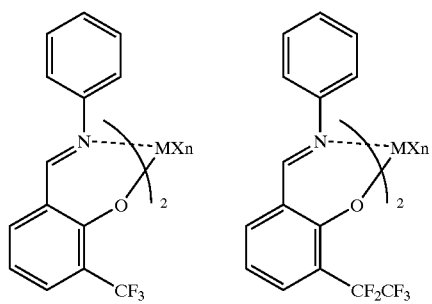
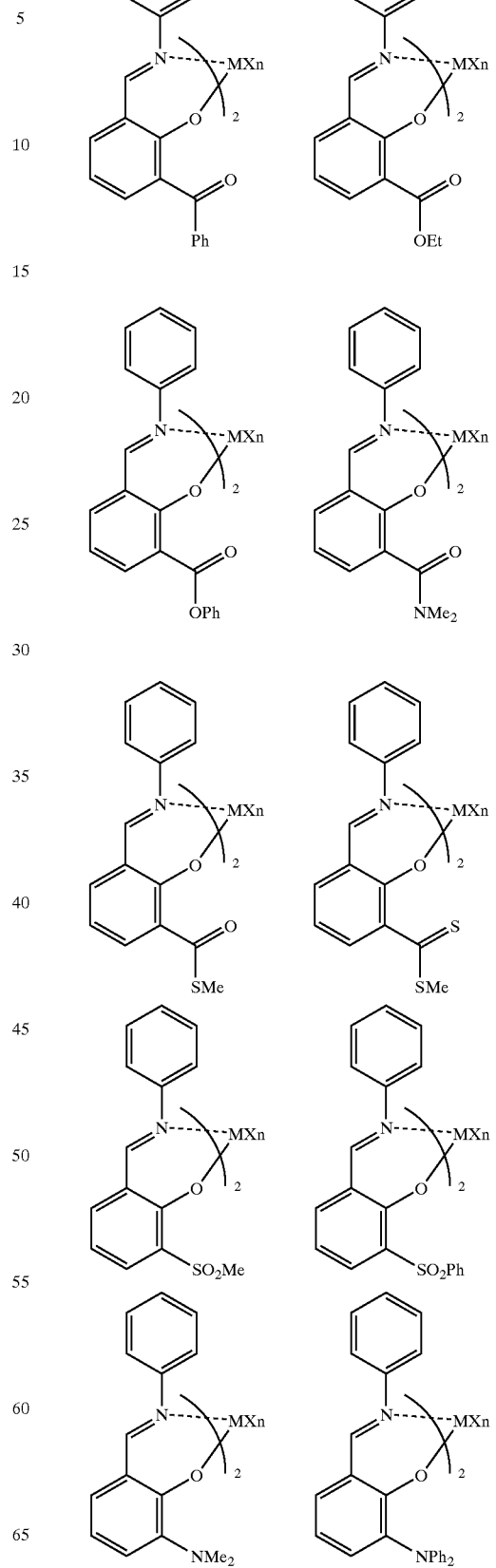

-continued
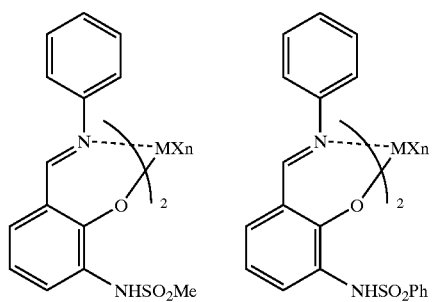
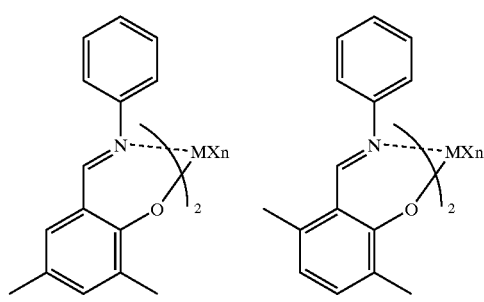
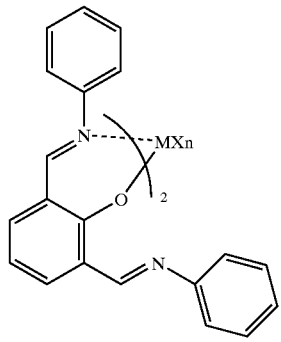
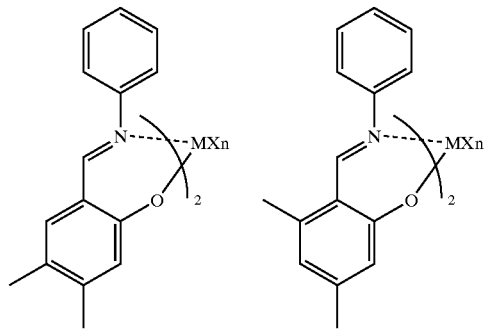
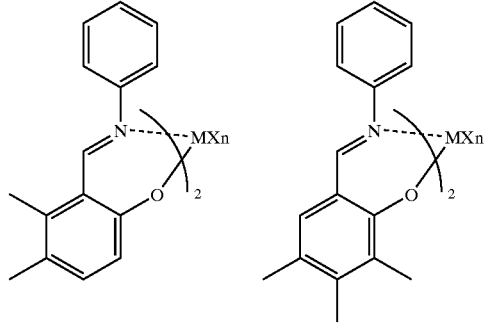
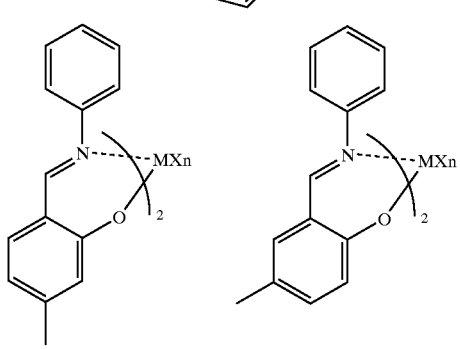
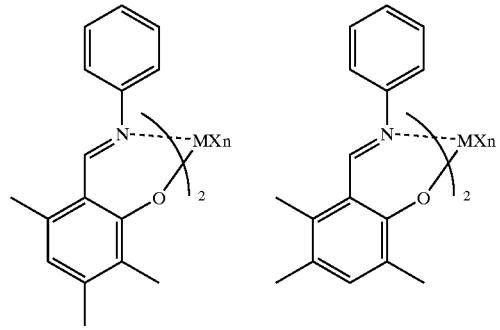
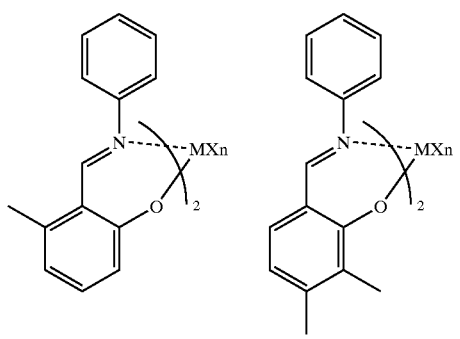
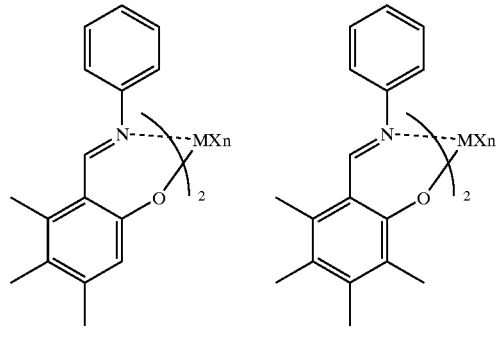

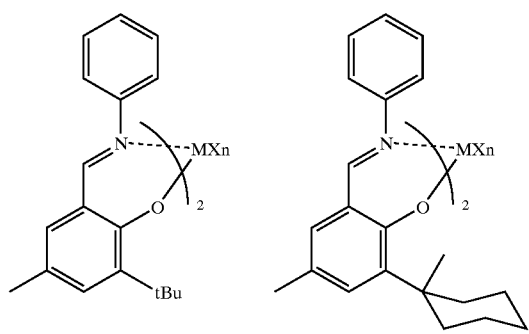
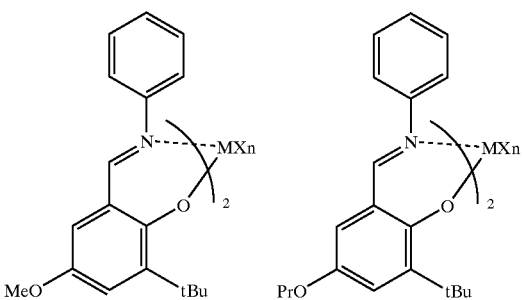
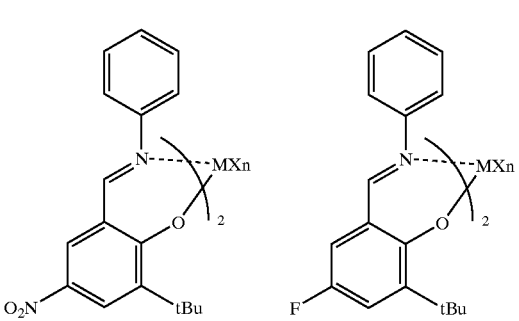
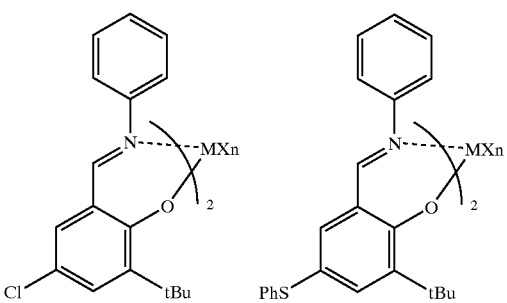
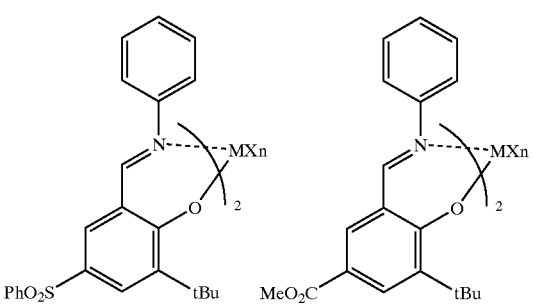
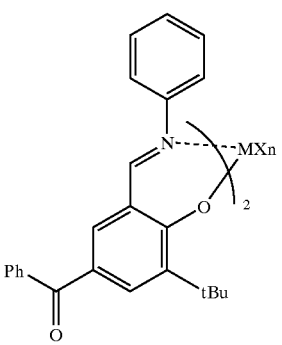

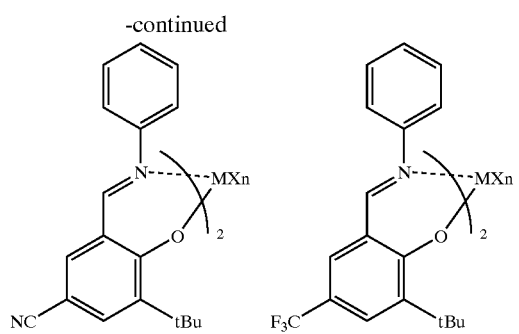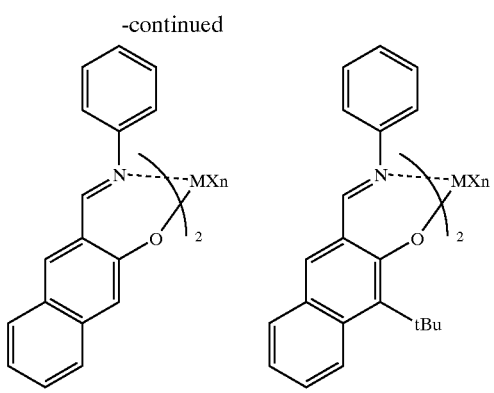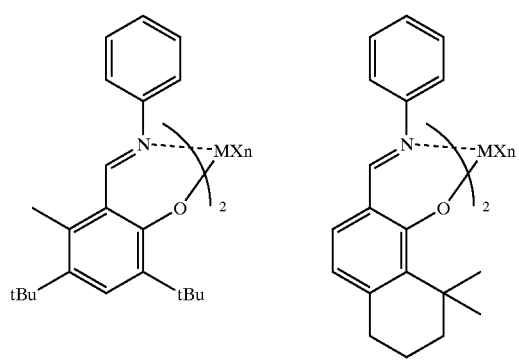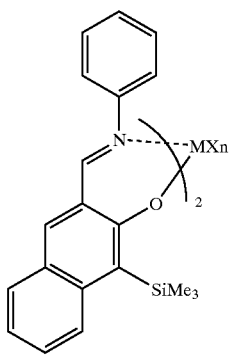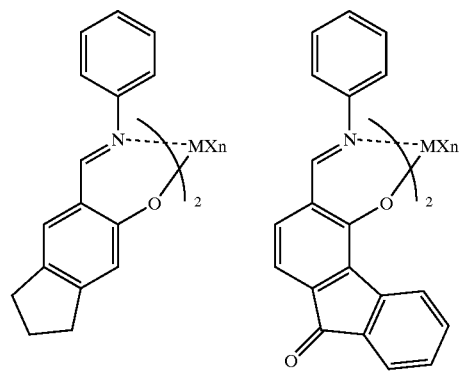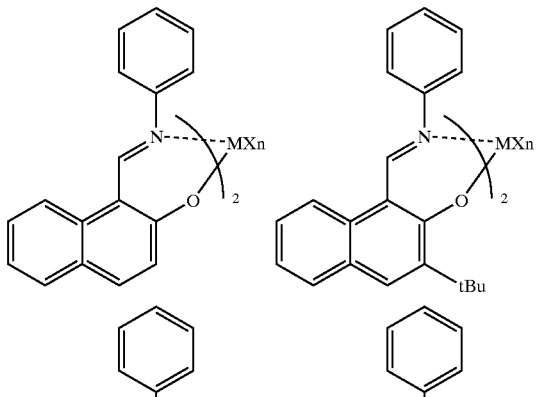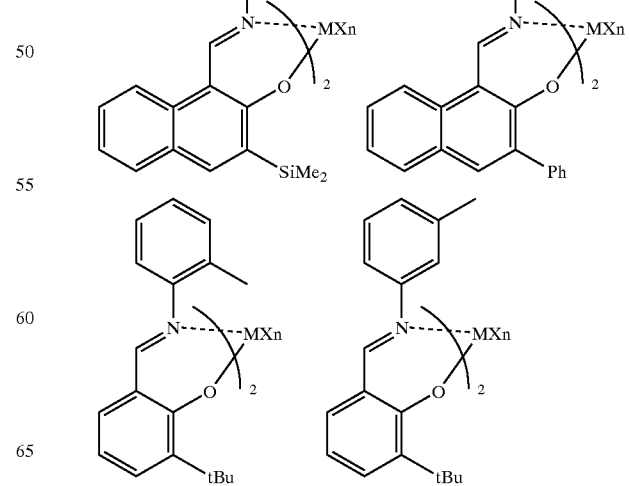

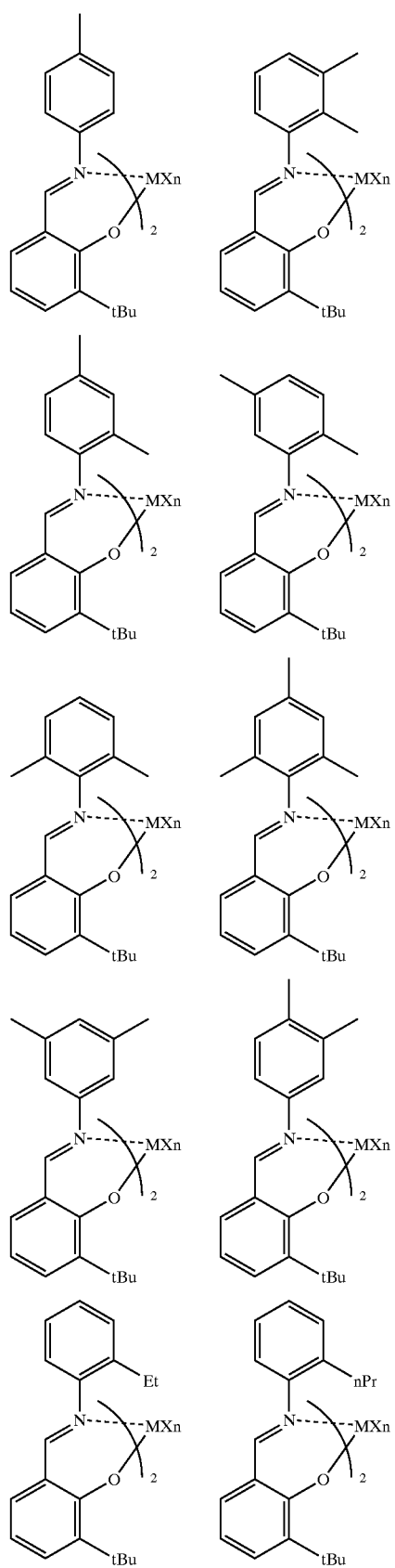
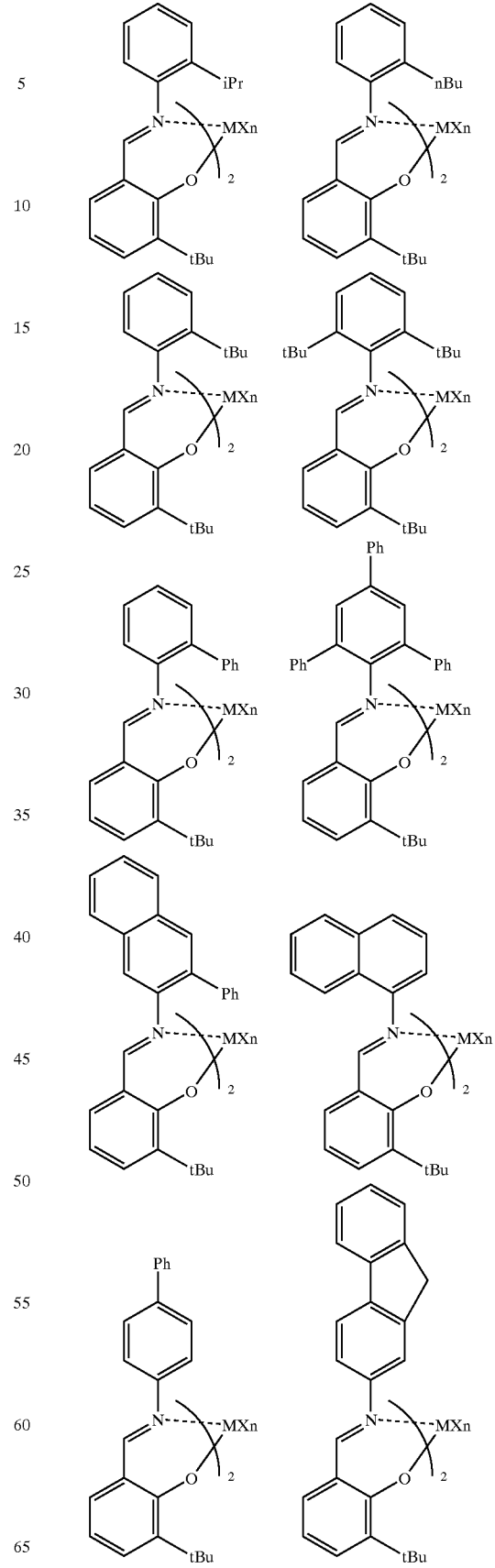

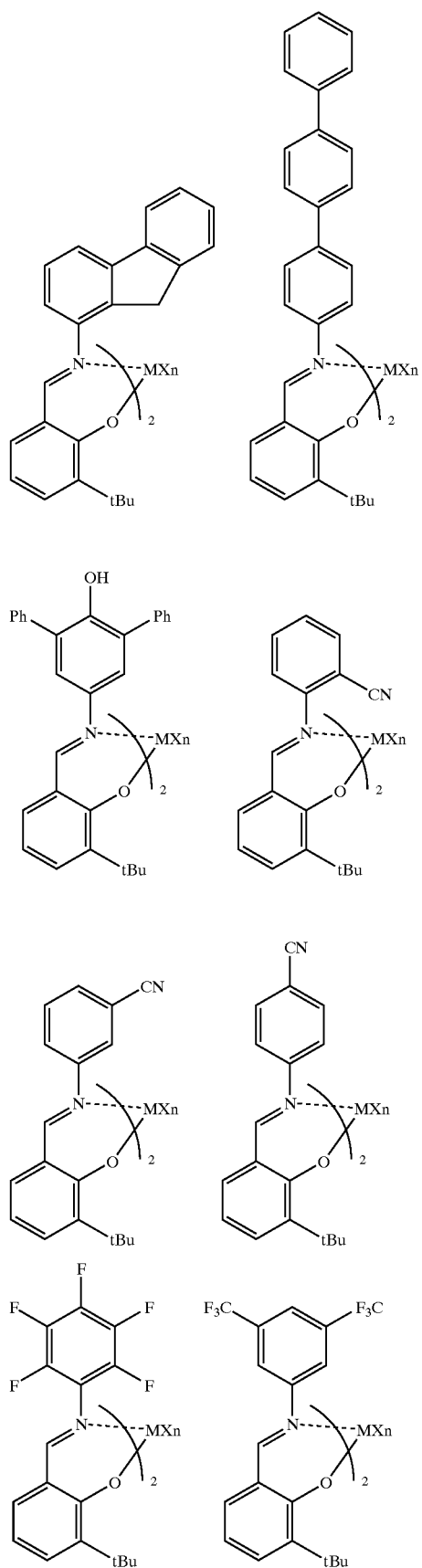
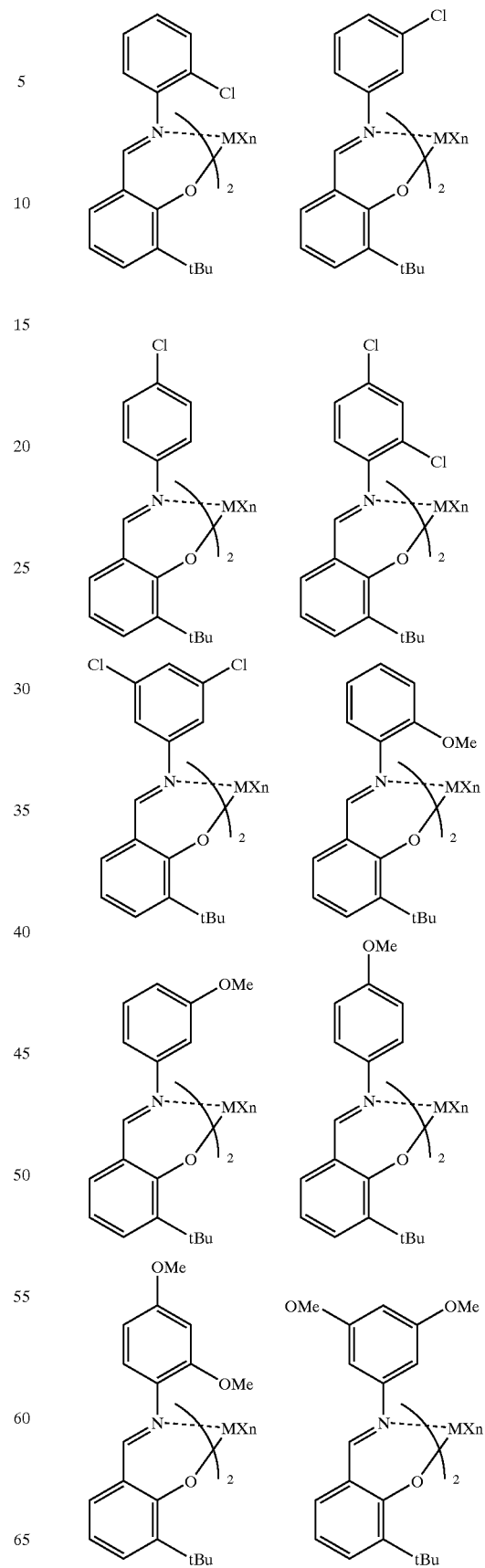

-continued
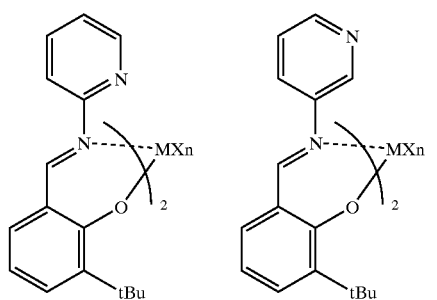
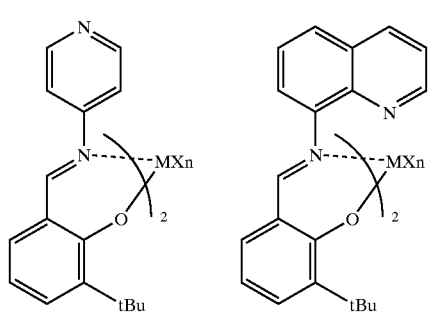
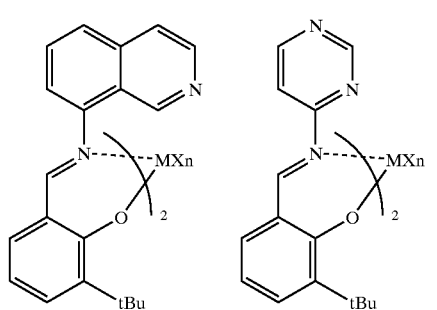
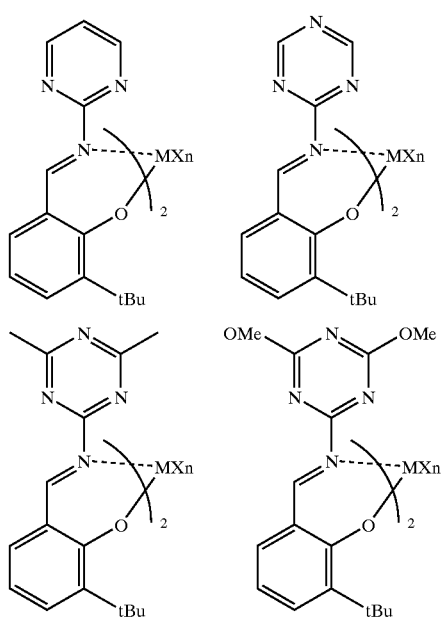
-continued
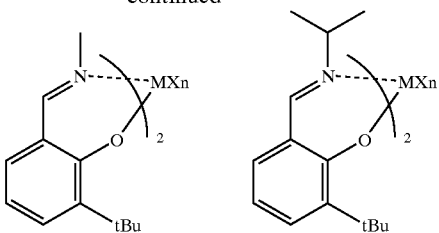
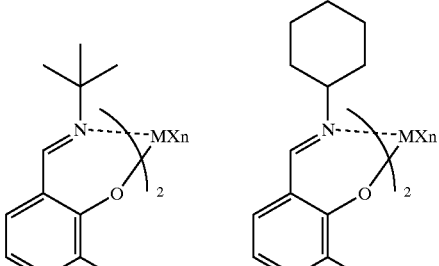
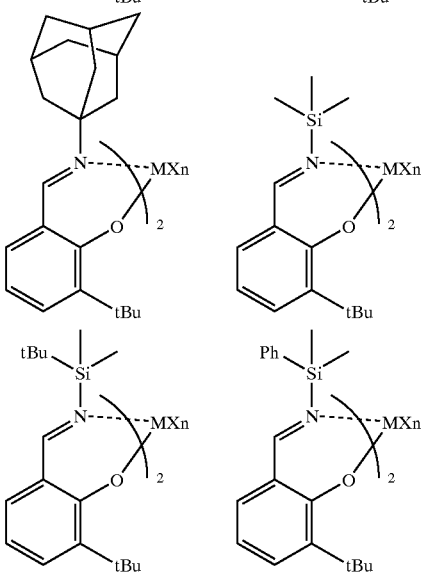
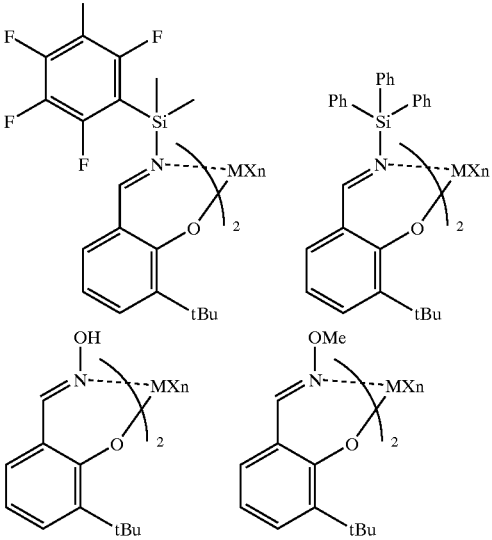

-continued
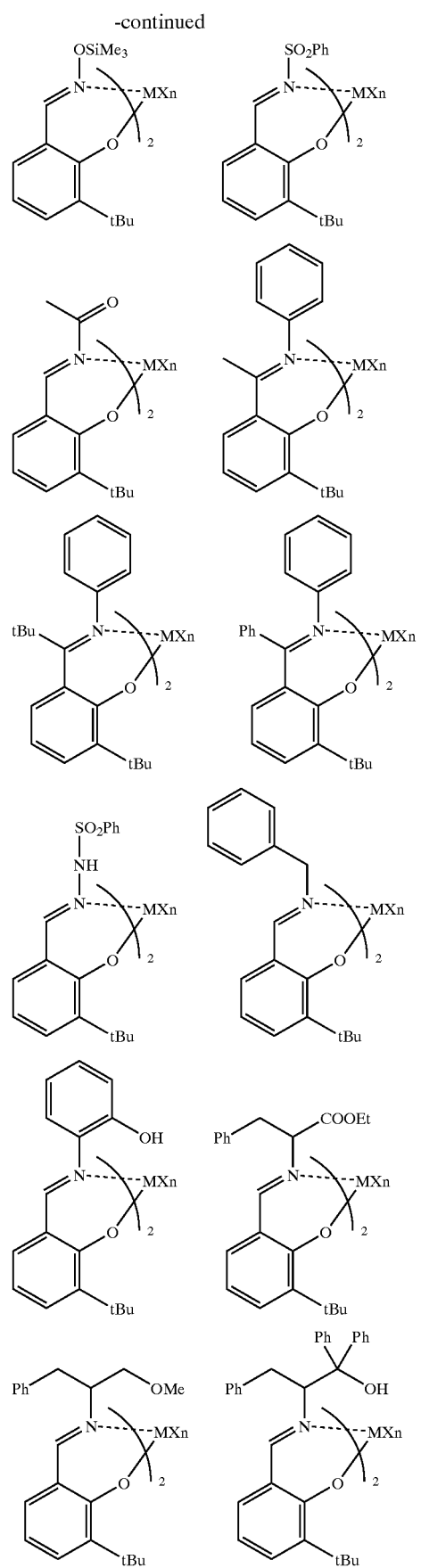
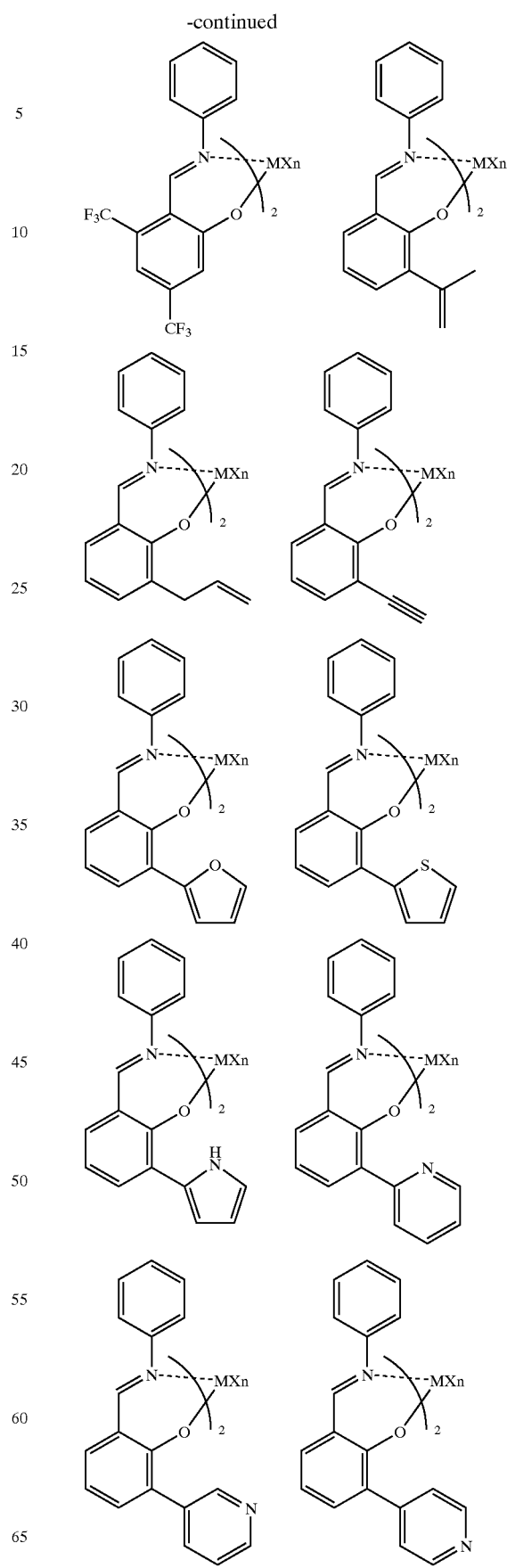

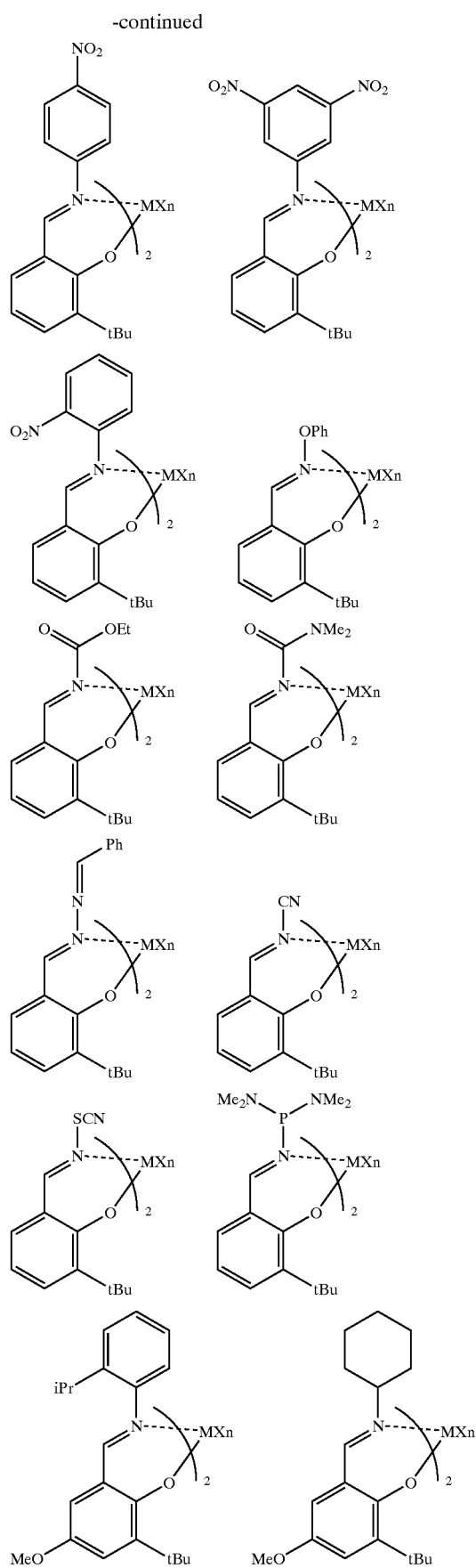
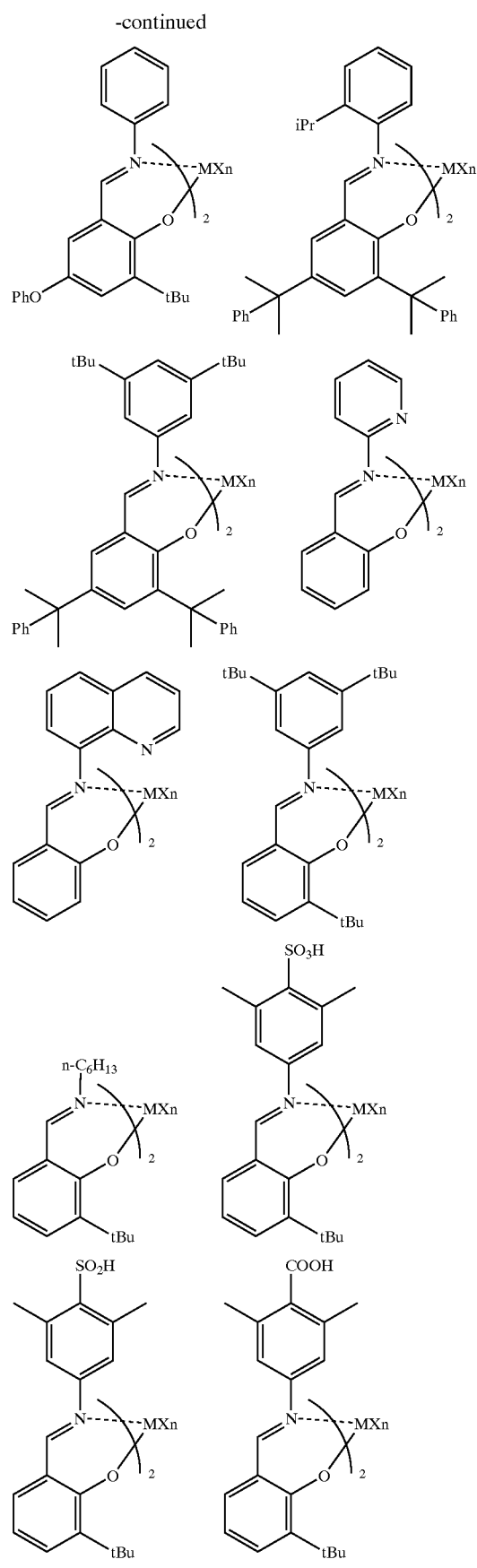

-continued
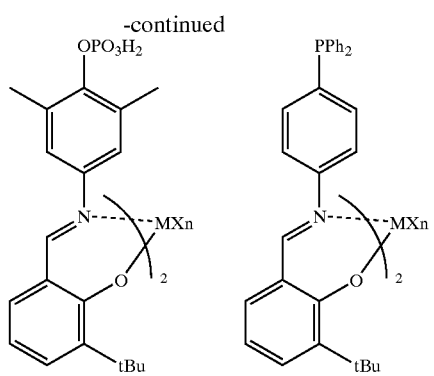
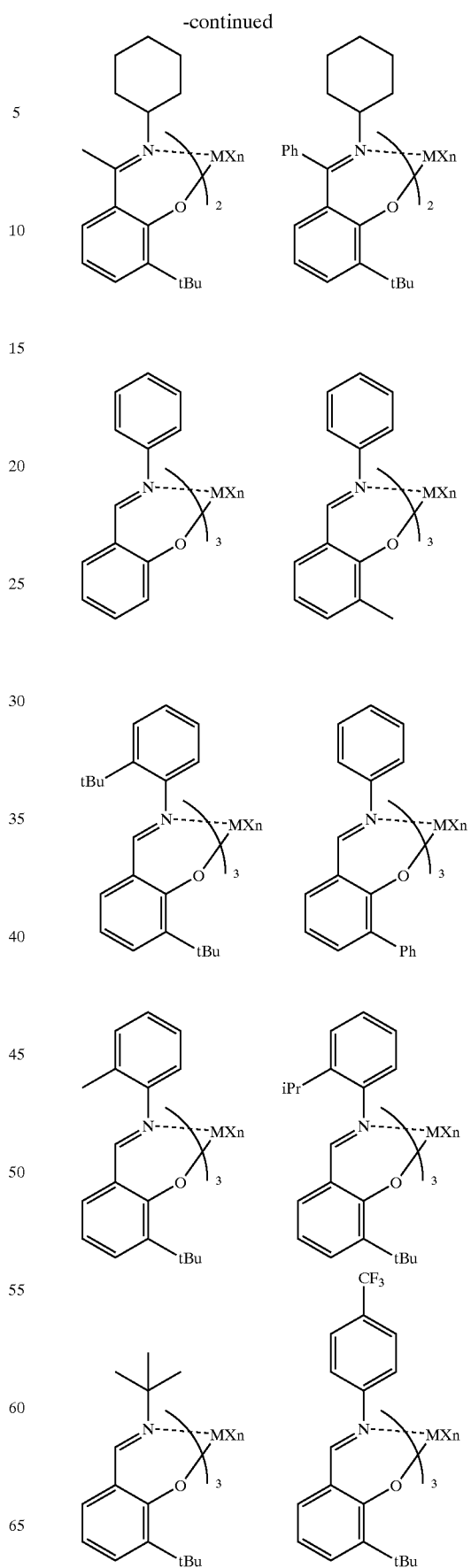

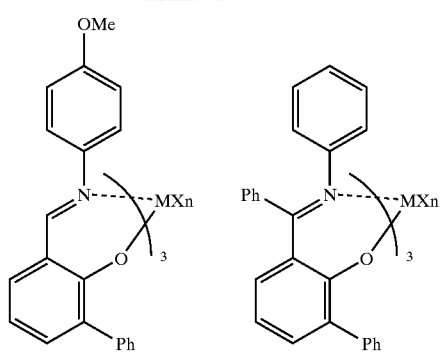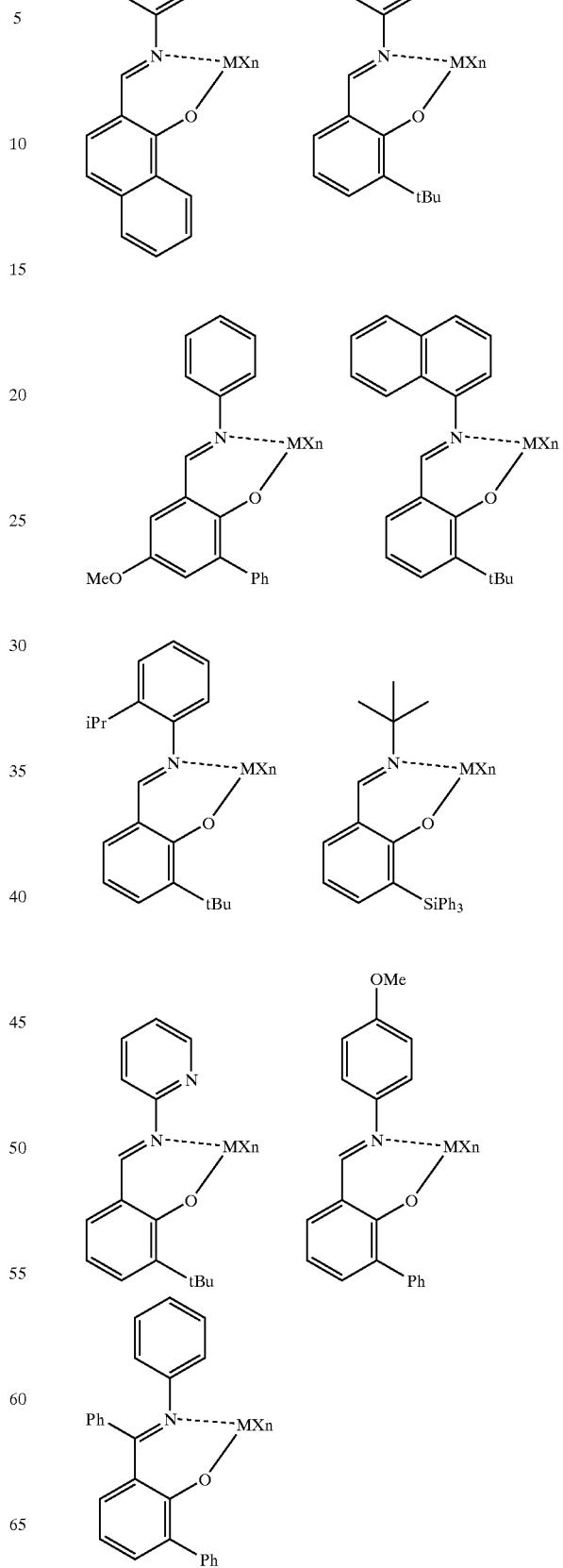

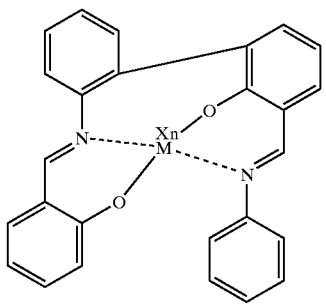
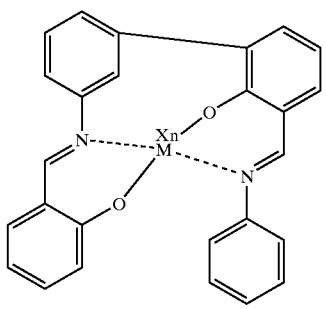
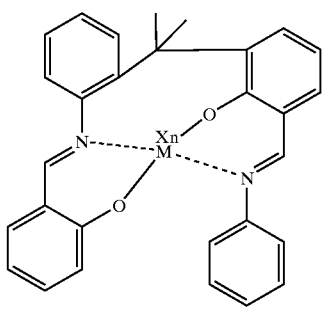
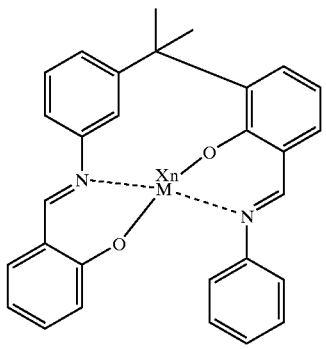
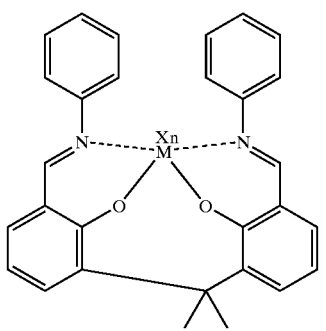
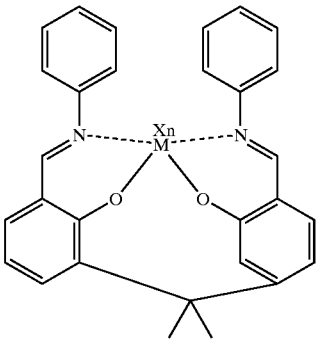
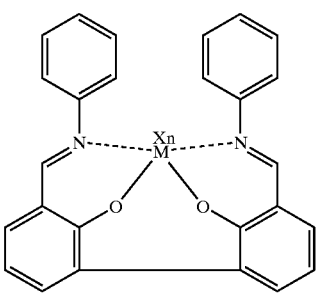
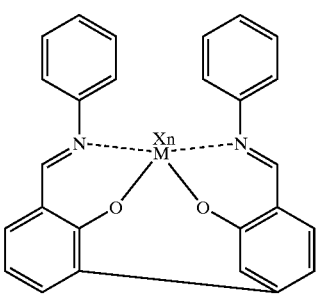
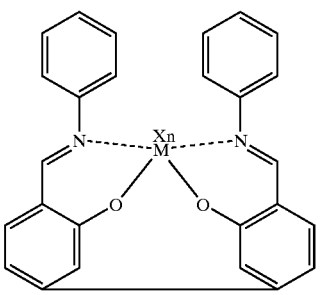
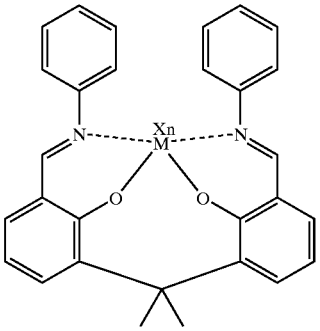

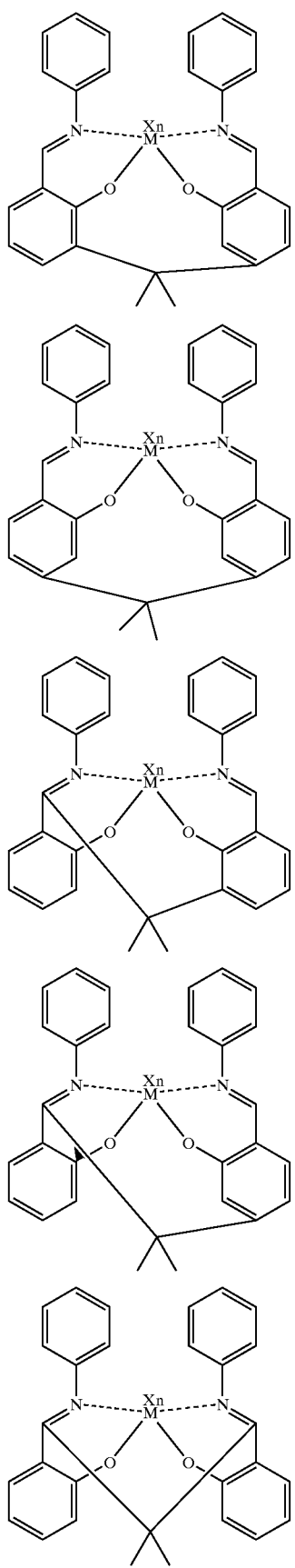
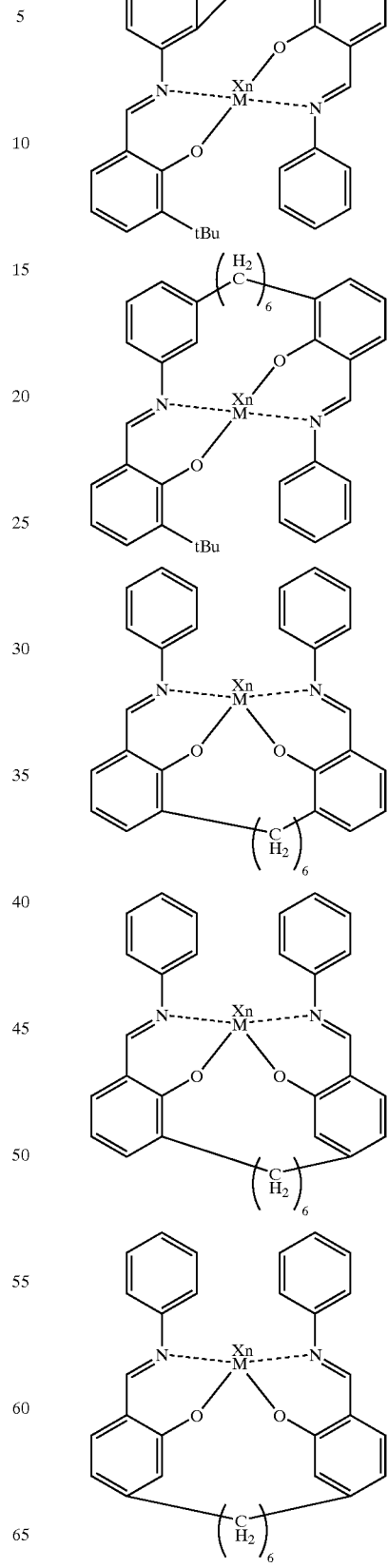

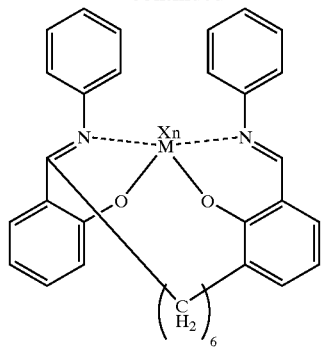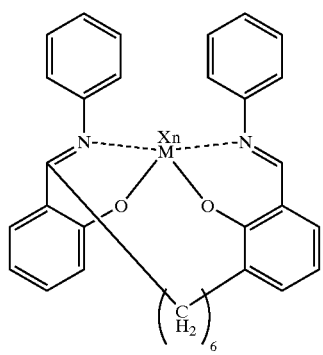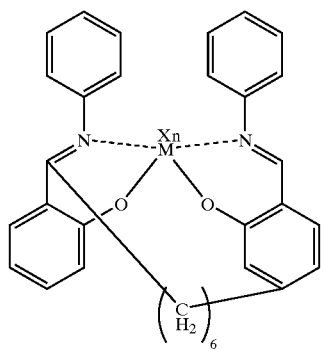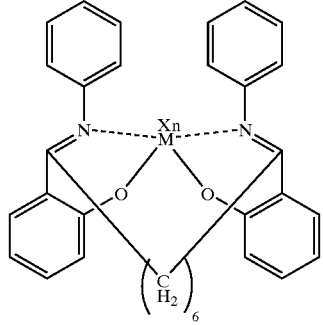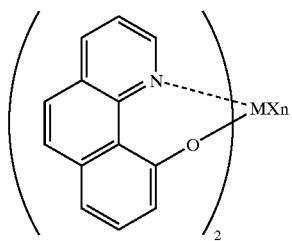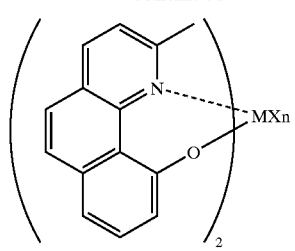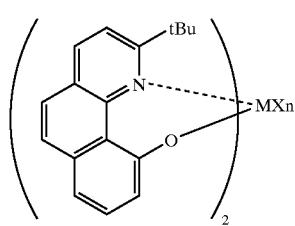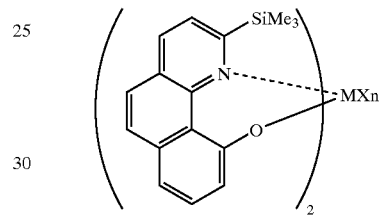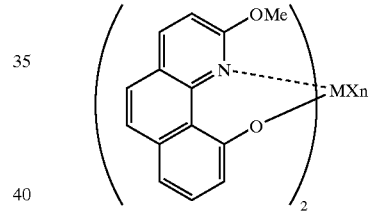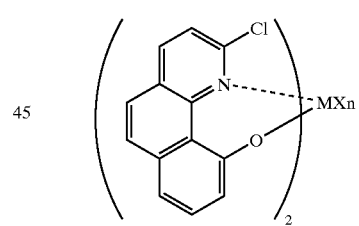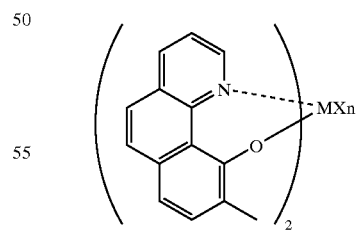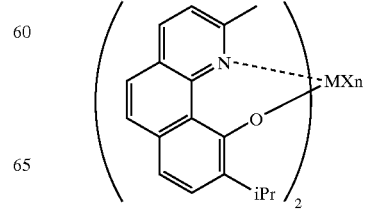

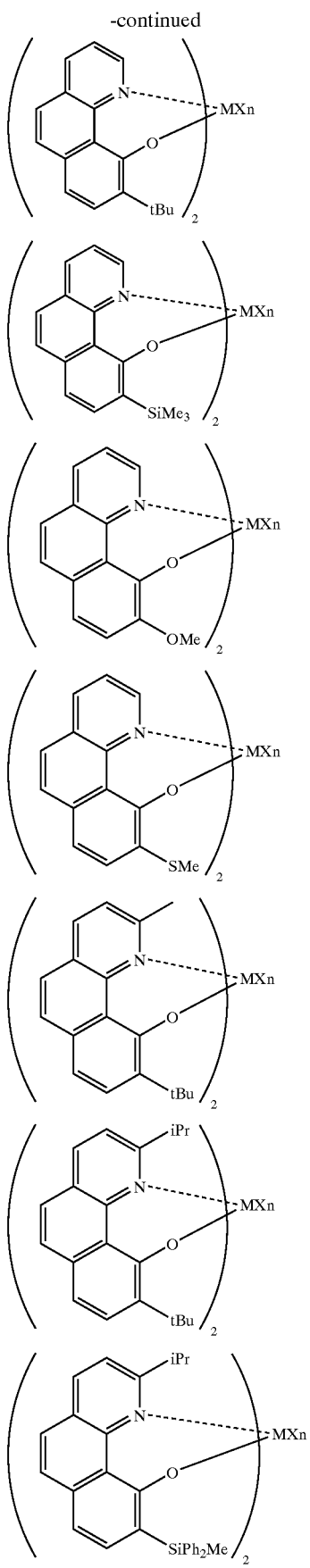
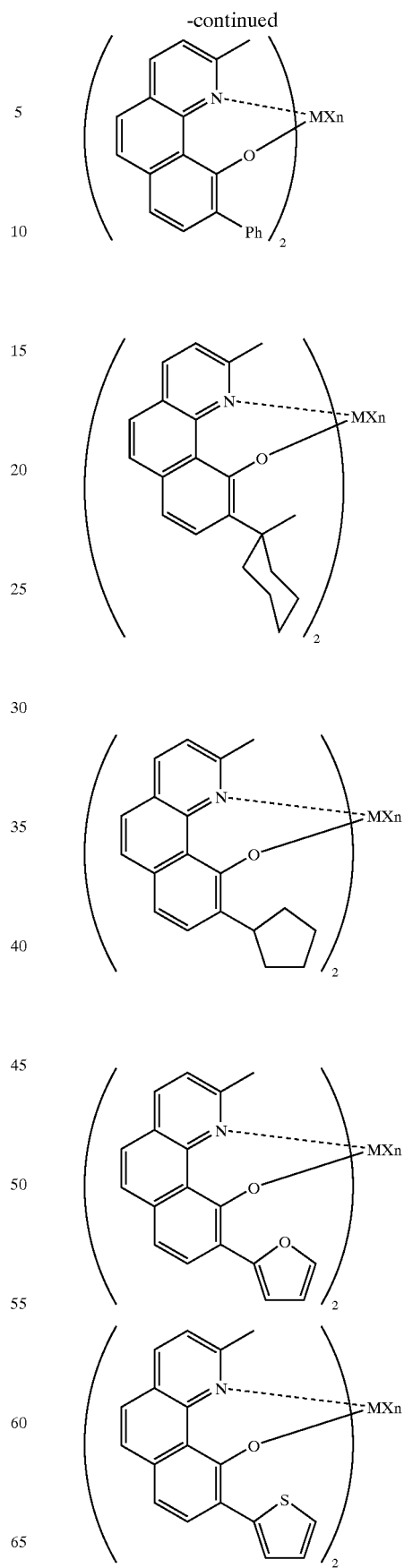

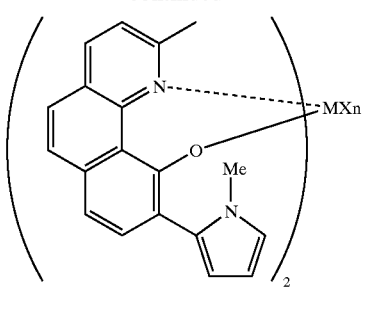
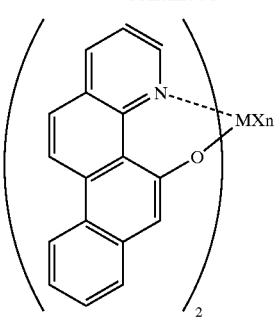
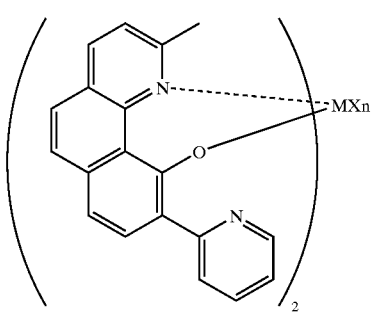
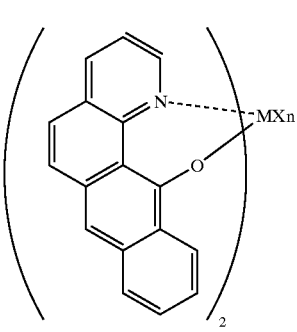
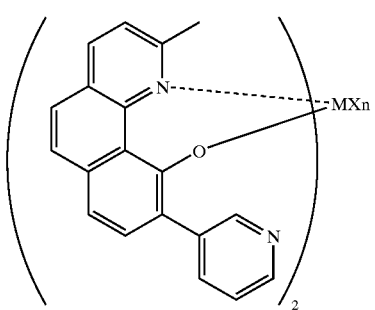
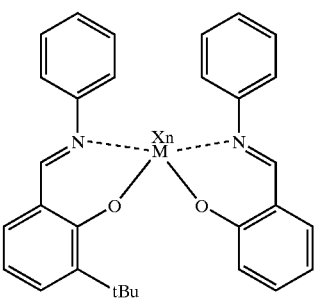
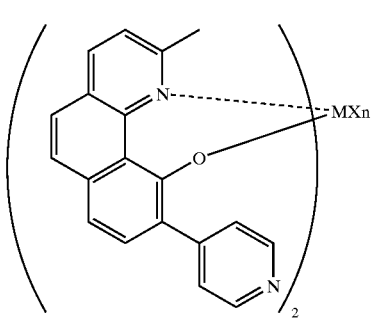
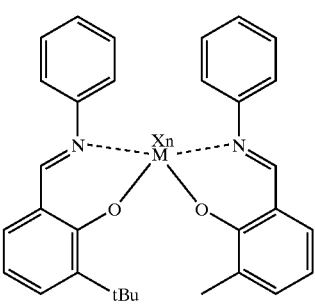
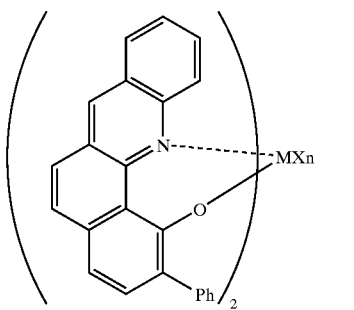
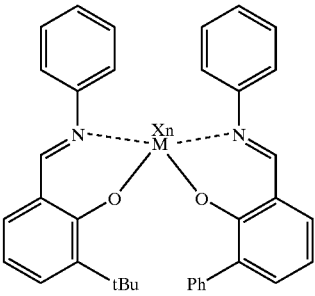

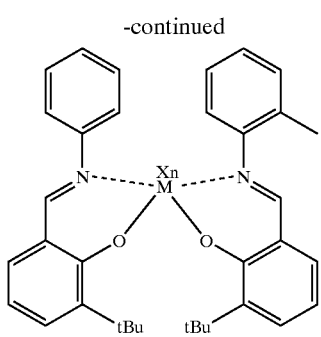
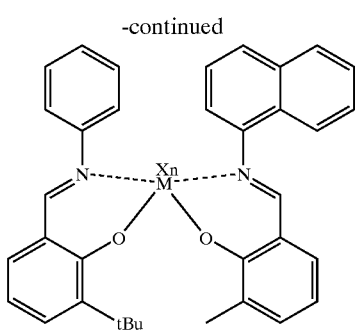
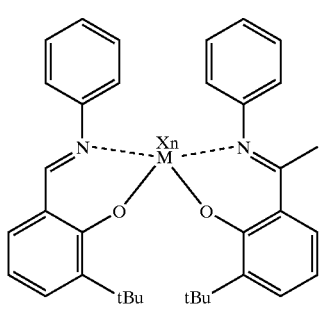
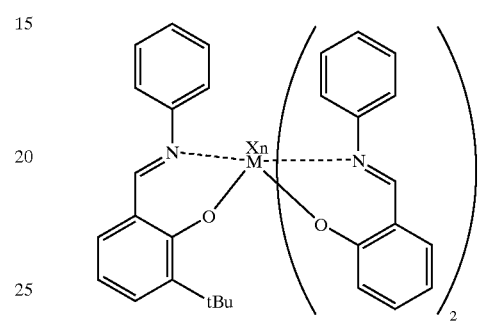
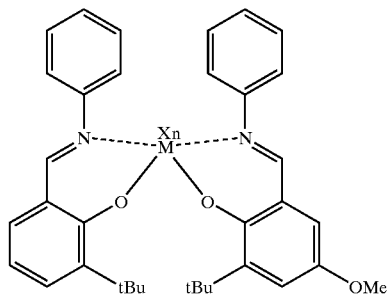
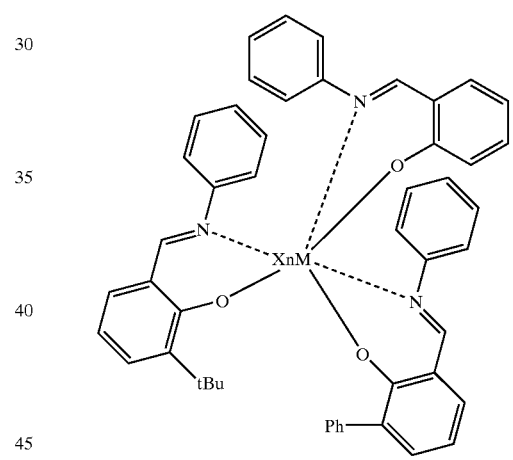
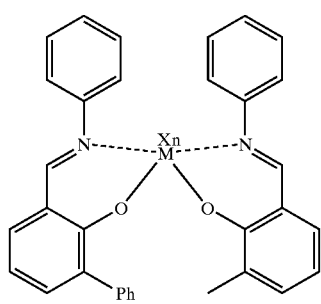
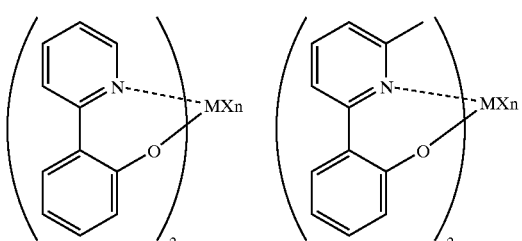
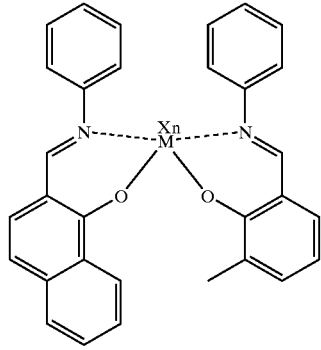
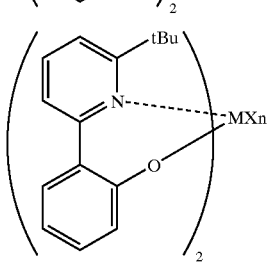

-continued
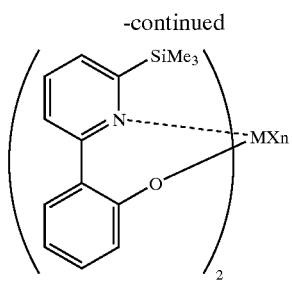
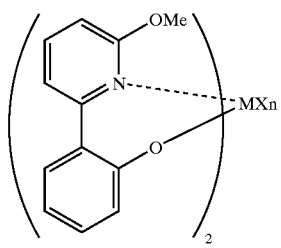
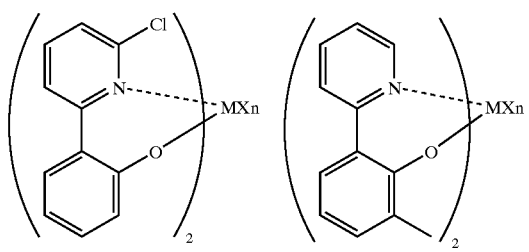
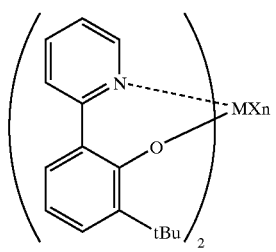
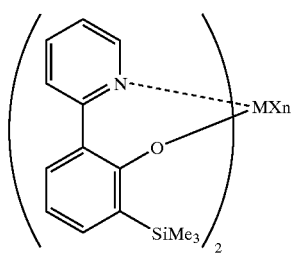
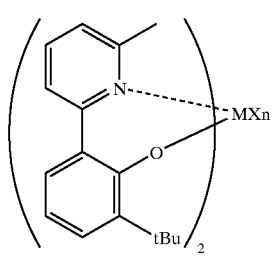
-continued
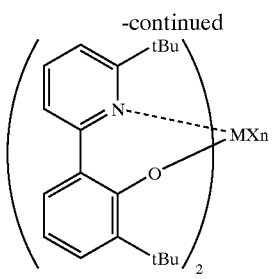
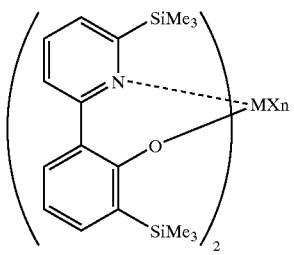
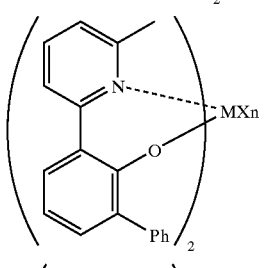
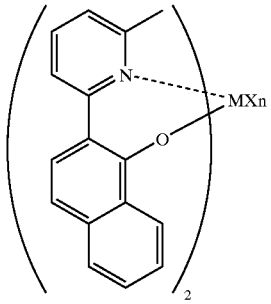
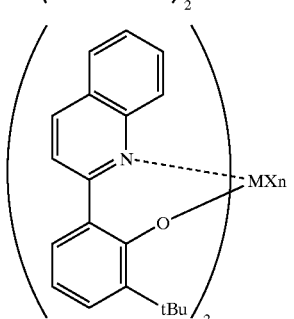
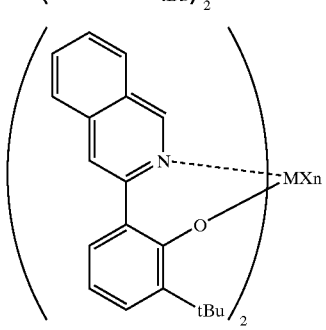

-continued
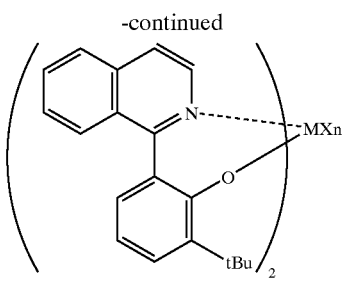
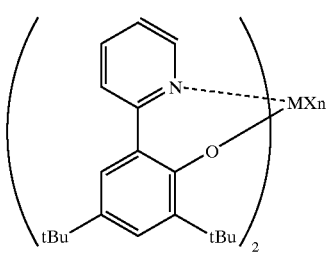
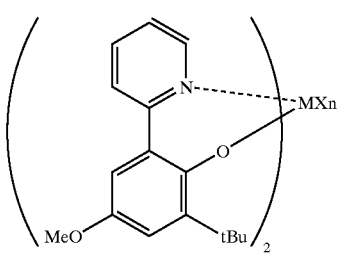
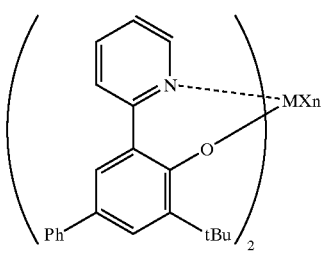
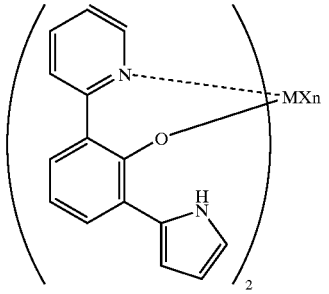
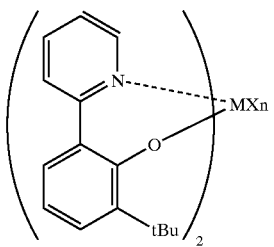
-continued
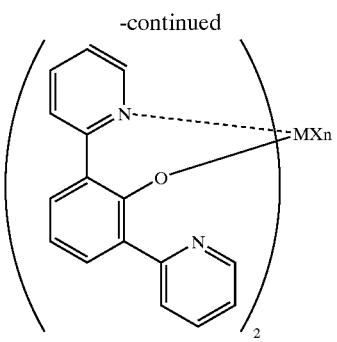
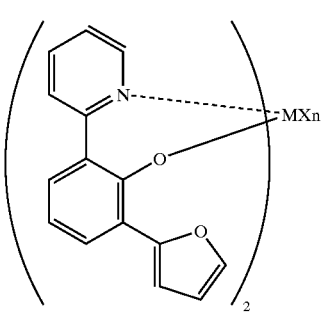
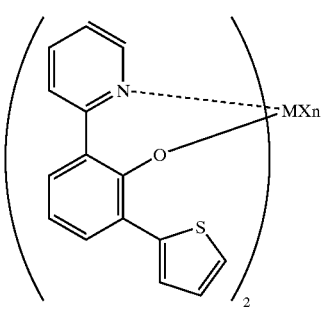
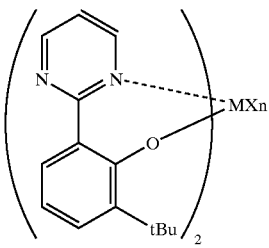
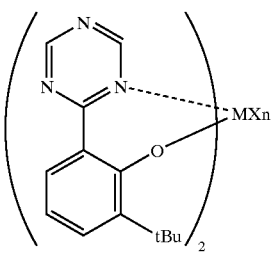
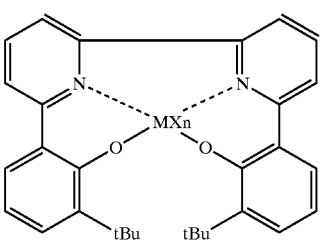

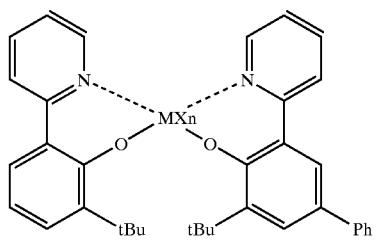
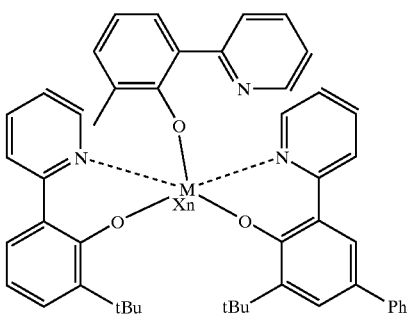
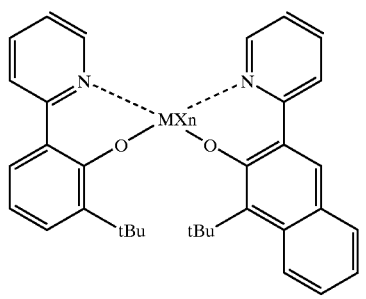
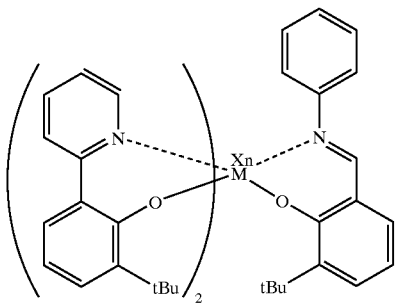
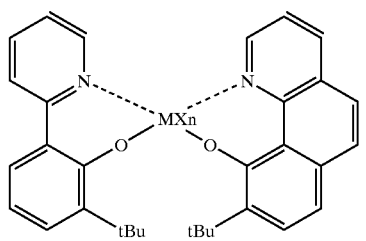
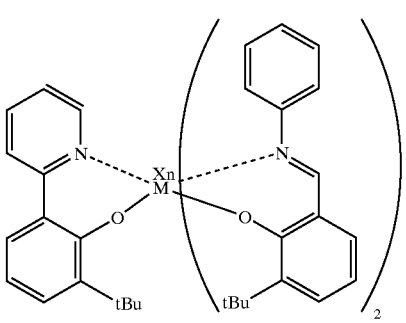
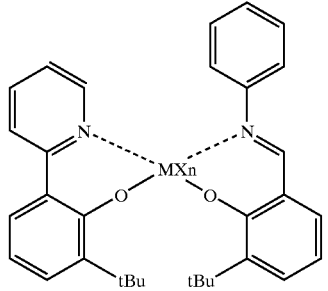
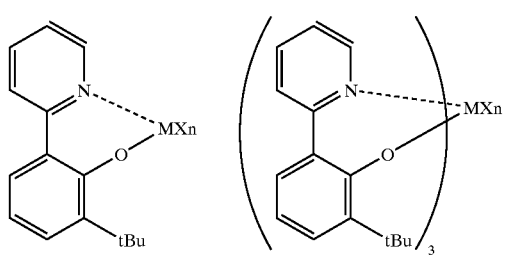
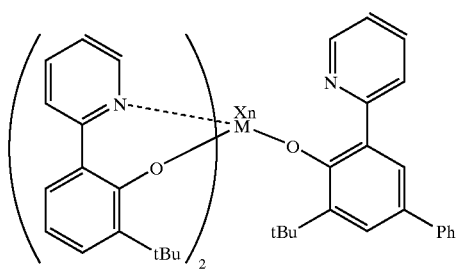
In the above chemical formulae, Me is methyl, Et is ethyl, iPr is isopropyl, tBu is tert-butyl and Ph is phenyl.
More specific examples of compounds having a center metal Ti are given below. There can also be mentioned those compounds in which titanium is replaced with zirconium, hafnium, cobalt or rhodium.
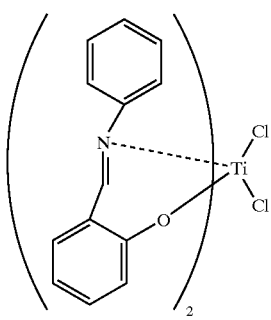

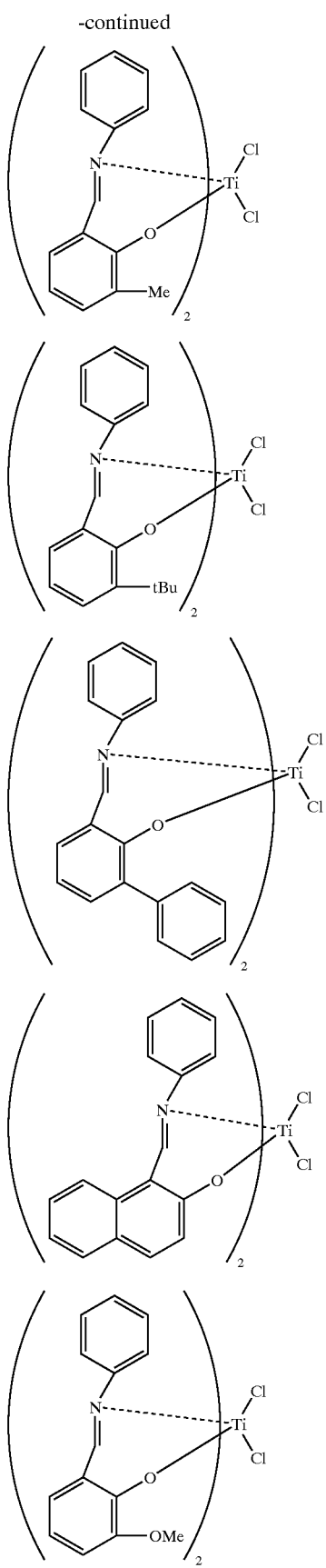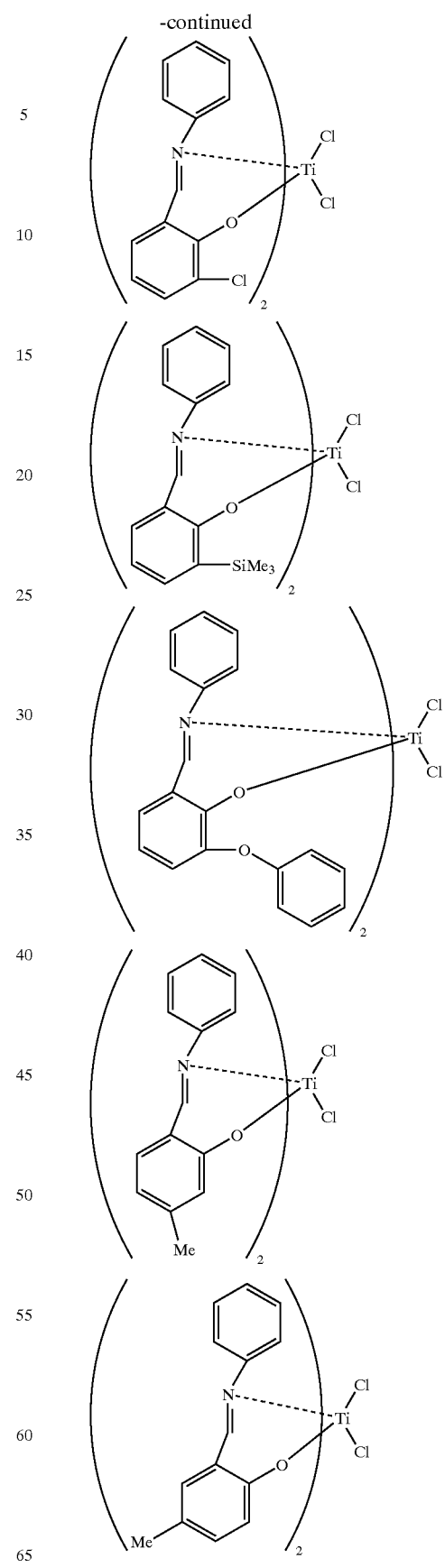

-continued
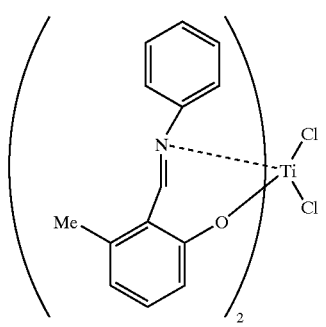
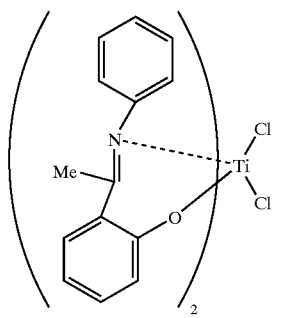
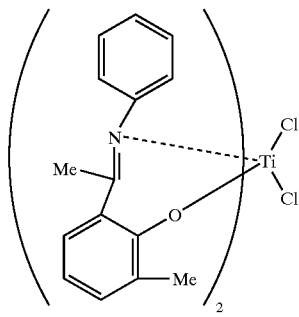
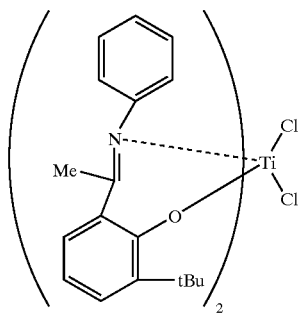
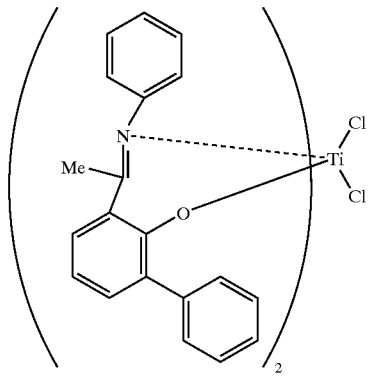
-continued
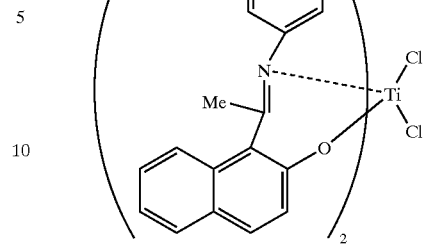
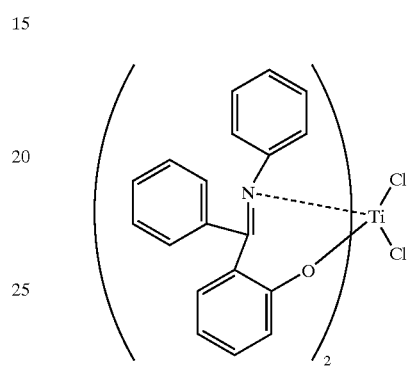
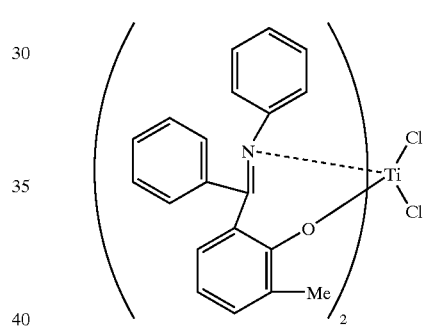
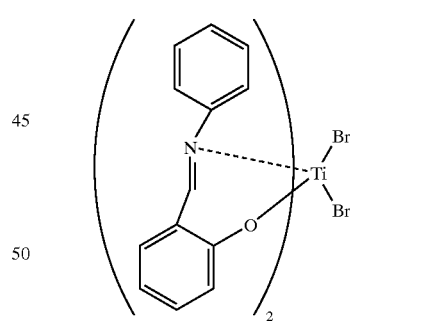
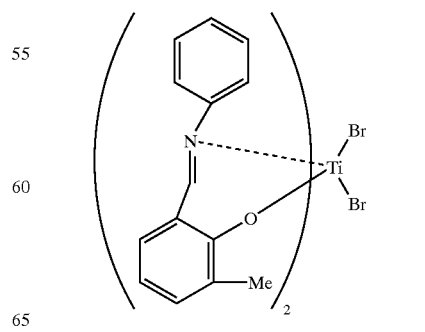

-continued
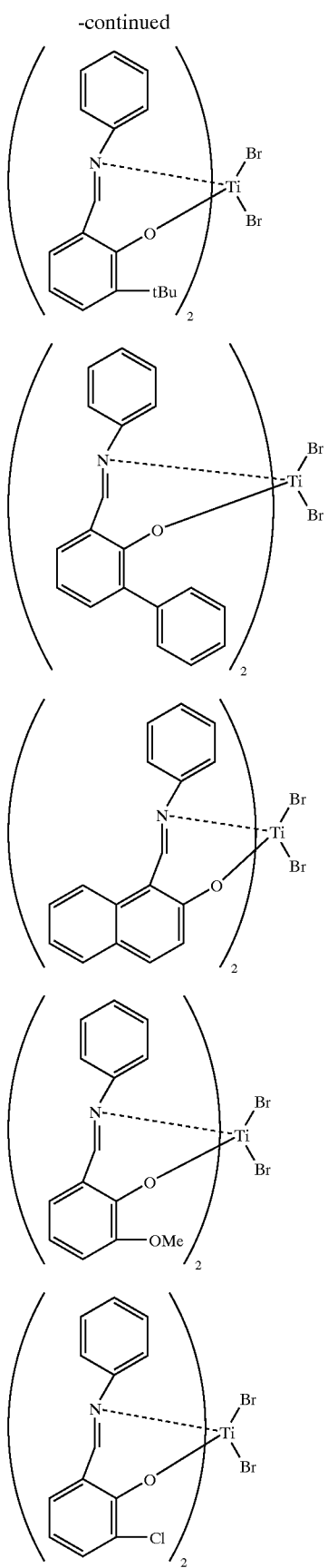
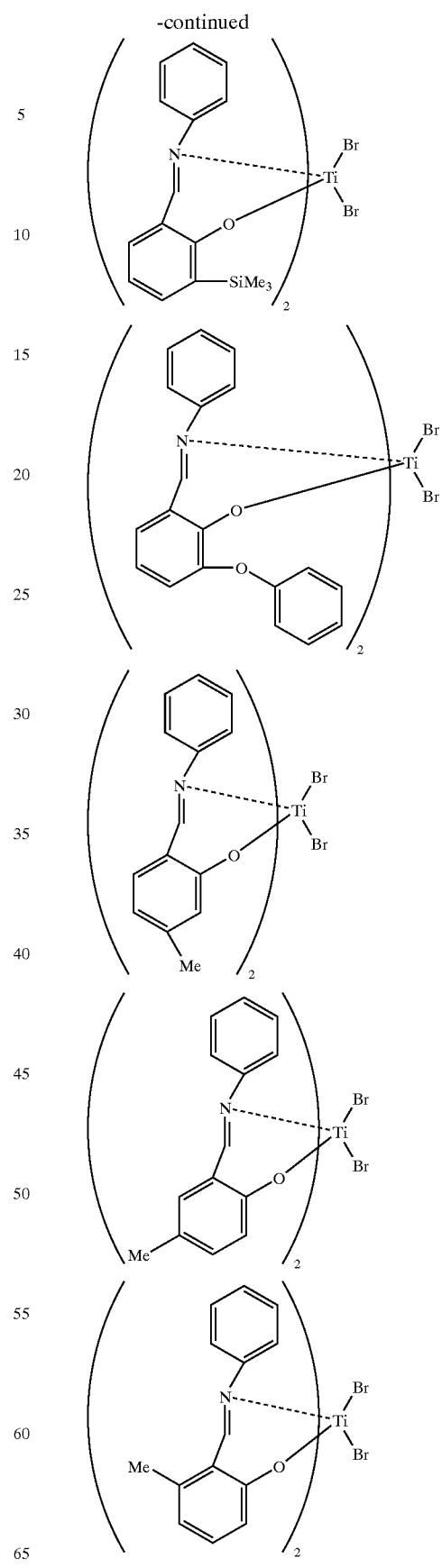

-continued
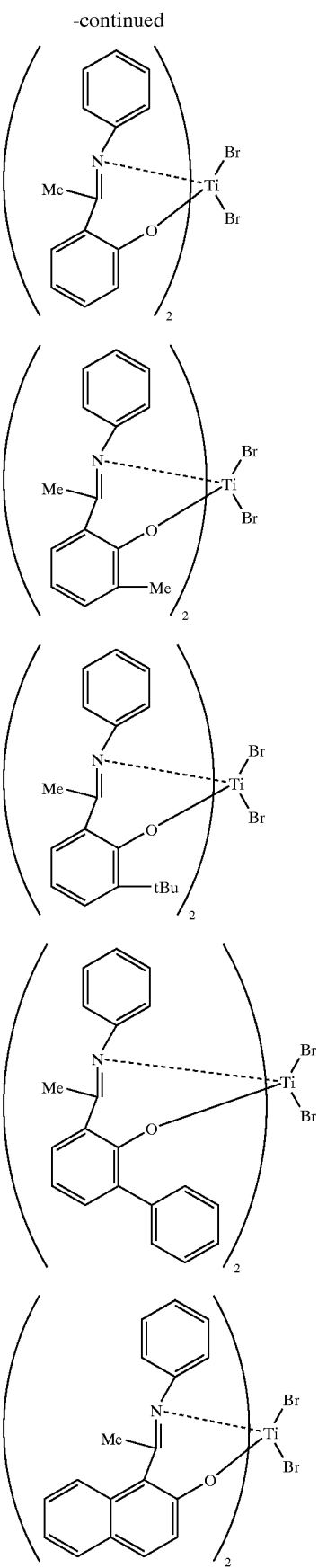
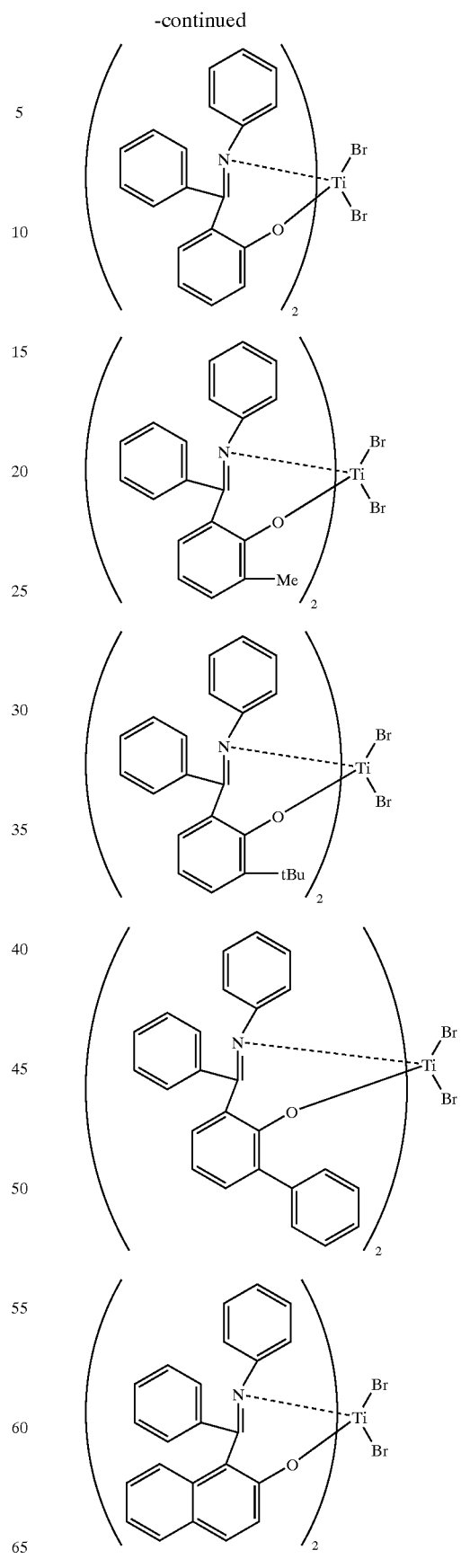

-continued
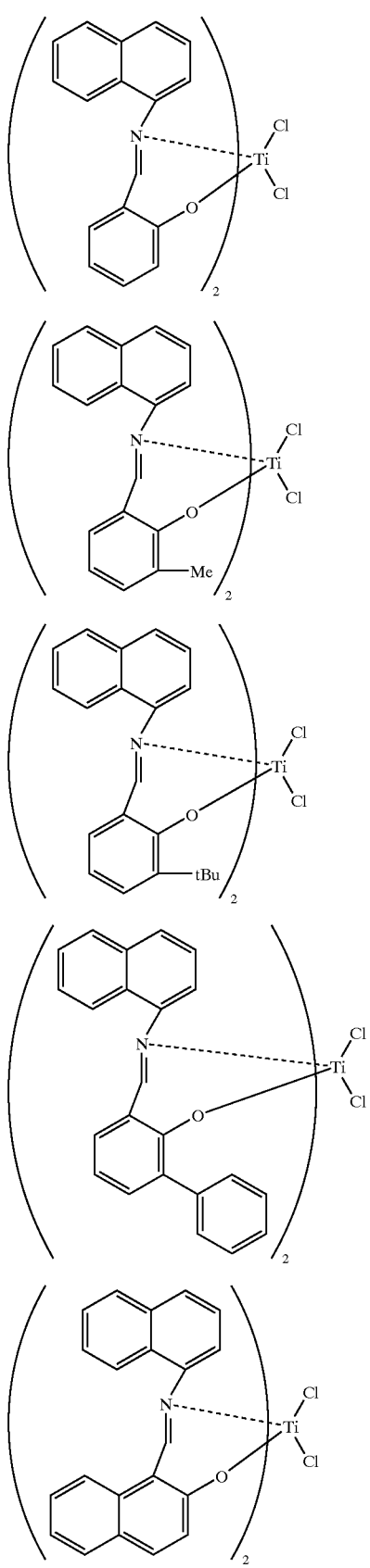
-continued
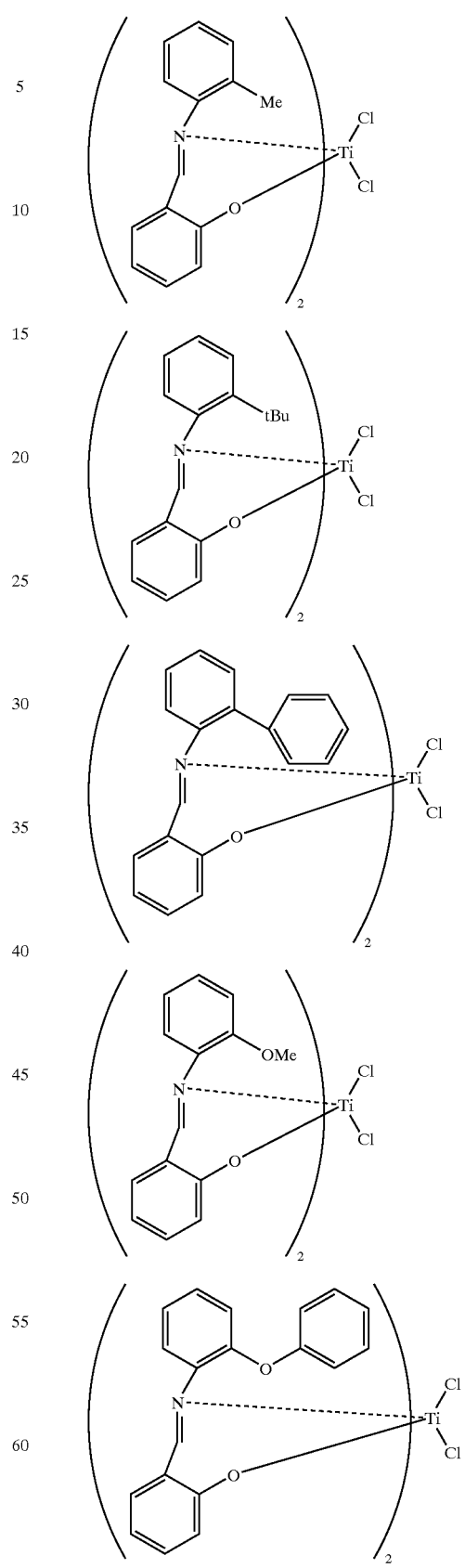

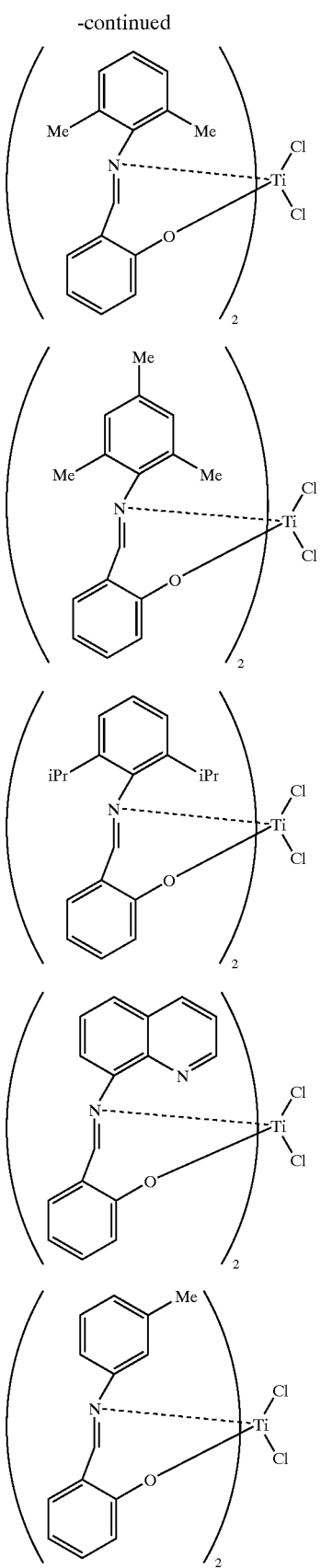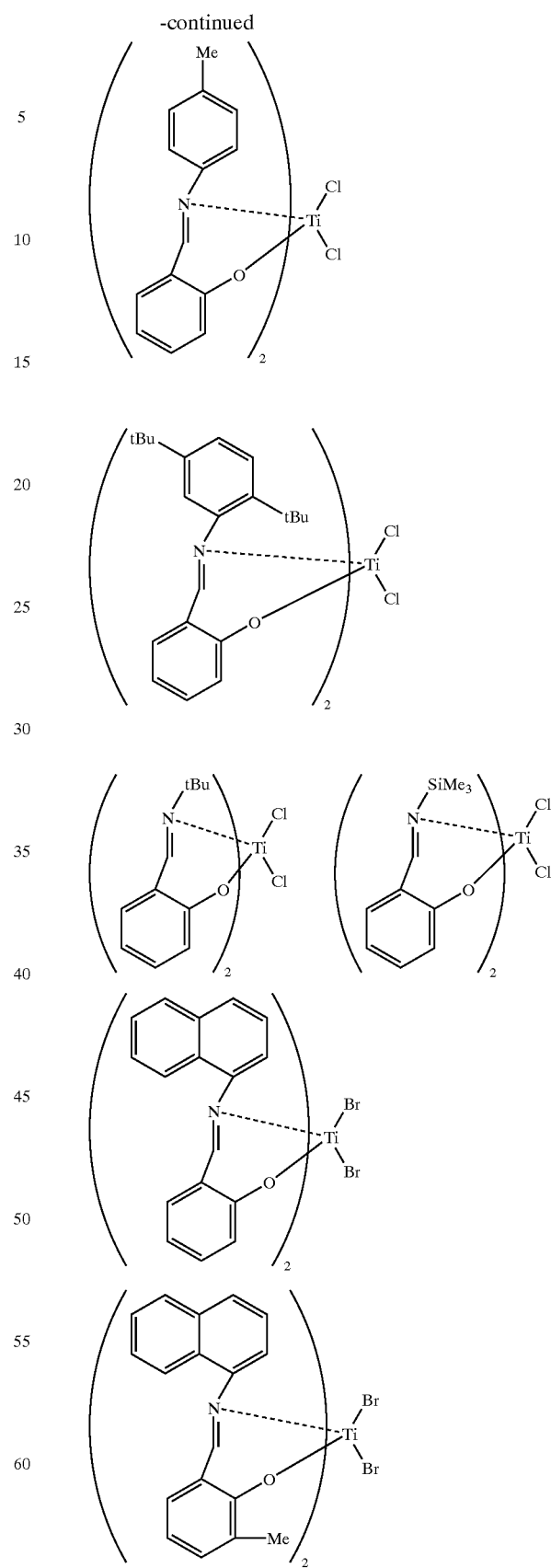

-continued
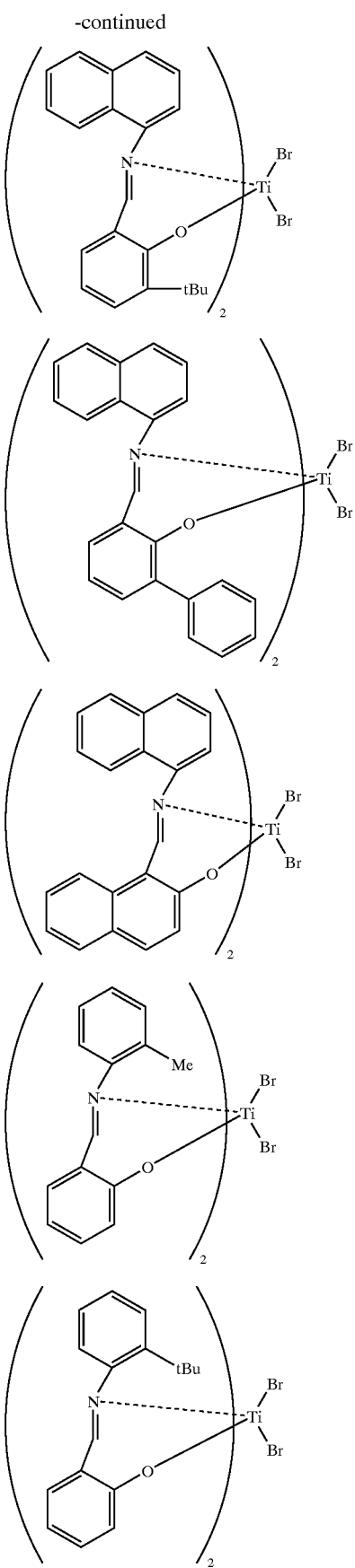
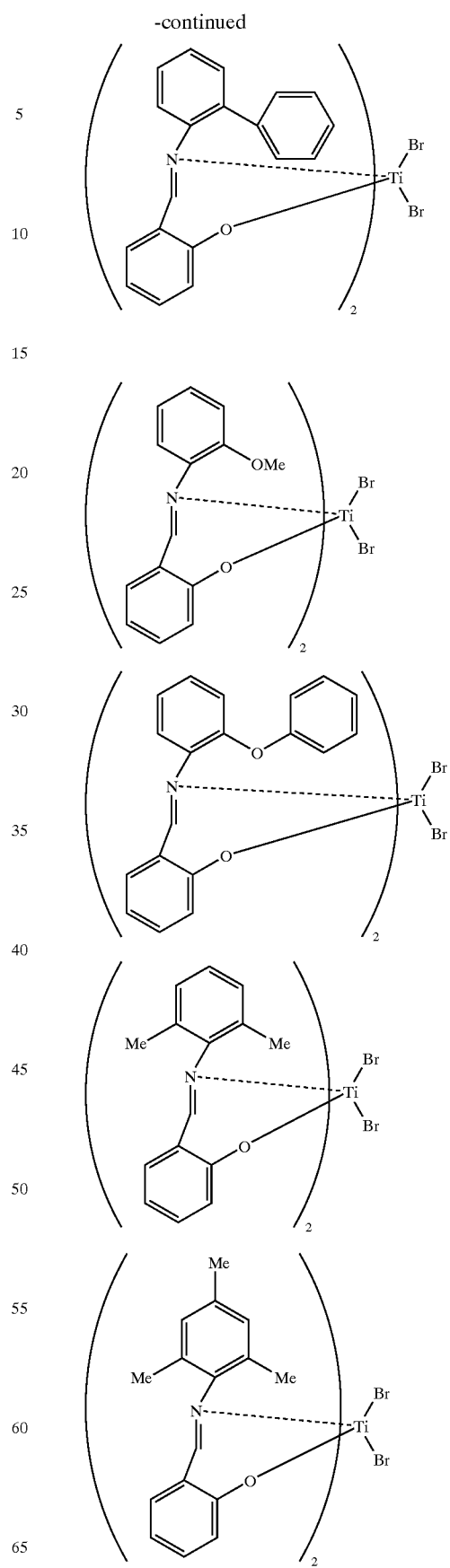

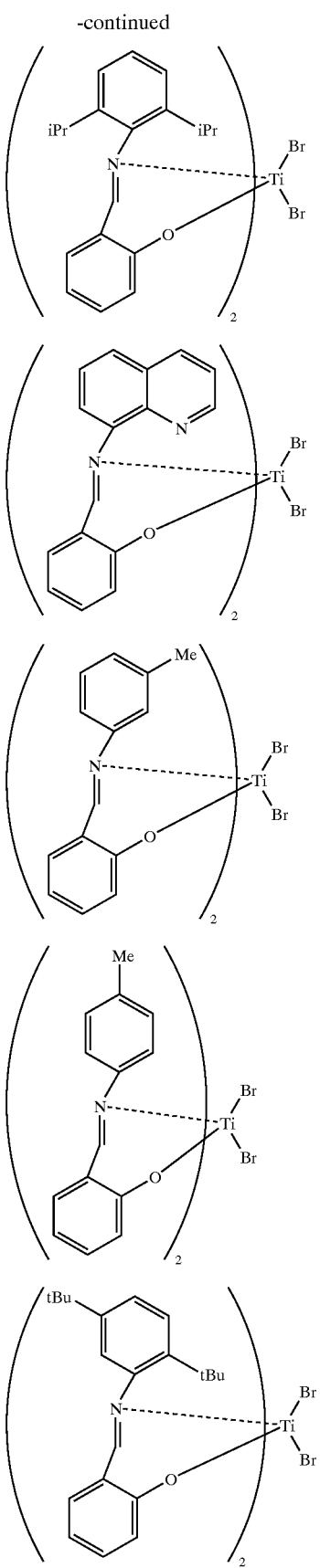
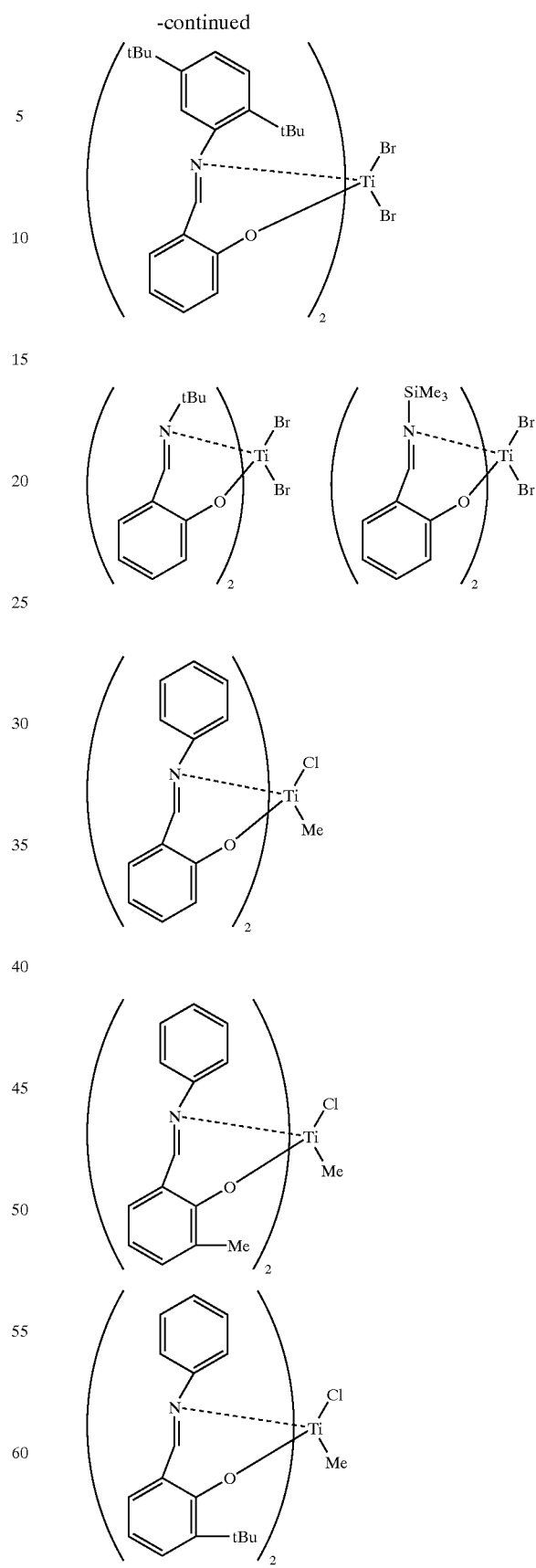

-continued
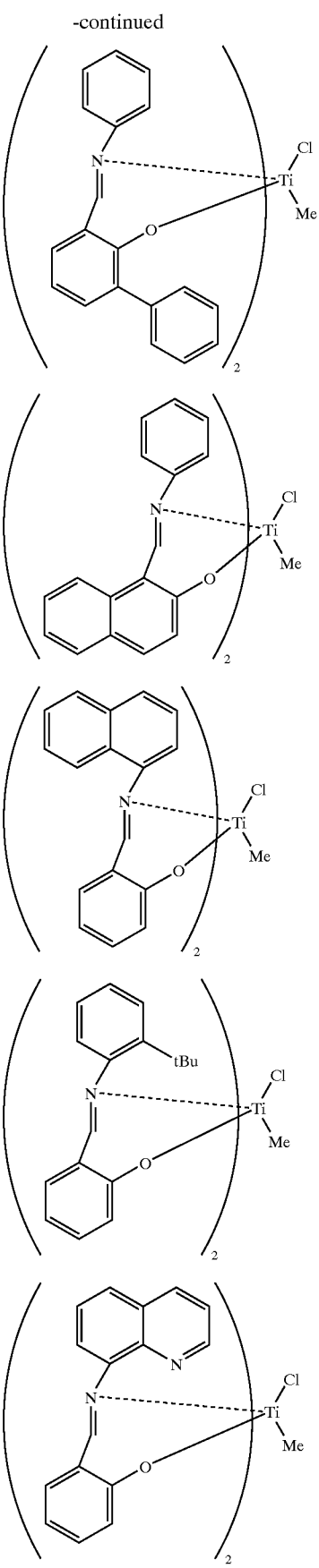
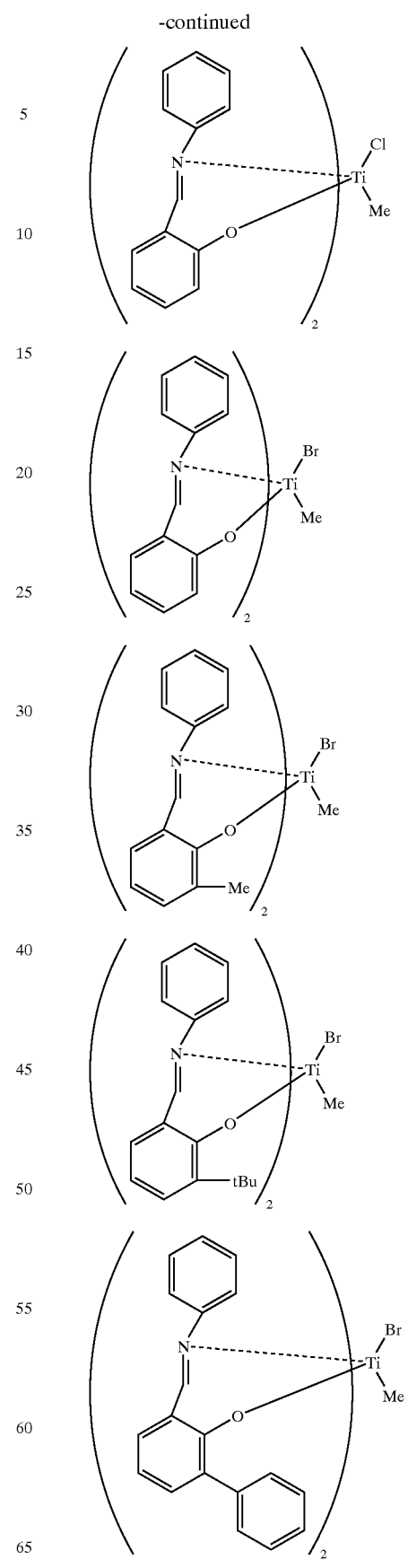

-continued
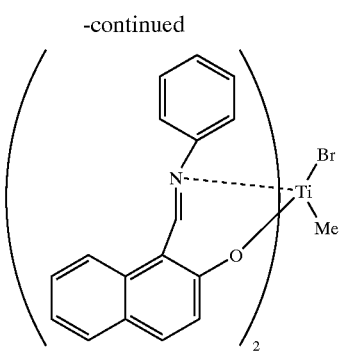
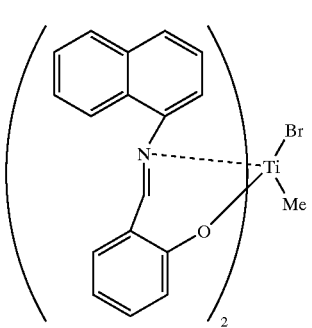
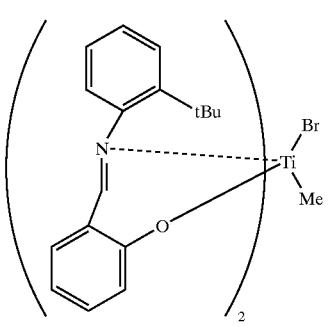
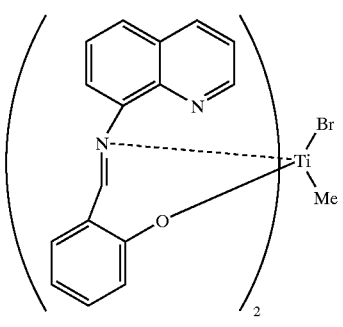
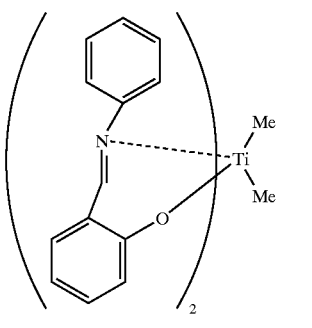
-continued
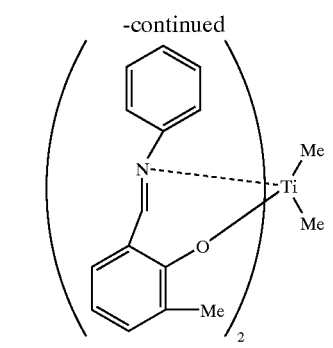
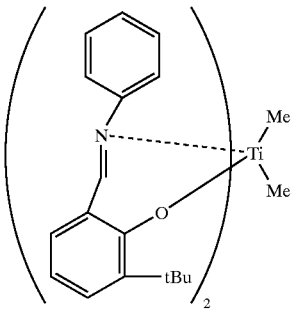
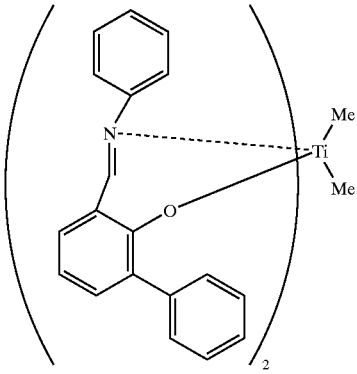
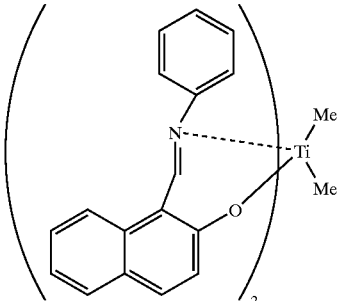
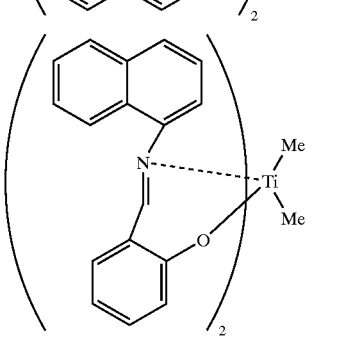

-continued
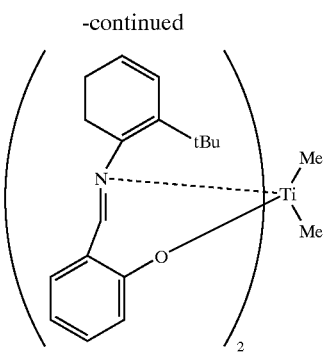
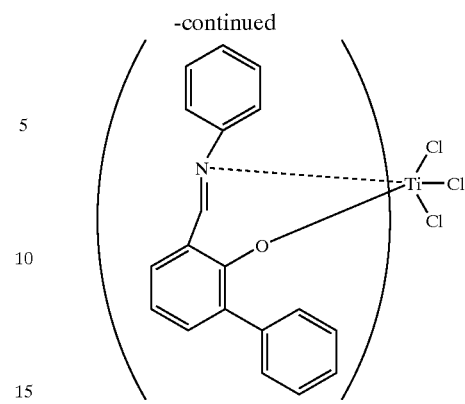
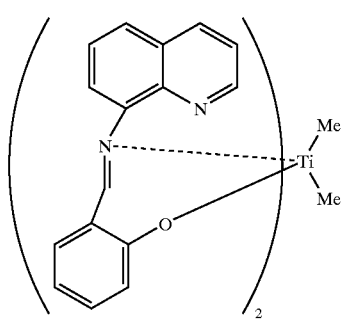
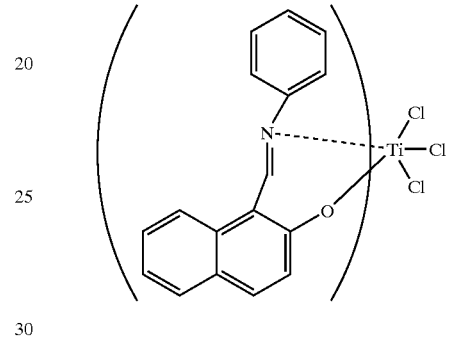
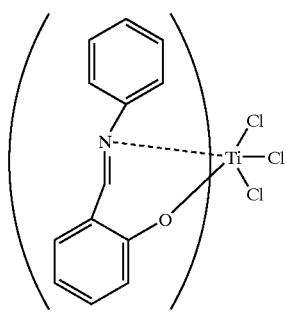
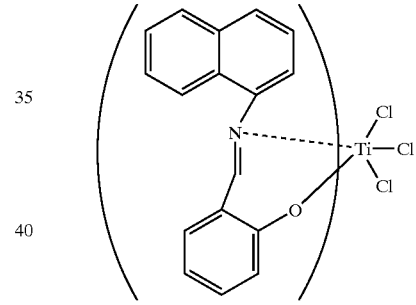
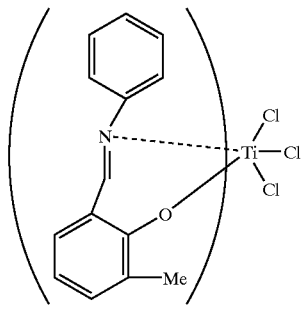
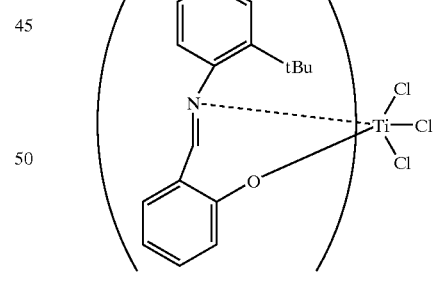
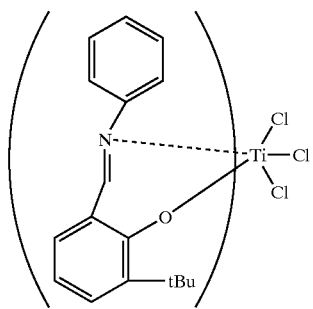
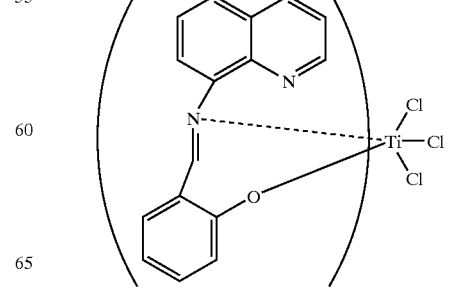

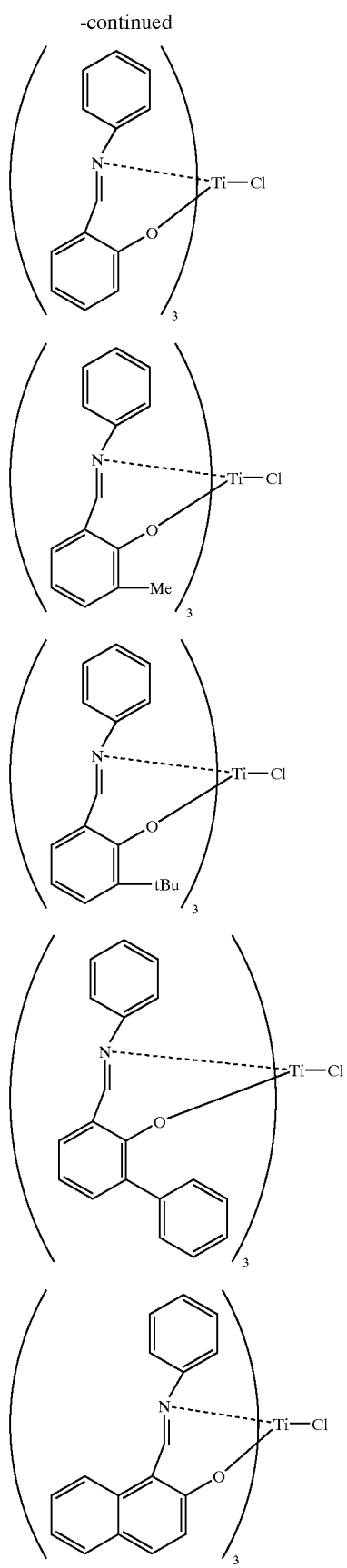
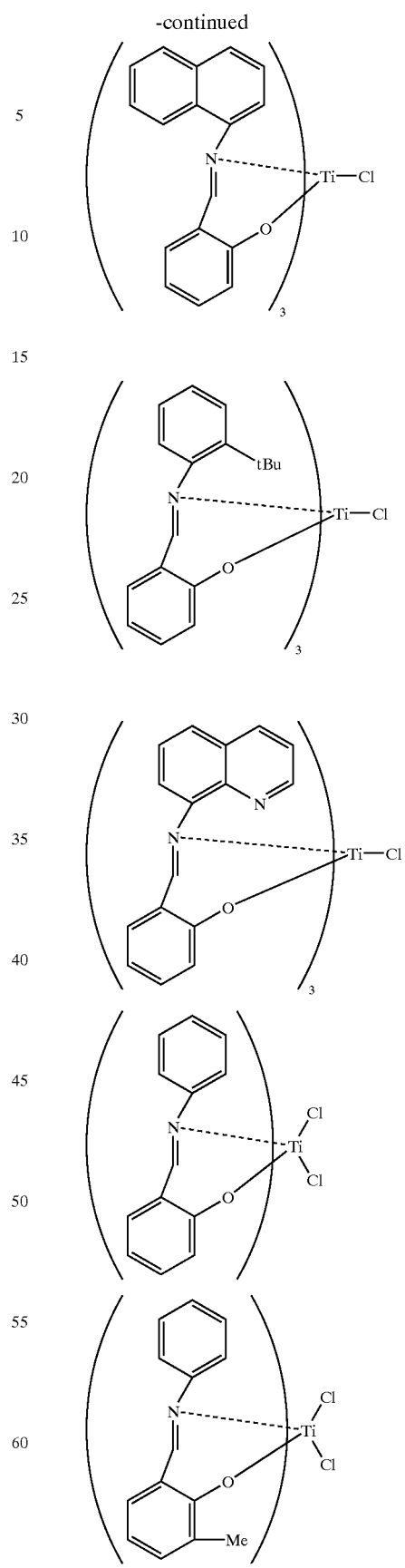

-continued
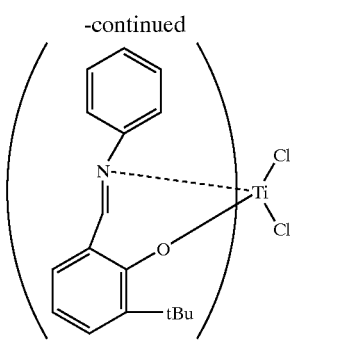
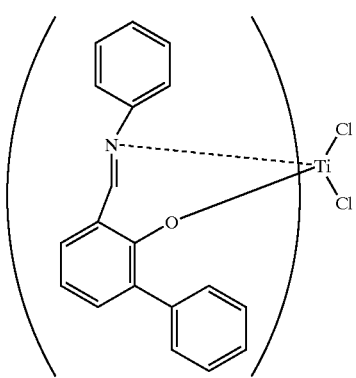
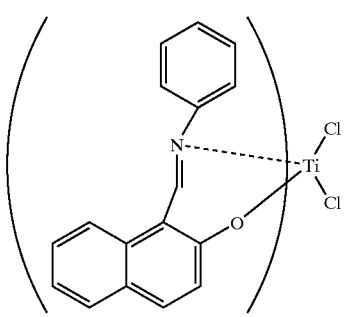
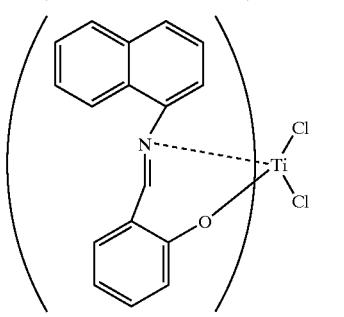
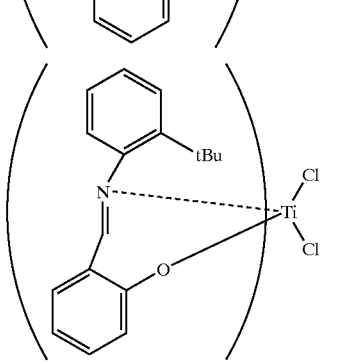
-continued
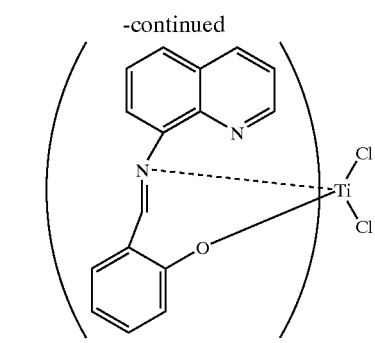
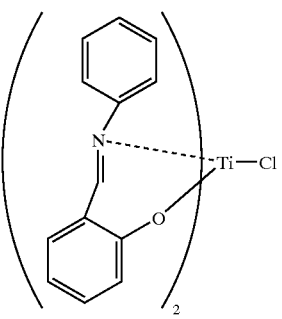
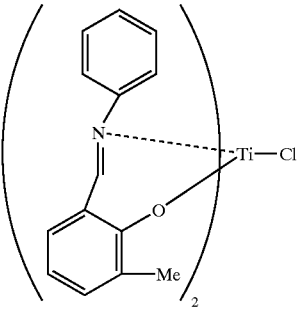
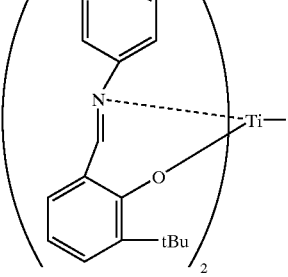
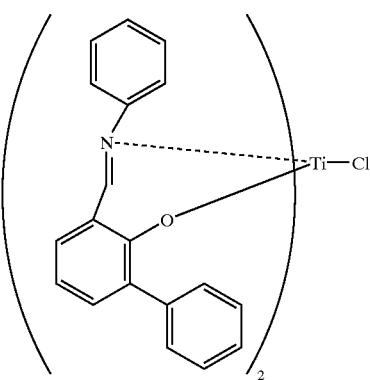

-continued
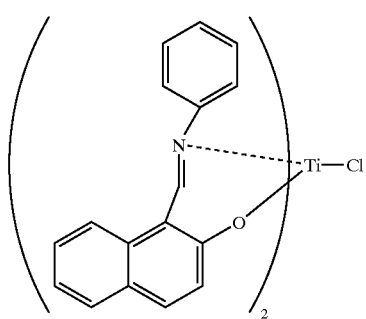
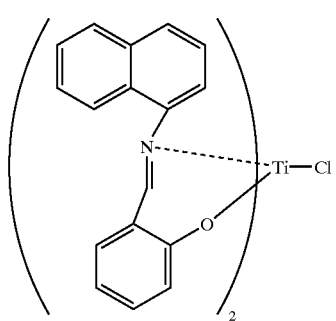
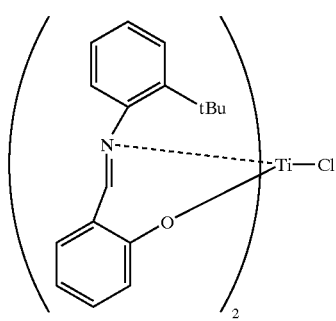
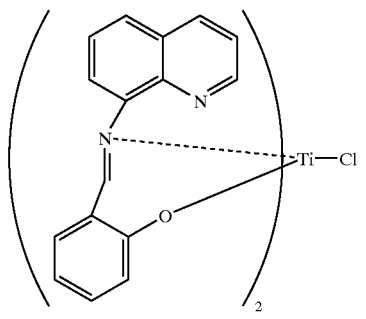
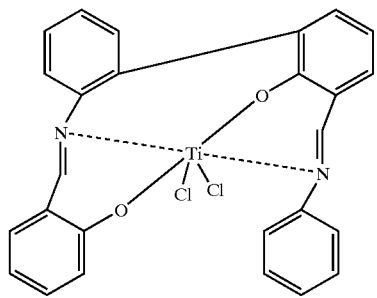
-continued
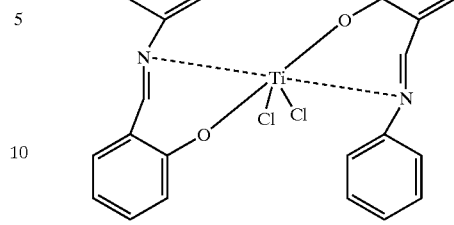
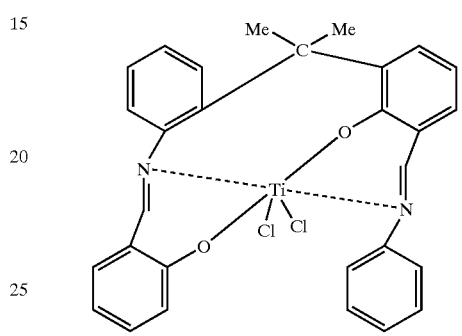
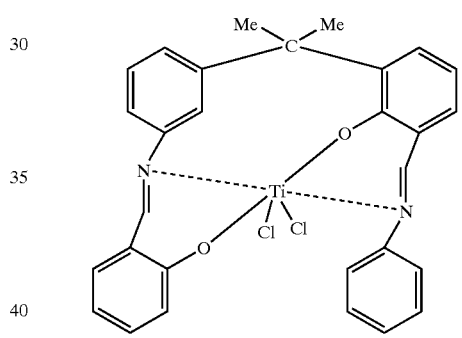
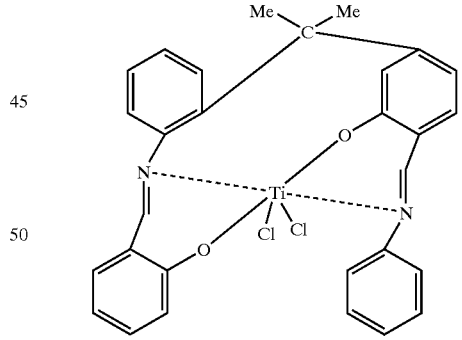
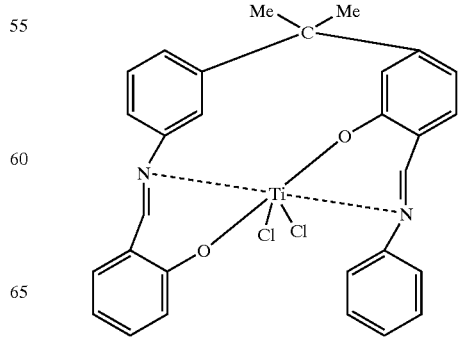

-continued

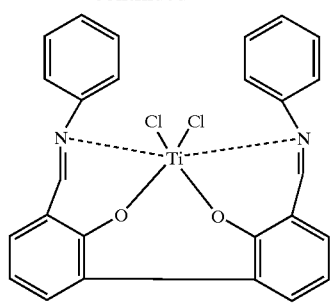

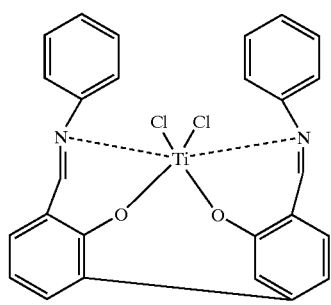

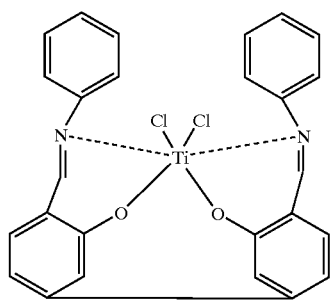

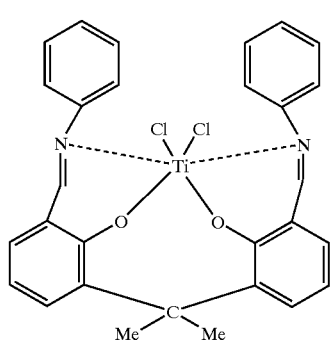

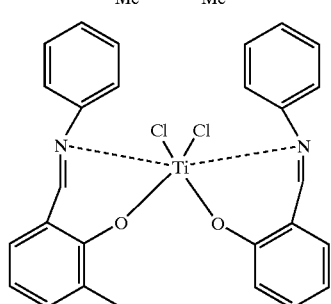

-continued

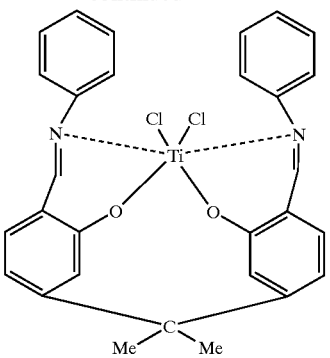

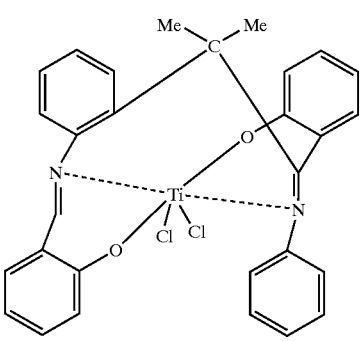

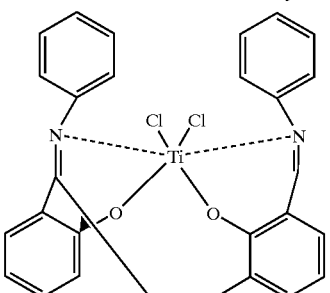

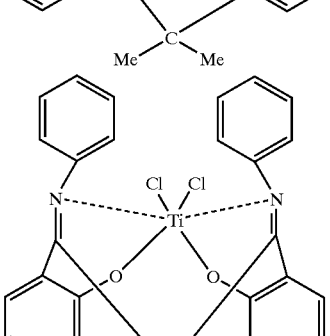

In the olefin polymerization catalyst according to the invention, it is particularly preferable to use a novel transition metal compound of the formula (III), which will be described in detail below, as the catalyst component (A').

Transition Metal Compound (I-b)

Also employable as the transition metal compound (A) in the invention is a transition metal compound represented by the following formula (I-b).

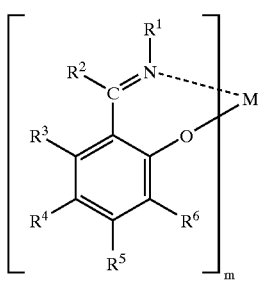
(I-b)

In the formula (I-b), M is a transition metal atom of Group 3 to Group 11 of the periodic table, preferably of Group 4 or Group 9, and particularly preferably, titanium, zirconium, hafnium, cobalt or rhodium.

m is an integer of 1 to 6, preferably 1 to 4.

$R^1$ to $R^6$ may be the same or different, and are each a hydrogen atom, a halogen atom, a hydrocarbon group, a hydrocarbon-substituted silyl group, an alkoxy group, an aryloxy group, an ester group, an amido group, an amino group, a sulfonamido group, a cyano group or a nitro group.

Of these, particularly preferable is a halogen atom, a hydrocarbon group, a hydrocarbon-substituted silyl group, an alkoxy group, an aryloxy group, an ester group, an amido group, an amino group, a sulfonamido group, a cyano group or a nitro group.

Examples of the groups $R^1$ to $R^6$ are those exemplified for the transition metal compounds of the formulae (I) and (I-a).

When m is 2 or greater, two or more groups $R^1$ to $R^6$, preferably adjacent groups, may be bonded to each other to form a ring, with the proviso that the groups $R^1$ are not bonded to each other.

Examples of the transition metal compounds represented by the formula (I-b) are given below, but not limited thereto.

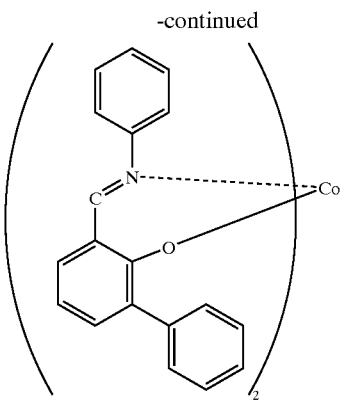

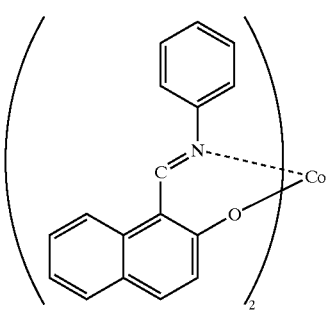

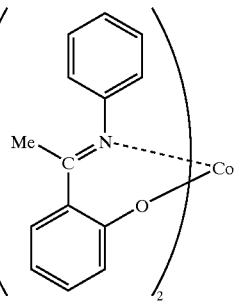

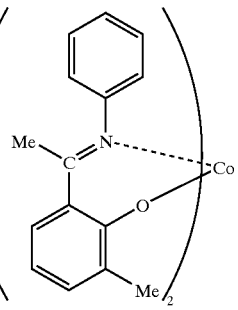

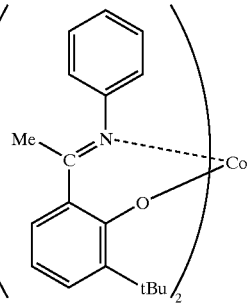

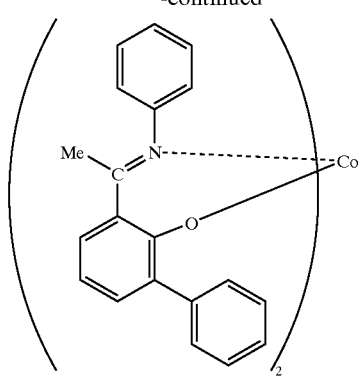
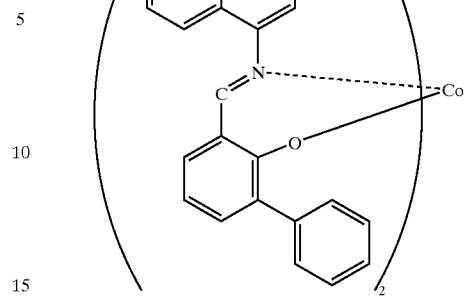
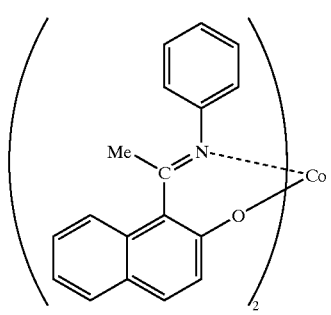
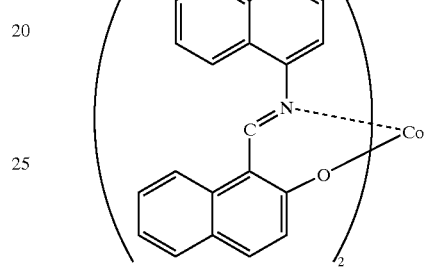
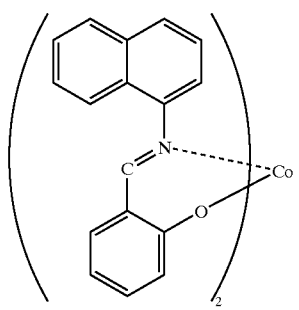
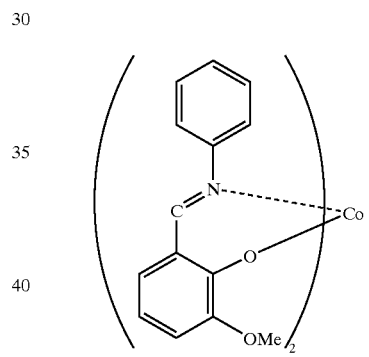
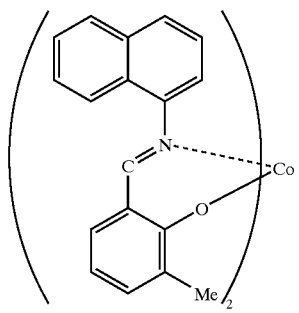
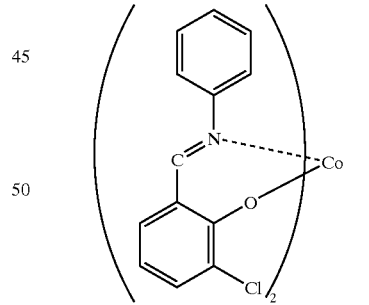
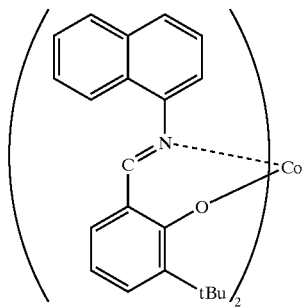
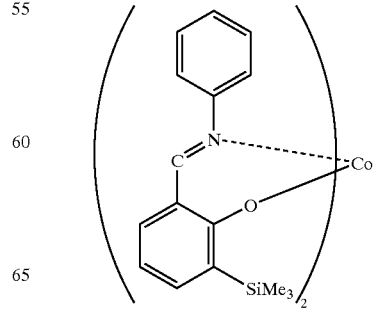

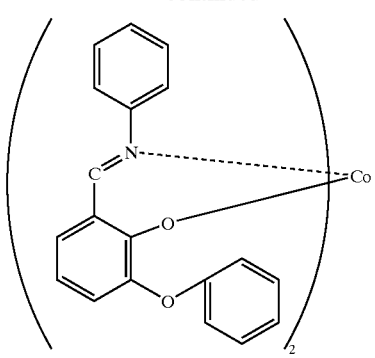
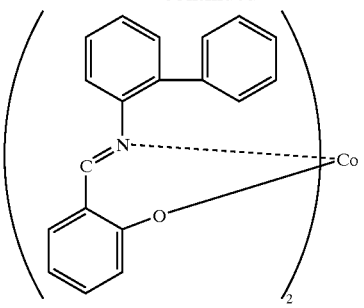
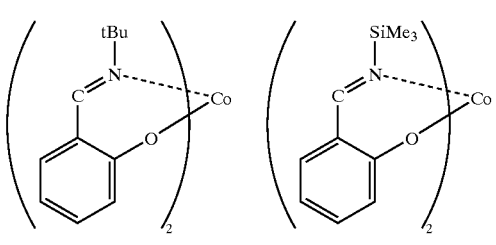
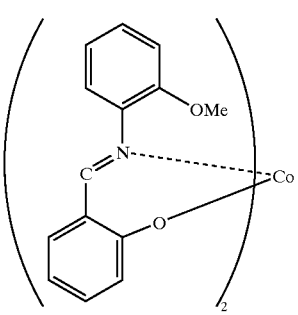
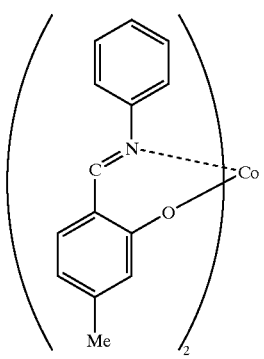
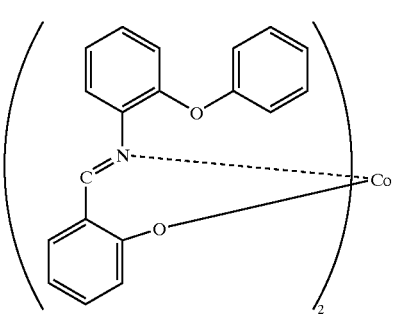
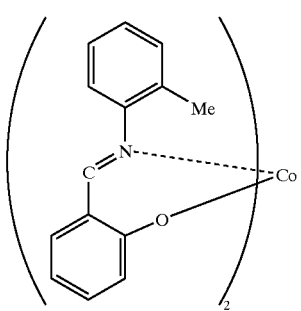
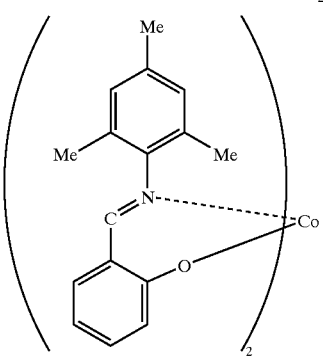
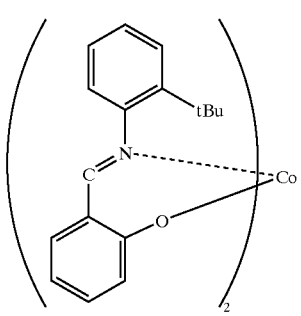
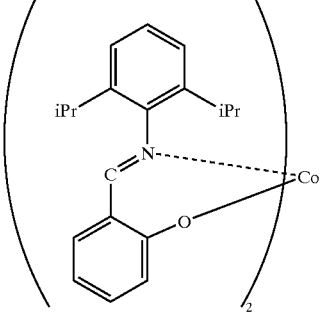

-continued

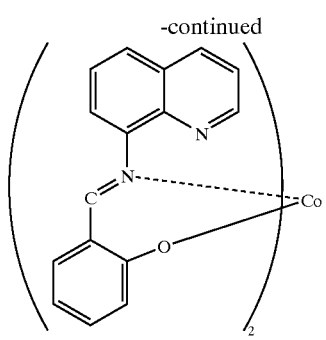

In the present invention, transition metal compounds wherein cobalt is replaced with titanium, zirconium, hafnium, iron, copper or rhodium in the above-exemplified compounds are also employable.

The transition metal compounds (A) mentioned above are used singly or in combination of two or more kinds, and they can be used in combination with other transition metal compounds, for example known transition metal compounds comprising a ligand which has a hetero atom such as nitrogen, oxygen, sulfur, boron or phosphorus.

Other Transition Metal Compound

Some examples of the other transition metal compounds are given below, but the compounds are not limited those examples.

(a-1) Transition metal imide compound (I-c)

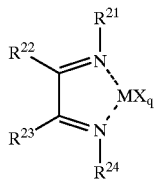

(I-c)

In the above formula, M is a transition metal atom of Group 8 to Group 10 of the periodic table, preferably nickel, palladium or platinum.

$R^{21}$ to $R^{24}$ may be the same or different, and are each a hydrocarbon group of 1 to 50 carbon atoms, a halogenated hydrocarbon group of 1 to 50 carbon atoms, a hydrocarbon-substituted silyl group, or a hydrocarbon group substituted with a substituent containing at least one element selected from nitrogen, oxygen, phosphorus, sulfur and silicon.

Two or more groups, preferably adjacent groups, of $R^{21}$ to $R^{24}$ may be bonded to each other to form a ring.

q is an integer of 0 to 4.

X is a hydrogen atom, a halogen atom, a hydrocarbon group of 1 to 20 carbon atoms, a halogenated hydrocarbon group of 1 to 20 carbon atoms, an oxygen-containing group, a sulfur-containing group, a silicon-containing group or nitrogen-containing group, and when q is 2 or greater, plural groups X may be the same or different.

(a-2) Transition metal amide compound (I-d)

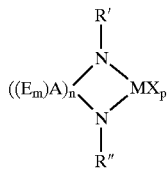

(I-d)

In the above formula, M is a transition metal atom of Group 3 to Group 6 of the periodic table, preferably titanium, zirconium or hafnium.

R' and R" may be the same or different, and are each a hydrogen atom, a hydrocarbon group of 1 to 50 carbon atoms, a halogenated hydrocarbon group of 1 to 50 carbon atoms, a hydrocarbon-substituted silyl group, or a substituent containing at least one element selected from nitrogen, oxygen, phosphorus, sulfur and silicon.

m is an integer of 0 to 2.

n is an integer of 1 to 5.

A is an atom of Group 13 to Group 16 of the periodic table, specifically boron, carbon, nitrogen, oxygen, silicon, phosphorus, sulfur, germanium, selenium, tin or the like, preferably carbon or silicon.

When n is 2 or greater, plural atoms A may be the same or different.

E is a substituent containing at least one element selected from carbon, hydrogen, oxygen, halogen, nitrogen, sulfur, phosphorus, boron and silicon. When plural groups E are present, they may be the same or different, and two or more groups E may be bonded to form a ring.

p is an integer of 0 to 4.

X is a hydrogen atom, a halogen atom, a hydrocarbon group of 1 to 20 carbon atoms, a halogenated hydrocarbon group of 1 to 20 carbon atoms, an oxygen-containing group, a sulfur-containing group, a silicon-containing group or nitrogen-containing group. When p is 2 or greater, plural groups X may be the same or different.

X is preferably a halogen atom, a hydrocarbon group of 1 to 20 carbon atoms or a sulfonato group.

(a-3) Transition metal diphenoxy compound (I-e)

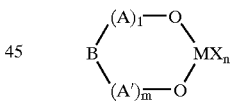

(I-e)

In the above formula, M is a transition metal atom of Group 3 to Group 11 of the periodic table; 1 and m are each an integer of 0 or 1; A and A' are each a hydrocarbon group of 1 to 50 carbon atoms, a halogenated hydrocarbon group of 1 to 50 carbon atoms, a hydrocarbon group having a substituent containing oxygen, sulfur or silicon, or a halogenated hydrocarbon group having a substituent containing oxygen, sulfur or silicon; and A and A' may be the same or different.

B is a hydrocarbon group of 0 to 50 carbon atoms, a halogenated hydrocarbon group of 1 to 50 carbon atoms, $R^1R^2Z$, oxygen or sulfur, where $R^1$ and $R^2$ are each a hydrocarbon group of 1 to 20 carbon atoms or a hydrocarbon group having 1 to 20 carbon atoms and containing at least one hetero atom, and Z is carbon, nitrogen, sulfur, phosphorus or silicon.

n is a number satisfying a valence of M.

X is a hydrogen atom, a halogen atom, a hydrocarbon group of 1 to 20 carbon atoms, a halogenated hydrocarbon group of 1 to 20 carbon atoms, an oxygen-containing group, a sulfur-containing group, a silicon-containing group or nitrogen-containing group, and when n is 2 or greater, plural groups X may the same or different and may be bonded to form a ring.

(a-4) Transition metal compound (I-f) containing at least one hetero atom and containing a ligand having cyclopentadienyl skeleton

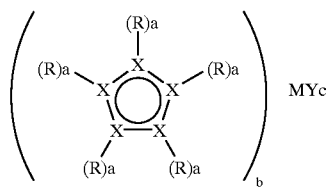

(I-f)

In the above formula, M is a transition metal atom of Group 3 to Group 11 of the periodic table. X is an atom of Group 13, Group 14 or Group 15, and at least one of X contains an element other than carbon.

Each R may be the same or different, and is a hydrogen atom, a halogen atom, a hydrocarbon group, a halogenated hydrocarbon group, a hydrocarbon-substituted silyl group or a hydrocarbon group substituted with a substituent containing at least one element selected from nitrogen, oxygen, phosphorus, sulfur and silicon. Two or more of R may be bonded to form a ring, and a is 0 or 1.

b is an integer of 1 to 4, when b is a number of 2 or greater, the moieties [((R)$_a$)$_5$X$_5$] may be the same or different, and the groups R may be bonded to form a bridge.

c is a number satisfying a valence of M.

Y is a hydrogen atom, a halogen atom, a hydrocarbon group of 1 to 20 carbon atoms, a halogenated hydrocarbon group of 1 to 20 carbon atoms, an oxygen-containing group, a sulfur-containing group, a silicon-containing group, or nitrogen-containing group. When c is a number of 2 or greater, plural groups Y may be the same or different and may be bonded to form a ring.

(a-5) Transition metal compound represented by the formula RB(Pz)$_3$MX$_n$

In the above formula, M is a transition metal atom of Group 3 to Group 11 of the periodic table; R is a hydrogen atom, a hydrocarbon group of 1 to 20 carbon atoms or a halogenated hydrocarbon group of 1 to 20 carbon atoms; and Pz is a pyrazolyl group or a substituted pyrazolyl group.

n is a number satisfying a valence of M.

X is a hydrogen atom, a halogen atom, a hydrocarbon group of 1 to 20 carbon atoms, a halogenated hydrocarbon group of 1 to 20 carbon atoms, an oxygen-containing group, a sulfur-containing group, a silicon-containing group or nitrogen-containing group, and when n is a number of 2 or greater, plural groups X may be the same or different and may be bonded to form a ring.

(a-6) Transition metal compound represented by the following formula (I-g)

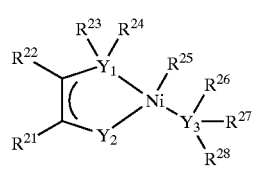

(I-g)

In the above formula, Y$_1$ and Y$_3$ are each an element of Group 15 of the periodic table; Y$_2$ is an element of Group 16 of the periodic table; and R$^{21}$ to R$^{28}$ may be the same or different, they are each a hydrogen atom, a halogen atom, a hydrocarbon group of 1 to 20 carbon atoms, a halogenated hydrocarbon group of 1 to 20 carbon atoms, an oxygen-containing group, a sulfur-containing group or a silicon-containing group, and two or more of them may be bonded to form a ring.

(a-7) Transition metal compound comprising a compound represented by the following formula (I-h) and a transition metal atom of Group VIII

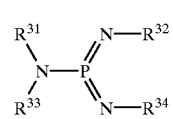

(I-h)

In the above formula, R$^{31}$ to R$^{34}$ may be the same or different, they are each a hydrogen atom, a halogen atom, a hydrocarbon group of 1 to 20 carbon atoms or a halogenated hydrocarbon group of 1 to 20 carbon atoms, and two or more of them may be bonded to form a ring.

(a-8) Transition metal compound represented by the following formula (I-i)

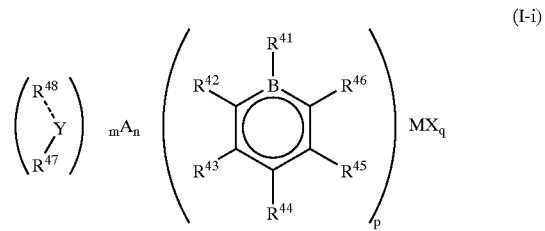

(I-i)

In the above formula, M is a transition metal atom of Group 3 to Group 11 of the periodic table.

m is an integer of 0 to 3.

n is an integer of 0 or 1.

p is an integer of 1 to 3.

q is a number satisfying a valence of M.

R$^{41}$ to R$^{48}$ may be the same or different, and are each a hydrogen atom, a halogen atom, a hydrocarbon group of 1 to 20 carbon atoms or a halogenated hydrocarbon group of 1 to 20 carbon atoms, an oxygen-containing group, a sulfur-containing group, a silicon-containing group or nitrogen-containing group, and two or more of them may be bonded to form a ring.

X is a hydrogen atom, a hologen atom, a hydrocarbon group of 1 to 20 carbon atoms, a halogenated hydrocarbon group of 1 to 20 carbon atoms, an oxygen-containing group, a sulfur-containing group, a silicon-containing group or a nitrogen-containing group, and when q is 2 or greater, plural X may be the same or different and may be bonded to each other to form a ring.

Y is a group bridging the borata benzen ring, and Y is carbon, silicon or germanium.

A is an element of Group 14, Group 15 or Group 16 of the periodic table.

(B-1) Organometallic Compound

As the organometallic compound (B-1), the below-described organometallic compounds of metals of Group 1, Group 2, Group 12 and Group 13 of the periodic table are employable in the invention.

(B-1a) Organoaluminum compound represented by the following formula:

$$R^a{}_m Al(OR^b)_n H_p X_q$$

wherein $R^a$ and $R^b$ may be the same or different, and are each a hydrocarbon group of 1 to 15 carbon atoms, preferably a hydrocarbon group of 1 to 4 carbon atoms; X is a halogen atom; and m, n, p and q are numbers satisfying the conditions of $0<m\leq 3$, $0\leq n<3$, $0\leq p<3$, $0\leq q<3$ and $m+n+p+q=3$.

(B-1b) Alkyl complex compound of Group 1 metal and aluminum, that is represented by the following formula:

$$M^2 Al R^a{}_4$$

wherein $M^2$ is Li, Na or K; and $R^a$ is a hydrocarbon group of 1 to 15 carbon atoms, preferably a hydrocarbon group of 1 to 4 carbon atoms.

(B-1c) Dialkyl compound of Group 2 metal or Group 12 metal, that is represented by the following formula:

$$R^a R^b M^3$$

wherein $R^a$ and $R^b$ may be the same or different, and are each a hydrocarbon group of 1 to 15 carbon atoms, preferably a hydrocarbon group of 1 to 4 carbon atoms; and $M^3$ is Mg, Zn or Cd.

Examples of the organoaluminum compounds (B-1a) include the following compounds.

Organoaluminum compound represented by the following formula:

$$R^a{}_m Al(OR^b)_{3-m}$$

wherein $R^a$ and $R^b$ may be the same or different, and are each a hydrocarbon group of 1 to 15 carbon atoms, preferably a hydrocarbon group of 1 to 4 carbon atoms; and m is preferably a number satisfying the condition of $1.5 \leq m \leq 3$.

Organoaluminum compound represented by the following formula:

$$R^a{}_m Al X_{3-m}$$

wherein $R^a$ is a hydrocarbon group of 1 to 15 carbon atoms, preferably a hydrocarbon group of 1 to 4 carbon atoms; X is a halogen atom; and m is preferably a number satisfying the condition of $0 \leq m \leq 3$.

Organoaluminum compound represented by the following formula:

$$R^a{}_m Al H_{3-m}$$

wherein $R^a$ is a hydrocarbon group of 1 to 15 carbon atoms, preferably a hydrocarbon group of 1 to 4 carbon atoms; and m is preferably a number satisfying the condition of $2 \leq m < 3$.

organoaluminum compound represented by the following formula:

$$R^a{}_m Al(OR^b)_n X_q$$

wherein $R^a$ and $R^b$ may be the same or different, and are each a hydrocarbon group of 1 to 15 carbon atoms, preferably a hydrocarbon group of 1 Lo 4 carbon atoms; X is a halogen atom; and m, n and q are numbers satisfying the conditions of $0<m\leq 3$, $0\leq n<3$, $0\leq q<3$ and $m+n+q=3$.

Particular examples of the organoaluminum compounds (B-1a) include:

tri-n-alkylaluminums, such as tri-methylaluminum, triethylaluminum, tri-n-butylaluminum, tripropylaluminum, tripentylaluminum, trihexylaluminum, trioctylalminum and tridecylaluminum;

branched-chain trialkylaluminums, such as triisopropylaluminum, triisobutylaluminum, tri-sec-butylaluminum, tri-tert-butylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum, and tri-2-ethylhexylaluminum;

tricycloalkylaluminums, such as tricyclohexylaluminum and tricyclooctylaluminum;

triarylaluminums, such as triphenylaluminum and tritolylaluminum;

dialkylaluminum hydrides, such as diisobutylaluminum hydride;

trialkenylaluminums represented by the formula $(i\text{-}C_4H_9)_x Al_y (C_5H_{10})_z$ (wherein x, y and z are positive numbers, and $z \geq 2x$), such as isoprenylaluminum;

alkylaluminum alkoxides, such as isobutylaluminum methoxide, isobutylaluminum ethoxide and isobutylaluminum isopropoxide;

dialkylaluminum alkoxides, such as dimethylaluminum methoxide, diethylaluminum ethoxide and dibutylaluminum butoxide;

alkylaluminum sesquialkoxides, such as ethylaluminum sesquiethoxide and butylaluminum sesquibutoxide;

partially alkoxylated alkylaluminums having an average composition represented by $R^a{}_{2.5} Al(OR^b)_{0.5}$;

dialkylaluminum aryloxides, such as diethylaluminum phenoxide, diethylaluminum(2,6-di-t-butyl-4-methylphenoxide), ethylaluminumbis(2,6-di-t-butyl-4-methylphenoxide), diisobutylaluminum(2,6-di-t-butyl-4-methylphenoxide) and isobutylaluminumbis(2,6-di-t-butyl-4-methylphenoxide);

dialkylaluminum halides, such as dimethylaluminum chloride, diethylaluminum chloride, dibutylaluminum chloride, diethylaluminum bromide and diisobutylaluminum chloride;

alkylaluminum sesquihalides, such as ethylaluminum sesquichloride, butylaluminum sesquichloride and ethylaluminum sesquibromide, partially halogenated alkylaluminums, such as ethylaluminum dichloride, propylaluminum dichloride and butylaluminum dibromide;

dialkylaluminum hydrides, such as diethylaluminum hydride and dibutylaluminum hydride;

partially hydrogenated alkylaluminums, e.g., alkylaluminum dihydrides, such as ethylaluminum dihydride and propylaluminum dihydride; and partially alkoxylated and halogenated alkylaluminums, such as ethylaluminum ethoxychloride, butylaluminum butoxychloride and ethylaluminum ethoxybromide.

Also employable are compounds analogous to the organoaluminum compound (B-1a). For example, there can be mentioned organoaluminum compounds wherein two or more aluminum compounds are combined through a nitrogen atom, such as $(C_2H_5)_2 AlN(C_2H_5) Al(C_2H_5)_2$.

Examples of the organoaluminum compounds (B-1b) include LiAl$(C_2H_5)_4$ and LiAl$(C_7H_{15})_4$.

Further, other compounds such as methyllithium, ethyllithium, propyllithium, butyllithium, methylmagnesium bromide, methylmagnesium chloride, ethylmagnesium bromide, ethylmagnesium chloride, propylmagnesium bromide, propylmagnesium chloride, butylmagnesium bromide, butylmagnesium chloride, dimethylmagnesium, diethylmagnesium, dibutylmagnesium and butylethylmagnesium are also employable as the organometallic compounds (B-1).

Furthermore, combinations of compounds capable of producing the above-mentioned organoaluminum compounds in the polymerization system, e.g., a combination of halogenated aluminum and alkyllithium and a combination of halogenated aluminum and alkylmagnesium, are also employable.

Of the organometallic compounds (B-1) mentioned above, the organoaluminum compounds are preferable.

The organometallic compounds (B-1) can be used singly or in combination of two or more kinds.

(B-2) Organoaluminum Oxy-compound

The organoaluminum oxy-compound (B-2) for use in the invention may be conventional aluminoxane or a benzene-insoluble organoaluminum oxy-compound exemplified in Japanese Patent Laid-Open Publication No. 78687/1990.

The conventional aluminoxane can be prepared by, for example, the following processes, and is generally obtained as a hydrocarbon solvent solution.

(1) An organoaluminum compound such as trialkylaluminum is added to a hydrocarbon medium suspension of a compound containing adsorbed water or a salt containing water of crystallization, e.g., magnesium chloride hydrate, copper sulfate hydrate, aluminum sulfate hydrate, nickel sulfate hydrate or cerous chloride hydrate, to allow the organoaluminum compound to react with the adsorbed water or the water of crystallization.

(2) Water, ice or water vapor is allowed to directly act on an organoaluminum compound such as trialkylaluminum in a medium such as benzene, toluene, ethyl ether or tetrahydrofuran.

(3) An organotin oxide such as dimethyltin oxide or dibutyltin oxide is allowed to react with an organoaluminum compound such as trialkylaluminum in a medium such as decane, benzene or toluene.

The aluminoxane may contain a small amount of an organometallic component. Further, it is possible that the solvent or the unreacted organoaluminum compound is distilled off from the recovered solution of aluminoxane and the remainder is redissolved in a solvent or suspended in a poor solvent for aluminoxane.

Examples of the organoaluminum compounds used for preparing the aluminoxane include the same organoaluminum compounds as described for the organoaluminum compound (B-1a).

Of these, preferable are trialkylaluminums and tricycloalkylaluminums. Particularly preferable is trimethylaluminum.

The organoaluminum compounds can be used singly or in combination of two or more kinds.

Examples of the solvents used for preparing the aluminoxane include aromatic hydrocarbons, such as benzene, toluene, xylene, cumene and cymene; aliphatic hydrocarbons, such as pentane, hexane, heptane, octane, decane, dodecane, hexadecane and octadecane; alicyclic hydrocarbons, such as cyclopentane, cyclohexane, cyclooctane and methylcyclopentane; petroleum fractions, such as gasoline, kerosine and gas oil; and halides of these aromatic, aliphatic and alicyclic hydrocarbons, particularly chlorides and bromides thereof. Also employable are ethers such as ethyl ether and tetrahydrofuran. Of the solvents, particularly preferable are aromatic hydrocarbons and aliphatic hydrocarbons.

In the benzene-insoluble organoaluminum oxy-compound for use in the invention, the content of Al component which is soluble in benzene at 60° C. is usually not more than 10%, preferably not more than 5%, particularly preferably not more than 2%, in terms of Al atom, and the benzene-insoluble organoaluminum oxy-compound is insoluble or sparingly soluble in benzene.

The organoaluminum oxy-compound employable in the invention is, for example, an organoaluminum oxy-compound containing boron and represented by the following formula (IV):

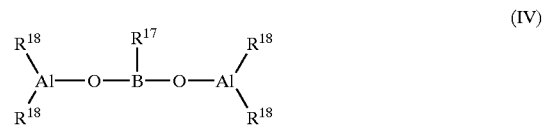

wherein $R^{17}$ is a hydrocarbon group of 1 to 10 carbon atoms; and each $R^{18}$ may be the same or different and is a hydrogen atom, a halogen atom or a hydrocarbon group of 1 to 10 carbon atoms.

The organoaluminum compound containing boron and represented by the formula (IV) can be prepared by causing an alkylboronic acid represented by the following formula (V) to react with an organoaluminum compound in an inert solvent under an inert gas atmosphere at a temperature of −80° C. to room temperature for 1 minute to 24 hours.

wherein $R^{17}$ is the same group as described above.

Examples of the alkylboronic acids represented by the formula (V) include methylboronic acid, ethylboronic acid, isopropylboronic acid, n-propylboronic acid, n-butylboronic acid, isobutylboronic acid, n-hexylboronic acid, cyclohexylboronic acid, phenylboronic acid, 3,5-difluoroboronic acid, pentafluorophenylboronic acid and 3,5-bis(trifluoromethyl)phenylboronic acid. Of these, preferable are methylboronic acid, n-butylboronic acid, isobutylboronic acid, 3,5-difluorophenylboronic acid and pentafluorophenylboronic acid. The alkylboronic acids are used singly or in combination of two or more kinds.

Examples of the organoaluminum compounds to be reacted with the alkylboronic acid include the same organoaluminum compounds as described for the organoaluminum compound (B-1a).

Of these, preferable are trialkylaluminums and tricycloalkylaluminums. Particularly preferable are trimethylaluminum, triethylaluminum and triisobutylaluminum. The organoaluminum compounds can be used singly or in combination of two or more kinds.

The organoaluminum oxy-compounds (B-2) mentioned above are used singly or in combination of two or more kinds.

(B-3) Compound which Reacts with the Transition Metal Compound to form Ion Pair The compound (B-3) which reacts with the transition metal compound to form an ion pair (referred to as "ionizing ionic compound" hereinafter), that is used in the invention, is a compound which reacts with the transition metal compound (A) to form an ion pair, and includes Lewis acid, an ionic compound, a borane compound and a carborane compound described in Japanese Patent Laid-Open Publications No. 501950/1989, No. 502036/1989, No. 179005/1991, No. 179006/1991, No. 207703/1991 and No. 207704/1991, and U.S. Pat. No. 5,321,106. Further, as ionizing ionic compound, heteropoly-compound or isopoly-compound may be used.

The Lewis acid is, for example, a compound represented by $BR_3$ (R is a phenyl group which may have a substituent such as fluorine, methyl or trifluoromethyl, or a fluorine atom). Examples of such compounds include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris(3,5-dimethylphenyl)boron.

The ionic compound is, for example, a compound represented by the following formula (VI).

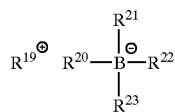

(VI)

In the above formula, $R^{19}$ is $H^+$, carbonium cation, oxonium cation, ammonium cation, phosphonium cation, cycloheptyltrienyl cation, ferrocenium cation having a transition metal, or the like.

$R^{20}$ to $R^{23}$ may be the same or different, and are each an organic group, preferably an aryl group or a substituted aryl group.

Examples of the carbonium cations include tri-substituted cations, such as triphenylcarbonium cation, tri(methylphenyl)carbonium cation and tri(dimethylphenyl)carbonium cation.

Examples of the ammonium cations include trialkylammonium cations, such as trimethylammonium cation, triethylammonium cation, tripropylammonium cation and tributylammonium cation; N,N-dialkylanilinium cations, such as N,N-dimethylanilinium cation, N,N-diethylanilinium cation and N,N-2,4,6-pentamethylanilinium cation; and dialkylammonium cations, such as di(isopropyl)ammonium cation and dicyclohexylammonium cation.

Examples of the phosphonium cations include triarylphosphonium cations, such as triphenylphosphonium cation, tri(methylphenyl)phosphonium cation and tri(dimethylphenyl)phosphonium cation.

$R^{19}$ is preferably carbonium cation or ammonium cation, particularly preferably triphenylcarbonium cation, N,N-dimethylanilinium cation or N,N-diethylanilinium cation.

Also available as the ionic compound is a trialkyl-substituted ammonium salt, a N,N-dialkylanilinium salt, a dialkylammonium salt and a triarylphosphonium salt.

Examples of the trialkyl-substituted ammonium salts include triethylammoniumtetra(phenyl)boron, tripropylammoniumtetra(phenyl)boron, tri(n-butyl)ammoniumtetra(phenyl)boron, trimethylammoniumtetra(p-tolyl)boron, trimethylammoniumtetra(o-tolyl)boron, tri(n-butyl)ammoniumtetra(pentafluorophenyl)boron, tripropylammoniumtetra(o,p-dimethylphenyl)boron, tri(n-butyl)ammoniumtetra(m,m-dimethylphenyl)boron, tri(n-butyl)ammoniumtetra(p-trifluoromethylphenyl)boron, tri(n-butyl)ammoniumtetra(3,5-ditrifluoromethylphenyl)boron and tri(n-butyl)ammoniumtetra(o-tolyl)boron.

Examples of the N,N-dialkylanilinium salts include N,N-dimethylaniliniumtetra(phenyl)boron, N,N-diethylaniliniumtetra(phenyl)boron and N,N-2,4,6-pentamethylaniliniumtetra(phenyl)boron.

Examples of the dialkylammonium salts include di(1-propyl)ammoniumtetra(pentafluorophenyl)boron and dicyclohexylammoniumtetra(phenyl)boron.

Further employable as the ionic compound is triphenylcarbeniumtetrakis(pentafluorophenyl)borate, N,N-dimethylaniliniumtetrakis(pentafluorophenyl)borate, ferroceniumtetra(pentafluorophenyl)borate, triphenylcarbeniumpentaphenylcyclopentadienyl complex, N,N-diethylaniliniumpentaphenylcyclopentadienyl complex or a boron compound represented by the following formula (VII) or (VIII).

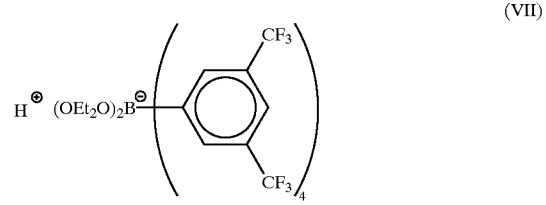

(VII)

wherein Et is an ethyl group.

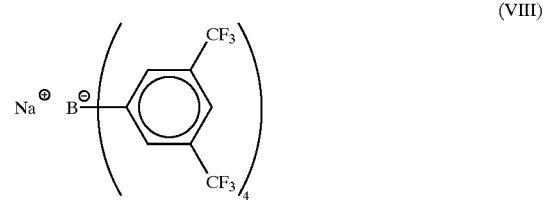

(VIII)

Examples of the borane compounds include:

decaborane(14);

salts of anions, such as bis[tri(n-butyl)ammonium] nonaborate, bis[tri(n-butyl)ammonium]decaborate, bis[tri(n-butyl)ammonium]undecaborate, bis[tri(n-butyl)ammonium]dodecaborate, bis[tri(n-butyl)ammonium] decachlorodecaborate and bis[tri(n-butyl)ammonium] dodecachlorododecaborate; and salts of metallic borane anions, such as tri(n-butyl)ammoniumbis(dodecahydridedodecaborate)cobaltate (III) and bis[tri(n-butyl)ammonium]bis-(dodecahydridedodecaborate)nickelate(III).

Examples of the carborane compounds include:

salts of anions, such as 4-carbanonaborane(14), 1,3-dicarbanonaborane(13), 6,9-dicarbadecaborane(14), dodecahydride-1-phenyl-1,3-dicarbanonaborane, dodecahydride-1-methyl-1,3-dicarbanonaborane, undecahydride-1,3-dimethyl-1,3-dicarbanonaborane, 7,8-dicarbaundecaborane(13), 2,7-dicarbaundecaborane(13), undecahydride-7,8-dimethyl-7,8-dicarbaundecaborane, dodecahydride-11-methyl-2,7-dicarbaundecaborane, tri(n-butyl)ammonium-1-carbadecaborate, tri(n-butyl)ammonium-1-carbaundecaborate, tri(n-butyl)ammonium-1-carbadodecaborate, tri(n-butyl)ammonium-1-trimethylsilyl-1-carbadecaborate, tri(n-butyl)ammoniumbromo-1-carbadodecaborate, tri(n-butyl)ammonium-6-carbadecaborate(14), tri(n-butyl)ammonium-6-carbadecaborate(12), tri(n-butyl)ammonium-7-carbaundecaborate(13), tri(n-butyl)

ammonium-7,8-dicarbaundecaborate(12), tri(n-butyl) ammonium-2,9-dicarbaundecaborate(12), tri(n-butyl) ammoniumdodecahydride-8-methyl-7,9-dicarbaundecaborate, tri(n-butyl) ammoniumundecahydride-8-ethyl-7,9-dicarbaundecaborate, tri(n-butyl) ammoniumundecahydride-8-butyl-7,9-dicarbaundecaborate, tri(n-butyl) ammoniumundecahydride-8-allyl-7,9-dicarbaundecaborate, tri(n-butyl) ammoniumundecahydride-9-trimethylsilyl-7,8-dicarbaundecaborate and tri(n-butyl) ammoniumundecahydride-4,6-dibromo-7-carbaundecaborate; and salts of metallic carborane anions, such as tri(n-butyl) ammoniumbis(nonahydride-1,3-dicarbanonaborate) cobaltate(III), tri(n-butyl) ammoniumbis (undecahydride-7,8-dicarbaundecaborate)ferrate(III), tri(n-butyl)ammoniumbis(undecahydride-7,8-dicarbaundecaborate)cobaltate(III), tri(n-butyl) ammoniumbis(undecahydride-7,8-dicarbaundecaborate)nickelate(III), tri(n-butyl) ammoniumbis(undecahydride-7,8-dicarbaundecaborate)cuprate(III), tri(n-butyl) ammoniumbis(undecahydride-7,8-dicarbaundecaborate)aurate(III), tri(n-butyl) anmoniumbis(nonahydride-7,8-dimethyl-7,8-dicarbaundecaborate)ferrate(III), tri(n-butyl) ammoniumbis(nonahydride-7,8-dimethyl-7,8-dicarbaundecaborate)chromate(III), tri(n-butyl) ammoniumbis(tribromooctahydride-7,8-dicarbaundecaborate)cobaltate(III), tris[tri(n-butyl) ammonium]bis(undecahydride-7-carbaundecaborate) chromate(III), bis[tri(n-butyl)ammonium]bis (undecahydride-7-carbaundecaborate)manganate(IV), bis[tri(n-butyl)ammonium]bis(undecahydride-7-carbaundecaborate)cobaltate(III) and bis[tri(n-butyl) ammonium]bis(undecahydride-7-carbaundecaborate) nickelate(IV).

The heteropoly-compounds comprise a heteroatom such as silicon, phosphorus, titanium, germanium, arsenic or tin, and at least one polyatom selected from vanadium, niobium molybdenum and tungsten. For example, phosphovanadic acid, germanovanadic acid, arsenovanadic acid, phosphoniobic acid, germanoniobic acid, siliconomolybdic acid, phosphomolybdic acid, titanomolybdic acid, germanomolybdic acid, arsenomolybdic acid, stannnomolybdic acid, phosphotungstic acid, germanotungstic acid, stannotungstic acid, phosphomolybdovanadic acid, phosphotungstovanadic acid, germanotungstovanadic acid, phosphomolybdotungstovanadic acid, germanomolybdotungstovanadic acid, phosphomolybdotungstic acid and phosphomolybdoniobic acid, salts of these acid with a metal of Group 1 or 2 of the periodic table such as lithium, sodium, potassium, rubidium, cesium, beryllium, magnesium, calcium, strontium or barium, and further organic salts such as triphenylethyl salts of the above acids, as well as isopoly-compounds, but not limited thereto.

The heteropoly-compounds and isopoly-compounds mentioned above may be used singly or in combination of two or more kind.

The ionizing ionic compounds (B-3) mentioned above can be used singly or in combination of two or more kinds.

If the transition metal compounds according to the invention are used as catalyst in combination with the organoaluminum oxy-compound (B-2) such as methylaluminoxane as a cocatalyst, olefin compounds can be polymerized with high polymerization activities. If the ionized ionic compound (B-3) such as triphenylcarbonium tetrakis (pentafluorophenyl)borate is used as a cocatalyst, polyolefins having a very high molecular weight is produced with good activities.

In the olefin polymerization catalyst of the invention, the below-described carrier (C) can be used if necessary, in addition to the above-mentioned transition metal compound (A) and at least one compound (B) selected from the organometallic compound (B-1), the organoaluminum oxy-compound (B-2) and the ionized ionic compound (B-3).

(C) Carrier

The carrier (C) for use in the invention is an inorganic or organic compound in the form of granular or particulate solid. As the inorganic compound, porous oxide, inorganic chloride, clay, clay mineral or an ion-exchange layered compound is preferable.

Examples of the porous oxides include $SiO_2$, $Al_2O_3$, MgO, ZrO, $TiO_2$, $B_2O_3$, CaO, ZnO, BaO, $ThO_2$; and mixtures containing these oxides, such as $SiO_2$—MgO, $SiO_2$—$Al_2O_3$, $SiO_2$—$TiO_2$, $SiO_2$—$V_2O_5$, $SiO_2$—$Cr_2O_3$ and $SiO_2$—$TiO_2$—MgO. Preferable are compounds each containing at least one of $SiO_2$ and $Al_2O_3$ as the main component.

The inorganic oxides may contain a small amount of carbonate, sulfate, nitrate or oxide component, such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ or $Li_2O$.

Though the porous oxides differ in their properties depending on the type and the preparation process thereof, the carrier preferably used in the invention has a particle diameter of 10 to 300 $\mu$m, preferably 20 to 200 $\mu$m, a specific surface area of 50 to 1,000 $m^2/g$, preferably 100 to 700 $m^2/g$, and a pore volume of 0.3 to 3.0 $cm^3/g$. The carrier can be used after calcined at 100 to 1,000° C., preferably 150 to 700° C., if desired.

Examples of the inorganic chlorides employable in the invention include $MgCl_2$, $MgBr_2$, $MnCl_2$ and $MnBr_2$. In the invention, the inorganic chloride may be used as it is, or can be used after pulverized by a ball mill, a vibration mill or the like. The inorganic chloride can be used as fine particles of a precipitate obtained by dissolving the inorganic chloride in a solvent such as alcohol and then precipitating using precipitating agent.

The clay for use in the invention is generally constituted mainly of clay mineral. The ion-exchange layered-compound is a compound having a crystal structure wherein planes formed by ionic bonding or the like are laminated in parallel to each other with a weak bond strength, and the ions contained therein are exchangeable. Most of clay minerals are ion-exchange layered compounds. As the clay, the clay minerals and the ion-exchange layered compounds, not only natural ones but also synthetic ones are employable.

Examples of such clay, clay minerals and ion-exchange layered compounds include clay, clay minerals and ion crystalline compounds having layered crystal structures such as hexagonal closest packing type, antimony type, $CdCl_2$ type and $CdI_2$ type.

Particular examples of the clay and the clay minerals include kaolin, bentonite, kibushi clay, gairome clay, allophane, hisingerite, pyrophyllite, mica, montmorillonite, vermiculite, chlorite, palygorskite, kaolinite, nacrite, dickite and halloysite. Particular examples of the ion-exchange layered compounds include crystalline acid salts of polyvalent metals, such as $\alpha$-Zr(HAsO_4)_2$\cdot$H_2O, $\alpha$-Zr(HPO_4)_2$, $\alpha$-Zr $(KPO_4)_2 \cdot 3H_2O$, $\alpha\text{-}Ti(HPO_4)_2$, $\alpha\text{-}Ti(HAsO_4)_2 \cdot H_2O$, $\alpha\text{-}Sn(HPO_4)_2 \cdot H_2O$, $\gamma\text{-}Zr(HPO_4)_2$, $\gamma\text{-}Ti(HPO_4)_2$ and $\gamma\text{-}Ti(NH_4PO_4)_2 \cdot H_2O$.

As the clay, the clay minerals and the ion-exchange layered compounds, preferable are those having a pore volume, as measured on pores having a radius of not less than 20 Å by a mercury penetration method, of not less than 0.1 cc/g, and particularly preferable are those having a pore volume of 0.3 to 5 cc/g. The pore volume is measured on the pores having a radius of 20 to $3 \times 10^4$ Å by a mercury penetration method using a mercury porosimeter. When a compound having a pore volume, as measured on pores having a radius of not less than 20 Å, of less than 0.1 cc/g is used, high polymerization activities are apt to be hardly obtained.

It is preferable that the clay and the clay minerals for use in the invention are subjected to chemical treatments. A surface treatment to remove impurities attached to the surface and a treatment having an influence on the crystal structure of the clay are both available. Examples of such treatments include acid treatment, alkali treatment, salt treatment and organic matter treatment. The acid treatment contributes to not only removing impurities from the surface but also eluting cations such as Al, Fe and Mg present in the crystal structure to thereby increase the surface area. The alkali treatment destroys the crystal structure of clay to bring about change in the structure of the clay. The salt treatment and the organic matter treatment can produce ionic complex, molecular complex or organic derivative to change the surface area or the distance between layers.

In the ion-exchange layered compound for use in the invention, the exchangeable ions between layers can be exchanged with other large and bulky ions utilizing ion exchange properties, whereby a layered compound having enlarged distance between layers can be obtained. That is, the bulky ion plays a pillar-like roll to support the layer structure and is called a "pillar". Introduction of other substances between layers of a layered material is called "intercalation".

Examples of the guest compounds to be intercalated include cationic inorganic compounds, such as $TiCl_4$ and $ZrCl_4$; metallic alcoholates, such as $Ti(OR)_4$, $Zr(OR)_4$, $PO(OR)_3$ and $B(OR)_3$ (R is a hydrocarbon group or the like); and metallic hydroxide ions, such as $[Al_{13}O_4(OH)_{24}]^{7+}$, $[Zr_4(OH)_{14}]^{2+}$ and $[Fe_3O(OCOCH_3)_6]^+$. These compounds can be used singly or in combination of two or more kinds. Intercalation of these compounds can be carried out in the presence of polymers obtained by hydrolysis of metallic alcoholates such as $Si(OR)_4$, $Al(OR)_3$ and $Ge(OR)_4$ (R is a hydrocarbon group or the like) or in the presence of colloidal inorganic compounds such as $SiO_2$. Examples of the pillars include oxides produced by intercalation of the above-mentioned hydroxide ions between layers and then dehydration under heating.

The clay, clay minerals and the ion-exchange layered compounds mentioned above may be used as they are, or may be used after subjected to a treatment of ball milling, sieving or the like. Moreover, they may be used after subjected to water adsorption or dehydration under heating. The clay, clay minerals and the ion-exchange layered compounds may be used singly or in combination of two or more kinds.

Of the above-mentioned materials, preferable are clay and clay minerals, and particularly preferable are montmorillonite, vermiculite, pectolite, teniolite and synthetic mica.

The organic compound is, for example, a granular or particulate organic compound having a particle diameter of 10 to 300 μm. Examples of such compounds include (co) polymers produced using, as main components, α-olefins of 2 to 14 carbon atoms such as ethylene, propylene, 1-butene and 4-methyl-1-pentene, (co)polymers produced using, as a main component, vinylcyclohexane or styrene, and modified products thereof.

In the olefin polymerization catalyst of the invention, the below-described specific organic compound (D) can be used if necessary, in addition to the transition metal compound (A), at least one compound (B) selected from the organometallic compound (B-1), the organoaluminum oxy-compound (B-2) and the ionized ionic compound (B-3), and the fine particle carrier (C).

(D) Organic Compound Component

The organic compound component which can be used if necessary functions to improve polymerizability and properties of the resulting polymers. Examples of the organic compounds include alcohol, a phenolic compound, a carboxylic acid, a phosphorus compound and sulfonate, but the organic compound employable in the invention is not limited thereto.

The alcohol and the phenolic compound are represented by $R^{31}$—OH wherein $R^{31}$ is a hydrocarbon group of 1 to 50 carbon atoms or a halogenated hydrocarbon group of 1 to 50 carbon atoms. The alcohol is preferably a halogen atom-containing hydrocarbon. The phenolic compound is preferably a phenolic compound wherein the α,α'-position of the hydroxyl group is substituted with a hydrocarbon group of 1 to 20 carbon atoms.

The carboxylic acid is represented by $R^{32}$—COOH wherein $R^{32}$ is a hydrocarbon group of 1 to 50 carbon atoms or a halogenated hydrocarbon group of 1 to 50 carbon atoms, preferably a halogenated hydrocarbon group of 1 to 50 carbon atoms.

Preferred examples of the phosphorus compounds include phosphoric acids having P—O—H bond, phosphates having P—OR bond or P=O bond, and phosphine oxide compounds.

The sulfonate is represented by the following formula (IX):

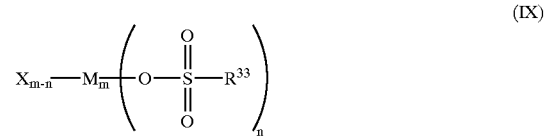

(IX)

wherein M is an atom of Group 1 to Group 14 of the periodic table; $R^{33}$ is a hydrocarbon group of 1 to 20 carbon atoms or a halogenated hydrocarbon group of 1 to 20 carbon atoms; X is a hydrogen atom, a halogen atom, a hydrocarbon group of 1 to 20 carbon atoms or a halogenated hydrocarbon group of 1 to 20 carbon atoms; m is an integer of 1 to 7; and $n \leq n \leq 7$.

FIG. 1 shows steps for preparing the first olefin polymerization catalyst according to the invention.

In the polymerization, the components can be used in any way and in any order. Some examples of the processes are given below.

(1) The component (A) and at least one component (B) selected from the organometallic compound (B-1), the organoaluminum oxy-compound (B-2) and the ionized ionic compound (B-3) (referred to simply as "component (B)" hereinafter) are fed to the polymerization reactor in an arbitrary order.

(2) A catalyst obtained by previously contacting the component (A) with the component (B) is fed to the polymerization reactor.

(3) A catalyst component obtained by previously contacting the component (A) with the component (B), and the component (B) are fed to the polymerization reactor in an arbitrary order. In this case, the components (B) may be the same or different.

(4) A catalyst component wherein the component (A) is supported on the carrier (C), and the component (B) are fed to the polymerization reactor in an arbitrary order.

(5) A catalyst component wherein the component (A) and the component (B) are supported on the carrier (C) is fed to the polymerization reactor.

(6) A catalyst component wherein the component (A) and the component (B) are supported on the carrier (C), and the component (B) are fed to the polymerization reactor in an arbitrary order. In this case, the components (B) may be the same or different.

(7) A catalyst component wherein the component (B) is supported on the carrier (C), and the component (A) are fed to the polymerization reactor in an arbitrary order.

(8) A catalyst component wherein the component (B) is supported on the carrier (C), the component (A) and the component (B) are fed to the polymerization reactor in an arbitrary order. In this case, the components (B) may be the same or different.

(9) A component wherein the component (A) is supported on the carrier (C) and a component wherein the component (B) is supported on the carrier (C) are fed to the polymerization reactor in an arbitrary order.

(10) A component wherein the component (A) is supported on the carrier (C), a component wherein the component (B) is supported on the component (C), and the component (B) are fed to the polymerization reactor in an arbitrary order. In this case, the components (B) may be the same or different.

(11) The component (A), the component (B) and the organic compound component (D) are fed to the polymerization reactor in an arbitrary order.

(12) A component obtained by previously contacting the component (B) with the component (D), and the component (A) are fed to the polymerization reactor in an arbitrary order.

(13) A component wherein the component (B) and the component (D) are supported on the carrier (C), and the component (A) are fed to the polymerization reactor in an arbitrary order.

(14) A catalyst component obtained by previously contacting the component (A) with the component (B), and the component (D) are fed to the polymerization reactor in an arbitrary order.

(15) A catalyst component obtained by previously contacting the component (A) with the component (B), the component (B) and the component (D) are fed to the polymerization reactor in an arbitrary order.

(16) A catalyst component obtained by previously contacting the component (A) with the component (B), and a component obtained by previously contacting the component (B) with the component (D) are fed to the polymerization reactor in an arbitrary order.

(17) A component wherein the component (A) is supported on the carrier (C), the component (B) and the component (D) are fed to the polymerization reactor in an arbitrary order.

(18) A component wherein the component (A) is supported on the carrier (C) and a component obtained by contacting the component (B) with the component (D) are fed to the polymerization reactor in an arbitrary order.

(19) A catalyst component obtained by previously contacting the component (A), the component (B) and the component (D) with each other is fed to the polymerization reactor.

(20) A catalyst component which is obtained by previously contacting the component (A), the component (B) and the component (D) with each other, and the component (B) are fed to the polymerization reactor in an arbitrary order. In this case, the components (B) may be the same or different.

(21) A catalyst component wherein the component (A), the component (B) and the component (D) are supported on the carrier (C) is fed to the polymerization reactor.

(22) A catalyst component wherein the component (A), the component (B) and the component (D) are supported on the carrier (C), and the component (B) are fed to the polymerization reactor in an arbitrary order. In this case, the components (B) may be the same or different.

An olefin may be prepolymerized onto the solid catalyst component wherein the component (A) and the component (B) are supported on the carrier (C).

In the process for olefin polymerization according to the invention, an olefin is polymerized or copolymerized in the presence of the above-described olefin polymerization catalyst to obtain an olefin polymer.

In the present invention, the polymerization can be carried out as any of liquid phase polymerization, such as solution polymerization or suspension polymerization, and gas phase polymerization.

Examples of the inert hydrocarbon media used in the liquid phase polymerization include aliphatic hydrocarbons, such as propane, butane, pentane, hexane, heptane octane, decane, dodecane and kerosine; alicyclic hydrocarbons, such as cyclopentane, cyclohexane and methylcyclopentane; aromatic hydrocarbons, such as benzene, toluene and xylene; halogenated hydrocarbons, such as ethylene chloride, chlorobenzene and dichloromethane; and mixtures of these hydrocarbons. The olefin itself can be used as the solvent.

In the polymerization of an olefin using the olefin polymerization catalyst, the component (A) is used in an amount of usually $10^{-12}$ to $10^{-2}$ mol, preferably $10^{-10}$ to $10^{-3}$ mol, based on 1 liter of the reaction volume. In the present invention, an olefin can be polymerized with high polymerization activities, even if the component (A) is used in a relatively low concentration.

The component (B-1) is used in such an amount that the molar ratio of the component (B-1) to the transition metal atom (M) in the component (A) ((B-1)/(M)) becomes usually 0.01 to 100,000, preferably 0.05 to 50,000. The component (B-2) is used in such an amount that the molar ratio of the aluminum atom in the component (B-2) to the transition metal atom (M) in the component (A) ((B-2)/(M)) becomes usually 10 to 500,000, preferably 20 to 100,000. The component (B-3) is used in such an amount that the molar ratio of the component (B-3) to the transition metal atom (M) in the component (A) ((B-3)/(M)) becomes usually 1 to 10, preferably 1 to 5.

The ratio of the component (D) to the component (B) is as follows. When the component (B) is the component (B-1), the component (D) is used in such an amount that the (D)/(B-1) ratio by mol becomes 0.01 to 10, preferably 0.1 to 5. When the component (B) is the component (B-2), the component (D) is used in such an amount that the molar ratio of the component (D) to the aluminum atom in the component (B-2) ((D)/(B-2)) becomes 0.001 to 2, preferably 0.005 to 1. When the component (B) is the component (B-3), the component (D) is used in such an amount that the (D)/(B-3) ratio by mol becomes 0.01 to 10, preferably 0.1 to 5.

The temperature for the olefin polymerization using the olefin polymerization catalyst is in the range of usually −50 to 200° C., preferably 0 to 170° C. The polymerization pressure is in the range of usually atmospheric pressure to 100 kg/cm², preferably atmospheric pressure to 50 kg/cm². The polymerization reaction can be carried out by any of batchwise, semi-continuous and continuous processes. The polymerization can be conducted in two or more stages under different reaction conditions.

The molecular weight of the resulting polymer can be adjusted by allowing hydrogen to exist in the polymerization system or by varying the polymerization temperature. Further, the molecular weight can be adjusted also by using the component (B) of different type.

Examples of the olefins which can be polymerized using the olefin polymerization catalyst include:

straight-chain or branched α-olefins of 2 to 30, preferably 3 to 20 carbon atoms, such as ethylene, propylene, 1-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene and 1-eicosene; and cycloolefins of 3 to 30, preferably 3 to 20 carbon atoms, such as cyclopentene, cycloheptene, norbornene, 5-methyl-2-norbornene, tetracyclododecene and 2-methyl-1,4,5,8-dimethano-1,2,3,4,4a,5,8,8a-octahydronaphthalene.

Also employable are polar monomers. Examples of such monomers include α,β-unsaturated carboxylic acids, such as acrylic acid, methacrylic acid, fumaric acid, maleic anhydride, itaconic acid, itaconic anhydride and bicyclo(2,2,1)-5-heptene-2,3-dicarboxylic acid; metallic salts of these acids, such as sodium salts, potassium salts, lithium salts, zinc salts, magnesium salts and calcium salts; α,β-unsaturated carboxylic esters, such as methyl acrylate, ethyl acrylate, n-propyl acrylate, isopropyl acrylate, n-butyl acrylate, isobutyl acrylate, tert-butyl acrylate, 2-ethylhexyl acrylate, methyl methacrylate, ethyl methacrylate, n-propyl methacrylate, isopropyl methacrylate, n-butyl methacrylate and isobutyl methacrylate; vinyl esters, such as vinyl acetate, vinyl propionate, vinyl caproate, vinyl caprate, vinyl laurate, vinyl stearate and vinyl trifluoroacetate; and unsaturated glycidyl esters, such as glycidyl acrylate, glycidyl methacrylate and monoglycidyl itaconate. Furthermore, vinylcyclohexane, diene, polyene and the like are also employable. The diene and the polyene are cyclic or chain compounds having 4 to 30, preferably 4 to 20 carbon atoms and having two or more double bonds. Examples of such compounds include butadiene, isoprene, 4-methyl-1,3-pentadiene, 1,3-pentadiene, 1,4-pentadiene, 1,5-hexadiene, 1,4-hexadiene, 1,3-hexadiene, 1,3-octadiene, 1,4-octadiene, 1,5-octadiene, 1,6-octadiene, 1,7-octadiene, ethylidene norbornene, vinyl norbornene and dicyclopentadiene;

7-methyl-1,6-octadiene, 4-ethylidene-8-methyl-1,7-nonadiene, 5,9-dimethyl-1,4,8-decatriene; and further aromatic vinyl compounds such as mono or poly alkyl-styrenes (e.g., styrene, o-methylstyrene, m-methylstyrene, p-methylstyrene, o,p-dimethylstyrene, o-ethylstyrene, m-ethylstyrene and p-ethylstyrene),functional group-containing styrene derivatives (e.g., methoxystyrene, ethoxystyrere, vinyl-benzoic acid, methyl vinylbenzoate, vinylbenzyl acetate, hydroxystyrene, o-chlorostyrene, p-chlorostyrene and divinylbenzene); and 3-phenylpropyrene, 4-phenylpropyrene and α-methylstyrene.

The olefin polymerization catalyst of the invention exhibits high polymerization activities, and by the use of the catalyst, polymers of narrow molecular weight distribution can be obtained. When two or more kinds of olefins are used, olefin copolymers of narrow composition distribution can be obtained.

The olefin polymerization catalyst of the invention can be used also for the copolymerization of an α-olefin and a conjugated diene.

Examples of the α-olefins used herein include the same straight-chain or branched α-olefins of 2 to 30, preferably 2 to 20 carbon atoms as described above. Of these, preferable are ethylene, propylene, 1-butene, 1-pentene, 1-hexene, 4-methyl-1-pentene and 1-octene. Particularly preferable are ethylene and propylene. These α-olefins can be used singly or in combination or two or more kinds.

Examples of the conjugated dienes include aliphatic conjugated dienes of 4 to 30, preferably 4 to 20 carbon atoms, such as 1,3-butadiene, isoprene, chloroprene, 1,3-cyclohexadiene, 1,3-pentadiene, 4-methyl-1,3-pentadiene, 1,3-hexadiene and 1,3-octadiene. These conjugated dienes can be used singly or in combination of two or more kinds.

In the copolymerization of the α-olefin and the conjugated diene, non-conjugated diene or polyene is further employable, and examples thereof include 1,4-pentadiene, 1,5-hexadiene, 1,4-hexadiene, 1,4-octadiene, 1,5-octadiene, 1,6-octadiene, 1,7-octadiene, ethylidene norbornene, vinyl norbornene, dicyclopentadiene, 7-methyl-1,6-octadiene, 4-ethylidene-8-methyl-1,7-nonadiene, 5,9-dimethyl-1,4,8-decatriene.

Second Olefin Polymerization Catalyst

The second olefin polymerization catalyst according to the invention is formed from:

(A') a transition metal compound represented by the below-described formula (II), and (B) at least one compound selected from:
(B-1) an organometallic compound,
(B-2) an organoaluminum oxy-compound, and
(B-3) a compound which reacts with the transition metal compound (A') to form an ion pair.

First, the components for forming the olefin polymerization catalyst of the invention are described.

(A') Transition Metal Compound

The transition metal compound (A') for use in the invention is a transition metal compound represented by the following formula (II):

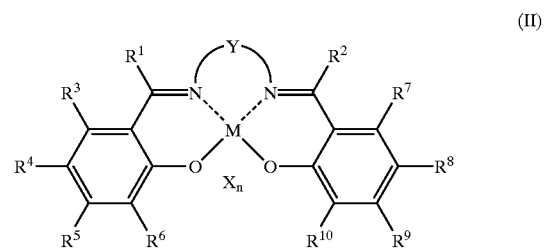

(II)

wherein M is a transition metal atom of Group 3 to Group 11 of the periodic table, R[1] to R[10] may be the same or different, and are each a hydrogen atom, a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group, and two or more of them may be bonded to each other to form a ring, n is a number satisfying a valence of M, X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, and when n is 2 or greater, plural groups X may be the same or different and may be bonded to each other to form a ring, and Y is a divalent bonding group containing at least one element selected from the group consisting of oxygen, sulfur, carbon, nitrogen, phosphorus, silicon, selenium, tin and boron, and when it is a hydrocarbon group, the hydrocarbon group has 3 or more carbon atoms.

It is preferable that at least one of R[6] and R[10], especially both of them, in the formula (II) is a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group.

As M, R[1] to R[10] and X in the formula (II), there can be used the same groups as mentioned for M, R[1] to R[6] and X in the formula (I), respectively. Specific examples of Y are described later on.

The transition metal compound represented by the formula (II) is preferably a transition metal compound represented by the following formula (II-a):

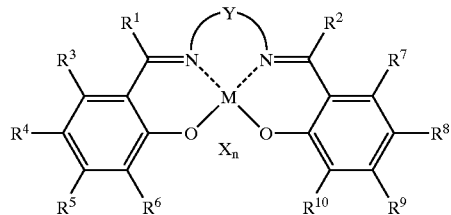

(II-a)

wherein M is a transition metal atom of Group 3 to Group 11, preferably Group 4 or 5, more preferably Group 4, of the periodic table, for example titanium, zirconium and halfnium, especially titanium.

R[1] to R[10] may be the same or different, and are each a hydrogen atom, a halogen atom, a hydrocarbon group, a hydrocarbon-substituted silyl group, an alkoxy group, an aryloxy group, an ester group, an amido group, an amino group, a sulfonamido group, a cyano group or a nitro group, and two or more of them may be bonded to each other to form a ring, n is a number satisfying a valence of M, usually an integer of 0 to 4, preferably 1 to 4, more preferably 1 to 3.

X is a hydrogen atom, a halogen atom, a hydrocarbon group of 1 to 20 carbon atoms, an oxygen-containing group, a sulfur-containing group or a silicon-containing group, and when n is 2 or greater, plural groups may be the same or different and may be bonded to each other to form a ring.

Y is a divalent bonding group containing at least one element selected from the group consisting of oxygen, sulfur, carbon, nitrogen, phosphorus, silicon, selenium, tin and boron, and when it is a hydrocarbon group, the hydrocarbon group has 3 or more carbon atoms.

The main chain of the bonding group Y has a structure comprising preferably 3 to 40, more preferably 4 to 10 atoms. The bonding group may have a substituent.

It is preferable that at least one of R[6] and R[10], preferably both of them in the formula (II-a) is a halogen atom, a hydrocarbon group, a hydrocarbon-substituted silyl group, an alkoxy group, an aryloxy group, an ester group, an amido group, an amino group, a sulfonamido group, a cyano group or a nitro group.

Specific examples of X and R[1] to R[10] in the formula (II-a) are the same as mentioned for X and R[1] to R[6] in the formulae (I) and (I-a). X is particularly preferably a halogen atom, a hydrocarbon group of 1 to 20 carbon atoms or a sulfinato group. When n is 2 or greater, plural groups X may be bonded to each other to form a ring such as an aromatic ring or an aliphatic ring.

Specific examples of the divalent bonding groups include chalcogen atoms, such as —O—, —S— and —Se—; nitrogen- or phosphorus-containing groups, such as —NH—, —N(CH₃)—, —PH— and —P(CH₃)—; silicon atom-containing groups, such as —SiH₂— and —Si(CH₃)₂; tin atom-containing groups, such as —SnH₂— and —Sn(CH₃)₂; and boron atom-containing groups, such as —BH—, —B(CH₃) and —BF. Examples of the hydrocarbon groups include saturated hydrocarbon groups of 3 to 20 carbon atoms, such as —(CH₂)₄—, —(CH₂)₅— and —(CH₂)₆—; cyclic saturated hydrocarbon groups, such as cyclohexylidene and cyclohexylene; groups wherein these saturated hydrocarbon groups are partially substituted with 1 to 10 groups or atoms selected from hydrocarbon groups, halogen atoms (e.g., fluorine, chlorine and bromine) and hetero atoms (e.g., oxygen, sulfur, nitrogen, phosphorus, silicon, selenium, tin and boron); residual groups of cyclic hydrocarbons of 6 to 20 carbon atoms, such as benzene, naphthalene and anthracene; residual groups of cyclic compounds containing hetero atoms and having 3 to 20 carbon atoms, such as pyridine, quinoline, thiophene and furan.

Examples of the transition metal compounds represented by the formula (II) are given below, but the transition metal compounds are not limited to those examples.

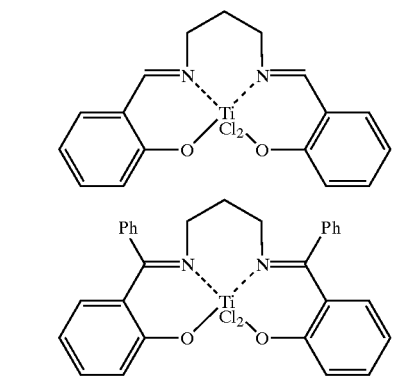

-continued
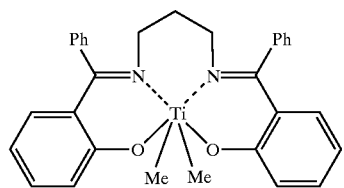
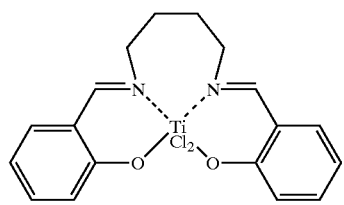
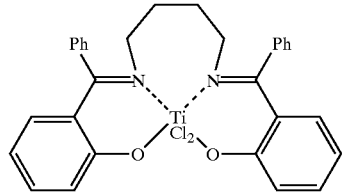
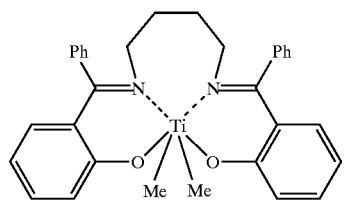
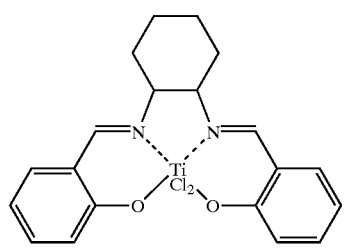
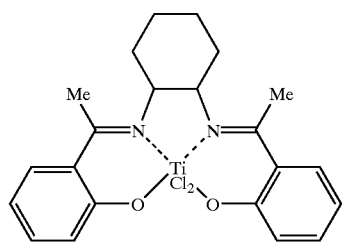
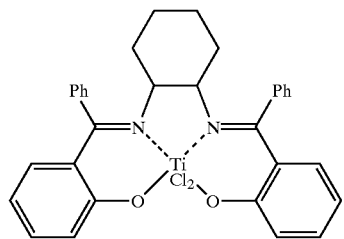
-continued
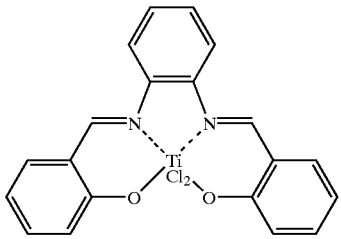
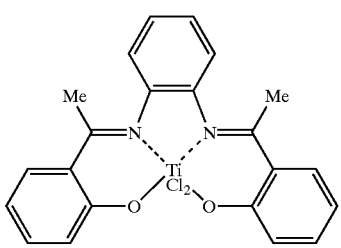
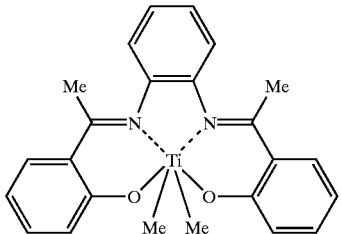
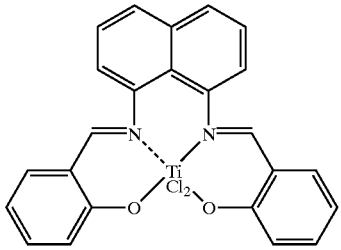
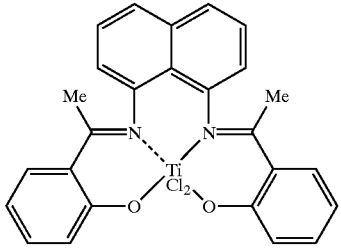
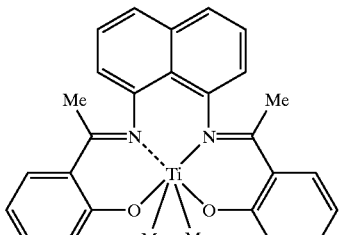
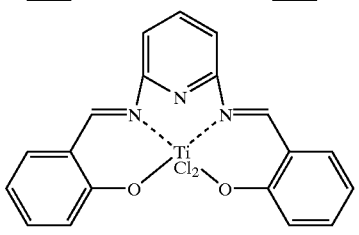

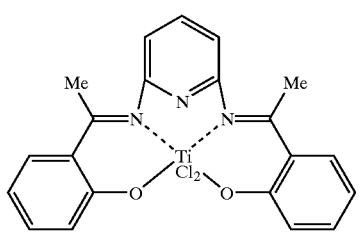
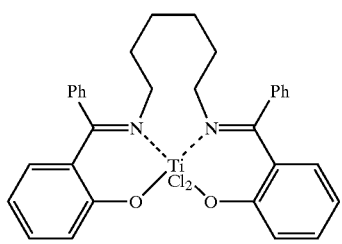
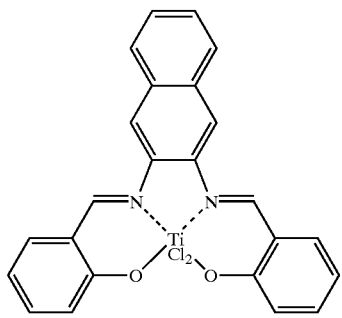
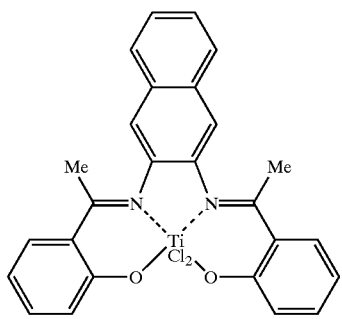
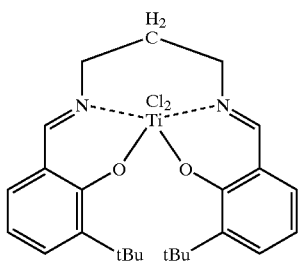
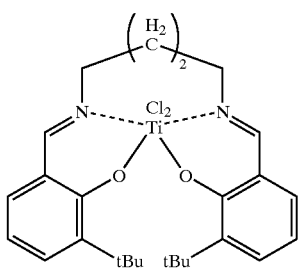
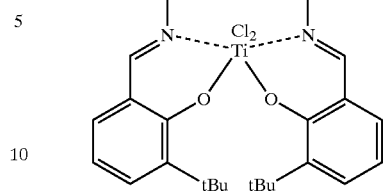
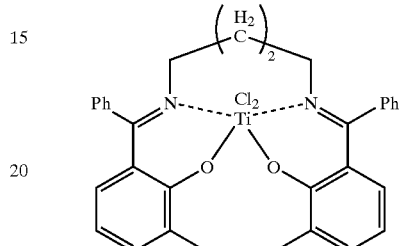
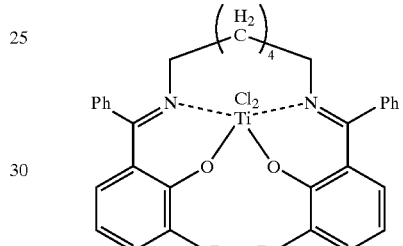
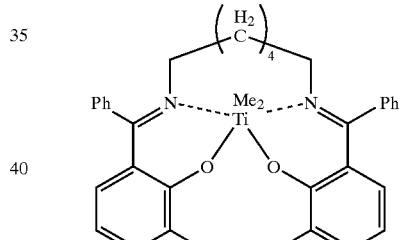
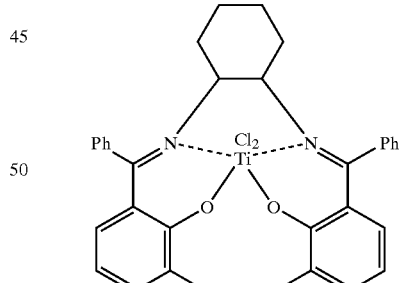
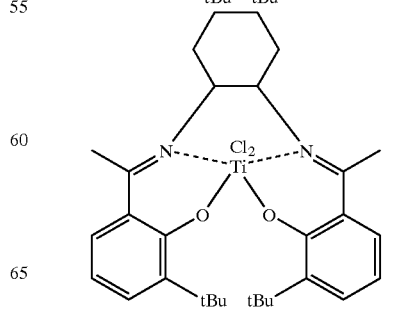

-continued

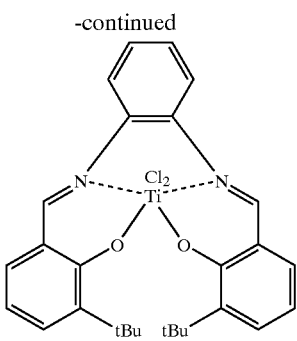

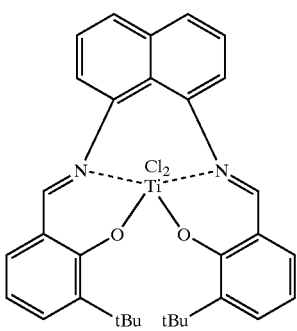

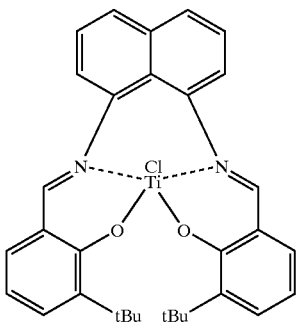

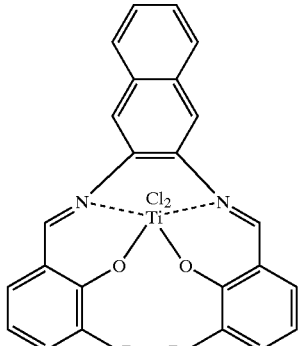

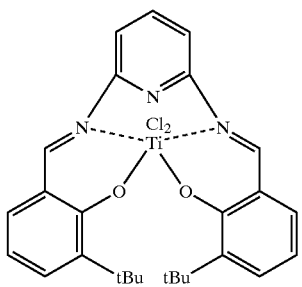

-continued

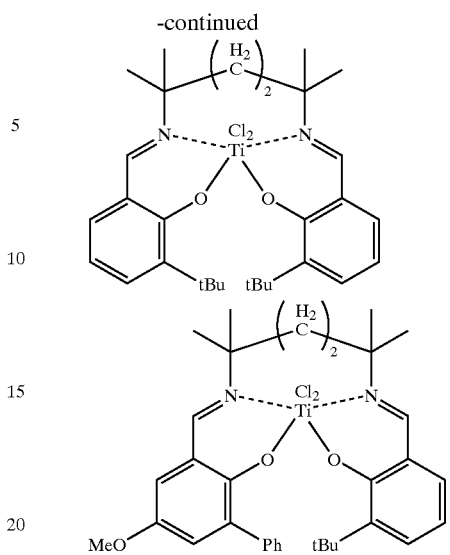

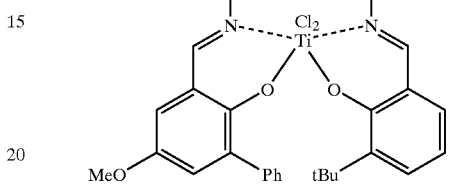

In the above examples, Me is methyl, Ph is phenyl.

In the present invention, transition metal compounds wherein titanium is replaced with other metals than titanium, such as zirconium or hafnium, in the above-exemplified compounds are also employable.

In the second olefin polymerization catalyst according to the invention, the transition metal compound (A') can be used in combination with other transition metal compounds, as for the aforesaid transition metal compound (A). Examples of the other transition metal compounds include the aforesaid compounds (a-1) to (a-8).

In the second olefin polymerization catalyst according to the invention, examples of the organometallic compounds (B-1), the organoaluminum oxy-compounds (B-2) and the compounds which react with the transition metal compound (A') to form an ion pair include those previously described.

In the second olefin polymerization catalyst according to the invention, the aforesaid carrier (C) can be used if necessary, in addition to the above-mentioned transition metal compound (A') and at least one compound (B) selected from the organometallic compound (B-1), the organoaluminum oxy-compound (B-2) and the ionized ionic compound (B-3), as in the first olefin polymerization catalyst. Further, the aforesaid specific organic compound (D) can also be used if necessary.

Figure 2:
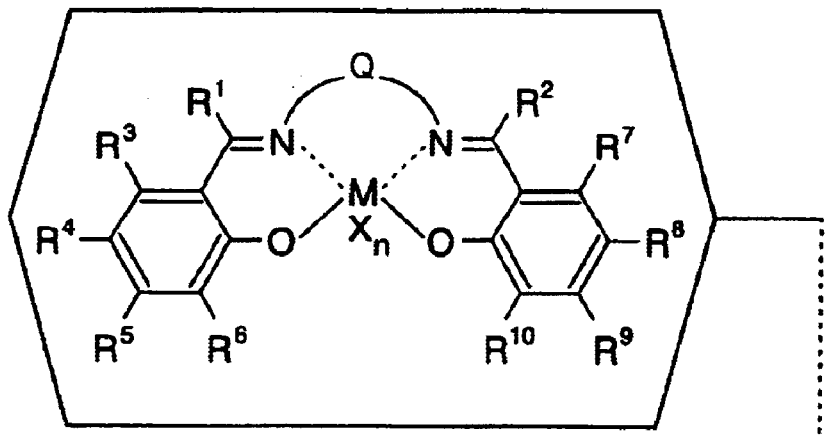
FIG. 2 shows steps for preparing the second olefin polymerization catalyst according to the invention.
Figure 2:
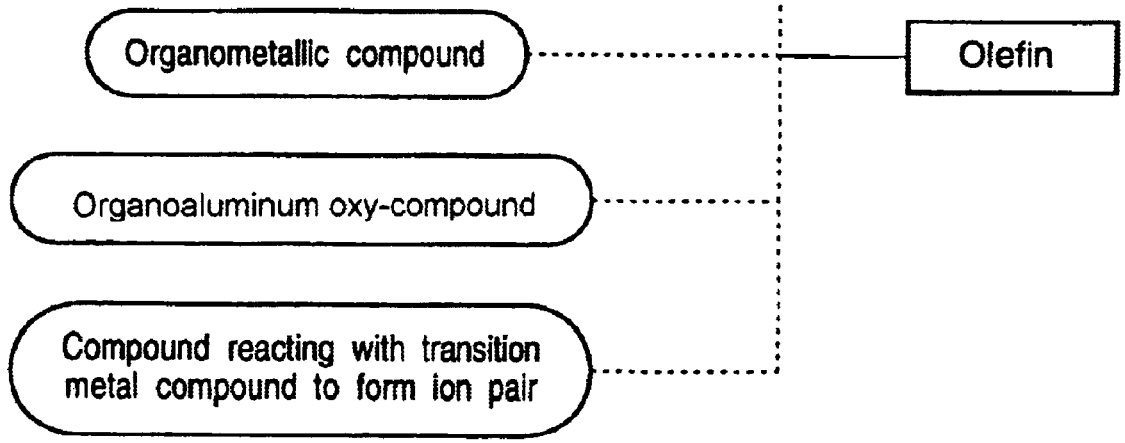

FIG. 2 shows steps for preparing the second olefin polymerization catalyst according to the invention.

The second olefin polymerization catalyst according to the invention can be used for polymerizing the same olefins under the same conditions as described for the first olefin polymerization catalyst.

Novel Transition Metal Compound

The novel transition metal compound according to the invention is represented by the following formula (III):

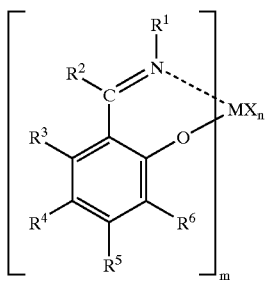

(III)

wherein M is a transition metal atom of Group 4 or Group 5 of the periodic table, m is an integer of 1 to 3, $R^1$ is a hydrocarbon group, a hydrocarbon-substituted silyl group, a hydrocarbon-substituted siloxy group, an alkoxy group, an alkylthio group, an aryloxy group, an arylthio group, an ester group, a thioester group, a sulfonester group or a hydroxyl group, $R^2$ to $R^5$ may be the same or different, and are each a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an ester group, a thioester group, an amido group, an imido group, an amino group, an imino group, a sulfonester group, a sulfonamido group, a cyano group, a nitro group, a carboxyl group, a sulfo group, a mercapto group or a hydroxyl group, $R^6$ is a halogen atom, a hydrocarbon group, a hydrocarbon-substituted silyl group, a hydrocarbon-substituted siloxy group, an alkoxy group, an alkylthio group, an aryloxy group, an arylthio group, an ester group, a thioester group, an amido group, an imido group, an imino group, a sulfonester group, a sulfonamido group or a cyano group, two or more of $R^1$ to $R^6$ may be bonded to each other to form a ring, when m is 2 or greater, two of the groups $R^1$ to $R^6$ may be bonded to each other, with the proviso that the groups $R^1$ are not bonded to each other, n is a number satisfying a valence of M, and X is a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, and when n is 2 or greater, plural groups X may be the same or different and may be bonded to each other to form a ring.

As the transition metal compound of the formula (III), preferable is a transition metal compound represented by the following formula (III-a).

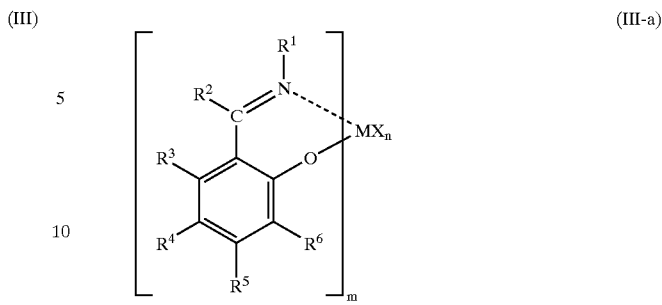

(III-a)

In the formula (III-a), M is a transition metal atom of Group 4 or Group 5 of the periodic table, specifically titanium, zirconium, hafnium, vanadium, niobium or tantalum.

m is an integer of 1 to 3, preferably 2.

$R^1$ to $R^5$ may be the same or different, and are each a hydrocarbon group, an alkoxy group or a hydrocarbon-substituted silyl group.

$R^6$ is a halogen atom, a hydrocarbon group, a hydrocarbon-substituted silyl group, an alkoxy group, an alkylthio group or a cyano group.

Two or more of $R^1$ to $R^6$ may be bonded to each other to form a ring.

When m is 2 or greater, two of the groups $R^1$ to $R^6$ may be bonded to each other, with the proviso that the groups $R^1$ are not bonded to each other.

n is a number satisfying a valence of M.

X is a halogen atom, a hydrocarbon group, an oxygen-containing group, a sulfur-containing group, a nitrogen-containing group, halogen-containing group or a silicon-containing group.

Preferable X is a halogen atom, a hydrocarbon group of 1 to 20 carbon atoms, a halogenated hydrocarbon group of 1 to 20 carbon atoms, an oxygen-containing, a sulfur-containing group or a silicon containing group.

When n is 2 or greater, plural groups X may be the same or different and may be bonded to each other to form a ring.

Specific examples of $R^1$ to $R^6$ and X include those described for the above-mentioned formula (I).

Some examples of the novel transition metal compounds are given below.

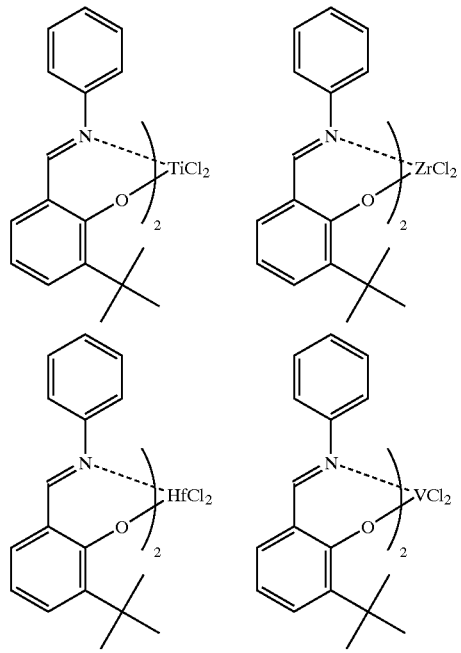

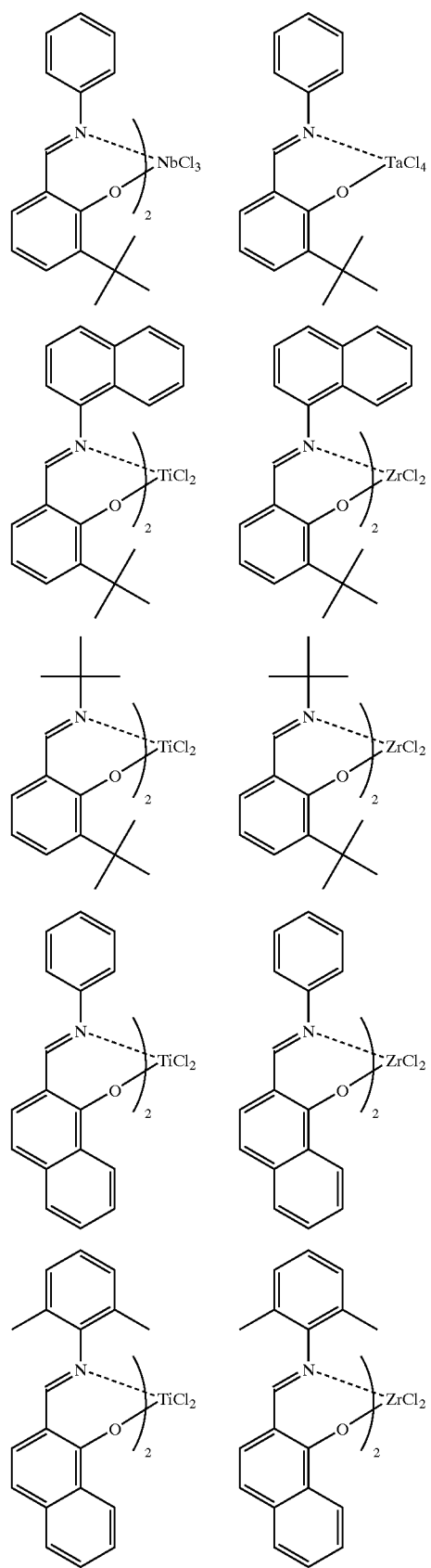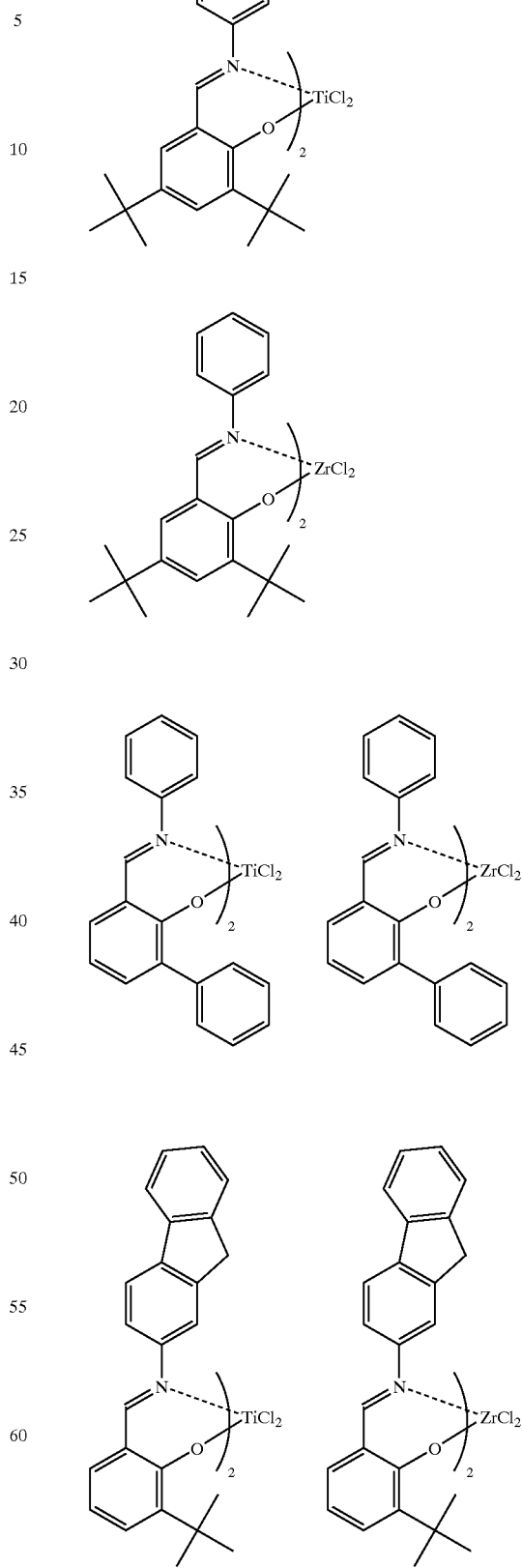

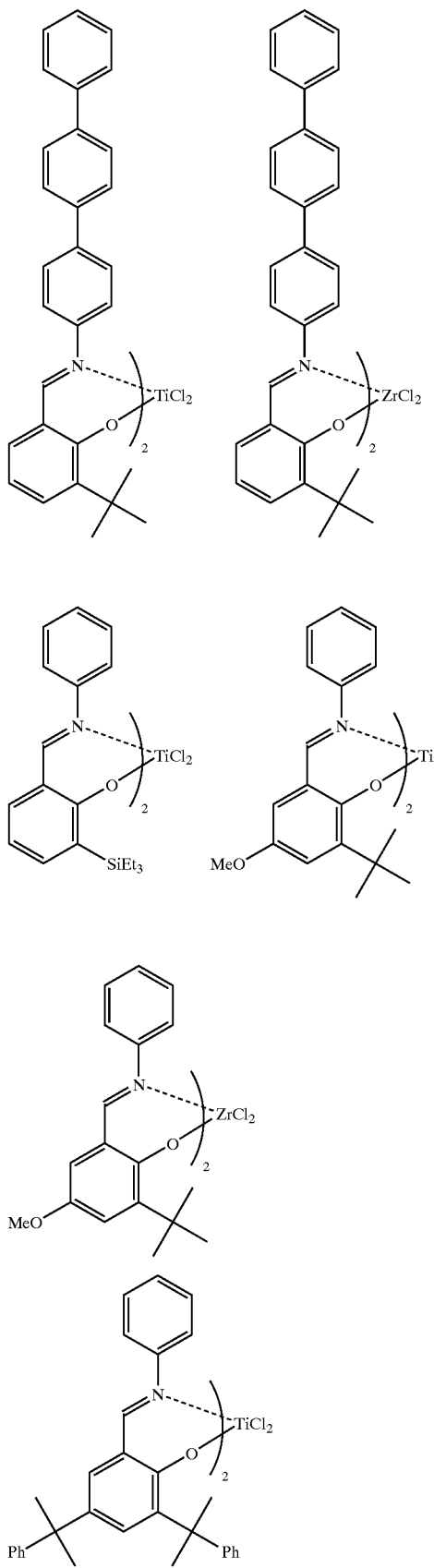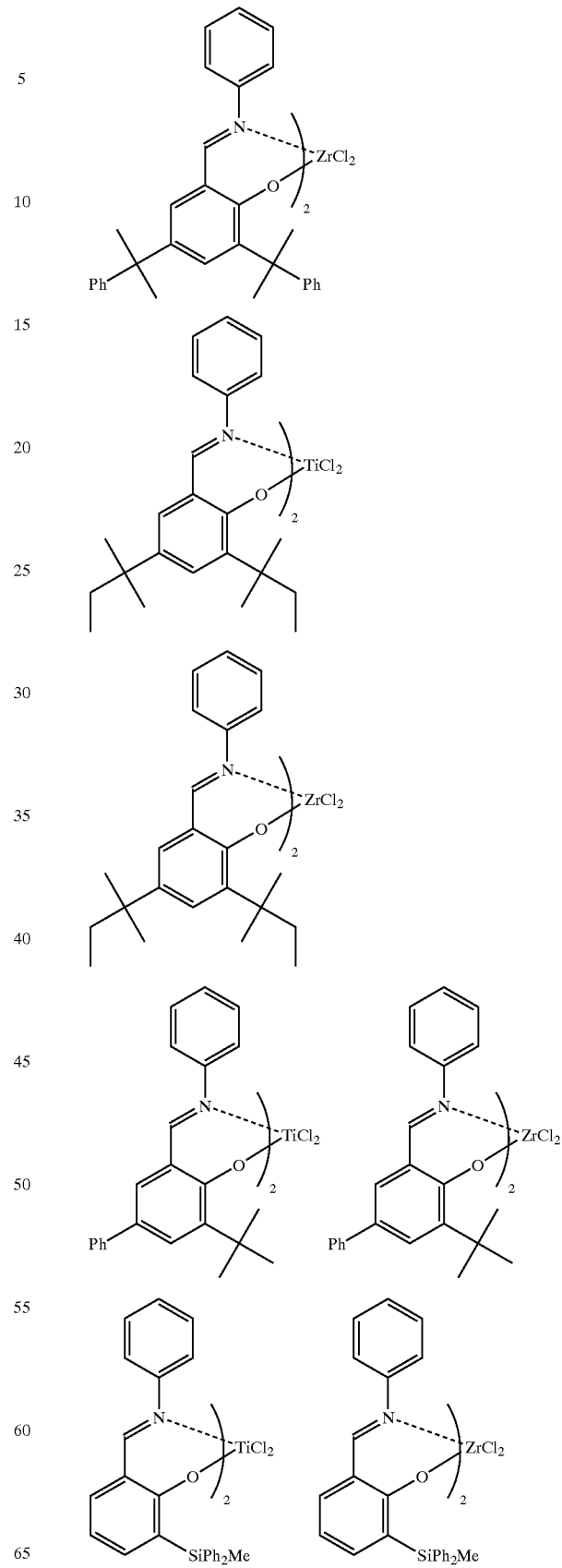

131
-continued
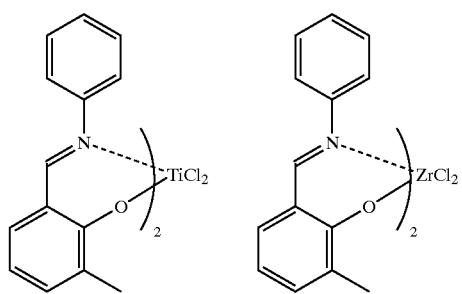
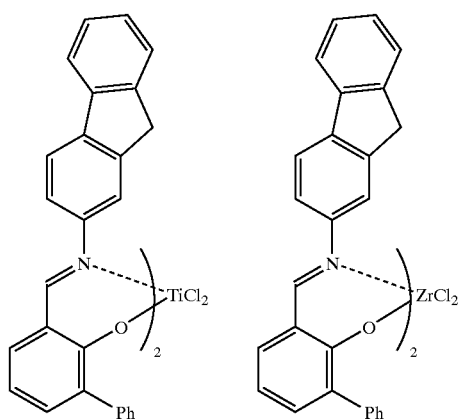
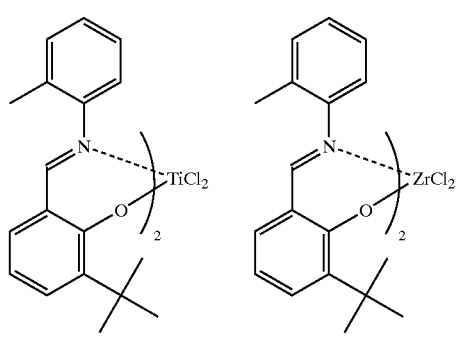
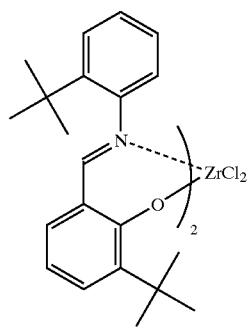
132
-continued
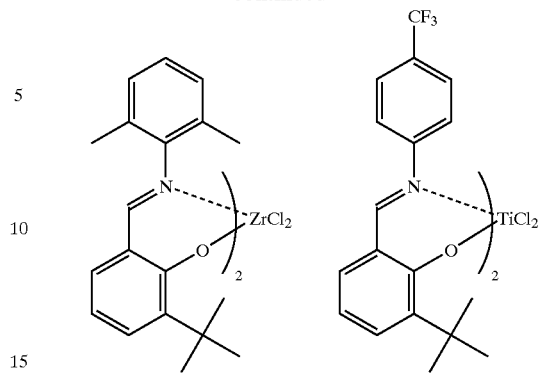
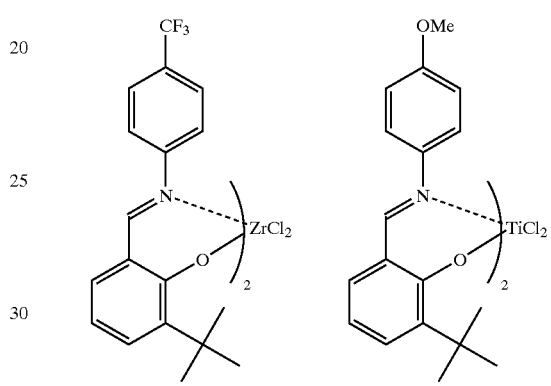
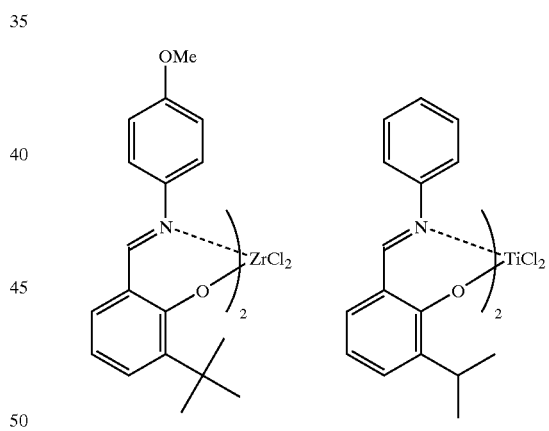
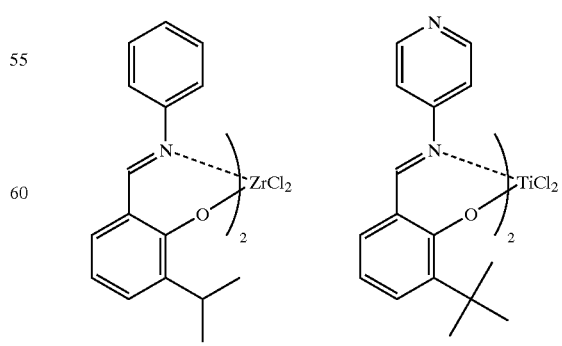

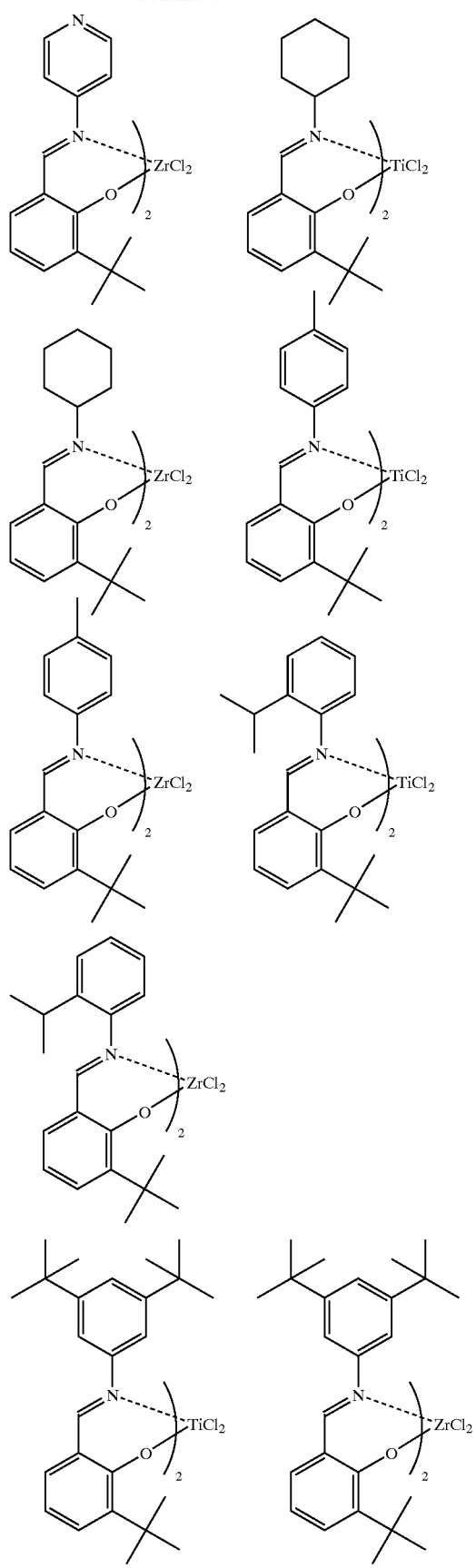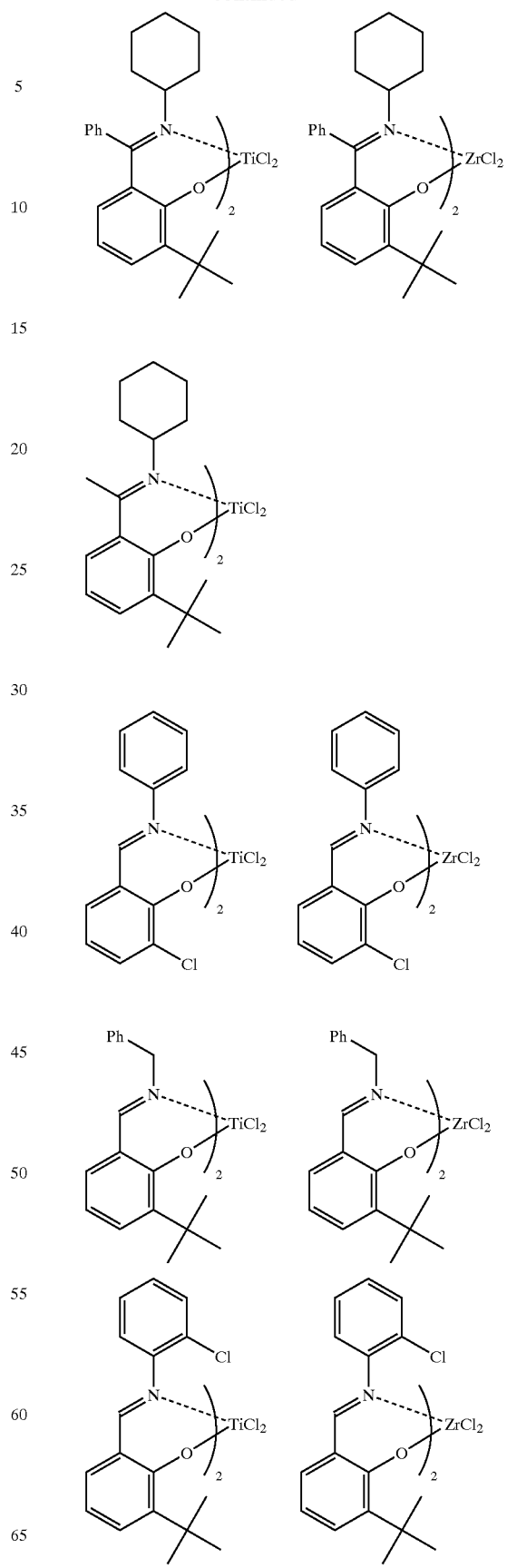

-continued

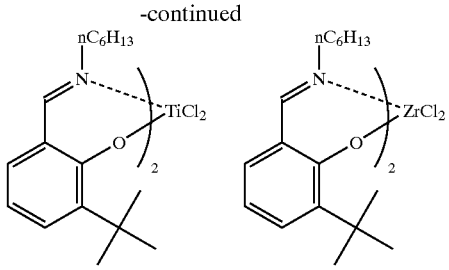

General Process for Preparing Transition Metal Compound

The transition metal compounds of the formulae (I), (II) and (III) can be prepared by any processes without specific limitation, for example, in the manner as described below. First, the ligand composing the transition metal compound can be obtained by reacting a salicylaldehyde compound with a primary amine compound of the formula $R^1$—$NH_2$ (where $R^1$ has the meanings as described above), for example an aniline compound or an alkylamine compound. In more detail, both starting compounds are dissolved in a solvent, for example those commonly used in such reactions, preferably alcohols such as methanol and ethanol, and hydrocarbon solvents such as toluene. The resulting solution is stirred for about 1 to 48 hours at room temperature to a reflux temperature to obtain the corresponding ligand in a good yield.

In the preparation of ligands, catalysts for example acid catalysts such as formic acid, acetic acid and toluenesulfonic acid can be used. In order to proceed the reaction effectively, it is also possible to use dehydrating agents such as molecular sieves, magnesium sulfate and sodium sulfate or to perform dehydration by the Dean Stark method.

The ligand thus obtained can then be reacted with a transition metal M-containing compound, to synthesize the desired transition metal compound. Specifically, the ligand is dissolved in a solvent, and if necessary, is contacted with a base to prepare a phenoxide salt, followed by mixing with a metal compound such as a metallic halide or a metallic alkylate at a low temperature and stirring for about 1 to 48 hours at $-78°$ C. to room temperature or under reflux. Any solvents usually used in such reactions may be employed and preferable are polar solvents such as ethers, e.g., tetrahydrofuran (THF) and hydrocarbon solvents such as toluene. Examples of the bases which may be used for preparing the phenoxide salt include, but not limited to metallic salts, such as lithium salts (e.g., n-butyllithium) and sodium salts (e.g., sodium hydride) and organic bases such as triethylamine and pyridine.

Depending on the properties of the compound, the step of preparing the phenoxide salt may be omitted, and the ligand can be directly reacted with the metal compound to synthesize the corresponding transition metal compound.

Further, it is possible that the transition metal M in the synthesized compound is replaced with another transition metal by conventional methods. Furthermore, any one of $R^1$ to $R^6$ which is H can be substituted by a substituent other than H at any synthesis steps.

The novel transition metal compound represented by the formula (III), preferably the formula (III-a), can be favorably used as an olefin polymerization catalyst.

If the transition metal compound is used as an olefin polymerization catalyst, (co)polymers of narrow molecular weight distribution can be synthesized with high polymerization activities.

α-Olefin/conjugated Diene Copolymer

The α-olefin/conjugated diene copolymer according to the invention comprises 1 to 99.9% by mol of constituent units derived from an α-olefin and 99 to 0.1% by mol of constituent units derived from a conjugated diene, and preferably comprises 50 to 99.9% by mol of constituent units derived from an α-olefin and 50 to 0.1% by mol of constituent units derived from a conjugated diene.

Examples of the α-olefins include the same straight-chain or branched α-olefins of 2 to 30, preferably 2 to 20 carbon atoms as described above. Of these, preferable are ethylene, propylene, 1-butene, 1-pentene, 1-hexene, 4-methyl-1-pentene and 1-octene. Particularly preferable are ethylene and propylene. These α-olefins can be used singly or in combination or two or more kinds.

Examples of the conjugated dienes include aliphatic conjugated dienes of 4 to 30, preferably 4 to 20, preferably 4 to 20 carbon atoms, such as 1,3-butadiene, isoprene, chloroprene, 1,3-cyclohexadiene, 1,3-pentadiene, 4-methyl-1,3-pentadiene, 1,3-hexadiene and 1,3-octadiene. These conjugated dienes can be used singly or in combination of two or more kinds.

In the copolymerization of the α-olefin and the conjugated diene, non-conjugated diene or polyene is further employable, and examples thereof include 1,4-pentadiene, 1,5-hexadiene, 1,4-hexadiene, 1,4-octadiene, 1,5-octadiene, 1,6-octadiene, 1,7-octadiene, ethylidene norbornene, vinyl norbornene, dicyclopentadiene, 7-methyl-1,6-octadiene, 4-ethylidene-8-methyl-1,7-nonadiene, 5,9-dimethyl-1,4,8-decatriene.

In the polymer chain of the α-olefin/conjugated diene copolymer of the invention, the content of 1,2-cyclopentane skeleton derived from the conjugated diene is not more than 1% by mol, preferably such a content that the 1,2-cyclopentadiene skeleton can be regarded to be substantially not contained (i.e., less than 0.1% by mol). When the content of the 1,2-cyclopentane skeleton is less than 0.1% by mol, the content is regarded to be lower than the detection limit and is not introduced into the calculation of all the conjugated diene units.

In the polymer chain of the α-olefin/conjugated diene copolymer of the invention, the proportion of the 1,2-cyclopentane skeleton to all the diene units is not more than 20%, preferably not more than 10%. The proportions of other insertions of the dienes (e.g., 1,4-cis, 1,4-trans, 1,2-vinyl) in the α-olefin/conjugated diene copolymer are arbitrary. The proportions can be determined by $^{13}$C-NMR and $^1$H-NMR in accordance with the method described in "Die Makromolekulare Chemie", volume 192, p. 2591 (1991).

The α-olefin/conjugated diene copolymer has a molecular weight distribution (Mw/Mn) of not more than 3.5 and has a uniform composition distribution. The weight average molecular weight (Mw) of the copolymer is not less than 1,000, preferably not less than 5,000.

Since the α-olefin/conjugated diene copolymer has double bonds in its main chain or side chain, it can be variously modified. For example, by virtue of modification with a peroxide, the double bonds can be epoxidized to introduce epoxy groups of high reactivity into the copolymer. Such a modification makes the copolymer possible to be used as a thermoplastic resin or a reactive resin. The double bonds can also be utilized in the Diels-Alder reaction or the Michael addition reaction. Further, in case of the copolymer having double bonds in the main chain, the copolymer can be improved in heat resistance and ozone resistance by selectively hydrogenating the double bonds to saturate them.

The α-olefin/conjugated diene copolymer of the invention may be modified partially or fully with an unsaturated carboxylic acid, its derivative or an aromatic vinyl compound, and the degree of modification is preferably in the range of 0.01 to 30% by weight.

The monomer used for the modification (referred to as "graft monomer" hereinafter) is, for example, an unsaturated carboxylic acid, its derivative or an aromatic vinyl compound. Examples of the unsaturated carboxylic acids include acrylic acid, methacrylic acid, maleic acid, fumaric acid and itaconic acid. Examples of the derivatives of unsaturated carboxylic acids include acid anhydrides, esters, amides, imides and metallic salts thereof, such as maleic anhydride, citraconic anhydride, itaconic anhydride, methyl acrylate, methyl methacrylate, ethyl acrylate, ethyl methacrylate, butyl acrylate, butyl methacrylate, glycidyl acrylate, glycidyl methacrylate, monoethyl maleate, diethyl maleate, monomethyl fumarate, dimethyl fumarate, monomethyl itaconate, diethyl itaconate, acrylamide, methacrylamide, maleic acid monoamide, maleic acid diamide, maleic acid-N-monoethylamide, maleic acid-N,N-diethylamide, maleic acid-N-monobutylamide, maleic acid-N,N-dibutylamide, fumaric acid monoamide, fumaric acid diamide, fumaric acid-N-monoethylamide, fumaric acid-N,N-diethylamide, fumaric acid-N-monobutylamide, fumaric acid-N,N-dibutylamide, maleimide, N-butylmaleimide, N-phenylmaleimide, sodium acrylate, sodium methacrylate, potassium acrylate and potassium methacrylate. Of the graft monomers, maleic anhydride is preferably employed.

Examples of the aromatic vinyl compounds include:

styrene;

mono or polyalkylstyrenes, such as o-methylstyrene, m-methylstyrene, p-methylstyrene, o,p-dimethylstyrene, o-ethylstyrene, m-ethylstyrene and p-ethylstyrene;

functional group-containing styrene derivatives, such as methoxystyrene, ethoxystyrene, vinylbenzoic acid, methyl vinylbenzoate, vinylbenzyl acetate, hydroxystyrene, o-chlorostyrene, p-chlorostyrene and divinylbenzene; and others, such as 3-phenylpropylene, 4-phenylbutene and a-methylstyrene. Of these, styrene or 4-methoxystyrene is preferable For graft copolymerizing the α-olefin/conjugated diene copolymer with the graft monomer to prepare a modified copolymer, various known processes are available.

For example, the α-olefin/conjugated diene copolymer and the graft monomer are heated at a high temperature in the presence or absence of a solvent and in the presence or absence of a radical initiator to perform graft copolymerization. In the reaction, the graft monomers may be used in combination.

In order to prepare a partially or wholly graft-modified α-olefin/conjugated diene copolymer having a graft ratio of 0.01 to 30% by weight, it is preferable from the viewpoint of industrial production that a graft-modified α-olefin/ conjugated diene copolymer having a high graft ratio is prepared and the thus graft-modified copolymer is then mixed with an unmodified α-olefin/conjugated diene copolymer to adjust the graft ratio, because the concentration of the graft monomer in the composition can be adjusted as desired. It is also possible that a given amount of a graft monomer is blended with the α-olefin/conjugated diene copolymer from the first to perform graft modification.

Referring to the degree of modification of the α-olefin/ conjugated diene copolymer with the graft monomer, the graft ratio to the whole resin composition is in the range of preferably 0.01 to 30% by weight, particularly preferably 0.05 to 10% by weight.

The α-olefin/conjugated diene copolymer of the invention (including the above-mentioned modified product) may be blended with (i) a polyolefin resin and optionally, with (ii) a filler to form resin compositions useful for various applications (i) Polyolefin Resin The polyolefin resin (i) which may be blended with the α-olefin/conjugated diene copolymer of the invention may be any of a crystalline polyolefin and an amorphous polyolefin, or may be a mixture of these polyolefin resins.

The crystalline polyolefin is, for example, a homopolymer or a copolymer of an α-olefin of 2 to 20 carbon atoms or a cycloolefin. The amorphous polyolefin is, for example, a copolymer of one or more α-olefins of 2 to 20 carbon atoms and one or more cycloolefins.

Examples of the α-olefins of 2 to 20 carbon atoms include ethylene, propylene, 1-butene, 2-butene, 1-pentene, 1-hexene, 4-methyl-1-pentene, 4,4-dimethyl-1-pentene, 3-methyl-1-pentene, 4-methyl-1-hexene, 3-ethyl-1-hexene, 4-ethyl-1-hexene, 4,4-dimethyl-1-hexene, 1-octene, 3-methyl-1-butene, 1-nonene, 1-decene, 1-undecene, 1-dodecene, 1-tetradecene, 1-hexadecene, 1-octadecene and 1-eicosene.

Examples of the cycloolefins include cyclopentene, cycloheptene, cyclohexene, norbornene, 5-ethyl-2-norbornene, tetracyclododecene and 2-ethyl-1,4,5,8-dimethano-1,2,3,4,4a,5,8,8a-octahydronaphthalene.

Examples of the crystalline polyolefin resins include the following (co)polymers (1) to (11). Of the copolymers, particularly preferable are the copolymers (3) and (5).

(1) Ethylene homopolymer (produced by any of low-pressure and high-pressure processes)
(2) Copolymer of ethylene and not more than 20% by mol of another α-olefin, vinyl monomer (e.g., vinyl acetate, ethyl acrylate) or cycloolefin
(3) Propylene homopolymer
(4) Random copolymer of propylene and not more than 20% by mol of another α-olefin
(5) Block copolymer of propylene and not more than 30% by mol of another α-olefin
(6) 1-Butene homopolymer
(7) Random copolymer of 1-butene and not more than 20% by mol of another α-olefin
(8) 4-Methyl-1-pentene homopolymer
(9) Random copolymer of 4-methyl-1-pentene and not more than 20% by mol of another α-olefin
(10) Cyclopentene homopolymer
(11) Random copolymer of cyclopentene and not more than 20% by mol of another α-olefin As the "another α-olefin" in the above (co)polymers (1) to (11), ethylene, propylene, 1-butene, 4-methyl-1-pentene, 1-hexene or 1-octene from among the aforesaid examples is preferably employed. As the cycloolefin, cyclopentene, cyclohexene, norbornene or tetracyclododecene is preferably employed.

The crystalline polyolefin resin desirably has a melt flow rate (measured at 230° C. under a load of 2.16 kg in accordance with ASTM D1238-65T) of 0.01 to 100 g/10 min, preferably 0.3 to 70 g/10 min, and a crystallinity, as measured by X-ray diffractometry, of usually 5 to 100%, preferably 20 to 80%.

The crystalline polyolefin resin can be prepared by a conventional process.

Examples of the amorphous polyolefin resins include the following (co)polymers.

(1) Norbornene homopolymer
(2) Copolymer of ethylene and norbornene, or copolymer of ethylene, norbornene and another α-olefin
(3) Copolymer of ethylene and tetracyclododecene, or copolymer of ethylene, tetracyclododecene and another α-olefin

(ii) Filler

As the fillers (ii), which may be blended with the α-olefin/conjugated diene copolymer of the invention, those generally used can be used without specific limitation.

Examples of the inorganic fillers include:

powdered fillers, such as silicates (e.g., powdered talc, kaolinite, calcined clay, pyrophillite, sericite, wollastonite), carbonates (precipitated calcium carbonate, heavy calcium carbonate, magnesium carbonate), hydroxides (e.g., aluminum hydroxide, magnesium hydroxide), oxides (e.g., zinc oxide, zinc white, magnesium oxide), and synthetic silicic acids or silicates (e.g., hydrated calcium silicate, hydrated aluminum silicate, hydrated silicic acid, silicic anhydride);

flaky fillers, such as mica;

fibrous fillers, such as basic magnesium sulfate whisker, calcium titanate whisker, aluminum borate whisker, sepiolite, PMF (processed mineral fiber), xonotlite, potassium titanate and ellestadite; and balloon fillers, such as glass balloon and fly ash balloon.

These fillers can be used singly or in combination of two or more kinds.

When the α-olefin/conjugated diene copolymer is blended with the polyolefin resin (i) and the filler (ii), the α-olefin/conjugated diene copolymer is desirably contained in an amount of 10 to 90 parts by weight, preferably 15 to 80 parts by weight, more preferably 20 to 75 parts by weight, based on 100 parts by weight of the total of the α-olefin/conjugated diene copolymer, the polyolefin resin (i) and the filler (ii).

If the content of the α-olefin/conjugated diene copolymer is used in this amount, the α-olefin/conjugated diene copolymer composition has excellent moldability and is capable of providing molded products having not only excellent impact resistance, weathering resistance and heat stability but also excellent rigidity, strength and heat resistance.

The polyolefin resin (i) is contained in an amount of 1 to 99 parts by weight, preferably 10 to 85 parts by weight, more preferably 10 to 85 parts by weight, based on 100 parts by weight of the total of the resulting composition.

If the polyolefin resin (i) is used in this amount, the composition having not only excellent impact resistance and cold resistance but also excellent rigidity, strength, heat resistance and moldability can be obtained.

The filler (ii) is contained in an amount of 0 to 40 parts by weight, preferably 0 to 30 parts by weight, based on 100 parts by weight of the total of the resulting composition. If the filler (ii) is contained in this amount, the composition having excellent rigidity, surface appearance and heat resistance can be obtained.

Further, to the α-olefin/conjugated diene copolymer composition, various additives, such as nucleating agents, antioxidants, hydrochloric acid absorbers, heat stabilizers, light stabilizers, ultraviolet light absorbers, lubricants, antistatic agensts, flame retardants, pigments, dyes, dispersants, copper harm inhibitors, neutralizing agents, foaming agents, plasticizers, anti-foaming agents, crosslinking agents, crosslinking aids, crosslinking accelerators, flow property improvers (e.g., peroxide), weld strength improvers, processing aids, weathering stabilizers and blooming inhibitors, may be added in an amount not detrimental to the objects of the invention. These optional additives may be used in combination of two or more kinds.

Effect of the Invention

The olefin polymerization catalyst according to the invention exhibits high polymerization activities on olefins.

In the process for olefin polymerization according to the invention, an olefin (co)polymer of narrow molecular distribution can be produced with high polymerization activities. When an α-olefin and a conjugated diene are copolymerized, a copolymer containing almost no 1,2-cyclopentane skeleton in the polymer chain can be produced.

The novel transition metal compound according to the invention is useful for an olefin polymerization catalyst, and provides an olefin (co)polymer of narrow molecular weight distribution with high polymerization activities.

The α-olefin/conjugated diene copolymer according to the invention has a narrow molecular weight distribution and contains almost no cyclopentane skeleton in the polymer chain.

EXAMPLE

The present invention is further described with reference to the following examples, but it should be construed that the invention is in no way limited to those examples.

Structures of the compounds obtained by Synthesis Examples were determined by 270 MHz $^1$H-NMR (GSH-270 of Japan Electron Optics Laboratory Co., Ltd.), FT-IR (SHIMAZU FTIR-8200D), FD-mass spectrometry (SX-102A of Japan Electron Optics Laboratory Co., Ltd.), metal content analysis (SHIMAZU ICPS-8000, ICP method after dry washing and dilute nitric acid dissolution), and carbon, hydrogen and nitrogen content analysis (CHNO type of Helaus Co.).

Structures of the compounds A-1 and B-1 were further decided by X-ray crystal structure analysis. The measurement was made by effecting Mo—K a-ray irradiation using a Rigaku AFC7R four-axis diffractometer. The structure analysis was made by a direct method (SIR92), and the structure optimization was made in accordance with TeXan crystal structure analysis program.

Further, the intrinsic viscosity [η] was measured in decahydronaphthalene at 135° C. The molecular weight distribution (Mw/Mn) was measured by the gas permeation chromatography (GPC) using o-dichlorobenzene as a solvent at 140° C.

Specific syntheses of ligands are given below.

Ligand Synthesis Example 1

Synthesis of Ligand (L1)

To a 100 ml reactor thoroughly purged with nitrogen, 40 ml of ethanol, 0.71 g (7.62 mmol) of aniline and 1.35 g (7.58 mmol) of 3-t-butylsalicylaldehyde were introduced, and they were stirred at room temperature for 24 hours. The reaction solution was concentrated under reduced pressure to remove the solvent. Then, 40 ml of ethanol was added again, and the mixture was stirred at room temperature for 12 hours. The reaction solution was concentrated under reduced pressure to obtain 1.83 g (7.23 mmol, yield: 95%) of a compound represented by the following formula (L1) as an orange oil.

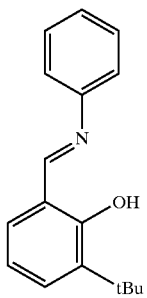

L1

¹H-NMR (CDCl₃): 1.47 (s, 9H), 6.88 (dd, 1H), 7.24–7.31 (m, 4H), 7.38–7.46 (m, 3H), 8.64 (s, 1H), 13.95 (s, 1H).

IR (neat): 1575, 1590, 1610 cm⁻¹.

FD-mass spectrometry: 253.

Ligand Synthesis Example 2

Synthesis of Ligand (L2)

To a 100 ml reactor thoroughly purged with nitrogen, 30 ml of ethanol, 1.34 g (9.99 mmol) of a-naphthylamine and 1.40 g (7.86 mmol) of 3-t-butylsalicylaldehyde were introduced. After addition of 5 g of molecular sieves 3A, the mixture was stirred under reflux for 8 hours and then at room temperature for 12 hours. The reaction solution was concentrated under reduced pressure and the residue was purified using a silica gel column to obtain 2.35 g (7.75 mmol, 98% yield) of a compound as an orange oil represented by the following formula (L2).

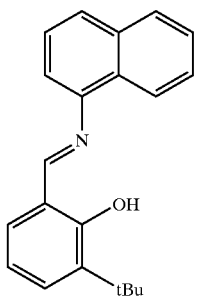

L2

¹H-NMR (CDCl3): 1.50 (s, 9H), 6.90–7.90 (m, 11H), 8.30–8.50 (m, 1H), 13.90 (s, 1H).

FD-mass spectrometry: 303.

Ligand Synthesis Example 3

Synthesis of Ligand (L3)

To a 100 ml reactor thoroughly purged with nitrogen, 30 ml of ethanol, 0.90 g (12.0 mmol) of t-butylamine and 1.78 g (10.0 mmol) of 3-t-butylsalicylaldehyde were introduced. After addition of 5 g of molecular sieves 3A, the mixture was stirred at room temperature for 12 hours. The reaction solution was concentrated under reduced pressure and the residue was purified using a silica gel column to obtain 2.17 g (9.3 mmol, 93% yield) of a compound as an fluorescent yellow oil represented by the following formula (L3).

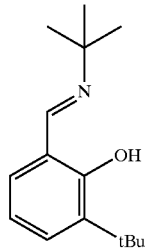

L3

¹H-NMR (CDCl₃): 1.20 (s, 9H), 1.42 (s, 9H), 6.50–7.50 (m, 3H), 8.38 (s, 1H), 13.80 (s, 1H).

FD-mass spectrometry: 233.

Ligand Synthesis Examples 4–42

Ligands L4 to L42 were synthesized in the similar manner as in the forgoing Ligand Synthesis Examples.

The identification of their structures were made by ¹H-NMR and FD-mass spectrometry.

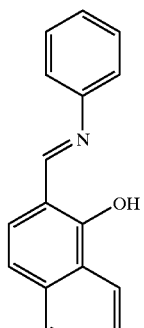

L4

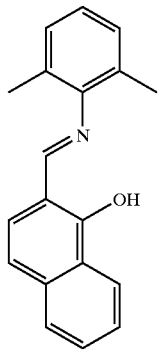

L5

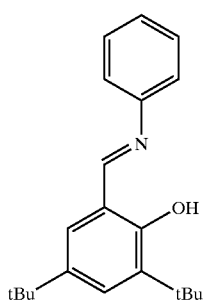

L6

L7 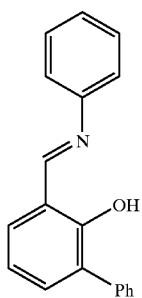
L8 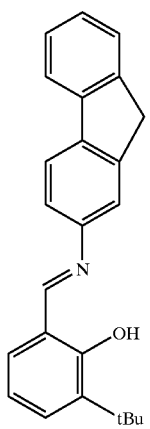
L9 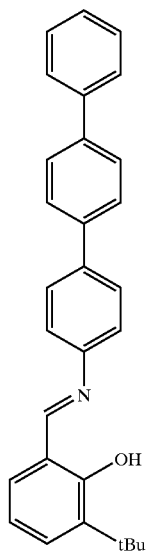
L10 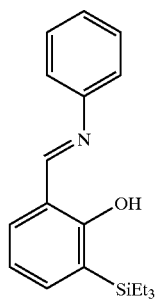
L11 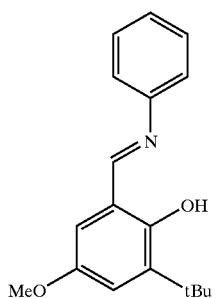
L12 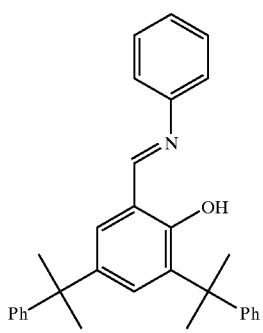
L13 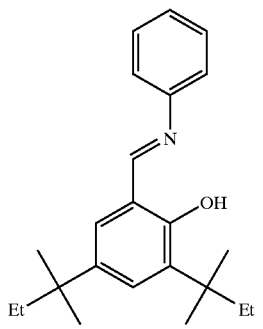
L14 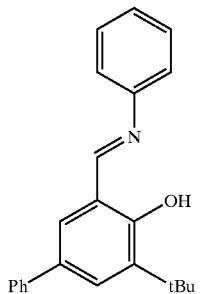
L15 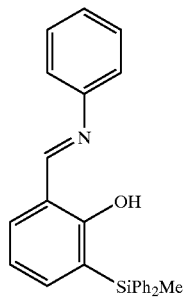

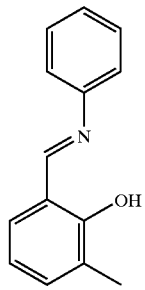
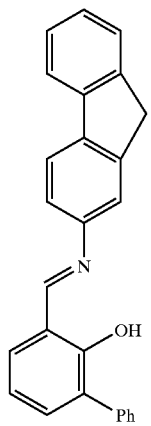
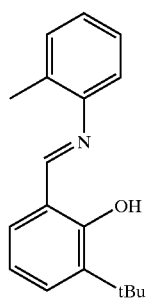
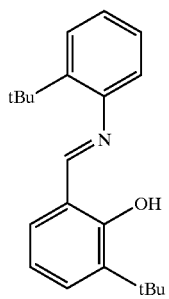
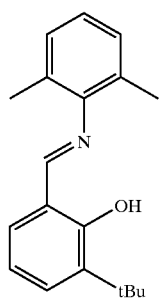
L16
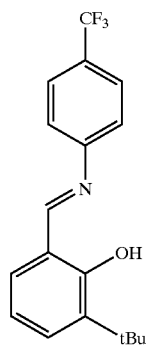
L17
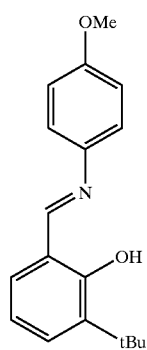
L18
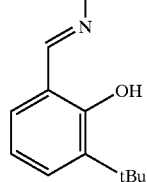
L19
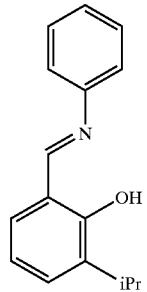
L20
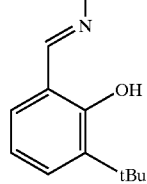
L21
L22
L23
L24
L25

-continued
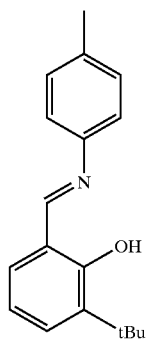
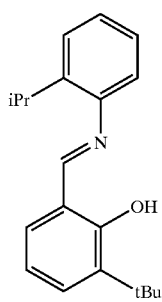
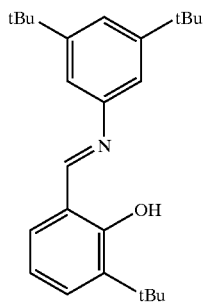
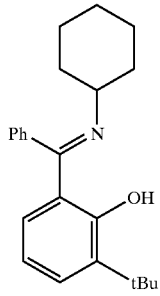
L30
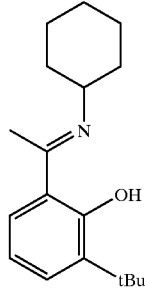
-continued
L26
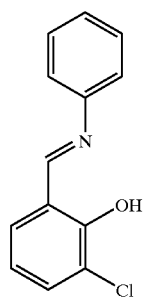
L27
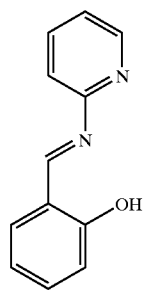
L28
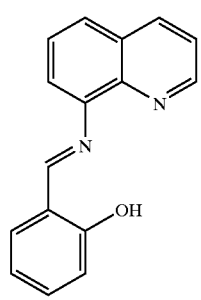
L29
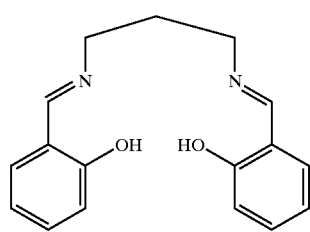
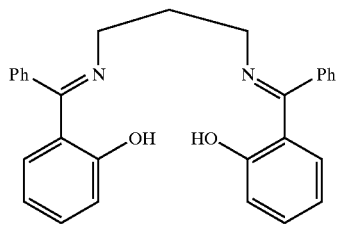
L31
L32
L33
L34
L35
L36

L37

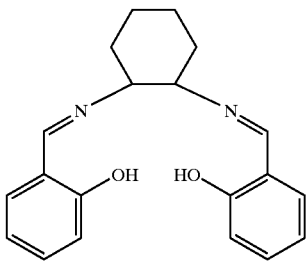

L38

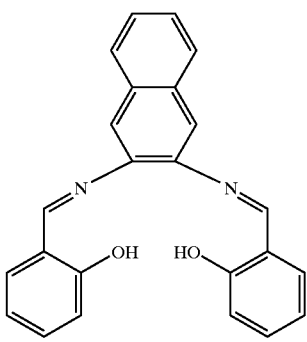

L39

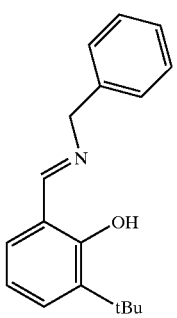

L40

L41

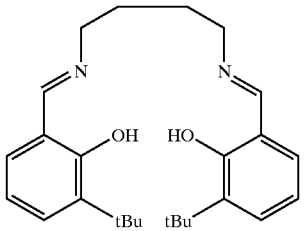

L42

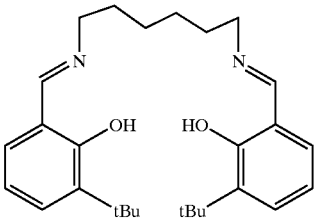

Specific syntheses of transition metal compounds according to the present invention are given below.

Synthesis of Compound A-1

To a 300 ml reactor thoroughly dried and purged with argon, 1.785 g (7.05 mmol) of compound L1 and 100 ml of diethyl ether were introduced, and they were cooled to −78° C. and stirred. After 4.78 ml of n-butyllithium (1.55 mmol/ml n-hexane solution, 7.40 mmol) was dropwise added over a period of 5 minutes, the temperature was slowly raised to room temperature, and stirring was continued for 4 hours at room temperature to prepare a lithium salt solution. The solution was slowly dropwise added to a mixture of 7.05 ml of a titanium tetrachloride solution (0.5 mmol/ml heptane solution, 3.53 mmol) and 40 ml of diethyl ether which had been cooled to −78° C.

After the dropwise addition was completed, the temperature was slowly raised to room temperature with stirring. After stirring for another 8 hours at room temperature, the reaction solution was filtered with a glass filter, and the resulting solid was dissolved and washed with 50 ml of methylene chloride to remove insolubles. The filtrate was concentrated under reduced pressure, and the solid precipitated was dissolved in 10 ml of methylene chloride. To the solution was then slowly added 70 ml of pentane with stirring. The mixture was allowed to stand at room temperature to precipitate red brown crystals. The crystals were separated by filtration with a glass filter, washed with pentane and then vacuum dried to obtain 1.34 g (2.15 mmol, yield: 61%) of compound A-1 represented by the following formula as red brown crystals.

Compound A-1

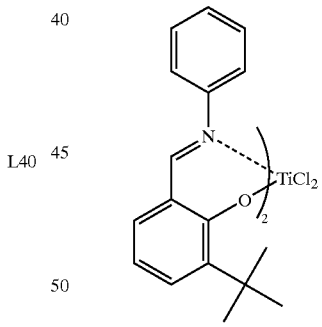

$^1$H-NMR (CDCl$_3$): 1.35 (s, 18H), 6.82–7.43 (m, 16H), 8.07 (s, 2H).

IR (KBr): 1550, 1590, 1600 cm$^{-1}$.

FD-mass spectrometry: 622 (M+).

Elemental analysis: Ti: 7.7% (7.7), C: 65.8% (65.5), H: 6.0% (5.8), N: 4.5% (4.5). Calculated values in pharentheses.

Melting point: 265° C.

Figure 3:
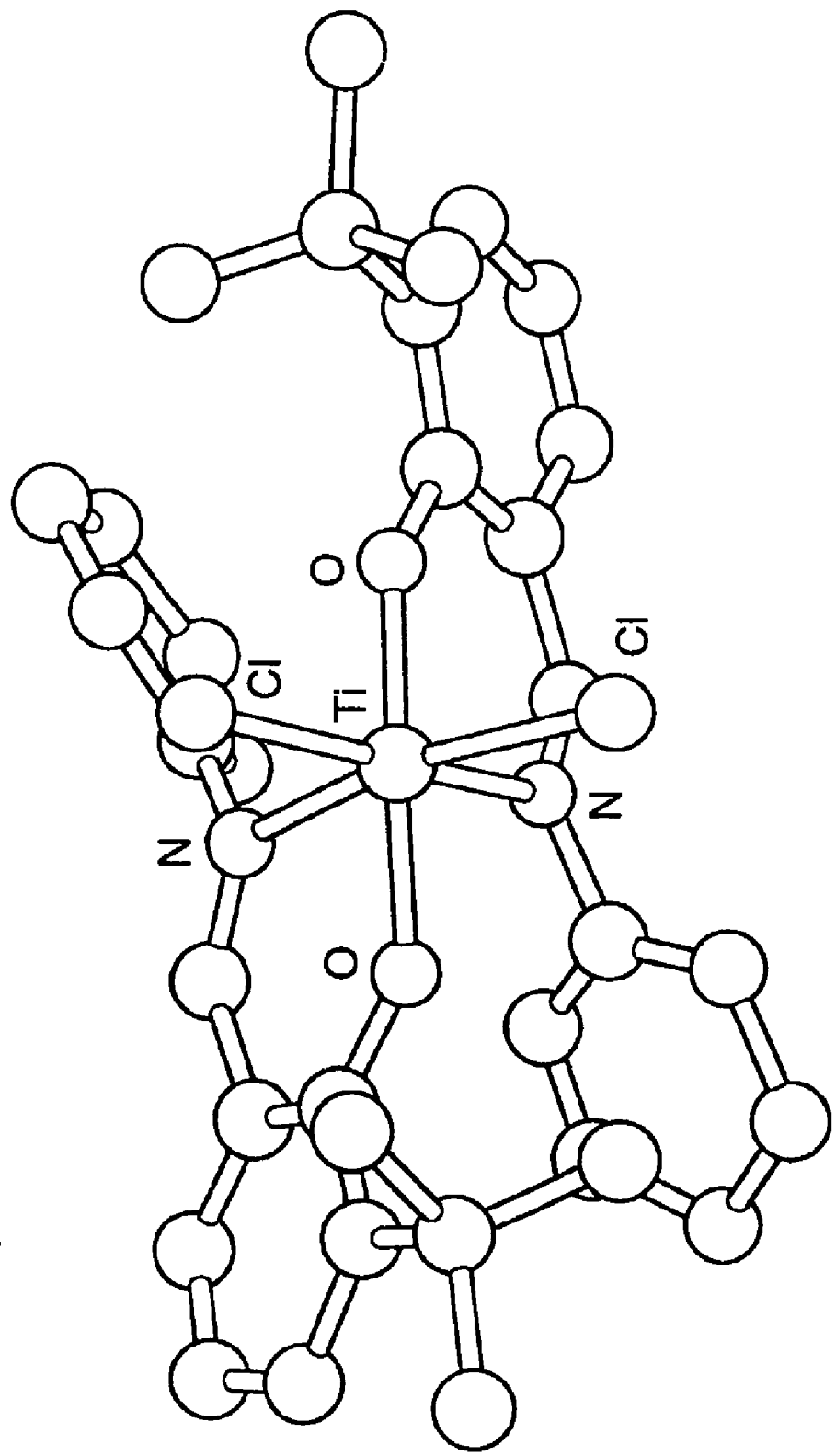
FIG. 3 shows the structure of transition metal compound A-1 prepared in Synthesis Example 1, which was determined by X-ray structure analysis.

X-ray crystal structure analysis: The structure of compound A-1 is shown in FIG. 3.

Synthesis Example 2

Synthesis of Compound B-1

To a 200 ml reactor thoroughly dried and purged with argon, 1.53 g (6.04 mmol) of compound L1 and 60 ml of tetrahydrofuran were introduced, and they were cooled to −78° C and stirred. After 4.1 ml of n-butyllithium (1.55 mmol/ml n-hexane solution, 6.34 mmol) was dropwise added over a period of 5 minutes, the temperature was slowly raised to room temperature, and stirring was continued at room temperature for 4 hours. To the reaction solution was added 10 ml of tetrahydrofuran, and the mixture was slowly added to a solution of 0.70 g of zirconium tetrachloride (purity: 99.9%, 3.02 mmol) in 30 ml of tetrahydrofuran which had been cooled to −78° C. After the addition, the temperature was slowly raised to room temperature. The reaction solution was stirred for 2 hours at room temperature and then further stirred for another 4 hours under reflux.

The reaction solution was concentrated under reduced pressure, and the solid precipitated was washed with 50 ml of methylene chloride and filtered with a glass filter to remove insolubles. The filtrate was concentrated under reduced pressure, and the solid precipitated was dissolved in 30 ml of diethyl ether. The solution was allowed to stand for one day at −20° C. in a nitrogen atmosphere to precipitate yellow crystals. The solid was separated by filtration, washed with hexane and then vacuum dried to obtain 1.09 g (1.63 mmol, yield: 54%) of compound B-1 represented by the following formula as fluorescent yellow crystals.

Compound B-1

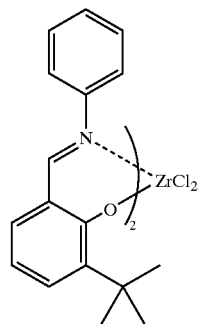

$^1$H-NMR (CDCl$_3$): 1.33 (s, 18H), 6.78–7.42 (m, 16H), 8.12 (2H).

IR (KBr): 1550, 1590, 1605 cm$^{-1}$.

FD-mass spectrometry: 664 (M+).

Elemental analysis: Zr: 13.5% (13.7), C: 61.0% (61.2), H: 5.5% (5.4), N: 4.2% (4.2). Calculated values in pharentheses.

Melting point: 287° C.

Figure 4:
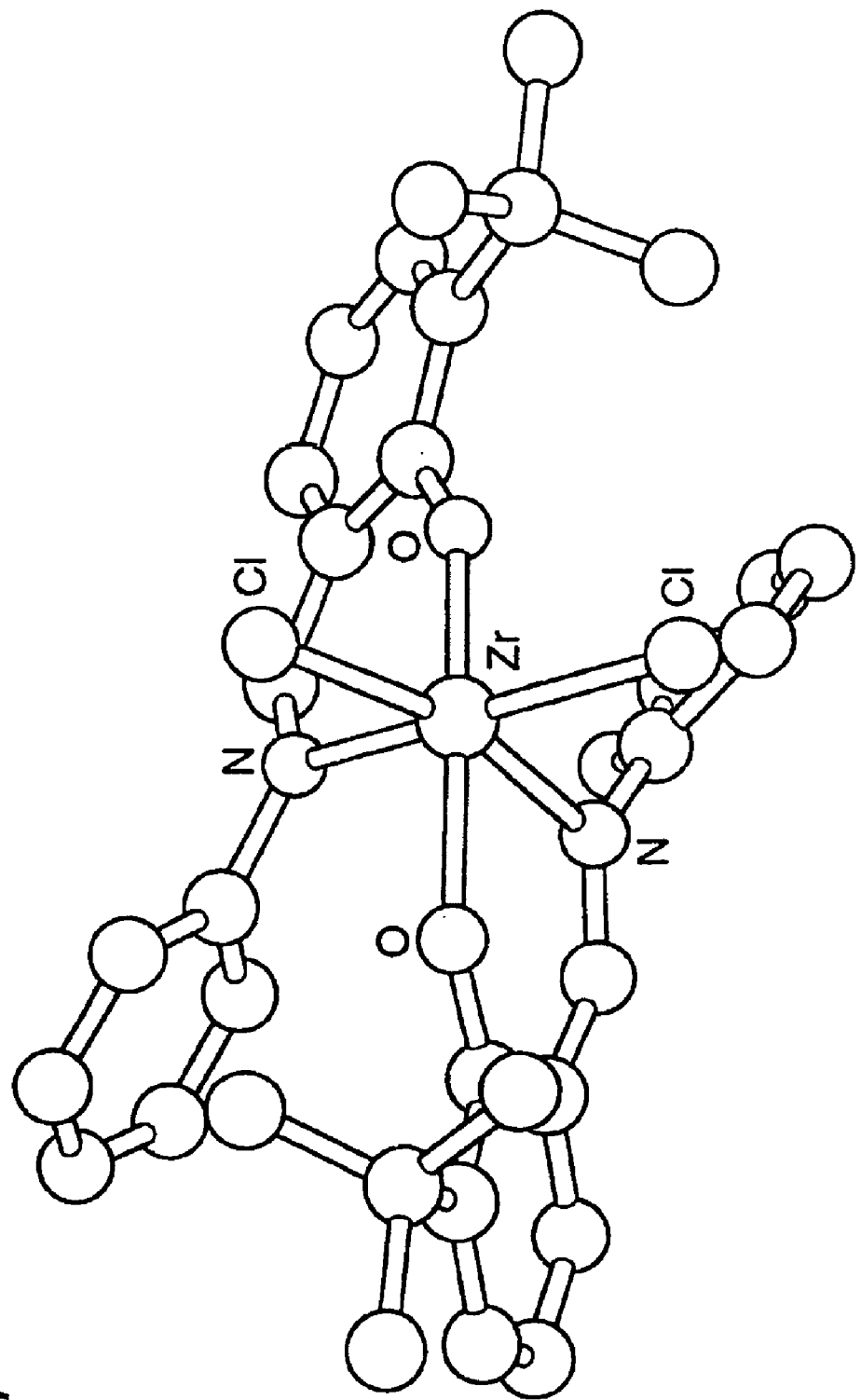
FIG. 4 shows the structure of transition metal compound B-1 prepared in Synthesis Example 2, which was determined by X-ray crystal structure analysis.

X-ray crystal structure analysis: The structure of compound B-1 is shown in FIG. 4.

Synthesis Example 3

Synthesis of Compound C-1

To a 100 ml reactor thoroughly dried and purged with argon, 0.66 g (2.60 mmol) of compound (L1) and 8 ml of diethyl ether were introduced, and they were cooled to −78° C. and stirred. After 1.81 ml of n-butyllithium (1.55 mmol/ml n-hexane solution, 2.80 mmol) was dropwise added over a period of 5 minutes, the temperature was slowly raised to room temperature, and stirring was continued at room temperature for 2 hours. To the reaction solution was added 10 ml of tetrahydrofuran, and the mixture was slowly added to a solution of 0.385 g of hafnium tetrachloride (purity: 99.9%, 3.02 mmol) in 10 ml of tetrahydrofuran which had been cooled to −78° C. After the addition, the temperature was slowly raised to room temperature. The reaction solution was stirred for 2 hours at room temperature and then further stirred for another 2 hours under heating at 50° C.

The reaction solution was concentrated under reduced pressure, and the solid precipitated was washed with 20 ml of methylene chloride and filtered with a glass filter to remove insolubles. The filtrate was concentrated under reduced pressure, and the solid precipitated was reslurried in 10 ml of diethyl ether at room temperature for 1 hour and separated by filtration. The solid was washed with hexane and then vacuum dried to obtain 0.33 g (0.40 mmol, yield: 33%) of compound C-1 represented by the following formula as fluorescent yellow white crystals.

Compound C-1

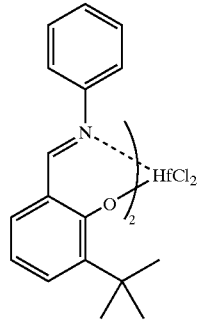

$^1$H-NMR (CDCl$_3$): 1.30 (s, 18H), 6.70–7.50 (m, 16H), 3.18 (s, 2H).

FD-mass spectrometry: 754 (M+).

Elemental analysis: Hf: 23.5% (23.7), C: 54.4% (54.2), H: 4.8% (4.8), N: 3.6% (3.7). Calculated values in pharentheses.

Melting point: 277° C.

Synthesis Example 4

Synthesis of Compound D-1

To a 100 ml reactor thoroughly dried and purged with argon, 0.61 g (2.40 mmol) of compound (L1) and 10 ml of diethyl ether were introduced, and they were cooled to −78° C. and stirred. After 1.61 ml of n-butyllithium (1.55 mmol/ml n-hexane solution, 2.50 mmol) was dropwise added over a period of 5 minutes, the temperature was slowly raised to room temperature, and stirring was continued at room temperature for 4 hours. The reaction solution was slowly added to a solution of 0.385 g of hafnium tetrachloride (purity: 99.9%, 3.02 mmol) in 10 ml of diethyl ether which had been cooled to −78° C. After the addition, the temperature was slowly raised to room temperature, and the reaction solution was stirred for 4 hours at room temperature.

The reaction solution was concentrated under reduced pressure, and the solid precipitated was washed with 20 ml of methylene chloride and filtered with a glass filter to remove insolubles. The filtrate was concentrated under reduced pressure, and the solid precipitated was dissolved in 1 ml of diethyl ether. To the solution was slowly added 10 ml of hexane with stirring to precipitate black green solid. The solid was separated by filtration, reslurried and washed with hexane at room temperature for 1 hour and then vacuum dried to obtain 0.55 g (0.88 mmol, yield: 73%) of compound D-1 represented by the following formula as a blue black powder.

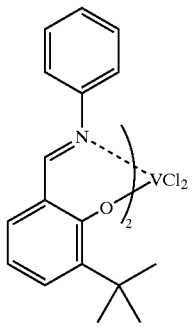

Compound D-1

$^1$H-NMR (CDCl$_3$): unmeasurable because of paramagnetic metal complex.

FD-mass spectrometry: 625 (M+). Elemental analysis: V: 8.4% (3.1), C: 65.3% (65.2), H: 5.5% (5.3), N: 4.5% (4.8). Calculated values in pharentheses.

Synthesis Example 5

Synthesis of Compound E-1

To a 100 ml reactor thoroughly dried and purged with argon, 0.61 g (2.40 mmol) of compound (L1) and 10 ml of diethyl ether were introduced, and they were cooled to −78° C. and stirred. After 1.60 ml of n-butyllithium (1.55 mmol/ml n-hexane solution, 2.50 mmol) was dropwise added over a period of 5 minutes, the temperature was slowly raised to room temperature, and stirring was continued at room temperature for 4 hours. To the reaction solution was added 5 ml of tetrahydrofuran, and the mixture was slowly added to a solution of 0.34 g of niobium pentachloride (purity: 95%, 1.20 mmol) in 10 ml of tetrahydrofuran which had been cooled to −78° C. After the addition, the temperature was slowly raised to room temperature, and the reaction solution was stirred at room temperature for 15 hours.

The reaction solution was concentrated under reduced pressure, and the solid precipitated was washed with 20 ml of methylene chloride and filtered with a glass filter to remove insolubles. The filtrate was concentrated under reduced pressure, and the solid precipitated was dissolved in 3 ml of diethyl ether. To the solution was slowly dropwise added 12 ml of hexane at room temperature with stirring to precipitate black solid. The solid was separated by filtration, reslurried and washed with hexane at room temperature for 1 hour and then vacuum dried to obtain 0.36 g (0.51 mmol, yield: 43%) of fluorescent yellow white compound E-1 represented by the following formula.

Compound E-1

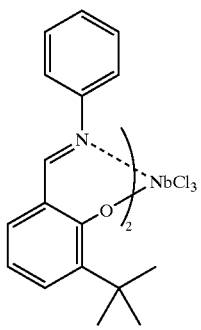

$^1$H-NMR (CDCl$_3$): 1.46 (s, 18H), 7.20–7.50 (m, 16H), 8.65 (s, 2H).

FD-mass spectrometry: 702 (M+).

Elemental analysis: Nb: 13.0% (13.2), C: 58.4% (53.0), H: 5.0% (5.2), N: 3.9% (4.0). Calculated values in pharenthesis.

Synthesis Example 6

Synthesis of Compound F-1

To a 100 ml reactor thoroughly dried and purged with argon, 0.61 g (2.40 mmol) of compound (L1) and 10 ml of toluene were introduced, and they were cooled to −40° C. and stirred. To the mixture, 0.43 g of solid tantalum pentachloride (purity: 99.99%, 1.20 mmol) was slowly added. After the addition, the temperature was slowly raised to room temperature, then further raised to 60° C., and stirring was continued for 16 hours.

To the reaction solution was added 30 ml of methylene chloride, and the insolubles were filtered. The filtrate was concentrated under reduced pressure, and to the concentrate was added 8 ml of hexane to separate out an orange viscous oil. The oil portion was separated and dissolved in 1 ml of diethyl ether. To the solution was slowly dropwise added 9 ml of hexane with stirring to precipitate bright yellow solid. The solid was separated by filtration, reslurried and washed hexane at room temperature for 1 hour and then vacuum dried to obtain 0.15 g (0.26 mmol, yield: 22%) of compound F-1 represented by the following formula as a bright yellow powder.

Compound F-1

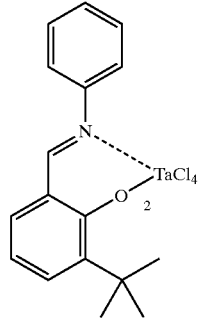

$^1$H-NMR (CDCl$_3$): 1.50 (s, 9H), 6.80–7.75 (m, 8H), 8.23 (s, 1H).

FD-mass spectrometry: 575 (M+).

Elemental analysis: Ta: 31.0% (31.5), C: 58.4% (58.0), H: 3.3% (3.2), N: 4.5% (4.8). Calculated values in pharentheses.

Synthesis Example 7

Synthesis of Compound A-2

After charging 0.91 g (3.0 mmol) of compound L2 and 20 ml of diethyl ether into a 100 ml reactor which had been adequately dried and substituted with argon, they were cooled to −78° C. and stirred. After dropwise adding 1.90 ml of n-butyllithium (1.54 mmol/ml n-hexane solution, 3.3 mmol) over 5 minutes, the temperature was slowly increased to room temperature and stirring was continued for 4 hours at room temperature to prepare a lithium salt solution. The solution was cooled to −78° C. and then slowly added dropwise to a mixture of 3.0 ml of a titanium tetrachloride solution (0.5 mmol/ml heptane solution, 1.50 mmol) and 10 ml of diethyl ether. After completion of the dropwise addition, stirring was continued while slowly increasing the temperature to room temperature. After further stirring for 8 hours at room temperature, the reaction solution was filtered with a glass filter. The resulting solid was dissolved and washed in 50 ml of methylene chloride, and the insoluble portion was removed by filtration. The filtrate was concentrated under reduced pressure, and the deposited solid was reprecipitated with diethyl ether and hexane and dried under reduced pressure to obtain 0.53 g (0.73 mmol, 49% yield) of compound A-2 as dark brown crystals represented by the formula given below.

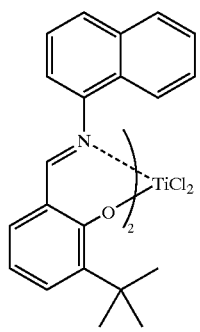

Compound A-2

$^1$H-NMR (CDCl$_3$): 0.86 (s, 18H), 6.85–7.05 (m, 6H), 7.15–7.30 (m, 4H), 7.35–7.90 (m, 10H), 8.45 (s, 2H).

FD-mass spectrometry: 722 (M+).

Elemental analysis: Ti: 6.6% (6.6), C: 69.9% (69.7), H: 5.5% (5.6), N: 3.4% (3.9). Calculated values in parentheses.

Synthesis Example 8

Synthesis of Compound B-2

After charging 0.91 g (3.0 mmol) of compound L2 and 20 ml of diethyl ether into a 100 ml reactor which had been adequately dried and substituted with argon, they were cooled to −78° C. and stirred. After dropwise adding 1.94 ml of n-butyllithium (1.55 mmol/ml n-hexane solution, 3.0 mmol) over 5 minutes, the temperature was slowly increased to room temperature and stirring was continued for 4 hours at room temperature to prepare a lithium salt solution. The solution was then slowly added dropwise to a 10 ml tetrahydrofuran solution containing zirconium tetrachloride (0.35 g, 1.50 mmol) which had been cooled to −78° C. After completion of the dropwise addition, stirring was continued while slowly increasing the temperature to room temperature. After further stirring for 8 hours at room temperature, the reaction solution was concentrated to dryness, the residue was dissolved and washed in 50 ml of methylene chloride, and then the insoluble portion was removed by filtration. The filtrate was concentrated under reduced pressure, and the deposited solid was reprecipitated with diethyl ether and hexane and dried under reduced pressure to obtain 0.21 g (0.73 mmol, 18% yield) of compound B-2 as yellow crystals represented by the formula given below.

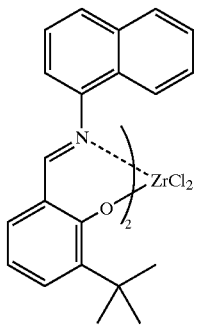

Compound B-2

$^1$H-NMR (CDCl$_3$): 1.11–1.70 (m, 18H), 6,80–8.30 (m, 20H), 8.33–8.48 (m, 2H).

FD-mass spectrometry: 766 (M+).

Elemental analysis: Zr: 12.1% (11.9). Calculated value in parentheses.

Synthesis Example 9

Synthesis of Compound A-3

After charging 0.70 g (3.0 mmol) of compound L3 and 30 ml of diethyl ether into a 100 ml reactor which had been adequately dried and substituted with argon, they were cooled to −78° C. and stirred. After dropwise adding 1.90 ml of n-butyllithium (1.54 mmol/ml n-hexane solution, 3.3 mmol) over 5 minutes, the temperature was slowly increased to room temperature and stirring was continued for 4 hours at room temperature to prepare a lithium salt solution. The solution was cooled to −78° C. and then 3.0 ml of a titanium tetrachloride solution (0.5 mmol/ml heptane solution, 1.50 mmol) was slowly added dropwise. After completion of the dropwise addition, stirring was continued while slowly increasing the temperature to room temperature. After further stirring for 15 hours at room temperature, the reaction solution was filtered with a glass filter. The resulting solid was dissolved and washed in 50 ml of methylene chloride, and the insoluble portion was removed by filtration. The filtrate was concentrated under reduced pressure, and the deposited solid was reprecipitated with diethyl ether and hexane and dried under reduced pressure to obtain 0.15 g (0.26 mmol, 17% yield) of compound A-3 as yellow brown crystals represented by the formula given below.

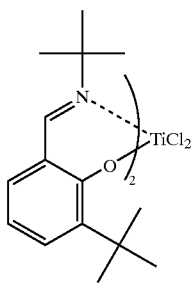

Compound A-3

$^1$H-NMR (CDCl$_3$): 1.20 (s, 18H), 1.41 (s, 18H), 6.85–7.05 (m, 2H), 7.20–7.80 (m, 4H), 8.58 (s, 2H).

FD-mass spectrometry: 582 (M+).

Elemental analysis: Ti: 8.2% (8.2), C: 62.1% (61.8), H: 7.1% (7.6), N: 4.7% (4.8). Calculated values in parentheses.

Synthesis Example 10

Synthesis of Compound B-3

After charging 0.70 g (3.0 mmol) of compound L3 and 30 ml of tetrahydrofuran into a 100 ml reactor which had been adequately dried and substituted with argon, they were cooled to −78° C. and stirred. After dropwise adding 1.90 ml of n-butyllithium (1.54 mmol/ml n-hexane solution, 3.3 mmol) over 5 minutes, the temperature was slowly increased to room temperature and stirring was continued for 4 hours at room temperature to prepare a lithium salt solution. The solution was cooled to −78° C. and solid zirconium tetrachloride (0.38 g, 1.65 mmol) was added. After completion of the addition, stirring was continued while slowly increasing the temperature to room temperature. After further stirring for 15 hours at room temperature, the solvent was distilled off from the reaction solution, the resulting solid was dissolved and washed in 50 ml of methylene chloride, and the insoluble portion was removed by filtration. The filtrate was concentrated under reduced pressure, and the deposited solid was reprecipitated with methylene chloride and hexane and dried under reduced pressure to obtain 0.31 g (0.50 mmol, 30% yield) of compound B-3 as a yellow powder represented by the formula given below.

Compound B-3

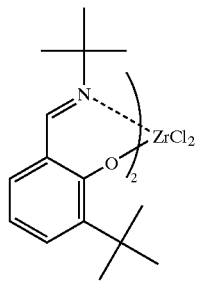

$^1$H-NMR (CDCl$_3$): 1.34 (s, 18H), 1.44 (s, 18H), 6.79 (dd, 2H), 7.11 (d, 2H), 7.27 (d, 2H), 8.34 (s, 2H).

FD-mass spectrometry: 626 (M+).

Elemental analysis: Zr: 15.0% (14.6), C: 52.9 (57.5), H: 7.2 (7.1), N: 4.7 (4.8). Calculated values in parentheses.

Synthesis Example 11

Synthesis of Compound A-4

After charging 0.50 g (2.02 mmol) of compound L4 and 30 ml of diethyl ether into a 100 ml reactor which had been adequately dried and substituted with argon, they were cooled to −78° C. and stirred. After dropwise adding 1.36 ml of n-butyllithium (1.54 mmol/ml n-hexane solution, 2.09 mmol) over 5 minutes, the temperature was slowly increased to room temperature and stirring was continued for 4 hours at room temperature to prepare a lithium salt solution. The solution was cooled to −78° C., and then 2.00 ml of a titanium tetrachloride solution (0.5 mmol/ml heptane solution, 1.00 mmol) was slowly added dropwise. After completion of the dropwise addition, stirring was continued while slowly increasing the temperature to room temperature. After further stirring for 8 hours at room temperature, the reaction solution was filtered with a glass filter. The resulting solid was dissolved and washed in 50 ml of methylene chloride, and the insoluble portion was removed by filtration. The filtrate was concentrated under reduced pressure, and the deposited solid was reprecipitated with methylene chloride and hexane and dried under reduced pressure to obtain 0.34 g (0.56 mmol, 56% yield) of compound A-4 as a dark brown powder represented by the formula given below.

Compound A-4

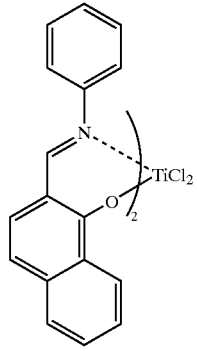

$^1$H-NMR (CDCl$_3$): 7.00–7.90 (m, 22H), 8.35–8.55 (m, 2H).

FD-mass spectrometry: 610 (M+).

Elemental analysis: Ti: 7.8% (7.8), C: 62.4% (66.8), H: 4.9% (4.4), N: 4.2% (4.6). Calculated values in parentheses.

Synthesis Example 12

Synthesis of Compound B-4

After charging 0.46 g (1.86 mmol) of compound L4 and 30 ml of diethyl ether into a 100 ml reactor which had been adequately dried and substituted with argon, they were cooled to −78° C. and stirred. After dropwise adding 1.30 ml of n-butyllithium (1.54 mmol/ml n-hexane solution, 2.00 mmol) over 5 minutes, the temperature was slowly increased to room temperature and stirring was continued for 4 hours at room temperature to prepare a lithium salt solution. The solution was cooled to −78° C., and then solid zirconium tetrachloride (0.21 g, 0.91 mmol) was added. After completion of the addition, stirring was continued while slowly increasing the temperature to room temperature. After further stirring for 16 hours at room temperature, 20 ml of diethyl ether was added and the insoluble portion was removed with a glass filter. The filtrate was concentrated under reduced pressure, and the deposited solid was reprecipitated with diethyl ether and hexane and dried under reduced pressure to obtain 0.25 g (0.38 mmol, 42% yield) of compound B-4 as a yellow-brownish green powder represented by the formula given below.

Compound B-4

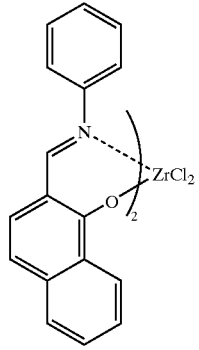

$^1$H-NMR (CDCl$_3$): 6.90–7.95 (m, 22H), 8.40–8.60 (m, 2H).

FD-mass spectrometry: 652 (M+).

Elemental analysis: Zr: 14.3% (13.9), Calculated value in parentheses.

Synthesis Example 13

Synthesis of Compound A-5

After charging 0.83 g (3.00 mmol) of compound L5 and 30 ml of diethyl ether into a 100 ml reactor which had been adequately dried and substituted with argon, they were cooled to −780° C. and stirred. After dropwise adding 2.00 ml of n-butyllithium (1.54 mmol/ml n-hexane solution, 3.08 mmol) over 5 minutes, the temperature was slowly increased to room temperature and stirring was continued for 4 hours at room temperature to prepare a lithium salt solution. The solution was cooled to −78° C., and then 3.00 ml of a titanium tetrachloride solution (0.5 mmol/ml heptane solution, 1.50 mmol) was slowly added dropwise. After completion of the dropwise addition, stirring was continued while slowly increasing the temperature to room temperature. After further stirring for 15 hours at room temperature, the reaction solution was filtered with a glass filter. The filtrate was concentrated under reduced pressure, and the deposited solid was reprecipitated with methylene chloride and hexane and dried under reduced pressure to obtain 0.07 g (0.10 mmol, 7% yield) of compound A-5 as an ocher powder represented by the formula given below.

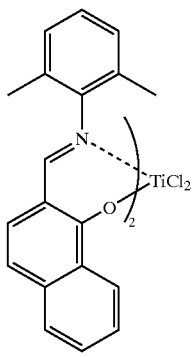

Compound A-5

FD-mass spectrometry: 666 (M+).

Elemental analysis: Ti: 7.3% (7.2). Calculated value in parentheses.

Synthesis Example 14

Synthesis of Compound B-5

After charging 0.50 g (1.82 mmol) of compound L5 and 15 ml of tetrahydrofuran into a 100 ml reactor which had been adequately dried and substituted with argon, they were cooled to −78° C. and stirred. After dropwise adding 1.36 ml of n-butyllithium (1.54 mmol/ml n-hexane solution, 2.09 mmol) over 5 minutes, the temperature was slowly increased to room temperature and stirring was continued for 4 hours at room temperature to prepare a lithium salt solution. The solution was cooled to −78° C. and then a 10 ml tetrahydrofuran solution containing a zirconium tetrachloride.2THF complex (0.38 g, 1.00 mmol) was added dropwise. After completion of the dropwise addition, stirring was continued while slowly increasing the temperature to room temperature. After further stirring for 10 hours at room temperature and 4 hours at 50° C., the insoluble portion was removed with a glass filter. The filtrate was concentrated under reduced pressure and the deposited solid was reprecipitated with methylene chloride, diethyl ether and hexane and dried under reduced pressure to obtain 0.04 g (0.05 mmol, 5% yield) of compound B-5 as a yellow-brownish green powder represented by the formula given below.

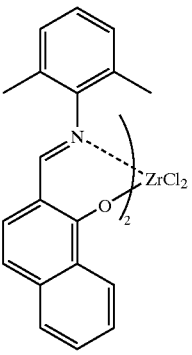

Compound B-5

FD-mass spectrometry: 710 (M+).

Elemental analysis: Zr: 13.3% (12.8). Calculated value in parentheses.

Synthesis Example 15

Synthesis of Compound A-6

After charging 0.93 g (3.01 mmol) of compound L6 and 30 ml of diethyl ether into a 100 ml reactor which had been adequately dried and substituted with argon, they were cooled to −78° C. and stirred. After dropwise adding 2.1 ml of n-butyllithium (1.54 mmol/ml n-hexane solution, 3.23 mmol) over 5 minutes, the temperature was slowly increased to room temperature and stirring was continued for 4 hours at room temperature to prepare a lithium salt solution. The solution was cooled to −78° C. and then 3.0 ml of a titanium tetrachloride solution (0.5 mmol/ml heptane solution, 1.50 mmol) was slowly added dropwise. After completion of the dropwise addition, stirring was continued while slowly increasing the temperature to room temperature. After further stirring for 15 hours at room temperature, the reaction solution was filtered with a glass filter. The filtrate was concentrated under reduced pressure, and the deposited solid was recrystallized with hexane at −78° C. and dried under reduced pressure to obtain 0.41 g (0.56 mmol, 37% yield) of compound A-6 as a brown powder represented by the formula given below.

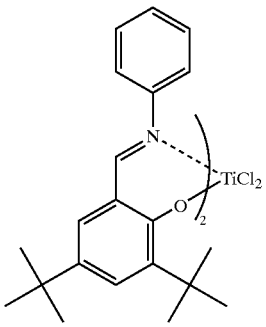

Compound A-6

$^1$H-NMR (CDCl$_3$): 1.21 (s, 18H), 1.30 (s, 18H), 6.70–7.70 (m, 14H), 8.08 (s, 2H).

FD-mass spectrometry: 734 (M+). Elemental analysis: Ti: 6.6% (6.5), C: 67.9% (68.6), H: 7.4% (7.1), N: 3.9% (3.8). Calculated values in parentheses.

Synthesis Example 16

Synthesis of Compound B-6

After charging 0.93 g (3.01 mmol) of compound L6 and 30 ml of diethyl ether into a 100 ml reactor which had been adequately dried and substituted with argon, they were cooled to −78° C. and stirred. After dropwise adding 2.1 ml of n-butyllithium (1.54 mmol/ml n-hexane solution, 3.23 mmol) over 5 minutes, the temperature was slowly increased to room temperature and stirring was continued for 4 hours at room temperature to prepare a lithium salt solution. The solution was cooled to −78° C. and then solid zirconium tetrachloride (0.35 g, 1.50 mmol) was added. After completion of the addition, stirring was continued while slowly increasing the temperature to room temperature. After further stirring for 14 hours at room temperature, 20 ml of methylene chloride was added, and the insoluble portion was removed with a glass filter. The filtrate was concentrated under reduced pressure, and the deposited solid was recrystallized with hexane at −78° C. and dried under reduced pressure to obtain 0.55 g (0.71 mmol, 47% yield) of compound B-6 as a brownish green powder represented by the formula given below.

Compound B-6

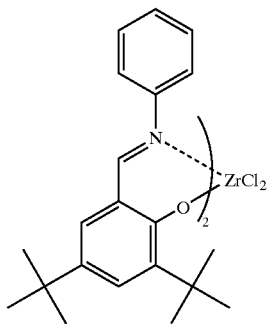

$^1$H-NMR (CDCl$_3$): 1.20–1.80 (m, 36H), 6.70–7.70 (m, 14H), 7.80–7.90 (m, 2H).

FD-mass spectrometry: 776 (M+).

Elemental analysis: Zr: 11.2% (11.7). Calculated value in parentheses.

Synthesis Example 17

Synthesis of Compound A-7

After charging 1.0 g (3.66 mmol) of compound L7 and 20 ml of diethyl ether into a 100 ml reactor which had been adequately dried and substituted with argon, they were cooled to −78° C. and stirred. After dropwise adding 2.48 ml of n-butyllithium (1.55 mmol/ml n-hexane solution, 3.84 mmol) over 5 minutes, the temperature was slowly increased to room temperature and stirring was continued for 4 hours at room temperature to prepare a lithium salt solution. The solution was then slowly added dropwise to a mixture of 3.66 ml of a titanium tetrachloride solution (0.5 mmol/ml heptane solution, 1.83 mmol) and 20 ml of diethyl ether which had been cooled to −78° C. After completion of the dropwise addition, stirring was continued while slowly increasing the temperature to room temperature. After further stirring for 15 hours at room temperature, the reaction solution was filtered with a glass filter. The filtrate was concentrated under reduced pressure, and the deposited solid was reslurried with hexane. The slurry was filtered to remove the solvent, and the solid was dried under reduced pressure to obtain 0.95 g (1.43 mmol, 78% yield) of compound A-7 as a brown powder represented by the formula given below.

Compound A-7

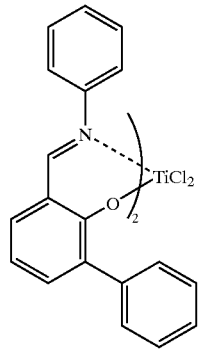

$^1$H-NMR (CDCl$_3$): 6.90–7.90 (m, 26H), 8.00 (s, 2H).

FD-mass spectrometry: 662 (M+).

Elemental analysis: Ti: 6.5% (6.5), C: 62.0% (62.2), H: 3.7% (3.8), N: 3.8% (3.8). Calculated values in parentheses.

Synthesis Example 18

Synthesis of Compound B-7

After charging 1.0 g (3.66 mmol) of compound L7 and 20 ml of diethyl ether into a 100 ml reactor which had been adequately dried and substituted with argon, they were cooled to −78° C. and stirred. After dropwise adding 2.48 ml of n-butyllithium (1.55 mmol/ml n-hexane solution, 3.84 mmol) over 5 minutes, the temperature was slowly increased to room temperature and stirring was continued for 4 hours at room temperature to prepare a lithium salt solution. The solution was then added dropwise to a mixture of zirconium tetrachloride (0.41 g, 1.77 mmol) in 30 ml of diethyl ether cooled to −78° C. After completion of the dropwise addition, stirring was continued while slowly increasing the temperature to room temperature. After further stirring for 15 hours at room temperature, 20 ml of methylene chloride was added, and the insoluble portion was removed with a glass filter. The filtrate was concentrated under reduced pressure, and the deposited solid was reslurried with hexane. The slurry was filtered to remove the solvent and the solid was dried under reduced pressure to obtain 0.94 g (1.33 mmol, 73% yield) of compound B-7 as a yellow green powder represented by the formula given below.

Compound B-7

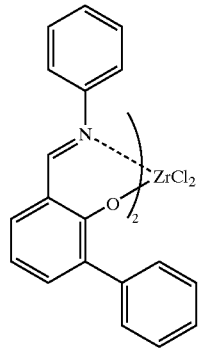

$^1$H-NMR (CDCl$_3$): 7.00–7.90 (m, 26H), 8.20 (s, 2H).

FD-mass spectrometry: 704 (M+).

Elemental analysis: Zr: 11.5% (11.7). Calculated values in parentheses.

Synthesis Example 19

Synthesis of Compound A-8

After charging 1.0 g (2.93 mmol) of compound L8 and 20 ml of diethyl ether into a 100 ml reactor which had been adequately dried and substituted with argon, they were cooled to −78° C. and stirred. After dropwise adding 2.0 ml of n-butyllithium (1.55 mmol/ml n-hexane solution, 3.10 mmol) over 5 minutes, the temperature was slowly increased to room temperature and stirring was continued for 4 hours at room temperature to prepare a lithium salt solution. The solution was then slowly added dropwise to a mixture containing 2.9 ml of a titanium tetrachloride solution (0.5 mmol/ml heptane solution, 1.45 mmol) and 20 ml of diethyl ether which had been cooled to −78° C. After completion of the dropwise addition, stirring was continued while slowly increasing the temperature to room temperature. After further stirring for 15 hours at room temperature, the reaction solution was filtered with a glass filter. The filtrate was concentrated under reduced pressure, and the deposited solid was reslurried with hexane. The slurry was filtered to remove the solvent and the solid was dried under reduced pressure to obtain 1.06 g (1.33 mmol, 91% yield) of compound A-8 as a brown powder represented by the formula given below.

Compound A-8

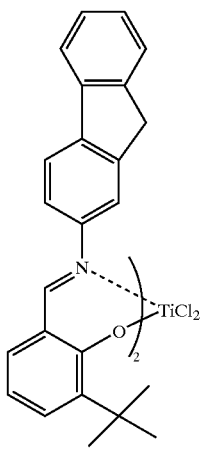

$^1$H-NMR (CDCl$_3$): 0.90–1.70 (m, 18H), 3.40–3.80 (m, 4H), 7.00–7.70 (m, 20H), 7.80–8.20 (m, 2H).

FD-mass spectrometry: 798 (M+).

Elemental analysis: Ti: 6.0% (6.0). Calculated value in parentheses.

Synthesis Example 20

Synthesis of Compound B-8

After charging 1.0 g (2.93 mmol) of compound L8 and 20 ml of diethyl ether into a 100 ml reactor which had been adequately dried and substituted with argon, they were cooled to −78° C. and stirred. After dropwise adding 2.0 ml of n-butyllithium (1.55 mmol/ml n-hexane solution, 3.10 mmol) over 5 minutes, the temperature was slowly increased to room temperature and stirring was continued for 4 hours at room temperature to prepare a lithium salt solution. The solution was then added dropwise to a mixture of zirconium tetrachloride (0.34 g, 1.44 mmol) in 20 ml of diethyl ether which had been cooled to −78° C. After completion of the dropwise addition, stirring was continued while slowly increasing the temperature to room temperature. After further stirring for 8 hours at room temperature, 20 ml of diethyl ether was added, and the insoluble portion was removed with a glass filter. The filtrate was concentrated under reduced pressure, and the deposited solid was reslurried with hexane. The slurry was filtered to remove the solvent and the solid was dried under reduced pressure to obtain 1.02 g (1.21 mmol, 83% yield) of compound B-8 as a yellow green powder represented by the formula given below.

Compound B-8

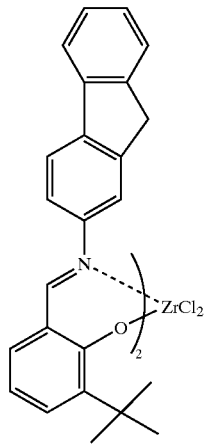

$^1$H-NMR (CDCl$_3$): 0.90–1.80 (m, 18H), 3.40–3.90 (m, 4H), 6.40–7.90 (m, 20H), 8.00–8.30 (m, 2H).

FD-mass spectrometry: 842 (M+).

Elemental analysis: Zr: 11.1% (10.8). Calculated value in parentheses.

Synthesis Example 21

Synthesis of Compound A-9

After charging 0.50 g (1.23 mmol) of compound L9 and 15 ml of diethyl ether into a 100 ml reactor which had been adequately dried and substituted with argon, they were cooled to −78° C. and stirred. After dropwise adding 0.84 ml of n-butyllithium (1.55 mmol/ml n-hexane solution, 1.30 mmol) over 5 minutes, the temperature was slowly increased to room temperature and stirring was continued for 4 hours at room temperature to prepare a lithium salt solution. The solution was then slowly added dropwise to a mixed solution containing 1.2 ml of a titanium tetrachloride solution (0.5 mmol/ml heptane solution, 0.60 mmol) and 15 ml of diethyl ether which had been cooled to −78° C. After completion of the dropwise addition, stirring was continued while slowly increasing the temperature to room temperature. After further stirring for 8 hours at room temperature, the reaction solution was filtered with a glass filter. The filtrate was concentrated under reduced pressure, and the deposited solid was reslurried with hexane. The slurry was filtered to remove the solvent and the solid was dried under reduced pressure to obtain 0.33 g (0.36 mmol, 58% yield) of compound A-9 as a brown powder represented by the formula given below.

Compound A-9

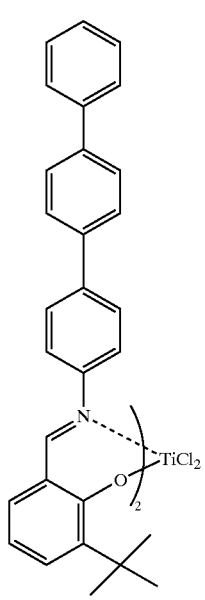

¹H-NMR (CDCl₃): 1.70–1.90 (m, 18H), 6.60–7.80 (m, 34H).

FD-mass spectrometry: 926 (M+).

Elemental analysis: Ti: 5.3% (5.2). Calculated value in parentheses.

Synthesis Example 22

Synthesis of Compound B-9

After charging 0.50 g (1.23 mmol) of compound L9 and 15 ml of diethyl ether into a 100 ml reactor which had been adequately dried and substituted with argon, they were cooled to −78° C. and stirred. After dropwise adding 0.84 ml of n-butyllithium (1.55 mmol/ml n-hexane solution, 1.30 mmol) over 5 minutes, the temperature was slowly increased to room temperature and stirring was continued for 4 hours at room temperature to prepare a lithium salt solution. The solution was then slowly added dropwise to a mixed solution of zirconium tetrachloride (0.14 g, 0.60 mmol) and 15 ml of diethyl ether which had been cooled to −78° C. After completion of the dropwise addition, stirring was continued while slowly increasing the temperature to room temperature. After further stirring for 15 hours at room temperature, the solvent was distilled off, the resulting solid was dissolved in 50 ml of methylene chloride and 10 ml of diethyl ether, and then the insoluble portion was removed with a glass filter. The filtrate was concentrated under reduced pressure, and the deposited solid was reslurried with hexane. The slurry was filtered to remove the solvent and the solid was dried under reduced pressure to obtain 0.19 g (0.20 mmol, 32% yield) of compound B-9 as a light yellow powder represented by the formula given below.

Compound B-9

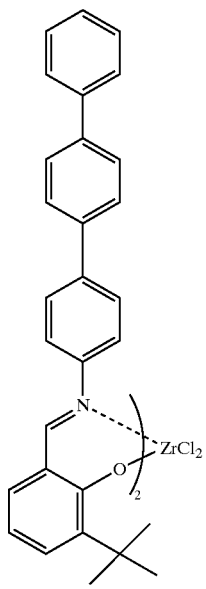

¹H-NMR (CDCl₃): 1.28–1.52 (m, 18H), 6.70–7.76 (m, 34H).

FD-mass spectrometry: 970 (M+).

Elemental analysis: Zr: 9.6% (9.4). Calculated value in parentheses.

Synthesis Example 23

Synthesis of Compound A-10

After charging 0.32 g (1.03 mmol) of compound L10 and 10 ml of diethyl ether into a 100 ml reactor which had been adequately dried and substituted with argon, they were cooled to −78° C. and stirred. After dropwise adding 0.77 ml of n-butyllithium (1.55 mmol/ml n-hexane solution, 1.19 mmol) over 5 minutes, the temperature was slowly increased to room temperature and stirring was continued for 4 hours at room temperature to prepare a lithium salt solution. The solution was then slowly added dropwise to a solution containing 1.0 ml of a titanium tetrachloride solution (0.5 mmol/ml heptane solution, 0.50 mmol) and 10 ml of diethyl ether which had been cooled to −78° C. After completion of the dropwise addition, stirring was continued while slowly increasing the temperature to room temperature. After further stirring for 15 hours at room temperature, the reaction solution was filtered with a glass filter. The filtrate was concentrated under reduced pressure, and the deposited solid was reprecipitated with methylene chloride and hexane and dried under reduced pressure to obtain 0.16 g (0.22 mmol, 43% yield) of compound A-10 as a brown powder represented by the formula given below.

Compound A-10

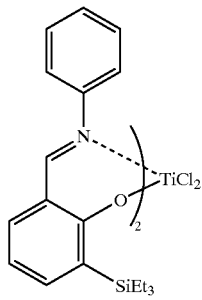

¹H-NMR (CDCl₃): 0.40–0.90 (m, 30H), 6.60–7.80 (m, 18H).

FD-mass spectrometry: 739 (M+).

Elemental analysis: Ti: 5.3% (5.2). Calculated value in parentheses.

Synthesis Example 24

Synthesis of Compound A-11

After charging 0.68 g (2.40 mmol) of compound L11 and 30 ml of diethyl ether into a 100 ml reactor which had been adequately dried and substituted with argon, they were cooled to −78° C. and stirred. After dropwise adding 1.49 ml of n-butyllithium (1.61 mmol/ml n-hexane solution, 2.40 mmol) over 5 minutes, the temperature was slowly increased to room temperature and stirring was continued for 4 hours at room temperature to prepare a lithium salt solution. The solution was then slowly added dropwise to a solution containing 2.4 ml of a titanium tetrachloride solution (0.5 mmol/ml heptane solution, 1.20 mmol) and 15 ml of diethyl ether which had been cooled to −78° C. After completion of the dropwise addition, stirring was continued while slowly increasing the temperature to room temperature. After further stirring for 15 hours at room temperature, the solvent of the reaction solution was distilled off, the resulting solid was dissolved in 50 ml of methylene chloride, and the insoluble portion was filtered off with a glass filter. The filtrate was concentrated under reduced pressure, and the deposited solid was reprecipitated with methylene chloride and hexane at 0° C. and dried under reduced pressure to obtain 0.37 g (0.54 mmol, 45% yield) of compound A-11 as a red brown powder.

Compound A-11

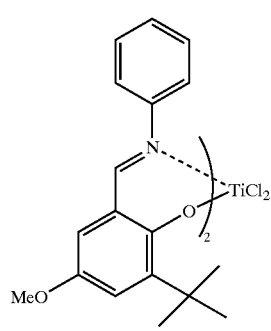

¹H-NMR (CDCl₃): 1.20–1.40 (m, 9H), 1.50–1.55 (m, 9H), 3.70–3.85 (m, 6H), 6.52–7.40 (m, 14H), 8.05–8.20 (m, 2H).

FD-mass spectrometry: 682 (M+).

Elemental analysis: Ti: 7.0% (7.0). Calculated value in parentheses.

Synthesis Example 25

Synthesis of Compound B-11

After charging 0.64 g (2.26 mmol) of compound L11 and 20 ml of diethyl ether into a 100 ml reactor which had been adequately dried and substituted with argon, they were cooled to −78° C. and stirred. After dropwise adding 1.40 ml of n-butyllithium (1.61 mmol/ml n-hexane solution, 2.26 mmol) over 5 minutes, the temperature was slowly increased to room temperature and stirring was continued for 4 hours at room temperature to prepare a lithium salt solution. The solution was then slowly added dropwise to a solution of zirconium tetrachloride.2THF (0.42 g, 1.10 mmol) in 20 ml of tetrahydrofuran which had been cooled to −78° C. After completion of the dropwise addition, stirring was continued while slowly increasing the temperature to room temperature. After further stirring for 15 hours at room temperature, the solvent of the reaction solution was distilled off. The resulting solid was dissolved in 50 ml of methylene chloride, and the insoluble portion was filtered off with a glass filter. The filtrate was concentrated under reduced pressure, and the deposited solid was reprecipitated with methylene chloride and hexane and dried under reduced pressure to obtain 0.25 g (0.34 mmol, 31% yield) of compound B-11 as a yellow green powder represented by the formula given below.

Compound B-11

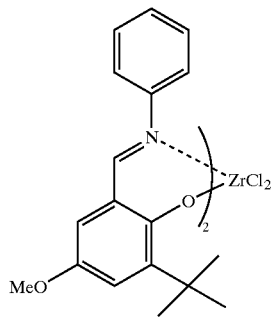

¹H-NMR (CDCl₃): 1.20–1.60 (m, 18H), 3.66–3.86 (m, 6H), 6.50–7.50 (m, 14H), 8.05–8.20 (m, 2H).

FD-mass spectrometry: 726 (M+).

Elemental analysis: Zr: 12.4% (12.6). Calculated value in parentheses.

Synthesis Example 26

Synthesis of Compound A-12

After charging 1.0 g (2.31 mmol) of compound L12 and 20 ml of diethyl ether into a 100 ml reactor which had been adequately dried and substituted with argon, they were cooled to −78° C. and stirred. After dropwise adding 1.56 ml of n-butyllithium (1.55 mmol/ml n-hexane solution, 2.42 mmol) over 5 minutes, the temperature was slowly increased to room temperature and stirring was continued for 4 hours at room temperature to prepare a lithium salt solution. The solution was then slowly added dropwise to a mixed solution containing 2.3 ml of a titanium tetrachloride solution (0.5 mmol/ml heptane solution, 1.15 mmol) and 20 ml of diethyl ether which had been cooled to −78° C. After completion of the dropwise addition, stirring was continued while slowly increasing the temperature to room temperature. After further stirring for 15 hours at room temperature, the insoluble portion was filtered off with a glass filter. The filtrate was concentrated under reduced pressure, and the deposited solid was reslurried with hexane. The slurry was filtered to remove the solvent and the solid was dried under reduced pressure to obtain 0.45 g (0.45 mmol, 40% yield) of compound A-12 as a red brown powder.

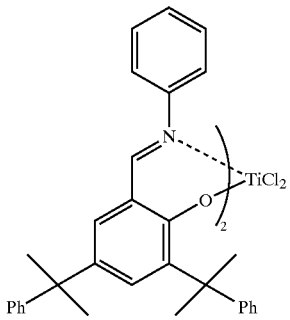

Compound A-12

$^1$H-NMR (CDCl$_3$): 1.30–2.20 (m, 24H), 6.20–7.40 (m, 34H). 7.50–7.70 (m, 2H).

FD-mass spectrometry: 982 (M+).

Elemental analysis: Ti: 5.0% (4.9). Calculated value in parentheses.

Synthesis Example 27

Synthesis of Compound B-12

After charging 1.0 g (2.31 mmol) of compound L12 and 20 ml of diethyl ether into a 100 ml reactor which had been adequately dried and substituted with argon, they were cooled to −78° C. and stirred. After dropwise adding 1.56 ml of n-butyllithium (1.55 mmol/ml n-hexane solution, 2.42 mmol) over 5 minutes, the temperature was slowly increased to room temperature and stirring was continued for 4 hours at room temperature to prepare a lithium salt solution. The solution was then slowly added dropwise to a mixed solution of zirconium tetrachloride (0.27 g, 1.15 mmol) and 20 ml of diethyl ether which had been cooled to −78° C. After completion of the dropwise addition, stirring was continued while slowly increasing the temperature to room temperature. After further stirring for 15 hours at room temperature, the insoluble portion was removed with a glass filter. The filtrate was concentrated under reduced pressure, and the deposited solid was reprecipitated with diethyl ether, hexane, heptane and pentane, reslurried and washed, and then dried under reduced pressure to obtain 0.02 g (0.02 mmol, 1% yield) of compound B-12 as a yellow green powder represented by the formula given below.

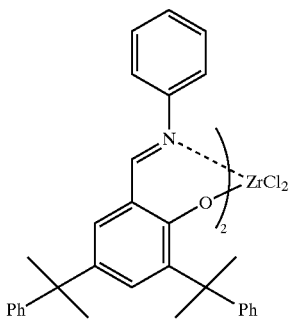

Compound B-12

$^1$H-NMR (CDCl$_3$): 1.20–2.10 (m, 24H), 6.20–7.40 (m, 34H), 7.50–8.00 (m, 2H).

FD-mass spectrometry: 1026 (M+).

Elemental analysis: Zr: 9.1% (8.9). Calculated value in parentheses.

Synthesis Example 28

Synthesis of Compound A-13

After charging 1.10 g (3.26 mmol) of compound L13 and 22 ml of diethyl ether into a 100 ml reactor which had been adequately dried and substituted with argon, they were cooled to −78° C. and stirred. After dropwise adding 2.2 ml of n-butyllithium (1.55 mmol/ml n-hexane solution, 3.41 mmol) over 5 minutes, the temperature was slowly increased to room temperature and stirring was continued for 4 hours at room temperature to prepare a lithium salt solution. The solution was then slowly added dropwise to a mixed solution containing 3.26 ml of a titanium tetrachloride solution (0.5 mmol/ml heptane solution, 1.13 mmol) and 22 ml of diethyl ether which had been cooled to −78° C. After completion of the dropwise addition, stirring was continued while slowly increasing the temperature to room temperature. After further stirring for 15 hours at room temperature, the solvent of the reaction solution was distilled off, the insoluble portion of the reaction solution was filtered off with a glass filter. The filtrate was concentrated under reduced pressure, and the deposited solid was reprecipitated with diethyl ether and pentane and dried under reduced pressure to obtain 0.22 g (0.28 mmol, 17% yield) of compound A-13 as a red brown powder.

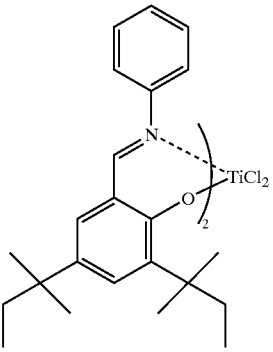

Compound A-13

$^1$H-NMR (CDCl$_3$): 0.60–2.41 (m, 44H), 6.70–7.60 (m, 34H), 7.91–8.10 (m, 2H).

FD-mass spectrometry: 790 (M+).

Elemental analysis: Ti: 6.3% (6.1). Calculated value in parentheses.

Synthesis Example 29

Synthesis of Compound B-13

After charging 1.03 g (3.02 mmol) of compound L13 and 20 ml of diethyl ether into a 100 ml reactor which had been adequately dried and substituted with argon, they were cooled to −78° C. and stirred. After dropwise adding 2.0 ml of n-butyllithium (1.55 mmol/ml n-hexane solution, 3.10 mmol) over 5 minutes, the temperature was slowly increased to room temperature and stirring was continued for 4 hours at room temperature to prepare a lithium salt solution. The solution was then slowly added dropwise to a mixed solution of zirconium tetrachloride (0.35 g, 1.50 mmol) and 20 ml of diethyl ether which had been cooled to −78° C. After completion of the dropwise addition, stirring was continued while slowly increasing the temperature to room temperature. After further stirring for 15 hours at room temperature, the insoluble portion was removed with a glass filter. The filtrate was concentrated under reduced pressure, the deposited solid was recrystallized with pentane and dried under reduced pressure to obtain 0.27 g (0.32 mmol, 21% yield) of compound B-13 as a yellow green powder represented by the formula given below.

Compound B-13

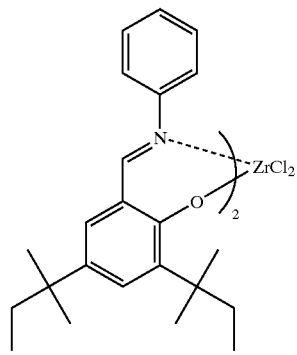

¹H-NMR (CDCl₃): 0.30–2.32 (m, 44H), 6.70–7.60 (m, 14H), 7.90–8.20 (m, 2H).

FD-mass spectrometry: 834 (M+).

Elemental analysis: Zr: 10.9% (10.9). Calculated value in parentheses.

Synthesis Example 30

Synthesis of Compound A-14

After charging 0.98 g (2.97 mmol) of compound L14 and 30 ml of diethyl ether into a 100 ml reactor which had been adequately dried and substituted with argon, they were cooled to −78° C. and stirred. After dropwise adding 2.0 ml of n-butyllithium (1.61 mmol/ml n-hexane solution, 3.22 mmol) over 5 minutes, the temperature was slowly increased to room temperature and stirring was continued for 4 hours at room temperature to prepare a lithium salt solution. The solution was then slowly added dropwise to a mixed solution containing 3.0 ml of a titanium tetrachloride solution (0.5 mmol/ml heptane solution, 1.50 mmol) and 15 ml of diethyl ether which had been cooled to −78° C. After completion of the dropwise addition, stirring was continued while slowly increasing the temperature to room temperature. After further stirring for 15 hours at room temperature, the insoluble portion of the reaction solution was filtered off, the filtered substance was dissolved in 30 ml of diethyl ether and 50 ml of methylene chloride, and the insoluble portion was filtered off with a glass filter. The filtrate was concentrated under reduced pressure, and the deposited solid was recrystallized with diethyl ether and dried under reduced pressure to obtain 0.66 g (0.85 mmol, 57% yield) of compound A-14 as a dark brown powder.

Compound A-14

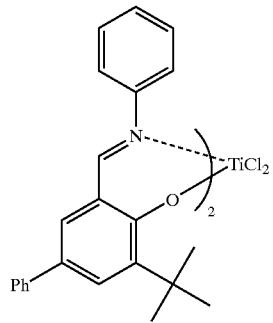

¹H-NMR (CDCl₃): 1.41 (s, 18H), 6.70–7.90 (m, 24H), 8.18 (s, 2H).

FD-mass spectrometry: 774 (M+).

Elemental analysis: Ti: 6.2% (6.2). Calculated value in parentheses.

Synthesis Example 31

Synthesis of Compound B-14

After charging 1.01 g (3.05 mmol) of compound L14 and 20 ml of diethyl ether into a 100 ml reactor which had been adequately dried and substituted with argon, they were cooled to −78° C. and stirred. After dropwise adding 2.0 ml of n-butyllithium (1.61 mmol/ml n-hexane solution, 3.22 mmol) over 5 minutes, the temperature was slowly increased to room temperature and stirring was continued for 4 hours at room temperature to prepare a lithium salt solution. The solution was then slowly added dropwise to a tetrahydrofuran solution containing zirconium tetrachloride (0.36 g, 1.52 mmol) which had been cooled to −78° C. After completion of the dropwise addition, stirring was continued while slowly increasing the temperature to room temperature. After further stirring for 8 hours at room temperature, the insoluble portion was removed with a glass filter. The filtrate was concentrated to dryness, and the deposited solid was reprecipitated with methylene chloride and hexane and dried under reduced pressure to obtain 0.61 g (0.74 mmol, 49% yield) of compound B-14 as a fluorescent yellow powder represented by the formula given below.

Compound B-14

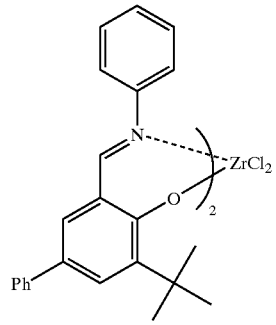

¹H-NMR (CDCl₃): 1.41 (s, 18H), 6.80–7.90 (m, 24H), 8.24 (s, 2H).

FD-mass spectrometry: 818 (M+).

Elemental analysis: Zr: 11.0% (11.1). Calculated value in parentheses.

Synthesis Example 32

Synthesis of Compound A-15

After charging 0.40 g (1.01 mmol) of compound L15 and 10 ml of diethyl ether into a 100 ml reactor which had been adequately dried and substituted with argon, they were cooled to −78° C. and stirred. After dropwise adding 0.77 ml of n-butyllithium (1.55 mmol/ml n-hexane solution, 1.19 mmol) over 5 minutes, the temperature was slowly increased to room temperature and stirring was continued for 4 hours at room temperature to prepare a lithium salt solution. The solution was then slowly added dropwise to a mixed solution containing 1.0 ml of a titanium tetrachloride solution (0.5 mmol/ml heptane solution, 0.50 mmol) and 10 ml of diethyl ether which had been cooled to −78° C. After completion of the dropwise addition, stirring was continued while slowly increasing the temperature to room temperature. After further stirring for 15 hours at room temperature, the insoluble portion was filtered off with a glass filter. The filtrate was concentrated under reduced pressure, and the deposited solid was reprecipitated with diethyl ether and hexane and dried under reduced pressure to obtain 0.19 g (0.21 mmol, 42% yield) of compound A-15 as a red brown powder.

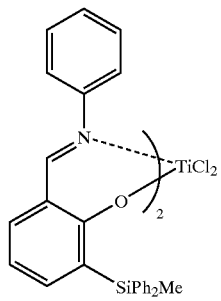

Compound A-15

$^1$H-NMR (CDCl$_3$): 0.60–1.30 (m, 6H), 6.50–7.80 (m, 36H), 7.80–7.90 (m, 2H).

FD-mass spectrometry: 900 (M+).

Elemental analysis: Ti: 5.5% (5.3). Calculated value in parentheses.

Synthesis Example 33

Synthesis of Compound B-15

After charging 0.40 g (1.02 mmol) of compound L15 and 10 ml of tetrahydrofuran into a 100 ml reactor which had been adequately dried and substituted with argon, they were cooled to −78° C. and stirred. After dropwise adding 0.77 ml of n-butyllithium (1.55 mmol/ml n-hexane solution, 1.19 mmol) over 5 minutes, the temperature was slowly increased to room temperature and stirring was continued for 4 hours at room temperature to prepare a lithium salt solution. After cooling the solution to −78° C., solid zirconium tetrachloride (0.12 g, 0.50 mmol) was added. After completion of the addition, stirring was continued while slowly increasing the temperature to room temperature. After further stirring for 15 hours at room temperature, the solvent of the reaction solution was distilled off. The resulting solid was dissolved in 50 ml of methylene chloride, and the insoluble portion was removed with a glass filter. The filtrate was concentrated under reduced pressure, and the deposited solid was reprecipitated with diethyl ether and hexane and dried under reduced pressure to obtain 0.20 g (0.21 mmol, 42% yield) of compound B-15 as a grayish white powder represented by the formula given below.

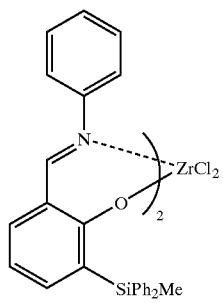

Compound B-15

$^1$H-NMR (CDCl$_3$): 0.70–1.00 (m, 6H), 6.60–7.60 (m, 36H), 7.70–7.80 (m, 2H).

FD-mass spectrometry: 944 (M+).

Elemental analysis: Zr: 9.4% (9.6). Calculated value in parentheses.

Synthesis Example 34

Synthesis of Compound A-16

After charging 1.0 g (4.73 mmol) of compound L16 and 20 ml of diethyl ether into a 100 ml reactor which had been adequately dried and substituted with argon, they were cooled to −78° C. and stirred. After dropwise adding 3.2 ml of n-butyllithium (1.55 mmol/ml n-hexane solution, 4.96 mmol) over 5 minutes, the temperature was slowly increased to room temperature and stirring was continued for 4 hours at room temperature to prepare a lithium salt solution. The solution was then slowly added dropwise to a mixed solution containing 4.7 ml of a titanium tetrachloride solution (0.5 mmol/ml heptane solution, 2.35 mmol) and 20 ml of diethyl ether which had been cooled to −78° C. After completion of the dropwise addition, stirring was continued while slowly increasing the temperature to room temperature. After further stirring for 15 hours at room temperature, the reaction solution was filtered, and the filtered substance was dissolved in 50 ml of methylene chloride. The insoluble portion was removed, the filtrate was concentrated under reduced pressure, and the deposited solid was reprecipitated with methylene chloride and hexane and dried under reduced pressure to obtain 0.96 g (1.78 mmol, 75% yield) of compound A-16 as a pale brown powder.

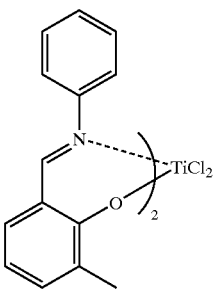

Compound A-16

$^1$H-NMR (CDCl$_3$): 1.90 (s, 6H), 6.50–7.30 (m, 16H), 7.90 (s, 2H).

FD-mass spectrometry: 538 (M+).

Elemental analysis: Ti: 9.0% (8.9). Calculated value in parentheses.

Synthesis Example 35

Synthesis of Compound B-16

After charging 1.0 g (4.73 mmol) of compound L16 and 20 ml of diethyl ether into a 100 ml reactor which had been adequately dried and substituted with argon, they were cooled to −78° C. and stirred. After dropwise adding 3.2 ml of n-butyllithium (1.55 mmol/ml n-hexane solution, 4.96 mmol) over 5 minutes, the temperature was slowly increased to room temperature and stirring was continued for 4 hours at room temperature to prepare a lithium salt solution. The solution was then added dropwise to a mixed solution of zirconium tetrachloride (0.55 g, 2.36 mmol) and 20 ml of diethyl ether which had been cooled to −78° C. After completion of the dropwise addition, stirring was continued while slowly increasing the temperature to room temperature. After further stirring for 15 hours at room temperature, the reaction solution was filtered off. The solvent of the filtrate was distilled off, and the resulting solid was recrystallized with diethyl ether, methylene chloride and hexane and dried under reduced pressure to obtain 0.49 g (0.84 mmol, 36% yield) of compound B-16 as a yellow green powder represented by the formula given below.

Compound B-16

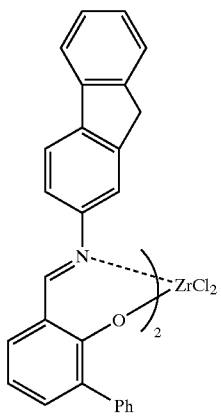

$^1$H-NMR (CDCl$_3$): 2.00 (s, 6H), 6.40–7.40 (m, 16H), 8.10 (s, 2H).

FD-mass spectrometry: 582 (M+).

Elemental analysis: Zr: 15.9% (15.7). Calculated value in parentheses.

Synthesis Example 36

Synthesis of Compound A-17

After charging 1.0 g (2.77 mmol) of compound L17 and 20 ml of diethyl ether into a 100 ml reactor which had been adequately dried and substituted with argon, they were cooled to −78° C. and stirred. After dropwise adding 1.87 ml of n-butyllithium (1.55 mmol/ml n-hexane solution, 2.90 mmol) over 5 minutes, the temperature was slowly increased to room temperature and stirring was continued for 4 hours at room temperature to prepare a lithium salt solution. The solution was then slowly added dropwise to a mixed solution containing 2.76 ml of a titanium tetrachloride solution (0.5 mmol/ml heptane solution, 1.38 mmol) and 20 ml of diethyl ether which had been cooled to −78° C. After completion of the dropwise addition, stirring was continued while slowly increasing the temperature to room temperature. After further stirring for 15 hours at room temperature, the insoluble portion was filtered off with a glass filter. The filtrate was concentrated under reduced pressure, and the deposited solid was reslurried with hexane. The slurry was filtered to remove the solvent and the solid was dried under reduced pressure to obtain 0.15 g (0.18 mmol, 13% yield) of compound A-17 as a brown powder.

Compound A-17

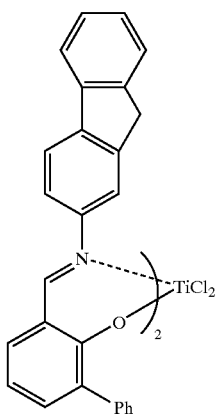

$^1$H-NMR (CDCl$_3$): 3.20–3.80 (m, 4H), 6.90–7.81 (m, 30H), 8.15 (s, 2H).

FD-mass spectrometry: 838 (M+).

Elemental analysis: Ti: 5.9% (5.7). Calculated value in parentheses.

Synthesis Example 37

Synthesis of Compound B-17

After charging 1.0 g (2.77 mmol) of compound L17 and 20 ml of diethyl ether into a 100 ml reactor which had been adequately dried and substituted with argon, they were cooled to −78° C. and stirred. After dropwise adding 1.87 ml of n-butyllithium (1.55 mmol/ml n-hexane solution, 2.90 mmol) over 5 minutes, the temperature was slowly increased to room temperature and stirring was continued for 4 hours at room temperature to prepare a lithium salt solution. The solution was then added dropwise to a mixed solution of zirconium tetrachloride (0.32 g, 1.37 mmol) and 20 ml of diethyl ether which had been cooled to −78° C. After completion of the dropwise addition, stirring was continued while slowly increasing the temperature to room temperature. After further stirring for 15 hours at room temperature, the insoluble portion in the reaction solution was removed with a glass filter. The filtrate was concentrated under reduced pressure, and the deposited solid was reslurried with hexane. The slurry was filtered to remove the solvent and the solid was dried under reduced pressure to obtain 0.71 g (0.88 mmol, 58% yield) of compound B-17 as a yellow green powder represented by the formula given below.

Compound B-17

$^1$H-NMR (CDCl$_3$): 3.30–3.80 (m, 4H), 6.71–7.72 (m, 30H), 8.25 (s, 2H).

FD-mass spectrometry: 882 (M+).

Elemental analysis: Zr: 10.6% (10.3). Calculated value in parentheses.

Synthesis Example 38

Synthesis of Compound A-18

After charging 0.59 g (2.20 mmol) of compound L18 and 10 ml of diethyl ether into a 100 ml reactor which had been adequately dried and substituted with argon, they were cooled to −78° C. and stirred. After dropwise adding 1.49 ml of n-butyllithium (1.55 mmol/ml n-hexane solution, 2.31 mmol) over 5 minutes, the temperature was slowly increased to room temperature and stirring was continued for 4 hours at room temperature to prepare a lithium salt solution. The solution was then slowly added dropwise to a mixed solution containing 2.2 ml of a titanium tetrachloride solution (0.5 mmol/ml heptane solution, 1.10 mmol) and 10 ml of tetrahydrofuran which had been cooled to −78° C. After completion of the dropwise addition, stirring was continued while slowly increasing the temperature to room temperature. After further stirring for 15 hours at room temperature, the mixture was concentrated to dryness, and the resulting solid was dissolved in 20 ml of methylene chloride. The insoluble portion was filtered off with a glass filter, the filtrate was concentrated under reduced pressure, and the deposited solid was reprecipitated with diethyl ether and hexane at −78° C. and dried under reduced pressure to obtain 0.27 g (0.41 mmol, 37% yield) of compound A-18 as a brown powder.

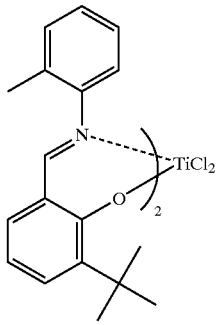

Compound A-18

¹H-NMR (CDCl₃): 1.22 (s, 18H), 2.40 (s, 6H), 6.44–7.80 (m, 14H), 8.21 (s, 2H).

FD-mass spectrometry: 650 (M+).

Elemental analysis: Ti: 7.1% (7.4). Calculated value in parentheses.

Synthesis Example 39

Synthesis of Compound B-18

After charging 0.60 g (2.25 mmol) of compound L18 and 10 ml of diethyl ether into a 100 ml reactor which had been adequately dried and substituted with argon, they were cooled to −78° C. and stirred. After dropwise adding 1.52 ml of n-butyllithium (1.55 mmol/ml n-hexane solution, 2.36 mmol) over 5 minutes, the temperature was slowly increased to room temperature and stirring was continued for 4 hours at room temperature to prepare a lithium salt solution. The solution was then added dropwise to a solution of zirconium tetrachloride (0.26 g, 1.12 mmol) in 10 ml of tetrahydrofuran which had been cooled to −78° C. After completion of the dropwise addition, stirring was continued while slowly increasing the temperature to room temperature. After further stirring for 8 hours at room temperature, the solvent of the reaction solution was distilled off. The resulting solid was dissolved in 20 ml of methylene chloride, and the insoluble portion was removed with a glass filter. The filtrate was concentrated under reduced pressure, and the deposited solid was reprecipitated with diethyl ether and hexane and dried under reduced pressure to obtain 0.16 g (0.24 mmol, 21% yield) of compound B-18 as a yellow green powder represented by the formula given below.

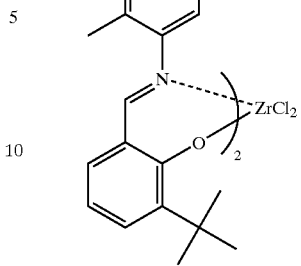

Compound B-18

¹H-NMR (CDCl₃): 1.13 (s, 18H), 2.39 (s, 6H), 6.50–7.75 (m, 14H), 8.26 (s, 2H).

FD-mass spectrometry: 694 (M+).

Elemental analysis: Zr: 13.1% (13.1). Calculated value in parentheses.

Synthesis Example 40

Synthesis of Compound B-19

After charging 0.70 g (2.25 mmol) of compound L19 and 10 ml of diethyl ether into a 100 ml reactor which had been adequately dried and substituted with argon, they were cooled to −78° C. and stirred. After dropwise adding 1.52 ml of n-butyllithium (1.55 mmol/ml n-hexane solution, 2.36 mmol) over 5 minutes, the temperature was slowly Increased to room temperature and stirring was continued for 4 hours at room temperature to prepare a lithium salt solution. The solution was then added dropwise to a solution of zirconium tetrachloride (0.26 g, 1.12 mmol) in 10 ml of tetrahydrofuran which had been cooled to −78° C. After completion of the dropwise addition, stirring was continued while slowly increasing the temperature to room temperature. After further stirring for 15 hours at room temperature, the solvent of the reaction solution was distilled off. The resulting solid was dissolved in 20 ml of methylene chloride, and the insoluble portion was removed with a glass filter. The filtrate was concentrated under reduced pressure, and the deposited solid was reprecipitated with diethyl ether and hexane and dried under reduced pressure to obtain 0.16 g (0.20 mmol, 18% yield) of compound B-19 as a yellow green powder represented by the formula given below.

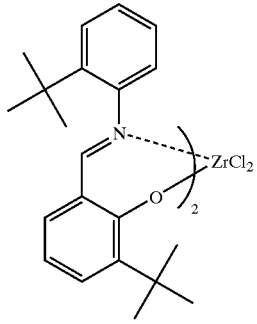

Compound B-19

¹H-NMR (CDCl₃): 1.43 (s, 18H), 1.47 (s, 18H), 6.90–7.60 (m, 14H), 8.40 (s, 2H).

FD-mass spectrometry: 778 (M+).

Elemental analysis: Zr: 12.1% (11.7). Calculated value in parentheses.

Synthesis Example 41

Synthesis of Compound B-20

After charging 0.63 g (2.25 mmol) of compound L20 and 10 ml of diethyl ether into a 100 ml reactor which had been adequately dried and substituted with argon, they were cooled to −78° C. and stirred. After dropwise adding 1.52 ml of n-butyllithium (1.55 mmol/ml n-hexane solution, 2.36 mmol) over 5 minutes, the temperature was slowly increased to room temperature and stirring was continued for 4 hours at room temperature to prepare a lithium salt solution. The solution was then added dropwise to a solution of zirconium tetrachloride (0.26 g, 1.12 mmol) in 10 ml of tetrahydrofuran which had been cooled to −78° C. After completion of the dropwise addition, stirring was continued while slowly increasing the temperature to room temperature. After further stirring for 15 hours at room temperature, the solvent of the reaction solution was distilled off. The resulting solid was dissolved in 25 ml of methylene chloride, and the insoluble portion was removed with a glass filter. The filtrate was concentrated under reduced pressure, and the deposited solid was reprecipitated with diethyl ether and hexane and dried under reduced pressure to obtain 0.35 g (0.48 mmol, 43% yield) of compound B-20 as a yellow powder represented by the formula given below.

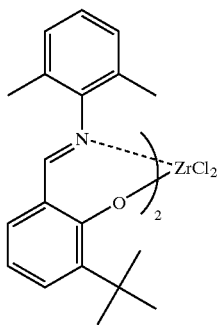

Compound B-20

$^{12}$H-NMR (CDCl$_3$): 1.40 (s, 18H), 1.50 (s, 18H), 2.21 (s, 12H), 6.70–7.40 (m, 12H), 8.33 (s, 2H).

FD-mass spectrometry: 720 (M+).

Elemental analysis: Zr: 12.8% (12.6). Calculated value in parentheses.

Synthesis Example 42

Synthesis of Compound A-21

After charging 0.80 g (2.50 mmol) of compound L21 and 10 ml of diethyl ether into a 100 ml reactor which had been adequately dried and substituted with argon, they were cooled to −78° C. and stirred. After dropwise adding 1.7 ml of n-butyllithium (1.55 mmol/ml n-hexane solution, 2.64 mmol) over 5 minutes, the temperature was slowly increased to 0° C., and stirring was continued for 4 hours at 0° C. to prepare a lithium salt solution. The solution was then slowly added dropwise to a mixed solution containing 2.5 ml of a titanium tetrachloride solution (0.5 mmol/ml heptane solution, 1.25 mmol) and 10 ml of diethyl ether which had been cooled to −78° C. After completion of the dropwise addition, stirring was continued while slowly increasing the temperature to room temperature. After further stirring for 8 hours at room temperature, the mixture was concentrated to dryness, and the resulting solid was dissolved in 50 ml of diethyl ether and 60 ml of methylene chloride. The insoluble portion was filtered off with a glass filter, the filtrate was concentrated under reduced pressure, and the deposited solid was recrystallized with diethyl ether and dried under reduced pressure to obtain 0.07 g (0.09 mmol, 8% yield) of compound A-21 as a red brown powder.

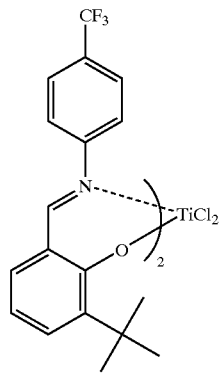

Compound A-21

$^1$H-NMR (CDCl$_3$): 1.34 (s, 18H), 6.75–7.75 (m, 14H), 8.10 (s, 2H).

FD-mass spectrometry: 758 (M+).

Elemental analysis: Ti: 6.5% (6.3). Calculated value in parentheses.

Synthesis Example 43

Synthesis of Compound B-21

After charging 1.03 g (3.20 mmol) of compound L21 and 10 ml of diethyl ether into a 100 ml reactor which had been adequately dried and substituted with argon, they were cooled to −78° C. and stirred. After dropwise adding 2.0 ml of n-butyllithium (1.61 mmol/ml n-hexane solution, 3.22 mmol) over 5 minutes, the temperature was slowly increased to −15° C. and stirring was continued for 2 hours at −15° C. to prepare a lithium salt solution. The solution was then added dropwise to a solution of zirconium tetrachloride (0.36 g, 1.54 mmol) in 10 ml of tetrahydrofuran which had been cooled to −78° C. After completion of the dropwise addition, stirring was continued while slowly increasing the temperature to room temperature. After further stirring for 15 hours at room temperature, the solvent of the reaction solution was distilled off. The residue was dissolved in 20 ml of toluene, and the reaction was continued for 3 hours under reflux conditions. The solvent was distilled off, the resulting solid was dissolved in 50 ml of methylene chloride, and the insoluble portion was removed with a glass filter. The filtrate was concentrated under reduced pressure, and the deposited solid was reprecipitated with diethyl ether and hexane and dried under reduced pressure to obtain 0.33 g (0.41 mmol, 27% yield) of compound B-21 as an ocher powder represented by the formula given below.

Compound B-21

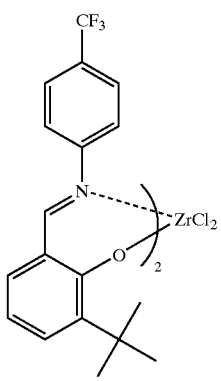

¹H-NMR (CDCl₃): 1.24 (s, 18H), 6.80–7.78 (m, 14H), 3.15 (s, 2H).

FD-mass spectrometry: 802 (M+).

Elemental analysis: Zr: 11.7% (11.4). Calculated value in parentheses.

Synthesis Example 44

Synthesis of Compound A-22

After charging 0.50 g (1.77 mmol) of compound L22 and 40 ml of diethyl ether into a 100 ml reactor which had been adequately dried and substituted with argon, they were cooled to −78° C. and stirred. After dropwise adding 1.20 ml of n-butyllithium (1.55 mmol/ml n-hexane solution, 1.86 mmol) over 5 minutes, the temperature was slowly increased to room temperature, and stirring was continued for 4 hours at room temperature to prepare a lithium salt solution. The solution was then slowly added dropwise to a mixed solution containing 1.77 ml of a titanium tetrachloride solution (0.5 mmol/ml heptane solution, 0.89 mmol) and 50 ml of diethyl ether which had been cooled to −78° C.

After completion of the dropwise addition, stirring was continued while slowly increasing the temperature to room temperature. After further stirring for 15 hours at room temperature, the reaction solution was filtered with a glass filter. After washing the filtered substance with diethyl ether, it was dissolved in methylene chloride. The insoluble portion was removed, the filtrate was concentrated under reduced pressure, and the deposited solid was reprecipitated with diethyl ether and hexane at −78° C. and dried under reduced pressure to obtain 0.31 g (0.45 mmol, 51% yield) of compound A-22 as a brown powder.

Compound A-22

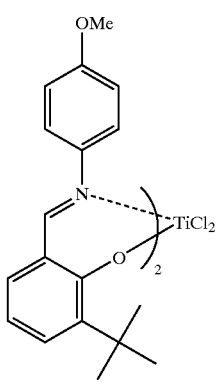

¹H-NMR (CDCl₃): 0.70–1.80 (m, 18H), 3.50–4.00 (m, 6H), 6.40–7.70 (m, 14H), 8.05 (s, 2H).

FD-mass spectrometry: 682 (M+).

Elemental analysis: Ti: 7.3% (7.0). Calculated value in parentheses.

Synthesis Example 45

Synthesis of Compound B-22

After charging 0.50 g (1.77 mmol) of compound L22 and 25 ml of diethyl ether into a 100 ml reactor which had been adequately dried and substituted with argon, they were cooled to −78° C. and stirred. After dropwise adding 1.20 ml of n-butyllithium (1.55 mmol/ml n-hexane solution, 1.86 mmol) over 5 minutes, the temperature was slowly increased to room temperature and stirring was continued for 4 hours at room temperature to prepare a lithium salt solution. The solution was then added dropwise to a mixed solution of zirconium tetrachloride (0.21 g, 0.99 mmol) in 10 ml of diethyl ether and 60 ml of tetrahydrofuran which had been cooled to −78° C. After completion of the dropwise addition, stirring was continued while slowly increasing the temperature to room temperature. After further stirring for 15 hours at room temperature, the solvent of the reaction solution was distilled off. The resulting solid was reslurried with 70 ml of hexane, and the insoluble portion was separated off with a glass filter. The filtered substance was dissolved in 100 ml of diethyl ether and 70 ml of hexane. After removing out the insoluble portion, the filtrate was concentrated under reduced pressure. The deposited solid was washed with hexane and dried under reduced pressure to obtain 0.08 g (0.11 mmol, 11% yield) of compound B-22 as a yellow green powder represented by the formula given below.

Compound B-22

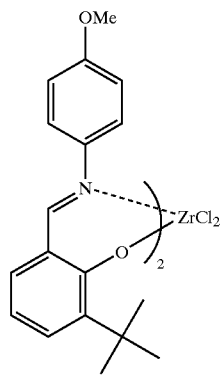

¹H-NMR (CDCl₃): 1.40 (s, 18H), 3.75 (s, 6H), 6.40–7.70 (m, 14H), 8.10 (s, 2H).

FD-mass spectrometry: 726 (M+).

Elemental analysis: Zr: 12.3% (12.6). Calculated value in parentheses.

Synthesis Example 46

Synthesis of Compound A-23

After charging 1.01 g (4.33 mmol) of compound L23 and 22 ml of diethyl ether into a 100 ml reactor which had been adequately dried and substituted with argon, they were cooled to −78° C. and stirred. After dropwise adding 2.9 ml of n-butyllithium (1.55 mmol/ml n-hexane solution, 4.50 mmol) over 5 minutes, the temperature was slowly increased to room temperature, and stirring was continued for 4 hours at room temperature to prepare a lithium salt solution. The solution was then slowly added dropwise to a mixed solution containing 4.25 ml of a titanium tetrachloride solution (0.5 mmol/ml heptane solution, 2.13 mmol) and 20 ml of diethyl ether which had been cooled to −78° C. After completion of the dropwise addition, stirring was continued while slowly increasing the temperature to room temperature. After further stirring for 15 hours at room temperature, the reaction solution was filtered, the filtrate was concentrated to dryness, and the resulting solid was reprecipitated with methylene chloride, diethyl ether and hexane and dried under reduced pressure to obtain 0.26 g (0.44 mmol, 21% yield) of compound A-23 as a brown powder.

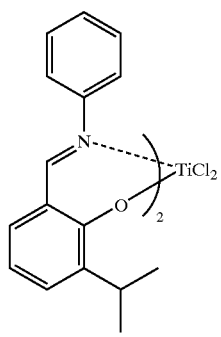

Compound A-23

¹H-NMR (CDCl₃): 0.82–1.40 (m, 12H), 2.90–3.30 (m, 2H), 6.60–7.40 (m, 16H), 8.10 (s, 2H).

FD-mass spectrometry: 594 (M+).

Elemental analysis: Ti: 8.0% (8.0). Calculated value in parentheses.

Synthesis Example 47

Synthesis of Compound B-23

After charging 1.02 g (4.25 mmol) of compound L23 and 20 ml of diethyl ether into a 100 ml reactor which had been adequately dried and substituted with argon, they were cooled to −78° C. and stirred. After dropwise adding 3.43 ml of n-butyllithium (1.55 mmol/ml n-hexane solution, 5.32 mmol) over 5 minutes, the temperature was slowly increased to room temperature, and stirring was continued for 4 hours at room temperature to prepare a lithium salt solution. The solution was then added dropwise to a mixed solution of zirconium tetrachloride (0.50 g, 2.15 mmol) and 20 ml of diethyl ether which had been cooled to −78° C. After completion of the dropwise addition, stirring was continued while slowly increasing the temperature to room temperature. After further stirring for 15 hours at room temperature, the insoluble portion was removed with a glass filter. The filtrate was concentrated under reduced pressure, and the deposited solid was reprecipitated with diethyl ether, methylene chloride and hexane and dried under reduced pressure to obtain 0.61 g (0.96 mmol, 45% yield) of compound B-23 as a yellow green powder represented by the formula given below.

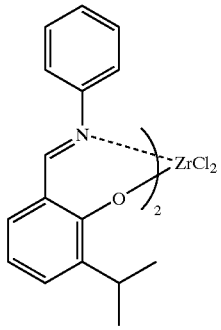

Compound B-23

¹H-NMR (CDCl₃): 0.80–1.30 (m, 12H), 2.90–3.25 (m, 2H), 6.72–7.43 (m, 16H), 8.20 (s, 2H).

FD-mass spectrometry: 638 (M+).

Elemental analysis: Zr: 14.0% (14.3). Calculated value in parentheses.

Synthesis Example 48

Synthesis of Compound A-24

After charging 0.52 g (2.05 mmol) of compound L24 and 40 ml of diethyl ether into a 100 ml reactor which had been adequately dried and substituted with argon, they were cooled to −78° C. and stirred. After dropwise adding 1.36 ml of n-butyllithium (1.55 mmol/ml n-hexane solution, 2.11 mmol) over 5 minutes, the temperature was slowly increased to room temperature and stirring was continued for 4 hours at room temperature to prepare a lithium salt slurry. The solution was slowly added dropwise to a mixed solution containing 2.04 ml of a titanium tetrachloride solution (0.5 mmol/ml heptane solution, 1.02 mmol), 40 ml of diethyl ether and 20 ml of tetrahydrofuran which had been cooled to −78° C. After completion of the dropwise addition, stirring was continued while slowly increasing the temperature to room temperature. After further stirring for 15 hours at room temperature, the solvent of the reaction solution was distilled off. The resulting solid was reslurried with 100 ml of diethyl ether, and the insoluble portion was separated off with a glass filter. The filtered substance was washed with diethyl ether and dissolved in methylene chloride. After removing the insoluble portion, the filtrate was concentrated under reduced pressure, and the deposited solid was washed with hexane and dried under reduced pressure to obtain 0.12 g (0.19 mmol, 19% yield) of compound A-24 as an orange powder.

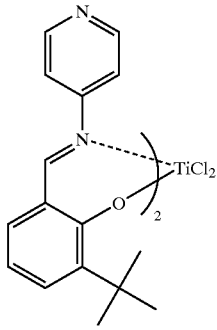

Compound A-24

$^1$H-NMR (CDCl$_3$): 0.80–2.30 (m, 18H), 6.30–9.20 (m, 14H), 8.35 (brs, 2H).

FD-mass spectrometry: 624 (M+).

Elemental analysis: Ti: 8.1% (7.7). Calculated value in parentheses.

Synthesis Example 49

Synthesis of Compound B-24

After charging 0.76 g (2.99 mmol) of compound L24 and 40 ml of diethyl ether into a 100 ml reactor which had been adequately dried and substituted with argon, they were cooled to −78° C. and stirred. After dropwise adding 1.91 ml of n-butyllithium (1.61 mmol/ml n-hexane solution, 3.08 mmol) over 5 minutes, the temperature was slowly increased to room temperature and stirring was continued for 4 hours at room temperature to prepare a lithium salt slurry. The solution was then added dropwise to a mixed solution of zirconium tetrachloride.2THF complex (0.563 g, 1.49 mmol) in 80 ml of tetrahydrofuran which had been cooled to −78° C. After completion of the dropwise addition, stirring was continued while slowly increasing the temperature to room temperature. After further stirring for 15 hours at room temperature, 50 ml of toluene was added, and the reaction solution was heated at 80° C. for 10 hours and then at 90° C. for 30 hours while stirring. The solvent of the reaction solution was distilled off, the resulting solid was reslurried with 150 ml of diethyl ether, and the insoluble portion was separated off with a glass filter. After washing the filtered substance with diethyl ether, it was dissolved in methylene chloride, the insoluble portion was removed out, and then the filtrate was concentrated under reduced pressure. The deposited solid was washed with hexane and dried under reduced pressure to obtain 0.43 g (0.64 mmol, 43% yield) of compound B-24 as a yellow powder represented by the formula given below.

Compound B-24

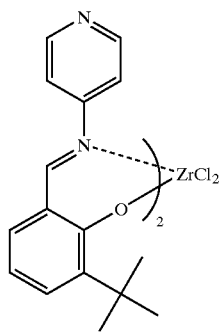

$^1$H-NMR (CDCl$_3$): 0.60–2.30 (m, 18H), 6.30–9.40 (m, 14H), 8.35 (brs, 2H).

FD-mass spectrometry: 668 (M+).

Elemental analysis: Zr: 13.2% (13.6). Calculated value in parentheses.

Synthesis Example 50

Synthesis of Compound A-25

After charging 0.50 g (1.93 mmol) of compound L25 and 20 ml of diethyl ether into a 100 ml reactor which had been adequately dried and substituted with argon, they were cooled to −78° C. and stirred. After dropwise adding 1.42 ml of n-butyllithium (1.55 mmol/ml n-hexane solution, 2.20 mmol) over 5 minutes, the temperature was slowly increased to room temperature and stirring was continued for 4 hours at room temperature to prepare a lithium salt solution. The solution was slowly added dropwise to a mixed solution containing 1.93 ml of a titanium tetrachloride solution (0.5 mmol/ml heptane solution, 0.97 mmol) and 50 ml of diethyl ether which had been cooled to −78° C. After completion of the dropwise addition, stirring was continued while slowly increasing the temperature to room temperature. After further stirring for 15 hours at room temperature, the reaction solution was filtered with a glass filter, and the filtered substance was washed with diethyl ether and dissolved in methylene chloride. After removing the insoluble portion, the filtrate was concentrated under reduced pressure, and the deposited solid was washed with hexane and dried under reduced pressure to obtain 0.11 g (0.17 mmol, 18% yield) of compound A-25 as a red brown powder.

Compound A-25

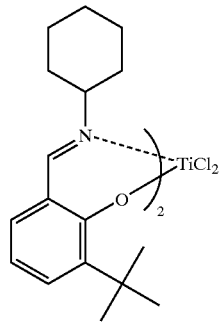

$^1$H-NMR (CDCl$_3$): 1.65 (s, 18H), 0.50–2.40 (m, 20H), 3.85 (brdt, 2H), 6.90–7.70 (m, 6H), 8.20 (s, 2H).

FD-mass spectrometry: 634 (M+).

Elemental analysis: Ti: 7.6% (7.5). Calculated value in parentheses

Synthesis Example 51

Synthesis of Compound B-25

After charging 0.50 g (1.93 mmol) of compound L25 and 20 ml of diethyl ether into a 100 ml reactor which had been adequately dried and substituted with argon, they were cooled to −78° C. and stirred. After dropwise adding 1.42 ml of n-butyllithium (1.55 mmol/ml n-hexane solution, 2.20 mmol) over 5 minutes, the temperature was slowly increased to room temperature and stirring was continued for 4 hours at room temperature to prepare a lithium salt solution. The solution was then added dropwise to a solution of zirconium tetrachloride (0.23 g, 0.99 mmol) in 50 ml of diethyl ether which had been cooled to −78° C. After completion of the dropwise addition, stirring was continued while slowly increasing the temperature to room temperature. After further stirring for 15 hours at room temperature, the reaction solution was filtered with a glass filter, and the filtrate was concentrated under reduced pressure. The deposited solid was washed with hexane and dried under reduced pressure to obtain 0.28 g (0.41 mmol, 43% yield) of compound B-25 as an ocher powder represented by the formula given below.

Compound B-25

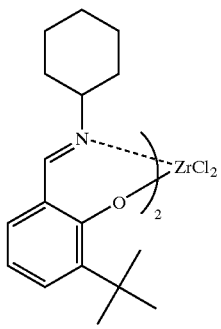

¹H-NMR (CDCl₃): 1.65 (s, 18H), 0.70–2.50 (m, 20H), 3.85 (brdt, 2H), 6.70–7.70 (m, 6H), 8.25 (s, 2H).

FD-mass spectrometry: 678 (M+).

Elemental analysis: Zr: 13.3% (13.4). Calculated value in parentheses.

Synthesis Example 52

Synthesis of Compound A-26

After charging 0.61 g (2.28 mmol) of compound L26 and 10 ml of diethyl ether into a 100 ml reactor which had been adequately dried and substituted with argon, they were cooled to −78° C. and stirred. After dropwise adding 1.6 ml of n-butyllithium (1.55 mmol/ml n-hexane solution, 2.48 mmol) over 5 minutes, the temperature was slowly increased to room temperature, and stirring was continued for 4 hours at room temperature to prepare a lithium salt solution. The solution was then slowly added dropwise to a mixed solution containing 2.2 ml of a titanium tetrachloride solution (0.5 mmol/ml heptane solution, 1.10 mmol) and 10 ml of tetrahydrofuran which had been cooled to −78° C. After completion of the dropwise addition, stirring was continued while slowly increasing the temperature to room temperature. After further stirring for 12 hours at room temperature, the insoluble portion was filtered out with a glass filter, the filtrate was concentrated under reduced pressure, and the deposited solid was reprecipitated with diethyl ether and hexane at −78° C. and dried under reduced pressure to obtain 0.36 g (0.55 mmol, 51% yield) of compound A-26 as a brown powder.

Compound A-26

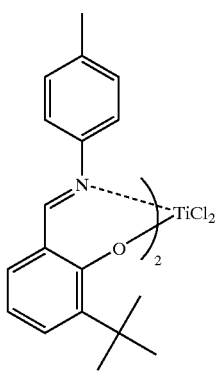

¹H-NMR (CDCl₃): 1.33 (s, 18H), 2.14 (s, 6H), 6.60–7.68 (m, 14H), 8.03 (s, 2H).

FD-mass spectrometry: 650 (M+).

Elemental analysis: Ti: 7.4% (7.3). Calculated value in parentheses.

Synthesis Example 53

Synthesis of Compound B-26

After charging 0.61 g (2.28 mmol) of compound L26 and 10 ml of diethyl ether into a 100 ml reactor which had been adequately dried and substituted with argon, they were cooled to −78° C. and stirred. After dropwise adding 1.6 ml of n-butyllithium (1.55 mmol/ml n-hexane solution, 2.48 mmol) over 5 minutes, the temperature was slowly increased to room temperature, and stirring was continued for 4 hours at room temperature to prepare a lithium salt solution. The solution was then added dropwise to a solution of zirconium tetrachloride (0.27 g, 1.15 mmol) in 10 ml of diethyl ether which had been cooled to −78° C. After completion of the dropwise addition, stirring was continued while slowly increasing the temperature to room temperature. After further stirring for 12 hours at room temperature, the insoluble portion was removed with a glass filter. The filtrate was concentrated under reduced pressure, and the deposited solid was reprecipitated with diethyl ether and hexane and dried under reduced pressure to obtain 0.14 g (0.20 mmol, 18% yield) of compound B-26 as a yellow green powder represented by the formula given below.

Compound B-26

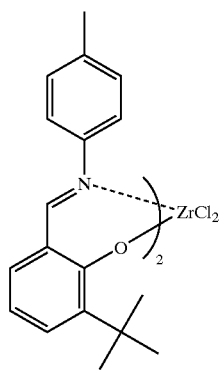

¹H-NMR (CDCl₃): 1.31 (s, 18H), 2.14 (s, 6H), 6.69–7.65 (m, 14H), 8.09 (s, 2H).

FD-mass spectrometry: 694 (M+).

Elemental analysis: Zr: 13.1% (13.1). Calculated value in parentheses.

Synthesis Example 54

Synthesis of Compound A-27

After charging 0.30 g (1.00 mmol) of compound L27 and 10 ml of diethyl ether into a 100 ml reactor which had been adequately dried and substituted with argon, they were cooled to −78° C. and stirred. After dropwise adding 0.65 ml of n-butyllithium (1.55 mmol/ml n-hexane solution, 1.00 mmol) over 5 minutes, the temperature was slowly increased to room temperature, and stirring was continued for 4 hours at room temperature to prepare a lithium salt solution. The solution was then slowly added dropwise to a mixed solution containing 1.0 ml of a titanium tetrachloride solution (0.5 mmol/ml heptane solution, 0.50 mmol) and 10 ml of diethyl ether which had been cooled to −78° C. After completion of the dropwise addition, stirring was continued while slowly increasing the temperature to room temperature. After first stirring for 12 hours at room temperature and then stirring for one hour under reflux, the insoluble portion was filtered out with a glass filter. The filtrate was concentrated under reduced pressure, and the deposited solid was reprecipitated with diethyl ether and hexane and dried under reduced pressure to obtain 0.18 g (0.25 mmol, 50% yield) of compound A-27 as an orange powder.

Compound A-27

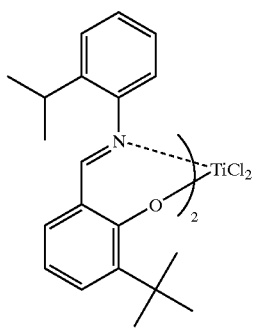

¹H-NMR (CDCl₃): 1.13 (s, 18H), 1.25 (brd, 6H), 1.28 (brd, 6H), 3.29 (brdq, 2H), 6.45–6.70 (m, 2H), 6.80–7.20 (m, 4H), 7.20–7.50 (m, 8H), 8.23 (s, 2H).

FD-mass spectrometry: 706 (M+).

Elemental analysis: Ti: 6.8% (6.8). Calculated value in parentheses.

Synthesis Example 55

Synthesis of Compound B-27

After charging 0.95 g (3.20 mmol) of compound L27 and 10 ml of diethyl ether into a 100 ml reactor which had been adequately dried and substituted with argon, they were cooled to −78° C. and stirred. After dropwise adding 2.08 ml of n-butyllithium (1.55 mmol/ml n-hexane solution, 3.22 mmol) over 5 minutes, the temperature was slowly increased to room temperature, and stirring was continued for 4 hours at room temperature to prepare a lithium salt solution. The solution was then added dropwise to a solution of zirconium tetrachloride (0.37 g, 1.60 mmol) in 10 ml of tetrahydrofuran which had been cooled to −78° C. After completion of the dropwise addition, stirring was continued while slowly increasing the temperature to room temperature. After first stirring for 12 hours at room temperature and then stirring for 6 hours under reflux, the solvent of the reaction solution was distilled off. The resulting solid was dissolved in 50 ml of methylene chloride, and the insoluble portion was removed with a glass filter. The filtrate was concentrated under reduced pressure, and the deposited solid was reprecipitated with methylene chloride and hexane and dried under reduced pressure to obtain 0.18 g (0.24 mmol, 15% yield) of compound B-27 as a yellow powder.

Compound B-27

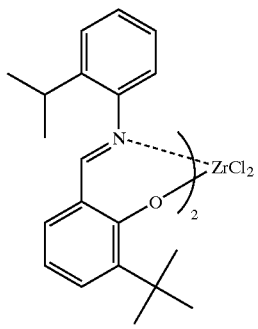

¹H-NMR (CDCl₃): 1.10 (s, 18H), 1.10–1.40 (m, 12H), 3.20–3.30 (m, 2H), 6.30–6.60 (m, 2H), 6.70–7.10–7.60 (m, 8H), 8.28 (s, 2H).

FD-mass spectrometry: 750 (M+).

Elemental analysis: Zr: 12.0% (12.2), C: 63.5% (64.0) H: 6.6% (6.4) N: 3.5% (3.7). Calculated values in parentheses.

Synthesis Example 56

Synthesis of Compound A-28

After charging 0.50 g (1.37 mmol) of compound L28 and 40 ml of diethyl ether into a 100 ml reactor which had been adequately dried and substituted with argon, they were cooled to −78° C. and stirred. After dropwise adding 0.92 ml of n-butyllithium (1.55 mmol/ml n-hexane solution, 1.43 mmol) over 5 minutes, the temperature was slowly increased to room temperature and stirring was continued for 4 hours at room temperature to prepare a lithium salt solution. The solution was then slowly added dropwise to a mixed solution containing 1.37 ml of a titanium tetrachloride solution (0.5 mmol/ml heptane, 0.69 mmol) and 40 ml of diethyl ether which had been cooled to −78° C. After completion of the dropwise addition, stirring was continued while slowly increasing the temperature to room temperature. After further stirring for 8 hours at room temperature, the reaction solution was filtered with a glass filter, the filtered substance was washed with diethyl ether, and then the insoluble portion was removed out by filtration. The filtrate was concentrated under reduced pressure, and the deposited solid was washed with hexane and dried under reduced pressure to obtain 0.17 g (0.20 mmol, 29% yield) of compound A-28 as a brown powder.

Compound A-28

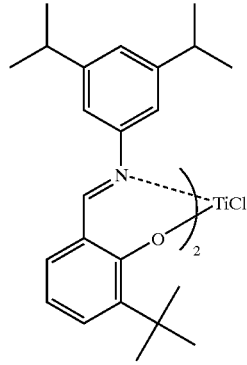

¹H-NMR (CDCl₃): 0.70–1.40 (m, 54H), 6.65–7.75 (m, 12H), 8.35 (s, 2H).

FD-mass spectrometry: 846 (M+).

Elemental analysis: Ti: 5.5% (5.7). Calculated value in parentheses.

Synthesis Example 57

Synthesis of Compound B-28

After charging 0.50 g (1.37 mmol) of compound L28 and 40 ml of diethyl ether into a 100 ml reactor which had been adequately dried and substituted with argon, they were cooled to −78° C. and stirred. After dropwise adding 0.92 ml of n-butyllithium (1.55 mmol/ml n-hexane solution, 1.43 mmol) over 5 minutes, the temperature was slowly increased to room temperature and stirring was continued for 4 hours at room temperature to prepare a lithium salt solution. The solution was then added dropwise to a mixed solution of zirconium tetrachloride (0.16 g, 0.69 mmol) in 20 ml of anhydrous diethyl ether and 50 ml of tetrahydrofuran which had been cooled to −78° C. After completion of the dropwise addition, stirring was continued while slowly increasing the temperature to room temperature. After further stirring for 12 hours at room temperature, the solvent of the reaction solution was distilled off. The resulting solid was reslurried with diethyl ether, the insoluble portion was removed off with a glass filter, and the filtrate was concentrated under reduced pressure. The deposited solid was reprecipitated with hexane at −78° C. and dried under reduced pressure to obtain 0.26 g (0.29 mmol, 43% yield) of compound B-28 as a yellow powder represented by the formula given below.

Compound B-28

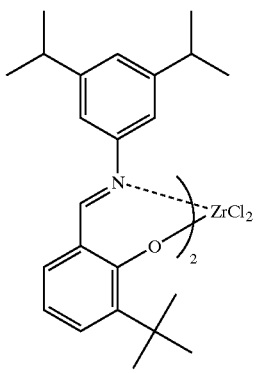

¹H-NMR (CDCl₃): 0.80–1.30 (m, 54H), 6.65 (m, 12H), 8.35 (s, 2H).

FD-mass spectrometry: 890 (M+).

Elemental analysis: Zr: 9.9% (10.2). Calculated value in parentheses.

Synthesis Example 58

Synthesis of Compound A-29

After charging 0.60 g (1.79 mmol) of compound L29 and 40 ml of diethyl ether into a 100 ml reactor which had been adequately dried and substituted with argon, they were cooled to −78° C. and stirred. After dropwise adding 1.17 ml of n-butyllithium (1.55 mmol/ml n-hexane solution, 1.81 mmol) over 5 minutes, the temperature was slowly increased to room temperature, and stirring was continued for 4 hours at room temperature to prepare a lithium salt solution. The solution was then slowly added dropwise to a mixed solution containing 1.79 ml of a titanium tetrachloride solution (0.5 mmol/ml heptane solution, 0.90 mmol) and 50 ml of diethyl ether which had been cooled to −78° C. After completion of the dropwise addition, stirring was continued while slowly increasing the temperature to room temperature. After stirring for 12 hours at room temperature, the reaction solution was filtered with a glass filter to remove the insoluble portion. The filtrate was concentrated under reduced pressure, and the deposited solid was washed with hexane and dried under reduced pressure to obtain 0.10 g (0.13 mmol, 14% yield) of compound A-29 as a red brown powder.

Compound A-29

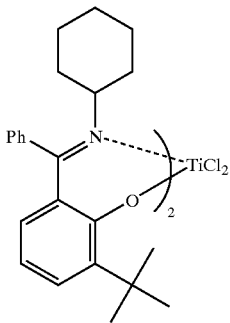

¹H-NMR (CDCl₃): 0.80–2.30 (m, 20H), 1.55 (s, 18H), 3.65 (brdt, 2H), 6.60–8.10 (m, 16H).

FD-mass spectrometry: 786 (M+).

Elemental analysis: Ti: 6.4% (6.1). Calculated value in parentheses.

Synthesis Example 59

Synthesis of Compound B-29

After charging 0.50 g (1.48 mmol) of compound L29 and 40 ml of diethyl ether into a 100 ml reactor which had been adequately dried and substituted with argon, they were cooled to −78° C. and stirred. After dropwise adding 1.02 ml of n-butyllithium (1.61 mmol/ml n-hexane solution, 1.64 mmol) over 5 minutes, the temperature was slowly increased to room temperature and stirring was continued for 4 hours at room temperature to prepare a lithium salt solution. The solution was then added dropwise to a solution of zirconium tetrachloride.2THF complex (0.26 g, 0.69 mmol) in 40 ml of tetrahydrofuran which had been cooled to −78° C. After completion of the dropwise addition, stirring was continued while slowly increasing the temperature to room temperature. After further stirring for 8 hours at room temperature, 70 ml of toluene was added, the reaction solution was heated at 80° C. for 20 hours while stirring. The solvent of the reaction solution was distilled off, the resulting solid was reslurried with 50 ml of diethyl ether. The slurry was filtered with a glass filter to remove off the insoluble portion, and then the filtrate was concentrated under reduced pressure. The deposited solid was reprecipitated with hexane at −78° C. and dried under reduced pressure to obtain 0.04 g (0.05 mmol, 7% yield) of compound B-29 as a yellowish white powder represented by the formula given below.

Compound B-29

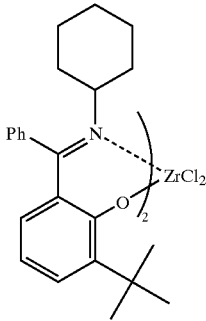

¹H-NMR (CDCl₃): 0.90–1.90 (m, 20H), 1.55 (s, 18H), 3.25 (brdt, 2H), 6.40–7.90 (m, 16H).

FD-mass spectrometry: 830 (M+).

Elemental analysis: Zr: 11.3% (11.0). Calculated value in parentheses.

Synthesis Example 60

Synthesis of Compound A-30

After charging 0.51 g (1.86 mmol) of compound L30 and 50 ml of diethyl ether into a 100 ml reactor which had been adequately dried and substituted with argon, they were cooled to −78° C. and stirred. After dropwise adding 1.20 ml of n-butyllithium (1.61 mmol/ml n-hexane solution, 1.93 mmol) over 5 minutes, the temperature was slowly increased to room temperature, and stirring was continued for 4 hours at room temperature to prepare a lithium salt solution. The solution was then slowly added dropwise to a solution containing 1.85 ml of a titanium tetrachloride solution (0.5 mmol/ml heptane solution, 0.93 mmol) and 60 ml of tetrahydrofuran which had been cooled to −78° C. After completion of the dropwise addition, stirring was continued while slowly increasing the temperature to room temperature. Further stirring for 8 hours at room temperature, the reaction solution was heated at 60° C. for 8 hours while stirring, and the solvent was then distilled off. The resulting solid was reslurried with diethyl ether and filtered with a glass filter, and the filtered substance was washed with diethyl ether and then dissolved in methylene chloride. After removal of the insoluble portion by filtration, the filtrate was concentrated under reduced pressure, and the deposited solid was washed with hexane and dried under reduced pressure to obtain 0.14 g (0.21 mmol, 23% yield) of compound A-30 as a red orange powder.

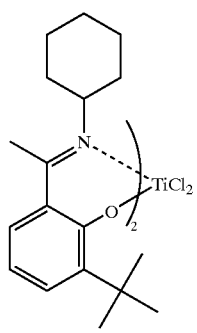

Compound A-30

$^1$H-NMR (CDCl$_3$): 1.10–2.10 (m, 20H), 1.45 (s, 18H), 2.40 (s, 6H), 3.85 (brdt, 2H), 6.70–7.70 (m, 6H).

FD-mass spectrometry: 662 (M+).

Elemental analysis: Ti: 7.1% (7.2). Calculated value in parentheses.

Synthesis Example 61

Synthesis of Compound B-30

After charging 0.51 g (1.86 mmol) of compound L30 and 50 ml of diethyl ether into a 100 ml reactor which had been adequately dried and substituted with argon, they were cooled to −78° C. and stirred. After dropwise adding 1.20 ml of n-butyllithium (1.61 mmol/ml n-hexane solution, 1.93 mmol) over 5 minutes, the temperature was slowly increased to room temperature and stirring was continued for 4 hours at room temperature to prepare a lithium salt solution. The solution was added dropwise to a solution of zirconium tetrachloride (0.22 g, 0.94 mmol) in 60 ml of tetrahydrofuran which had been cooled to −78° C. After completion of the dropwise addition, stirring was continued while slowly increasing the temperature to room temperature. After further stirring for 12 hours at room temperature, 60 ml of toluene was added, and the reaction solution was heated at 85° C. for 12 hours while stirring.

The solvent of the reaction solution was distilled off. The resulting solid was reslurried with 100 ml of diethyl ether, the slurry was filtered with a glass filter to remove off the insoluble portion, and then the filtrate was concentrated under reduced pressure. The deposited solid was washed with hexane and dried under reduced pressure to obtain 0.10 g (0.14 mmol, 15% yield) of compound B-30 as a milky white powder represented by the formula given below.

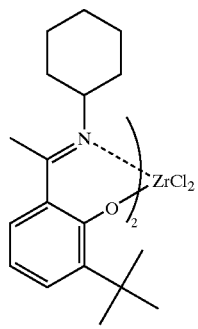

Compound B-30

$^1$H-NMR (CDCl$_3$): 0.80–2.10 (m, 20H), 1.45 (s, 18H), 2.40 (s, 6H), 3.75 (brdt, 2H), 6.50–7.80 (m, 6H).

FD-mass spectrometry: 704 (M+).

Elemental analysis: Zr: 13.3% (12.9). Calculated value in parentheses.

Synthesis Example 62

Synthesis of Compound A-31

After charging 1.00 g (4.22 mmol) of compound L31 and 20 ml of diethyl ether into a 100 ml reactor which had been adequately dried and substituted with argon, they were cooled to −78° C. and stirred. After dropwise adding 2.75 ml of n-butyllithium (1.61 mmol/ml n-hexane solution, 4.43 mmol) over 5 minutes, the temperature was slowly increased to room temperature, and stirring was continued for 4 hours at room temperature to prepare a lithium salt solution. The solution was then slowly added dropwise to a mixed solution containing 4.22 ml of a titanium tetrachloride solution (0.5 mmol/ml heptane solution, 2.11 mmol) and 20 ml of diethyl ether which had been cooled to −78° C.

After completion of the dropwise addition, stirring was continued while-slowly increasing the temperature to room temperature. After stirring for 12 hours at room temperature, the reaction solution was filtered with a glass filter. The filtered substance was dissolved in 50 ml of methylene chloride, and the insoluble portion was removed. The filtrate was evaporated to dryness under reduced pressure, and the resulting solid was reprecipitated with methylene chloride and diethyl ether and dried under reduced pressure to obtain 0.90 g (1.55 mmol, 72% yield) of compound A-31 as a brown powder.

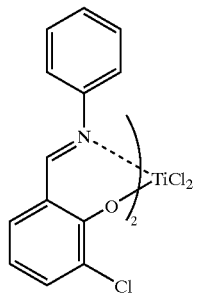

Compound A-31

$^1$H-NMR (CDCl$_3$): 6.70–7.40 (m, 16H), 7.90–8.20 (m, 2H).

FD-mass spectrometry: 578 (M+).

Elemental analysis: Ti: 8.0% (8.3). Calculated value in parentheses.

Synthesis Example 63

Synthesis of Compound B-31

After charging 1.20 g (5.18 mmol) of compound L31 and 24 ml of diethyl ether into a 100 ml reactor which had been adequately dried and substituted with argon, they were cooled to −78° C. and stirred. After dropwise adding 3.38 ml of n-butyllithium (1.61 mmol/ml n-hexane solution, 5.44 mmol) over 5 minutes, the temperature was slowly increased to room temperature, and stirring was continued for 4 hours at room temperature to prepare a lithium salt solution. The solution was then added dropwise to a mixed solution containing zirconium tetrachloride (0.60 g, 2.57 mmol) and 24 ml of diethyl ether which had been cooled to −78° C. After completion of the dropwise addition, stirring was continued while slowly increasing the temperature to room temperature. After stirring for 12 hours at room temperature, the reaction solution was filtered with a glass filter. The filtered substance was dissolved in 60 ml of methylene chloride and the insoluble portion was removed. The filtrate was concentrated under reduced pressure, and the deposited solid was reprecipitated with methylene chloride and hexane and dried under reduced pressure to obtain 0.20 g (0.32 mmol, 12% yield) of compound B-31 as a green powder.

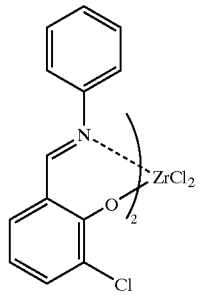

Compound B-31

$^1$H-NMR (CDCl$_3$): 6.70–7.45 (m, 16H), 7.90–8.25 (m, 2H).

FD-mass spectrometry: 621 (M+).

Elemental analysis: Zr: 14.9% (14.6). Calculated value in parentheses.

Synthesis Example 64

Synthesis of Compound A-32

After charging 1.00 g (5.05 mmol) of compound L32 and 50 ml of diethyl ether into a 100 ml reactor which had been adequately dried and substituted with argon, they were cooled to −78° C. and stirred. After dropwise adding 3.25 ml of n-butyllithium (1.63 mmol/ml n-hexane solution, 5.30 mmol) over 5 minutes, the temperature was slowly increased to room temperature, and stirring was continued for 4 hours at room temperature to prepare a lithium salt solution. The solution was cooled to −78° C., and then 2.52 ml of a titanium tetrachloride solution (0.5 mmol/ml heptane solution, 1.26 mmol) was slowly added dropwise. After completion of the dropwise addition, stirring was continued while slowly increasing the temperature to room temperature. After further stirring for 12 hours at room temperature, the reaction solution was filtered with a glass filter and the filtered substance was washed with diethyl ether followed by dissolution in methylene chloride. After removal of the insoluble portion, the filtrate was concentrated under reduced pressure, and the deposited solid was washed with hexane and dried under reduced pressure to obtain 0.23 g (0.45 mmol, 18% yield) of compound A-32 as an orange powder.

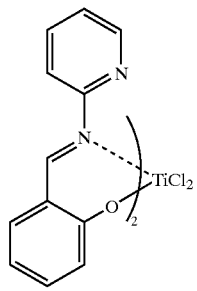

Compound A-32

FD-mass spectrometry: 512 (M+).

Synthesis Example 65

Synthesis of Compound A-33

After charging 1.09 g (4.39 mmol) of compound L33 and 70 ml of diethyl ether into a 100 ml reactor which had been adequately dried and substituted with argon, they were cooled to −78° C. and stirred. After dropwise adding 2.80 ml of n-butyllithium (1.63 mmol/ml n-hexane solution, 4.56 mmol) over 5 minutes, the temperature was slowly increased to room temperature, and stirring was continued for 4 hours at room temperature to prepare a lithium salt solution. The solution was cooled to −78° C., and then 8.78 ml of a titanium tetrachloride solution (0.5 mmol/ml heptane solution, 4.39 mmol) was slowly added dropwise. After completion of the dropwise addition, stirring was continued while slowly increasing the temperature to room temperature. After further stirring for 12 hours at room temperature, the reaction solution was filtered with a glass filter and the filtered substance was washed with diethyl ether followed by dissolution in methylene chloride. After removal of the insoluble portion, the filtrate was concentrated under reduced pressure, and the deposited solid was washed with diethyl ether and dried under reduced pressure to obtain 0.22 g (0.36 mmol, 16% yield) of compound A-33 as a brown powder.

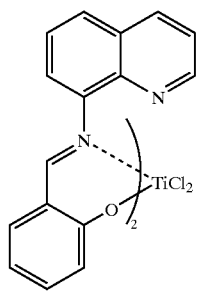

Compound A-33

FD-mass spectrometry: 612 (M+).

Synthesis Example 66

Synthesis of Compound A-34

After charging 0.60 g (2.13 mmol) of compound L34 and 40 ml of diethyl ether into a 100 ml reactor which had been adequately dried and substituted with argon, they were cooled to −78° C. and stirred. After dropwise adding 2.75 ml of n-butyllithium (1.63 mmol/ml n-hexane solution, 4.48 mmol) over 5 minutes, the temperature was slowly increased to room temperature, and stirring was continued for 4 hours at room temperature to prepare a lithium salt solution. The solution was cooled to −78° C., and then 0.71 g (2.13 mmol) of a titanium tetrachloride.tetrahydrofuran complex was slowly added. After completion of the addition, stirring was continued while slowly increasing the temperature to room temperature. After further stirring for 8 hours at room temperature, the reaction solution was filtered with a glass filter and the filtered substance was washed with diethyl ether followed by dissolution in methylene chloride. After removal of the insoluble portion, the filtrate was concentrated under reduced pressure, and the deposited solid was washed with hexane and dried under reduced pressure to obtain 0.19 g (0.48 mmol, 23% yield) of compound A-34 as a red powder.

Compound A-34

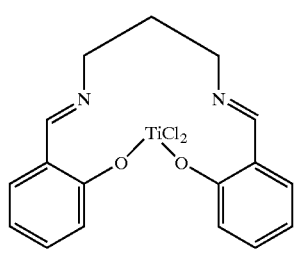

FD-mass spectrometry: 398 (M+).

Synthesis Example 67

Synthesis of Compound A-35

After charging 0.19 g of sodium hydride (60 wt % product, 4.75 mmol) and 50 ml of tetrahydrofuran into a 100 ml reactor which had been adequately dried and substituted with argon, a solution of 1.00 g (2.30 mmol) of compound L35 in 20 ml of tetrahydrofuran was added dropwise over 5 minutes while stirring at room temperature, after which the temperature was slowly increased to room temperature, and stirring was continued for 2 hours at 50° C. to prepare a sodium salt solution. The solution was then slowly added dropwise to a solution of 0.77 g (2.31 mmol) of a titanium tetrachloride.tetrahydrofuran complex in 50 ml of tetrahydrofuran while stirring at room temperature. After completion of the dropwise addition, stirring was continued while slowly increasing the temperature to room temperature. After further stirring for 8 hours at room temperature, the reaction solution was filtered with a glass filter and the filtered substance was washed with diethyl ether followed by removal of the insoluble portion. The filtrate was concentrated under reduced pressure, the deposited solid was reslurried with diethyl ether, the reaction solution was filtered with a glass filter. The filtered substance was washed with diethyl ether and dissolved in methylene chloride, and the impurities were removed. The filtrate was concentrated under reduced pressure, and the deposited solid was washed with hexane and dried under reduced pressure to obtain 1.10 g (2.00 mmol, 87% yield) of compound A-35 as a red orange powder.

Compound A-35

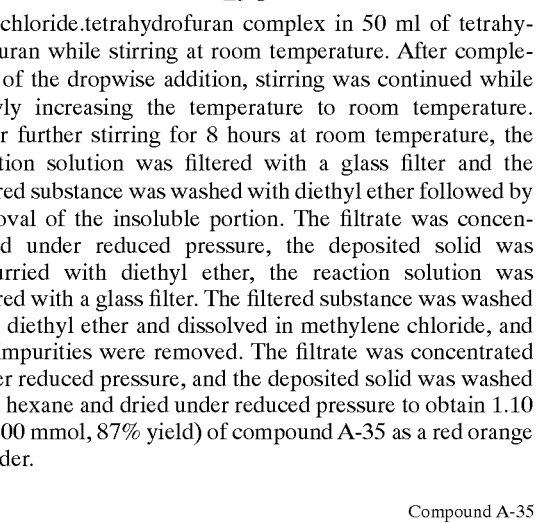

FD-mass spectrometry: 550 (M+).

Synthesis Example 68

Synthesis of Compound A-36

After charging 0.19 g of sodium hydride (60 wt % product, 4.75 mmol) and 50 ml of tetrahydrofuran into a 100 ml reactor which had been adequately dried and substituted with argon, a solution of 1.00 g (2.23 mmol) of compound L36 in 20 ml of tetrahydrofuran was added dropwise over 5 minutes while stirring at room temperature, after which the temperature was slowly increased to room temperature, and stirring was continued for 2 hours at 50° C. to prepare a sodium salt solution. The solution was cooled to −78° C., and then 4.50 ml of a titanium tetrachloride solution (0.5 mmol/ml heptane solution, 2.25 mmol) was slowly added dropwise. After completion of the dropwise addition, stirring was continued while slowly increasing the temperature to room temperature. After further stirring for 8 hours at room temperature, the reaction solution was filtered with a glass filter and the filtered substance was washed with diethyl ether and dissolved in methylene chloride. After removal of the insoluble portion, the filtrate was concentrated under reduced pressure, and the deposited solid was washed with hexane and dried under reduced pressure to obtain 0.55 g (0.97 mmol, 44% yield) of compound A-36 as an orange powder.

Compound A-36

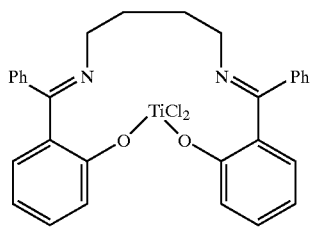

FD-mass spectrometry: 564 (M+).

Synthesis Example 69

Synthesis of Compound B-37

After charging 0.30 g of sodium hydride (60 wt % product, 7.50 mmol) and 50 ml of tetrahydrofuran into a 100 ml reactor which had been adequately dried and substituted with argon, a solution of 1.00 g (3.16 mmol) of compound L37 in 20 ml of tetrahydrofuran was added dropwise over 5 minutes while stirring at room temperature, after which the temperature was slowly increased to room temperature, and stirring was continued for 2 hours at 60° C. to prepare a sodium salt solution. The solution was then slowly added dropwise to a solution of 1.19 g (3.15 mmol) of zirconium tetrachloride.2THF complex in 50 ml of tetrahydrofuran while stirring at room temperature. After completion of the dropwise addition, stirring was continued while slowly increasing the temperature to room temperature. After further stirring for 8 hours at room temperature, the reaction solution was filtered with a glass filter, the filtered substance was washed with tetrahydrofuran and the insoluble portion was removed. The filtrate was concentrated under reduced pressure to about ⅓, the deposited solid was filtered with a glass filter, and the filtered substance was washed with cold tetrahydrofuran and dried under reduced pressure to obtain 1.00 g (2.10 mmol, 66% yield) of compound B-37 as a yellow powder.

Compound B-37

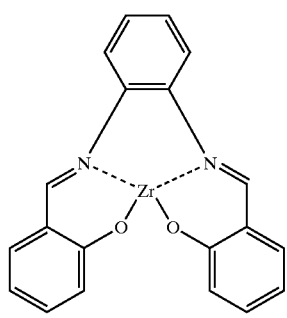

FD-mass spectrometry: 474 (M+).

Synthesis Example 70

Synthesis of Compound B-38

After charging 0.23 g of sodium hydride (60 wt % product, 5.75 mmol) and 50 ml of tetrahydrofuran into a 100 ml reactor which had been adequately dried and substituted with argon, a solution of 1.00 g (2.73 mmol) of compound L38 in 20 ml of tetrahydrofuran was added dropwise over 5 minutes while stirring at room temperature, after which the temperature was slowly increased to room temperature, and stirring was continued for 2 hours at 50° C. to prepare a sodium salt solution. The solution was then slowly added dropwise to a solution of 1.03 g (2.73 mmol) of zirconium tetrachloride.2THF complex in 50 ml of tetrahydrofuran while stirring at room temperature. After completion of the dropwise addition, stirring was continued while slowly increasing the temperature to room temperature. After further stirring for 8 hours at room temperature, the reaction solution was filtered with a glass filter, the filtered substance was washed with tetrahydrofuran and the insoluble portion was removed by filtration. The filtrate was allowed to stand for 2 hours, upon which a solid was deposited. The deposited solid was filtered with a glass filter, and the filtered substance was washed with cold tetrahydrofuran and dried under reduced pressure to obtain 1.15 g (2.18 mmol, 80% yield) of compound B-38 as a yellow powder.

Compound B-38

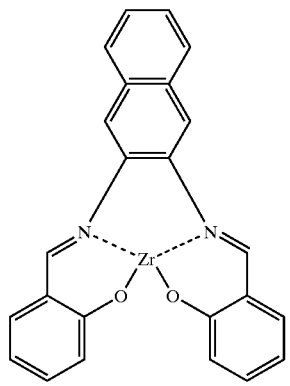

FD-mass spectrometry: 524 (M+).

Synthesis Example 71

Synthesis of Compound A-39

After charging 0.50 g (1.87 mmol) of compound L39 and 50 ml of diethyl ether into a 100 ml reactor which had been adequately dried and substituted with argon, they were cooled to −78° C. and stirred. After dropwise adding 1.20 ml of n-butyllithium (1.61 mmol/ml n-hexane solution, 1.93 mmol) over 5 minutes, the temperature was slowly increased to room temperature, and stirring was continued for 4 hours at room temperature to prepare a lithium salt solution. The solution was slowly added dropwise to a mixed solution containing 1.87 ml of a titanium tetrachloride solution (0.5 mmol/ml heptane solution, 0.94 mmol) and 70 ml of diethyl ether which had been cooled to −78° C. After completion of the dropwise addition, stirring was continued while slowly increasing the temperature to room temperature. After further stirring for 8 hours at room temperature, the reaction solution was filtered with a glass filter, and the filtered substance was washed with diethyl ether and then dissolved in methylene chloride. The insoluble portion was removed, the filtrate was then concentrated under reduced pressure, and the deposited solid was washed with hexane and dried under reduced pressure to obtain 0.11 g (0.17 mmol, 18% yield) of compound A-39 as a red powder.

Compound A-39

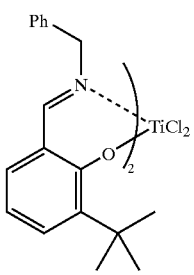

¹H-NMR (CDCl₃): 1.65 (s, 18H), 4.65 (d, 2H), 5.00 (d, 2H), 6.75–7.70 (m, 16H), 7.75 (s, 2H).

FD-mass spectrometry: 650 (M+).

Elemental analysis: Ti: 7.2% (7.3). Calculated value in parentheses.

Synthesis Example 72

Synthesis of Compound B-39

After charging 0.50 g (1.87 mmol) of compound L39 and 40 ml of diethyl ether into a 100 ml reactor which had been adequately dried and substituted with argon, they were cooled to −78° C. and stirred. After dropwise adding 1.20 ml of n-butyllithium (1.61 mmol/ml n-hexane solution, 1.93 mmol) over 5 minutes, the temperature was slowly increased to room temperature and stirring was continued for 4 hours at room temperature to prepare a lithium salt solution. The solution was then added dropwise to a solution of zirconium tetrachloride.2THF complex (0.352 g, 0.93 mmol) in 50 ml of tetrahydrofuran which had been cooled to −78° C. After completion of the dropwise addition, stirring was continued while slowly increasing the temperature to room temperature. After further stirring for 8 hours at room temperature, the reaction solution was heated at 60° C. for 3 hours while stirring, and the solvent was then distilled off. The resulting solid was reslurried with 50 ml of diethyl ether and the insoluble portion was separated off with a glass filter. The filtered substance was washed with 100 ml of diethyl ether and dissolved in methylene chloride, the insoluble portion was removed off, and the filtrate was concentrated under reduced pressure. The deposited solid was washed with hexane and dried under reduced pressure to obtain 0.30 g (0.43 mmol, 46% yield) of compound B-39 as a yellowish white powder represented by the formula given below.

Compound B-39

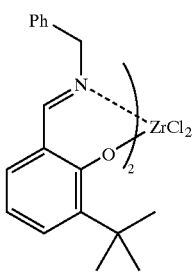

¹H-NMR (CDCl₃): 1.60 (s, 18H), 4.65 (d, 2H), 4.95 (d, 2H), 6.70–7.70 (m, 16H), 7.85 (s, 2H).

FD-mass spectrometry: 694 (M+).

Elemental analysis: Zr: 12.9% (13.1). Calculated value in parentheses.

Synthesis Example 73

Synthesis of Compound A-40

After charging 0.58 g (2.02 mmol) of compound L40 and 40 ml of diethyl ether into a 100 ml reactor which had been adequately dried and substituted with argon, they were cooled to −78° C. and stirred. After dropwise adding 1.50 ml of n-butyllithium (1.61 mmol/ml n-hexane solution, 2.42 mmol) over 5 minutes, the temperature was slowly increased to room temperature and stirring was continued for 4 hours at room temperature to prepare a lithium salt solution. The solution was then slowly added dropwise to a mixed solution containing 2.00 ml of a titanium tetrachloride solution (0.5 mmol/ml heptane solution, 1.00 mmol) and 80 ml of diethyl ether which had been cooled to −78° C. After completion of the dropwise addition, stirring was continued while slowly increasing the temperature to room temperature. After further stirring for 8 hours at room temperature, the reaction solution was filtered with a glass filter, the insoluble portion was removed, and the filtrate was concentrated under reduced pressure. The deposited solid was reprecipitated with hexane at −78° C. and dried under reduced pressure to obtain 0.19 g (0.28 mmol, 28% yield) of compound A-40 as a red orange powder.

Compound A-40

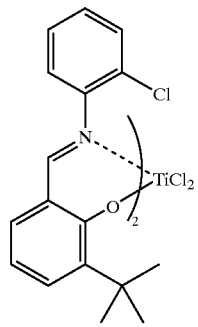

¹H-NMR (CDCl₃): 0.80–1.80 (m, 18H), 6.50–7.90 (m, 14H), 8.00–8.20 (m, 2H).

FD-mass spectrometry: 692 (M+).

Elemental analysis: Ti: 7.0% (6.9). Calculated value in parentheses.

Synthesis Example 74

Synthesis of Compound B-40

After charging 0.58 g (2.02 mmol) of compound L40 and 40 ml of diethyl ether into a 100 ml reactor which had been adequately dried and substituted with argon, they were cooled to −78° C. and stirred. After dropwise adding 1.50 ml of n-butyllithium (1.61 mmol/ml n-hexane solution, 2.42 mmol) over 5 minutes, the temperature was slowly increased to room temperature and stirring was continued for 4 hours at room temperature to prepare a lithium salt solution. The solution was then slowly added dropwise to a mixed solution containing a zirconium tetrachloride.2THF complex (0.38 g, 1.00 mmol) and 80 ml of tetrahydrofuran which had been cooled to −78° C. After completion of the dropwise addition, stirring was continued while slowly increasing the temperature to room temperature. After further stirring for 8 hours at room temperature, the solvent of the reaction solution was distilled off. The resulting solid was reslurried with 150 ml of diethyl ether, the insoluble portion was removed off with a glass filter, and then the filtrate was concentrated under reduced pressure. The deposited solid was reprecipitated with hexane at −78° C. and dried under reduced pressure to obtain 0.23 g (0.31 mmol, 31% yield) of compound B-40 as a yellow powder represented by the formula given below.

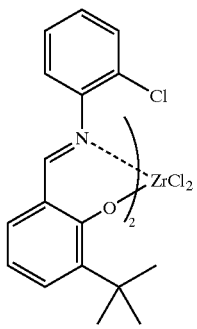

Compound B-40

¹H-NMR (CDCl₃): 0.80–1.70 (m, 18H), 6.50–7.90 (m, 14H), 8.20 (s, 2H).

FD-mass spectrometry: 734 (M+).

Elemental analysis: Zr: 12.2% (12.4). Calculated value in parentheses.

Synthesis Example 75

Synthesis of Compound A-41

After charging 0.50 g (1.15 mmol) of compound L41 and 10 ml of diethyl ether into a 100 ml reactor which had been adequately dried and substituted with argon, they were cooled to −78° C. and stirred. After dropwise adding 1.47 ml of n-butyllithium (1.61 mmol/ml n-hexane solution, 2.36 mmol) over 5 minutes, the temperature was slowly increased to room temperature and stirring was continued for 4 hours at room temperature to prepare a lithium salt solution. The solution was then slowly added dropwise to a mixed solution containing 2.3 ml of a titanium tetrachloride solution (0.5 mmol/ml heptane solution, 1.15 mmol) and 10 ml of diethyl ether which had been cooled to −78° C. After completion of the dropwise addition, stirring was continued while slowly increasing the temperature to room temperature. After further stirring for 8 hours at room temperature, the solvent of the reaction solution was distilled off, and the resulting solid was dissolved in 25 ml of methylene chloride. The insoluble portion was filtered off with a glass filter, the filtrate was concentrated under reduced pressure, and the deposited solid was reprecipitated with diethyl ether, methylene chloride and hexane and dried under reduced pressure to obtain 0.49 g (0.93 mmol, 76% yield) of compound A-41 as an orange powder.

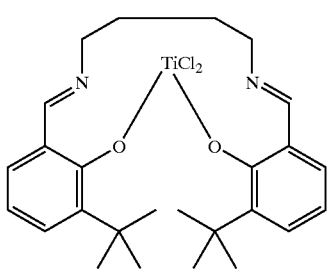

Compound A-41

FD-mass spectrometry: 525 (M+).

Elemental analysis: Ti: 8.9% (9.1). Calculated value in parentheses.

Synthesis Example 76

Synthesis of Compound B-41

After charging 0.50 g (1.15 mmol) of compound L41 and 10 ml of diethyl ether into a 100 ml reactor which had been adequately dried and substituted with argon, they were cooled to −78° C. and stirred. After dropwise adding 1.47 ml of n-butyllithium (1.61 mmol/ml n-hexane solution, 2.36 mmol) over 5 minutes, the temperature was slowly increased to room temperature, and stirring was continued for 4 hours at room temperature to prepare a lithium salt solution. The solution was then added dropwise to a solution of zirconium tetrachloride.2THF (0.43 g, 1.15 mmol) in 10 ml of tetrahydrofuran which had been cooled to −78° C. After completion of the dropwise addition, stirring was continued while slowly increasing the temperature to room temperature. After first stirring for 8 hours at room temperature and then stirring for 12 hours under reflux, the solvent of the reaction solution was distilled off. The resulting solid was dissolved in 25 ml of methylene chloride, and the insoluble portion was removed with a glass filter. The filtrate was concentrated under reduced pressure, and the deposited solid was reprecipitated with methylene chloride, diethyl ether and hexane and dried under reduced pressure to obtain 0.36 g (0.63 mmol, 51% yield) of compound B-41 as a yellow powder.

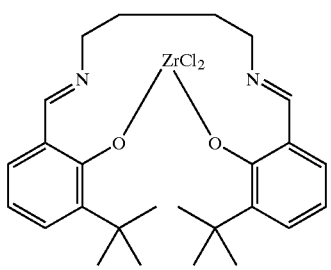

Compound B-41

¹H-NMR (CDCl₃): 1.41 (s, 18H), 2.10 (s, 2H), 3.70 (s, 2H), 6.94 (t, 2H), 7.30 (dd, 2H), 7.50 (dd, 2H), 8.39 (s, 2H).

FD-mass spectrometry: 568 (M+).

Elemental analysis: Zr: 16.2% (16.0). Calculated value in parentheses.

Synthesis Example 77

Synthesis of Compound A-42

After charging 0.500 g (1.22 mmol) of compound L42 and 10 ml of diethyl ether into a 100 ml reactor which had been adequately dried and substituted with argon, they were cooled to −78° C. and stirred. After dropwise adding 1.52 ml of n-butyllithium (1.61 mmol/ml n-hexane solution, 2.45 mmol) over 5 minutes, the temperature was slowly increased to room temperature, and stirring was continued for 4 hours at room temperature to prepare a lithium salt solution. The solution was then slowly added dropwise to a mixed solution containing 2.45 ml of a titanium tetrachloride solution (0.5 mmol/ml heptane solution, 1.23 mmol) and 10 ml of diethyl ether which had been cooled to −78° C. After completion of the dropwise addition, stirring was continued while slowly increasing the temperature to room temperature. After stirring for 8 hours at room temperature, the solvent of the reaction solution was distilled off, and the resulting solid was dissolved in 25 ml of methylene chloride. After filtering the insoluble portion with a glass filter, the filtrate was concentrated under reduced pressure, and the deposited solid was reprecipitated with diethyl ether, methylene chloride and hexane and dried under reduced pressure to obtain 0.25 g (0.45 mmol, 40% yield) of compound A-42 as a red brown powder.

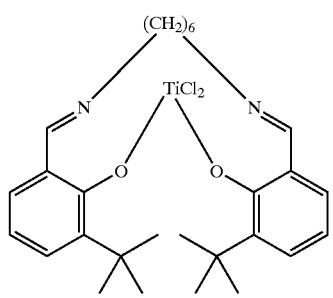

Compound A-42

FD-mass spectrometry: 552 (M+).

Elemental analysis: Ti: 9.0% (8.7). Calculated value in parentheses.

Synthesis Example 78

Synthesis of Compound B-42

After charging 0.50 g (1.22 mmol) of compound L42 and 10 ml of diethyl ether into a 100 ml reactor which had been adequately dried and substituted with argon, they were cooled to −78° C. and stirred. After dropwise adding 1.52 ml of n-butyllithium (1.61 mmol/ml n-hexane solution, 2.45 mmol) over 5 minutes, the temperature was slowly increased to room temperature, and stirring was continued for 4 hours at room temperature to prepare a lithium salt solution. The solution was then added dropwise to a solution of zirconium tetrachloride.2THF (0.46 g, 1.22 mmol) in 10 ml of tetrahydrofuran which had been cooled to −78° C. After completion of the dropwise addition, stirring was continued while slowly increasing the temperature to room temperature. After first stirring for 8 hours at room temperature and then stirring for 6 hours under reflux, the solvent of the reaction solution was distilled off. The resulting solid was dissolved in 25 ml of methylene chloride, and the insoluble portion was removed with a glass filter. The filtrate was concentrated under reduced pressure, and the deposited solid was reprecipitated with methylene chloride, diethyl ether and hexane and dried under reduced pressure to obtain 0.22 g (0.37 mmol, 32% yield) of compound B-42 as a yellow powder represented by the formula given below.

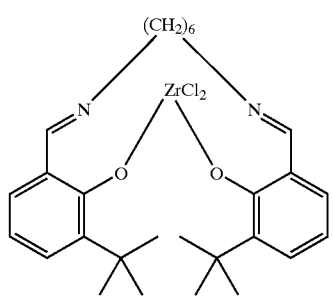

Compound B-42

FD-mass spectrometry: 596 (M+).

Elemental analysis: Zr: 15.5% (15.3). Calculated value in parentheses.

All the procedures for transition metal complex synthesis were conducted under an argon or nitrogen atmosphere, and the solvent employed was a commercially available anhydrous solvent.

Specific examples for polymerization processes according to the present invention are given below.

Example 1

To a 500 ml glass autoclave thoroughly purged with nitrogen, 250 ml of toluene was introduced, and the liquid phase and the gas phase were saturated with 100 l/hr of ethylene. Thereafter, 1.1875 mmol (in terms of aluminum atom) of methylaluminoxane (MAO) was added, and successively 0.00475 mmol of the compound A-1 obtained in Synthesis Example 1 was added to initiate polymerization. The reaction was conducted at 25° C. for 30 minutes in an ethylene gas atmosphere at normal pressure, and then a small amount of isobutanol was added to terminate the polymerization. After the polymerization was completed, the reaction product was introduced into a large amount of methanol to precipitate a polymer in the whole amount. Then, hydrochloric acid was added, and filtration was effected using a,glass filter. The resulting polymer was vacuum dried at 80° C. for 10 hours, to obtain 8.02 g of polyethylene (PE).

The polymerization activity was 3,400 g/mmol-Ti·hr, and the intrinsic viscosity [η] of the polyethylene was 8.44 dl/g.

Example 2

To a 500 ml glass autoclave thoroughly purged with nitrogen, 250 ml of toluene was introduced, and the liquid phase and the gas phase were saturated with 100 l/hr of ethylene. Thereafter, 1.25 mmol (in terms of aluminum atom) of methylaluminoxane and 0.005 mmol of the compound A-1 were added to initiate polymerization. The polymerization was conducted at 50° C. for 10 minutes, and then a small amount of isobutanol was added to terminate the polymerization.

The polymer suspension obtained was introduced into 1.5 liters of methanol containing a small amount of hydrochloric acid to precipitate a polymer. Then, filtration was effected using a glass filter to remove the solvent. The resulting polymer was washed with methanol and vacuum dried at 80° C. for 10 hours, to obtain 3.30 g of polyethylene. The polymerization activity was 3,960 g/mmol-Ti·hr, and the intrinsic viscosity [η] of the polyethylene was 6.37 dl/g.

Example 3

Polymerization was carried out in the same manner as in Example 2, except that the polymerization temperature was varied to 75° C. The results are set forth in Table 1.

Example 4

Polymerization was carried out in the same manner as in Example 2, except that the polymerization temperature was varied to 25° C. and 2 l/hr of hydrogen was fed together with ethylene. The results are set forth in Table 1.

Example 5

(TA-1, B)

To a 500 ml glass autoclave thoroughly purged with nitrogen, 250 ml of toluene was introduced, and the liquid phase and the gas phase were saturated with 100 l/hr of ethylene. Thereafter, 0.25 mmol of triisobutylaluminum (TIBA) was added, and successively 0.005 mmol of the compound A-1 and 0.006 mmol of triphenylcarbeniumtetrakis(pentafluorophenyl)borate (TrB) were added to initiate polymerization. The reaction was conducted at 25° C. for 1 hour in an ethylene gas atmosphere at normal pressure, and then a small amount of isobutanol was added to terminate the polymerization. After the polymerization was completed, the reaction product was introduced into a large amount of methanol to precipitate a polymer in the whole amount. Then, hydrochloric acid was added, and filtration was effected using a glass filter. The resulting polymer was vacuum dried at 80° C. for 10 hours, to obtain 0.50 g of polyethylene.

The polymerization activity was 100 g/mmol-Ti·hr, and the intrinsic viscosity [η] of the polyethylene was 10.6 dl/g.

Example 6

To a 500 ml glass autoclave thoroughly purged with nitrogen, 250 ml of toluene was introduced, and the liquid phase and the gas phase were saturated with 100 l/hr of ethylene. Thereafter, 0.25 mmol of triisobutylaluminum, 0.005 mmol of the compound A-1 and 0.006 mmol of triphenylcarbeniumtetrakis(pentafluorophenyl)borate were added to initiate polymerization. The polymerization was conducted at 75° C. for 30 minutes, and then a small amount of isobutanol was added to terminate the polymerization.

The polymer suspension obtained was introduced into 1.5 liters of methanol containing a small amount of hydrochloric acid to precipitate a polymer. Then, filtration was effected using a glass filter to remove the solvent. The resulting polymer was washed with methanol and vacuum dried at 80° C. for 10 hours, to obtain 0.71 g of polyethylene. The polymerization activity was 280 g/mmol-Ti·hr, and the intrinsic viscosity [η] of the polyethylene was 7.22 dl/g.

Example 7

To a 500 ml glass autoclave thoroughly purged with nitrogen, 250 ml of toluene was introduced, and the liquid phase and the gas phase were saturated with 100 l/hr of ethylene. Thereafter, 2.5 mmol (in terms of aluminum atom) of methylaluminoxane was added, and successively 0.005 mmol of the zirconium, compound B-1 was added to initiate polymerization. The reaction was conducted at 25° C. for 5 minutes in an ethylene gas atmosphere at normal pressure, and then a small amount of isobutanol was added to terminate the polymerization.

After the polymerization was completed, the reaction product was introduced into a large amount of methanol to precipitate a polymer in the whole amount. Then, hydrochloric acid was added, and filtration was effected using a glass filter. The resulting polymer was vacuum dried at 80° C. for 10 hours, to obtain 6.10 g of polyethylene.

The polymerization activity was 14,600 g/mmol-Zr·hr, and the intrinsic viscosity [η] of the polyethylene was 0.30 dl/g.

Examples 8–24

Ethylene polymerization was carried out in the same manner as in Example 7, except that the polymerization conditions were varied to those shown in Table 1. The results are set forth in Table 1.

Example 25

To a 500 ml glass autoclave thoroughly purged with nitrogen, 250 ml of toluene was introduced, and the liquid phase and the gas phase were saturated with 100 l/hr of ethylene. Thereafter, 0.25 mmol of triisobutylaluminum was added, and then a pre-mixed solution of 0.05 mmol of triisobutylaluminum, 0.005 mmol of the compound B-1 and 0.006 mmol of triphenylcarbeniumtetrakis(pentafluorophenyl)borate was added to initiate polymerization. The polymerization was conducted at 25° C. for 5 minutes, and then a small amount of isobutanol was added to terminate the polymerization. The polymer solution obtained was introduced into 1.5 liters of methanol containing a small amount of hydrochloric acid to precipitate a polymer. The polymer was washed with methanol and vacuum dried at 80° C. for 10 hours, to obtain 0.99 g of polyethylene. The polymerization activity was 2,380 g/mmol-Zr·hr, and the intrinsic viscosity [η] of the polyethylene was 22.4 dl/g.

Example 26

To a 500 ml glass autoclave thoroughly purged with nitrogen, 250 ml of toluene was introduced, and the liquid phase and the gas phase were saturated with ethylene. Thereafter, 0.25 mmol of triisobutylaluminum was added, and successively 0.0005 mmol of the zirconium compound B-1 and 0.001 mmol of triphenylcarbeniumtetrakis (pentafluoro-phenyl)borate were added to initiate polymerization. The reaction was conducted at 25° C. for 10 minutes in an ethylene gas atmosphere at normal pressure. After the polymerization was completed, the reaction product was introduced into a large amount of methanol to precipitate a polymer in the whole amount. Then, hydrochloric acid was added, and filtration was effected using a glass filter. The resulting polymer was vacuum dried at 80° C. for 10 hours, to obtain 0.34 g of polyethylene (PE).

The polymerization activity was 4,080 g/mmol-Zr·hr, and the intrinsic viscosity [η] of the polyethylene was 12.6 dl/g.

Examples 27–31

Ethylene polymerization was carried out in the same manner as in Example 26, except that the polymerization conditions were varied to those shown in Table 1. The results are set forth in Table 1.

TABLE 1

Results of ethylene polymerization at normal pressure

| Ex. | Compound | Amount (mmol) | Cocatalyst | Amount (mmol) | Temp. (° C.) | Time (min) | Yield (g) | Activity (g/mmol-M · h) | [η] (dl/g) |
|---|---|---|---|---|---|---|---|---|---|
| 1 | A-1 | 0.00475 | MAO | 1.1875 | 25 | 30 | 8.02 | 3400 | 8.44 |
| 2 | A-1 | 0.005 | MAO | 1 25 | 50 | 10 | 3 30 | 3960 | 6.37 |
| 3 | A-1 | 0 005 | MAO | 1 25 | 75 | 10 | 3.14 | 3770 | 5.48 |
| 4 | A-1 | 0 005 | MAO | 1.25 | 25 | 10 | 3.23 | 3880 | 3.53 |
| 5 | A-1 | 0.005 | TrB/TIBA | 0.006/0 25 | 25 | 60 | 0 50 | 100 | 10.6 |
| 6 | A-1 | 0.005 | TrB/TIBA | 0.006/0.25 | 75 | 30 | 0 71 | 280 | 7 22 |
| 7 | B-1 | 0 005 | MAO | 2.5 | 25 | 5 | 6 10 | 14600 | 0.30 |
| 8 | B-1 | 0.0005 | MAO | 0.5 | 25 | 5 | 4.85 | 116000 | 0.31 |
| 9 | B-1 | 0.0002 | MAO | 1.25 | 25 | 5 | 3.29 | 197000 | 0.32 |
| 10 | B-1 | 0.0001 | MAO | 0.5 | 25 | 5 | 2.72 | 326000 | 0.21 |
| 11 | B-1 | 0.00002 | MAO | 1.25 | 25 | 5 | 0.77 | 462000 | 0.28 |
| 12 | B-1 | 0.00002 | MA0 | 1 25 | 40 | 5 | 0 90 | 540000 | 0.33 |
| 13 | B-1 | 0.0002 | MAO | 1 25 | 0 | 5 | 3.09 | 185000 | 0.27 |
| 14 | B-1 | 0.0002 | MAO | 1 25 | 10 | 5 | 3.64 | 218000 | 0.29 |
| 15 | B-1 | 0.0002 | MAO | 1 25 | 30 | 5 | 3.70 | 222000 | 0.26 |

TABLE 1-continued

Results of ethylene polymerization at normal pressure

| Ex. | Com-pound | Amount (mmol) | Cocatalyst | Amount (mmol) | Temp. (° C.) | Time (min) | Yield (g) | Activity (g/mmol-M · h) | [η] (dl/g) |
|---|---|---|---|---|---|---|---|---|---|
| 16 | B-1 | 0.0002 | MAO | 1 25 | 40 | 5 | 4.21 | 253000 | 0.33 |
| 17 | B-1 | 0.0002 | MAO | 1 25 | 50 | 5 | 2.95 | 177000 | 0.30 |
| 18 | B-1 | 0.0002 | MAO | 1 25 | 60 | 5 | 2.99 | 179000 | 0.39 |
| 19 | B-1 | 0.0002 | MAO | 1 25 | 70 | 5 | 2.11 | 127000 | 0.41 |
| 20 | B-1 | 0.00008 | MAO | 1.25 | 25 | 5 | 2.67 | 401000 | 0.28 |
| 21 | B-1 | 0.00008 | MAO | 1 25 | 25 | 15 | 7.58 | 379000 | 0.30 |
| 22 | B-1 | 0.00008 | MAO | 1 25 | 25 | 30 | 12.42 | 311000 | 0.31 |
| 23 | B-1 | 0.0002 | MAO | 1 25 | 50 | 15 | 5.89 | 118000 | 0.60 |
| 24 | B-1 | 0.0002 | MAO | 1 25 | 50 | 30 | 9 67 | 96700 | 1 23 |
| 25 | B-1 | 0 005 | TrB/TIBA | 0 006/0.30 | 25 | 5 | 0 99 | 2380 | 22.40 |
| 26 | B-1 | 0.0005 | TrB/TIBA | 0.001/0 25 | 25 | 10 | 0 34 | 4080 | 12.6 |
| 27 | B-1 | 0.001 | TrB/TIBA | 0.002/0.25 | 25 | 10 | 0.31 | 1860 | 15.0 |
| 28 | B-1 | 0 0025 | TrB/TIBA | 0 005/0.25 | 25 | 10 | 1 28 | 3070 | 14 8 |
| 29 | B-1 | 0 0005 | TrB/TIBA | 0.001/0.25 | 25 | 10 | 0 27 | 3240 | 20.1 |
| 30 | B-1 | 0 0005 | TrB/TIBA | 0 001/0.25 | 50 | 10 | 0 22 | 2640 | 21 1 |
| 31 | B-1 | 0.0005 | TrB/TIBA | 0 001/0.25 | 75 | 10 | 0 12 | 1440 | 16 3 |

MAO: Methylalminoxane
TIBA: Triisobutylaluminum
TrB: Triphenylcarbeniumtetrakis (pentafluoro-phenyl) borate Examples 32–36

Ethylene polymerization was carried out in the same manner as in Example 7, except that the compounds shown in Table 2 were used and the polymerization conditions were varied to those shown in Table 2. The results are set forth in Table 2.

TABLE 2

Results of ethylene polymerization at normal pressure

| Ex. | Com-pound | Amount (mmol) | Cocatalyst | Amount (mmol) | Temp. (° C.) | Time (min) | Yield (g) | Activity (g/mmol-M · h) | [η] (dl/g) |
|---|---|---|---|---|---|---|---|---|---|
| 32 | C-1 | 0 005 | MAO | 1 25 | 25 | 5 | 2.69 | 6460 | 0 75 |
| 33 | C-1 | 0 005 | MAO | 1.25 | 75 | 5 | 3 47 | 8330 | 0.47 |
| 34 | D-1 | 0.005 | MAO | 1.25 | 25 | 30 | 0 03 | 12 | 8.32 |
| 35 | E-1 | 0.005 | MAO | 1 25 | 25 | 30 | 0 02 | 8 | 2.51 |
| 36 | F-1 | 0.005 | MAO | 1 25 | 25 | 30 | 0.01 | 4 | 1 05 |

Examples 37–52

In the case where methylaluminoxane was used as a cocatalyst, ethylene polymerization was carried out in the same manner as in Example 7, except that the compounds shown in Table 3 were used and the polymerization conditions were varied to those shown in Table 3. In the case where triisobutylaluminum and triphenylcarbeniumtetrakis (pentafluorophenyl)borate were used as cocatalysts, ethylene polymerization was carried out in the same manner as in Example 26, except that the compounds shown in Table 3 were used and the polymerization conditions were varied to those shown in Table 3. The results are set forth in Table 3.

TABLE 3

| EX. | Com-pound | Amount (mmol) | Cocatalyst | Amount (mmol) | Temp. (° C.) | Time (min) | Yield (g) | Activity (g/mmol-M · h) | [η] (dl/g) |
|---|---|---|---|---|---|---|---|---|---|
| 37 | B-2 | 0.005 | MAO | 1.25 | 25 | 30 | 0.69 | 270 | 8.32 |
| 38 | B-3 | 0.005 | MAO | 1.25 | 25 | 30 | 2.15 | 860 | 0.4 |
| 39 | A-6 | 0.005 | MAO | 1.25 | 25 | 5 | 0.54 | 1300 | 4.31 |
| 40 | A-6 | 0.005 | MAO | 1.25 | 75 | 5 | 0.76 | 1820 | 4.31 |
| 41 | B-6 | 0.0005 | MAO | 1.25 | 25 | 5 | 1.38 | 33100 | 0.24 |
| 42 | A-7 | 0.005 | MAO | 1.25 | 25 | 5 | 1.93 | 4630 | 6.84 |
| 43 | A-7 | 0.005 | MAO | 1 25 | 75 | 5 | 1.48 | 3550 | 5.34 |
| 44 | B-7 | 0.005 | MAO | 1.25 | 25 | 5 | 1.72 | 4130 | 0.10 |
| 45 | A-8 | 0.005 | MAO | 1.25 | 25 | 30 | 0.90 | 360 | 5.70 |
| 46 | A-8 | 0.005 | TrB/TIBA | 0.006/0.25 | 25 | 30 | 1.03 | 410 | 4.70 |
| 47 | B-8 | 0.0001 | MAO | 0.5 | 25 | 5 | 1.01 | 121000 | 0.21 |
| 48 | B-8 | 0.005 | TrB/TIBA | 0.006/0.25 | 25 | 30 | 2.57 | 1030 | 14.2 |

TABLE 3-continued

| EX. | Compound | Amount (mmol) | Cocatalyst | Amount (mmol) | Temp. (° C.) | Time (min) | Yield (g) | Activity (g/mmol-M · h) | [η] (dl/g) |
|---|---|---|---|---|---|---|---|---|---|
| 49 | A-9 | 0.005 | TrB/TIBA | 0.006/0.25 | 25 | 30 | 0.25 | 100 | 11.7 |
| 50 | B-9 | 0.0001 | MAO | 0.5 | 25 | 5 | 0.27 | 32400 | 0.24 |
| 51 | B-9 | 0.005 | TrB/TIBA | 0.006/0.25 | 25 | 5 | 2.87 | 6890 | 0.30 |
| 52 | A-10 | 0.005 | MAO | 1.25 | 25 | 60 | 0.48 | 96 | 11.0 |

Examples 53–78

In the case where methylaluminoxane was used as a cocatalyst, ethylene polymerization was carried out in the same manner as in Example 7, except that the compounds shown in Table 4 were used and the polymerization conditions were varied to those shown in Table 4. In the case where triisobutylaluminum and triphenylcarbeniumtetrakis(pentafluorophenyl)borate were used as cocatalysts, ethylene polymerization was carried out in the same manner as in Example 26, except that the compounds shown in Table 4 were used and the polymerization conditions were varied to those shown in Table 4. The results are set forth in Table 4.

TABLE 4

| EX. | Compound | Amount (mmol) | Cocatalyst | Amount (mmol) | Temp. (° C.) | Time (min) | Yield (g) | Activity (g/mmol-M·h) | [η] (dl/g) |
|---|---|---|---|---|---|---|---|---|---|
| 53 | A-11 | 0.005 | MAO | 1.25 | 25 | 5 | 2.57 | 6160 | 3.71 |
| 54 | A-11 | 0.005 | TrB/TIBA | 0.006/0.25 | 25 | 30 | 0.95 | 380 | 7.22 |
| 55 | B-11 | 0.0005 | MAO | 1.25 | 25 | 5 | 3.34 | 80000 | 0.42 |
| 56 | B-11 | 0.005 | TrB/TIBA | 0.006/0.25 | 25 | 5 | 2.59 | 6220 | 0.48 |
| 57 | A-12 | 0.005 | MAO | 1.25 | 25 | 5 | 3.28 | 7870 | 4.40 |
| 58 | A-12 | 0.005 | TrB/TIBA | 0.006/0.25 | 25 | 30 | 1.81 | 724 | 10.0 |
| 59 | B-12 | 0.0001 | MAO | 1.25 | 25 | 5 | 3.71 | 445200 | 0.45 |
| 60 | B-12 | 0.005 | TrB/TIBA | 0.006/0.25 | 25 | 5 | 4.63 | 11100 | 0.46 |
| 61 | A-13 | 0.005 | MAO | 1.25 | 25 | 5 | 1.13 | 2710 | 3.54 |
| 62 | A-13 | 0.005 | TrB/TIBA | 0.006/0.25 | 25 | 30 | 0.92 | 370 | 5.57 |
| 63 | B-13 | 0.0001 | MAO | 1.25 | 25 | 5 | 2.78 | 333600 | 0.22 |
| 64 | B-13 | 0.005 | TrB/TIBA | 0.006/0.25 | 25 | 10 | 3.30 | 3960 | 10.7 |
| 65 | A-14 | 0.005 | MAO | 1.25 | 25 | 5 | 1.93 | 4640 | 4.86 |
| 66 | A-14 | 0.005 | TrB/TIBA | 0.006/0.25 | 25 | 30 | 0.29 | 120 | 7.63 |
| 67 | B-14 | 0.0001 | MAO | 1.25 | 25 | 5 | 2.02 | 242400 | 0.31 |
| 68 | B-14 | 0.005 | TrB/TIBA | 0.006/0.25 | 25 | 5 | 1.83 | 4390 | 0.69 |
| 69 | A-15 | 0.005 | MAO | 1.25 | 25 | 10 | 2.05 | 2460 | 4.90 |
| 70 | B-15 | 0.005 | MAO | 1.25 | 25 | 10 | 3.22 | 3870 | 0.74 |
| 71 | A-16 | 0.005 | MAO | 1.25 | 25 | 30 | 0.71 | 280 | 3.47 |
| 72 | B-16 | 0.005 | MAO | 1.25 | 25 | 10 | 0.41 | 490 | 0.58 |
| 73 | A-17 | 0.005 | MAO | 1.25 | 25 | 30 | 1.52 | 608 | 5.50 |
| 74 | B-17 | 0.005 | MAO | 1.25 | 25 | 30 | 2.16 | 860 | 0.40 |
| 75 | A-18 | 0.005 | MAO | 1.25 | 25 | 30 | 0.34 | 136 | 3.98 |
| 76 | B-18 | 0.0005 | MAO | 1.25 | 25 | 5 | 1.68 | 40300 | 4.42 |
| 77 | B-18 | 0.005 | TrB/TIBA | 0.006/0.25 | 25 | 5 | 2.22 | 5330 | 1.87 |
| 78 | B-19 | 0.005 | TrB/TIBA | 0.006/0.25 | 25 | 30 | 0.50 | 200 | 24.40 |

Examples 79–111

In the case where methylaluminoxane was used as a cocatalyst, ethylene polymerization was carried out in the same manner as in Example 7, except that the compounds shown in Table 5 were used and the polymerization conditions were varied to those shown in Table 5. In the case where triisobutylaluminum and triphenylcarbeniumtetrakis(pentafluorophenyl)borate were used as cocatalysts, ethylene polymerization was carried out in the same manner as in Example 26, except that the compounds shown in Table 5 were used and the polymerization conditions were varied to those shown in Table 5. The results are set forth in Table 5.

TABLE 5

| EX. | Com-pound | Amount (mmol) | Cocatalyst | Amount (mmol) | Temp (° C.) | Time (min) | Yield (g) | Activity (g/mmol-M · h) | [η] (dl/g) |
|---|---|---|---|---|---|---|---|---|---|
| 79 | A-21 | 0.005 | MAO | 1.25 | 25 | 5 | 3.22 | 7730 | 6.34 |
| 80 | A-21 | 0.005 | TrB/TIBA | 0.006/0.25 | 25 | 30 | 0.57 | 230 | 9.06 |
| 81 | B-21 | 0.0001 | MAO | 1.25 | 25 | 5 | 1.24 | 148800 | 0.27 |
| 82 | B-21 | 0.005 | TrB/TIBA | 0.006/0.25 | 25 | 5 | 1.18 | 2830 | 3.06 |
| 83 | A-22 | 0.005 | MAO | 1.25 | 25 | 5 | 1.78 | 4270 | 4.00 |
| 84 | B-22 | 0.0002 | MAO | 1.25 | 25 | 5 | 1.60 | 96000 | 0.41 |
| 85 | B-22 | 0.005 | TrB/TIBA | 0.006/0.25 | 25 | 5 | 4.64 | 11100 | 0.24 |
| 86 | A-23 | 0.005 | MAO | 1.25 | 25 | 10 | 0.38 | 460 | 1.53 |
| 87 | B-23 | 0.005 | MAO | 1.25 | 25 | 30 | 2.34 | 940 | 0.31 |
| 88 | A-24 | 0.005 | TrB/TIBA | 0.006/0.25 | 25 | 30 | 0.44 | 176 | 7.11 |
| 89 | B-24 | 0.005 | MAO | 1.25 | 25 | 15 | 1.62 | 1300 | 2.03 |
| 90 | B-24 | 0.005 | TrB/TIBA | 0.006/0.25 | 25 | 30 | 1.10 | 440 | 0.57 |
| 91 | A-25 | 0.005 | MAO | 1.25 | 25 | 5 | 1.71 | 4100 | 6.55 |
| 92 | A-25 | 0.005 | TrB/TIBA | 0.006/0.25 | 25 | 15 | 1.30 | 1040 | 10.5 |
| 93 | B-25 | 0.0002 | MAO | 1.25 | 25 | 5 | 1.89 | 113000 | 0.44 |
| 94 | B-25 | 0.005 | TrB/TIBA | 0.006/0.25 | 25 | 5 | 4.34 | 10400 | 0.44 |
| 95 | A-26 | 0.005 | MAO | 1.25 | 25 | 5 | 1.04 | 2450 | 3.44 |
| 96 | B-26 | 0.0001 | MAO | 61.25 | 25 | 5 | 2.62 | 314000 | 0.43 |
| 97 | B-26 | 0.005 | TrB/TIBA | 0.006/0.25 | 25 | 5 | 0.95 | 2300 | 12.5 |
| 98 | A-27 | 0.005 | MAO | 1.25 | 25 | 15 | 0.31 | 240 | 1.81 |
| 99 | B-27 | 0.005 | MAO | 1.25 | 25 | 5 | 5.11 | 12300 | 6.34 |
| 100 | B-27 | 5E-05 | MAO | 0.25 | 25 | 5 | 2.41 | 57800 | 10.6 |
| 101 | B-27 | 2E-05 | MAO | 0.25 | 25 | 5 | 1.31 | 78400 | 7.73 |
| 102 | B-27 | 0.005 | TrB/TIBA | 0.006/0.25 | 25 | 5 | 1.98 | 4750 | 5.67 |
| 103 | A-28 | 0.005 | MAO | 1.25 | 25 | 5 | 1.35 | 3240 | 4.92 |
| 104 | A-28 | 0.005 | TrB/TIBA | 0.006/0.25 | 25 | 30 | 0.34 | 140 | 12.4 |
| 105 | B-28 | 0.0001 | MAO | 1.25 | 25 | 5 | 2.03 | 244000 | 0.76 |
| 106 | B-28 | 0.005 | TrB/TIBA | 0.006/0.25 | 25 | 10 | 4.20 | 5040 | 19.6 |
| 107 | A-29 | 0.005 | TrB/TIBA | 0.006/0.25 | 25 | 30 | 0.18 | 72 | 13.2 |
| 108 | B-29 | 0.005 | MAO | 1.25 | 25 | 30 | 0.49 | 200 | 8.43 |
| 109 | A-30 | 0.005 | TrB/TIBA | 0.006/0.25 | 25 | 30 | 0.16 | 60 | 19.7 |
| 110 | B-30 | 0.005 | MAO | 1.25 | 25 | 30 | 0.30 | 120 | 12.0 |
| 111 | B-30 | 0.005 | TrB/TIBA | 0.006/0.25 | 25 | 30 | 0.45 | 180 | 23.0 |

Examples 112–121

In the case where methylaluminoxane was used as a cocatalyst, ethylene polymerization was carried out in the same manner as in Example 7, except that the compounds shown in Table 6 were used and the polymerization conditions were varied to those shown in Table 6. In the case where triisobutylaluminum and triphenylcarbeniumtetrakis (pentafluorophenyl)borate were used as cocatalysts, ethylene polymerization was carried out in the same manner as in Example 26, except that the compounds shown in Table 6 were used and the polymerization conditions were varied to those shown in Table 6.

The results are set forth in Table 6.

TABLE 6

| EX. | Com-pound | Amount (mmol) | Cocatalyst | Amount (mmol) | Temp. (° C.) | Time (min) | Yield (g) | Activity (g/mmol-M · h) | [η] (dl/g) |
|---|---|---|---|---|---|---|---|---|---|
| 112 | A-31 | 0.005 | MAO | 1.25 | 25 | 30 | 0.63 | 250 | 5.49 |
| 113 | A-31 | 0.005 | TrB/TIBA | 0.006/0.25 | 25 | 30 | 0.49 | 200 | 15.30 |
| 114 | B-31 | 0.005 | MAO | 1.25 | 25 | 30 | 1.38 | 550 | 0.99 |
| 115 | A-32 | 0.005 | MAO | 1.25 | 25 | 60 | 0.02 | 2 | 8.81 |
| 116 | A-35 | 0.005 | MAO | 1.25 | 25 | 60 | 0.01 | 4 | 9.09 |
| 117 | A-39 | 0.005 | MAO | 1.25 | 25 | 30 | 0.10 | 40 | 1.66 |
| 118 | B-39 | 0.005 | MAO | 1.25 | 25 | 5 | 1.06 | 2540 | 0.29 |
| 119 | B-39 | 0.005 | TrB/TIBA | 0.006/0.25 | 25 | 20 | 1.10 | 660 | 4.42 |
| 120 | A-40 | 0.005 | MAO | 1.25 | 25 | 30 | 1.10 | 440 | 4.59 |
| 121 | B-40 | 0.005 | MAO | 1.25 | 25 | 30 | 0.25 | 200 | 1.28 |

Examples 122–130

In the case where methylaluminoxane was used as a cocatalyst, ethylene polymerization was carried out in the same manner as in Example 7, except that the compounds shown in Table 7 were used and the polymerization conditions were varied to those shown in Table 7. In the case where triisobutylaluminum and triphenylcarbeniumtetrakis (pentafluorophenyl)borate were used as cocatalysts, ethylene polymerization was carried out in the same manner as in Example 26, except that the compounds shown in Table 7 were used and the polymerization conditions were varied to those shown in Table 7.

The results are set forth in Table 7.

TABLE 7

| EX. | Com-pound | Amount (mmol) | Cocatalyst | Amount (mmol) | Temp. (° C.) | Time (min) | Yield (g) | Activity (g/mmol-M · h) | [η] (dl/g) |
|---|---|---|---|---|---|---|---|---|---|
| 122 | A-34 | 0.005 | MAO | 1.25 | 25 | 60 | 0.01 | 2 | 6.31 |
| 123 | A-35 | 0.005 | MAO | 1.25 | 25 | 60 | 0.05 | 10 | 5.88 |
| 124 | A-36 | 0.005 | MAO | 1.25 | 25 | 60 | 0.03 | 6 | 7.77 |
| 125 | B-37 | 0.005 | MAO | 1.25 | 25 | 60 | 0.01 | 2 | 6.09 |
| 126 | B-38 | 0.005 | MAO | 1.25 | 25 | 60 | 0.01 | 2 | 8.03 |
| 127 | A-41 | 0.005 | MAO | 1.25 | 25 | 15 | 0.96 | 770 | 4.00 |
| 128 | B-41 | 0.005 | TrB/TIBA | 0.006/0.25 | 25 | 5 | 0.59 | 1420 | 7.07 |
| 129 | A-43 | 0.005 | TrB/TIBA | 0.006/0.25 | 25 | 15 | 0.18 | 140 | 6.81 |
| 130 | B-43 | 0.005 | TrB/TIBA | 0.006/0.25 | 25 | 15 | 1.35 | 1080 | 0.84 |

Example 131

To a 500 ml glass autoclave thoroughly purged with nitrogen, 250 ml of toluene was introduced, and the liquid phase and the gas phase were saturated with a mixed gas of 50 l/hr of ethylene and 150 l/hr of propylene. Thereafter, 1.25 mmol (in terms of aluminum atom) of methylaluminoxane and 0.005 mmol of the compound A-1 were added to initiate polymerization. The polymerization was conducted at 25° C. for 15 minutes, and then a small amount of isobutanol was added to terminate the polymerization.

The polymer suspension obtained was introduced into 1.5 liters of methanol containing a small amount of hydrochloric acid to precipitate a polymer. Then, filtration was effected using a glass filter to remove the solvent. The resulting polymer was washed with methanol and vacuum dried at 80° C. for 10 hours, to obtain 0.95 g of an ethylene/propylene copolymer. The polymerization activity was 760 g/mmol-Ti·hr, the propylene content as measured by IR was 4.67% by mol, and the intrinsic viscosity [η] of the copolymer was 2.21 dl/g.

Example 132

To a 500 ml glass autoclave thoroughly purged with nitrogen, 250 ml of toluene was introduced, and the liquid phase and the gas phase were saturated with a mixed gas of 100 l/hr of ethylene and 100 l/hr of propylene. Thereafter, 0.25 mmol of triisobutylaluminum was added, and then a pre-mixed solution of 0.025 mmol of triisobutylaluminum, 0.0025 mmol of the compound B-1 and 0.005 mmol of triphenylcarbeniumtetrakis(pentafluorophenyl)borate (TrB) was added to initiate polymerization. The polymerization was conducted at 50° C. for 5 minutes, and then a small amount of isobutanol was added to terminate the polymerization.

The polymer solution obtained was introduced into 1.5 liters of methanol containing a small amount of hydrochloric acid to precipitate a polymer. The polymer was washed with methanol and vacuum dried at 130° C. for 10 hours, to obtain 1.63 g of an ethylene/propylene copolymer. The polymerization activity was 7,820 g/mmol-Zr·hr, the propylene content as measured by IR was 20.7% by mol, and the intrinsic viscosity [η] of the copolymer was 13.4 dl/g.

Example 133

Copolymerization was carried out in the same manner as in Example 132, except that the compound B-1 was used, the flow rates of ethylene and propylene were varied to 50 l/hr and 150 l/hr, respectively, and the polymerization temperature and the amounts of the catalysts were varied to those shown in Table 8.

The results are set forth in Table 8.

Examples 134–149

Copolymerization was carried out in the same manner as in Example 131, except that the compounds shown in Table 8 were used.

The results are set forth in Table 8.

TABLE 8

Results of ethylene/propylene copolymerization at normal pressure

| Ex. | Com-pound | Amount (mmol) | Cocatalyst | Amount (mmol) | Temp. (° C.) | Time (min) | Yield (g) | Activity (g/mmol-M · h) | [η] (dl/g) | Propylene content (mol %) |
|---|---|---|---|---|---|---|---|---|---|---|
| 131 | A-1 | 0 005 | MAO | 1 25 | 25 | 15 | 0 95 | 760 | 2.21 | 4.67 |
| 132 | B-1 | 0.0025 | TrB/TIBA | 0.005/0.275 | 50 | 5 | 1 63 | 7820 | 13.40 | 20.7 |
| 133 | B-1 | 0.005 | TrB/TIBA | 0 006/0.3 | 25 | 10 | 1 28 | 1540 | 12.40 | 31 3 |
| 134 | B-1 | 0.005 | MAO | 1 25 | 25 | 10 | 8.42 | 10100 | 0 03 | 29 2 |
| 135 | C-1 | 0.005 | MAO | 1 25 | 25 | 10 | 2.30 | 2760 | 0 32 | 7.19 |
| 136 | B-6 | 0.005 | MAO | 1 25 | 25 | 10 | 3.64 | 4370 | 0.14 | 10.2 |
| 137 | B-8 | 0 005 | MAO | 1 25 | 25 | 10 | 4 15 | 4980 | 0 13 | 12.43 |
| 138 | B-9 | 0.005 | MAO | 1 25 | 25 | 10 | 3 31 | 3970 | 0.13 | 8.3 |
| 139 | A-11 | 0.005 | MAO | 1 25 | 25 | 10 | 0.69 | 830 | 0 80 | 7 8 |
| 140 | A-12 | 0 005 | MAO | 1 25 | 25 | 10 | 0 37 | 400 | 0.41 | 3.8 |
| 141 | A-12 | 0.005 | MAO | 1 25 | 25 | 10 | 4 14 | 4970 | 0.11 | 18.5 |
| 142 | B-13 | 0 005 | MAO | 1 25 | 25 | 10 | 7 86 | 9430 | 0 05 | 30.1 |
| 143 | B-18 | 0 005 | MAO | 1.25 | 25 | 10 | 1 92 | 2300 | 3.63 | 3.09 |

TABLE 8-continued

Results of ethylene/propylene copolymerization at normal pressure

| Ex. | Com-pound | Amount (mmol) | Cocatalyst | Amount (mmol) | Temp. (° C.) | Time (min) | Yield (g) | Activity (g/mmol-M · h) | [η] (dl/g) | Propylene content (mol %) |
|---|---|---|---|---|---|---|---|---|---|---|
| 144 | A-21 | 0 005 | MAO | 1 25 | 25 | 10 | 0 74 | 890 | 1 92 | 8.2 |
| 145 | A-22 | 0 005 | MAO | 1 25 | 25 | 10 | 6.85 | 8220 | 0 08 | 15.4 |
| 146 | B-25 | 0 005 | MAO | 1 25 | 25 | 10 | 3.86 | 4630 | 0 16 | 12.1 |
| 147 | B-26 | 0.005 | MAO | 1.25 | 25 | 10 | 4 28 | 5140 | 0 05 | 26.3 |
| 148 | B-27 | 0 005 | MAO | 1 25 | 25 | 10 | 3.55 | 4260 | 1 11 | 6.5 |
| 149 | B-28 | 0.005 | MAO | 1 25 | 25 | 10 | 4.51 | 5410 | 0.19 | 14 5 |

Example 150

To a 500 ml glass autoclave thoroughly purged with nitrogen, 250 ml of toluene was introduced. Then, 100 l/hr of ethylene and 20 l/hr of butadiene were passed through the system. After 10 minutes, 5.0 mmol (in terms of aluminum atom) of methylaluminoxane was added, and successively 0.01 mmol of the titanium compound A-1 was added to initiate polymerization. The reaction was conducted at 25° C. for 20 minutes with passing the mixed gas of ethylene and butadiene at normal pressure, and then a small amount of methanol was added to terminate the polymerization. The reaction product was introduced into a large amount of hydrochloric acid/methanol to precipitate a polymer in the whole amount. The polymer was filtered with a glass filter and vacuum dried at 80° C. for 10 hours, to obtain 0.53 g of an ethylene/butadiene copolymer.

The polymerization activity per 1 mmol of titanium was 149 g, and the intrinsic viscosity [η] of the copolymer was 1.46 dl/g. The content of all the butadiene units in the copolymer, as determined by NMR analysis, was 0.9% by mol (1,4-cis form+1,4-trans form: 0.8% by mol, 1,2-vinyl form: 0.1% by mol, cyclopentane skeleton: less than 0.1% by mol (lower than the detection limit)).

Example 151

Polymerization was carried out in the same manner as in Example 150, except that a zirconium compound B-1 was used in place of the titanium compound A-1. The yield of the copolymer was 2.65 g.

The polymerization activity per 1 mmol of zirconium was 3,180 g, and the intrinsic viscosity [η] of the copolymer was 0.70 dl/g. The content of all the butadiene units in the copolymer, as determined by NMR analysis, was 1.2% by mol (1,4-cis form+1,4-trans form: 1.1% by mol, 1,2-vinyl form: 0.1% by mol, cyclopentane skeleton: less than 0.1% by mol (lower than the detection limit)).

Example 152

Polymerization was carried out in the same manner as in Example 151, except that the polymerization time was varied to 20 minutes and the flow rates of ethylene and butadiene were varied to 20 l/hr and 80 l/hr, respectively. The yield of the copolymer was 0.74 g.

The polymerization activity per 1 mmol of zirconium was 446 g, and the intrinsic viscosity [η] of the copolymer was 0.87 dl/g. The content of all the butadiene units in the copolymer, as determined by NMR analysis, was 5.3% by mol (1,4-cis form+1,4-trans form: 4.7% by mol, 1,2-vinyl form: 0.6% by mol, cyclopentane skeleton: less than 0.1% by mol (lower than the detection limit)).

Example 153

Polymerization was carried out in the same manner as in Example 151, except that the polymerization time was varied to 5 minutes and the flow rates of ethylene and butadiene were varied to 50 l/hr and 50 l/hr, respectively. The yield of the copolymer was 0.57 g.

The polymerization activity per 1 mmol of zirconium was 342 g, and the intrinsic viscosity [η] of the copolymer was 0.34 dl/g. The content of all the butadiene units in the copolymer, as determined by NMR analysis, was 2.4% by mol (1,4-cis form+1,4-trans form: 2.3% by mol, 1,2-vinyl form: 0.1% by mol, cyclopentane skeleton: less than 0.1% by mol (lower than the detection limit)).

Example 154

Polymerization was carried out in the same manner as in Example 153, except that the polymerization temperature was varied to 50° C. The yield of the copolymer was 0.627 g.

The polymerization activity was 1,488 g/mmol-Zr·hr, and the intrinsic viscosity [η] of the copolymer was 0.16 dl/g. The content of the butadiene units in the copolymer, as determined by NMR analysis, was 3.3% by mol (1,4-cis form+1,4-trans form: 3.2% by mol, 1,2-vinyl form: 0.1% by mol, cyclopentane skeleton: less than 0.1% by mol (lower than the detection limit)).

Example 155

Polymerization was carried out in the same manner as in Example 153, except that the polymerization temperature was varied to 50° C. and the flow rates of ethylene and butadiene were varied to 40 l/hr and 60 l/hr, respectively. The yield of the copolymer was 0.37 g.

The polymerization activity was 888 g/mmol-Zr·hr, and the intrinsic viscosity [η] of the copolymer was 0.17 dl/g. The content of the butadiene units in the copolymer, as determined by NMR analysis, was 4.8% by mol (1,4-cis form+1,4-trans form: 4.6% by mol, 1,2-vinyl form: 0.2% by mol, cyclopentane skeleton: less than 0.1% by mol (lower than the detection limit)).

Example 156

Polymerization was carried out in the same manner as in Example 153, except that the polymerization temperature was varied to 60° C. and the flow rates of ethylene and butadiene were varied to 40 l/hr and 60 l/hr, respectively. The yield of the copolymer was 0.417 g.

The polymerization activity was 984 g/mmol-Zr·hr, and the intrinsic viscosity [η] of the copolymer was 0.12 dl/g. The content of the butadiene units in the copolymer, as determined by NMR analysis, was 5.8% by mol (1,4-cis form+1,4-trans form: 5.6% by mol, 1,2-vinyl form: 0.2% by mol, cyclopentane skeleton: less than 0.1% by mol (lower than the detection limit)). The molecular weight distribution (Mw/Mn) as measured by the GPC was 1.85.

Example 157

Polymerization was carried out in the same manner as in Example 153, except that the polymerization temperature was varied to 50° C. and the flow rates of ethylene and butadiene were varied to 30 l/hr and 70 l/hr, respectively. The yield of the copolymer was 0.24 g.

The polymerization activity was 576 g/mmol-Zr·hr, and the intrinsic viscosity [η] of the copolymer was 0.14 dl/g. The content of the butadiene units in the copolymer, as determined by NMR analysis, was 6.6% by mol (1,4-cis form+1,4-trans form: 6.3% by mol, 1,2-vinyl form: 0.2% by mol, cyclopentane skeleton: less than 0.1% by mol (lower than the detection-limit)). The molecular weight distribution (Mw/Mn) as measured by the GPC was 2.05.

Example 158

To a 1-liter SUS autoclave thoroughly purged with nitrogen, 500 ml of heptane was introduced, and the gas phase and the liquid were saturated with ethylene at 50° C. Then, 1.25 mmol (in terms of aluminum) of methylaluminoxane and 0.001 mmol of the compound A-1 were added, and polymerization was performed for 15 minutes under an ethylene pressure of 8 kg/cm$^2$-G.

To the polymer suspension obtained, 1.5 liters of methanol containing a small amount of hydrochloric acid was added to precipitate a polymer. Then, filtration was effected using a glass filter to remove the solvent. The resulting polymer was washed with methanol and vacuum dried at 80° C. for 10 hours, to obtain 11.22 g of polyethylene. The polymerization activity was 44.9 g/mmol-Ti·hr, and the intrinsic viscosity [η] of the polyethylene was 7.91 dl/g.

Examples 159–162

Polymerization was carried out in the same manner as in Example 158, except that the compounds shown in Table 9 were used and the polymerization conditions were varied to those shown in Table 9.

The results are set forth in Table 9.

TABLE 9

Examples of ethylene polymerization under pressure

| Ex. | Compound | Amount (mmol) | Cocatalyst | Amount (mmol) | Temp. (° C.) | Time (min) | Yield (g) | Activity (g/mmol-M · h) | [η] (dl/g) |
|---|---|---|---|---|---|---|---|---|---|
| 158 | A-1 | 0 001 | MAO | 1 25 | 50 | 15 | 11 22 | 44 9 | 7 91 |
| 159 | A-1 | 0.001 | MAO | 1 25 | 75 | 15 | 11 96 | 47 8 | 7 31 |
| 160 | B-1 | 0.00005 | MAO | 1 25 | 50 | 15 | 14 90 | 1192 | 1 15 |
| 161 | C-1 | 0 00025 | MAO | 1 25 | 50 | 15 | 8 28 | 132 | 2.30 |
| 162 | A-7 | 0 001 | MAO | 1 25 | 50 | 15 | 4 83 | 19 3 | 4.44 |

Example 163

Preparation of Solid Catalyst Component

In 154 liters of toluene, 10 kg of silica having been dried at 250° C. for 10 hours was suspended, and the suspension was cooled to 0° C. Then, 57.5 liters of a methylaluminoxane solution (Al=1.33 mol/l) was dropwise added over a period of 1 hour. During the addition, the temperature of the system was maintained at 0° C., and the reaction was conducted at 0° C. for 30 minutes. Then, the temperature of the system was raised up to 95° C. over a period of 1.5 hours, and at this temperature the reaction was conducted for 20 hours. The temperature of the system was then lowered to 60° C., and the supernatant liquid was removed by decantation. The resulting solid catalyst component was washed twice with toluene and resuspended in toluene, to obtain a solid catalyst component (A) (whole volume: 200 liters).

22.4 Milliliters of the suspension of the solid catalyst component (A) as obtained above was transferred into a 200 ml glass flask, and then 175 ml of toluene and 4.8 ml of a toluene solution of the compound A-1 (Ti=0.01 mmol/l) were added. The mixture was stirred at room temperature for 2 hours. The resulting suspension was washed three times with 200 ml of hexane, and hexane was added to give 200 ml of a suspension and a solid catalyst component (B).

Polymerization

To a 2-liter SUS autoclave thoroughly purged with nitrogen, 1 liter of heptane was introduced, and the gas phase and the liquid were saturated with ethylene at 50° C. Then, 1.0 mmol of triisobutylaluminum and 0.005 mmol (in terms of Ti atom) of the solid catalyst component (B) were added, and polymerization was performed for 90 minutes under an ethylene pressure of 8 kg/cm$^2$-G.

The polymer suspension obtained was filtered with a glass filter, washed twice with 500 ml of hexane and vacuum dried at 80° C. for 10 hours, to obtain 8.96 g of polyethylene. The polymerization activity was 1,790 g/mmol-Ti·hr, and the intrinsic viscosity [η] of the polyethylene was 11.7 dl/g.

Example 164

To a 200 ml reactor thoroughly purged with nitrogen, 60 ml of heptane and 40 ml of 1-hexene were introduced, and they were stirred at 25° C. Thereafter, 0.25 mmol of triisobutylaluminum was added, and then a mixed solution of 0.1 mmol of triisobutylaluminum, 0.01 mmol of the compound A-1 and 0.012 mmol of triphenylcarbeniumtetrakis (penta-fluorophenyl)borate was added to initiate polymerization. The reaction was conducted at 25° C. for 1 hour, and then a small amount of isobutanol was added to terminate the polymerization.

The polymer suspension obtained was added little by little to 1 liter of acetone to precipitate a polymer. The polymer was separated from the solvent and vacuum dried at 130° C. for 10 hours, to obtain 3.15 g of polyhexene. The polymerization activity was 315 g/mmol-Ti·hr. The molecular weight (Mw), as measured by GPC, was 1,460,000 (in terms of polystyrene), and the molecular weight distribution (Mw/Mn) was 2.06.

Example 165

To a 500 ml reactor thoroughly purged with nitrogen, 250 ml of toluene was introduced, and the liquid phase and the gas phase were saturated with ethylene at 25° C. Thereafter, while passing 80 l/hr of butadiene, 1.0 mmol of triisobutylaluminum was added, and successively 0.01 mmol of the titanium compound A-1 and 0.02 mmol of triphenylcarbeniumtetrakis(pentafluorophenyl)borate were added to initiate polymerization. The reaction was conducted at 25° C. for 20 minutes, and then a small amount of isobutanol was added to terminate the polymerization. After the polymerization was completed, the reaction product was introduced into a large amount of methanol to precipitate a polymer in the whole amount. Then, hydrochloric acid was added, and filtration was effected using a glass filter. The resulting polymer was vacuum dried at 80° C. for 10 hours, to obtain 1.481 g of polybutadiene.

The polymerization activity was 444 g/mmol-Ti·hr, and the molecular weight (Mw) of the copolymer was 1,760,000 (in terms of polystyrene).

What is claimed is:

1. An olefin polymerization catalyst comprising:
   a transition metal compound; and
   at least one compound selected from the group consisting of an organometallic compound, an organoaluminum oxy-compound and a compound which reacts with said transition metal compound to form an ion pair,
   wherein said transition metal compound has the following formula I:

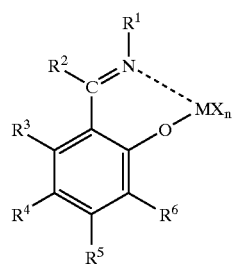

(I)

wherein M is a transition metal atom selected from the group consisting of Groups 3–7 and 11 of the periodic table,
$R^1$ to $R^6$ are the same or different, and are each a hydrogen atom, a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group, and two or more of them may be bonded to each other to form a ring,
n is a number making (I) electrically neutral, and
X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, and when n is 2 or greater, plural groups X may be the same or different.

2. The olefin polymerization catalyst as claimed in claim 1, wherein $R^6$ in the formula (I) is a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group.

3. The olefin polymerization catalyst as claimed in claim 1, wherein
   $R^1$ to $R^6$ may be the same or different, and are each a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group, a carboxyl group, a sulfo group, a mercapto group or a hydroxyl group, and two or more of them may be bonded to each other to form a ring.

4. The olefin polymerization catalyst as claimed in claim 3, wherein $R^6$ is a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group, a carboxyl group, a sulfo group, a mercapto group or a hydroxyl group.

5. The olefin polymerization catalyst as claimed in claim 1, wherein
   $R^1$ to $R^6$ are the same or different, and are each a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group or a hydroxyl group, and two or more of them may be bonded to each other to form a ring, and
   X is a hydrogen atom, a halogen atom, a hydrocarbon group of 1 to 20 carbon atoms, a halogenated hydrocarbon group of 1 to 20 carbon atoms, an oxygen-containing group, a sulfur-containing group or a silicon-containing group, and when n is 2 or greater, plural groups X are the same or different.

6. The olefin polymerization catalyst as claimed in claim 5, wherein $R^6$ is a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amido group, an imido group, an amino group, an imino group, a sulfonester group, a sulfonamido group, a cyano group, a nitro group or a hydroxyl group.

7. The olefin polymerization catalyst as claimed in claim 1, wherein
   $R^1$ to $R^6$ are the same or different, and are each a hydrogen atom, a halogen atom, a hydrocarbon group, a hydrocarbon-substituted silyl group, an alkoxy group, an aryloxy group, an ester group, an amido group, an amino group, a sulfonamido group, a cyano group or a nitro group, and two or more of them may be bonded to each other to form a ring.

8. The olefin polymerization catalyst as claimed in claim 7, wherein $R^6$ is a halogen atom, a hydrocarbon group, a hydrocarbon-substituted silyl group, an alkoxy group, an aryloxy group, an ester group, an amido group, an amino group, a sulfonamido group, a cyano group or a nitro group.

9. The olefin polymerization catalyst as claimed in claim 1, wherein M in the transition metal compound is a transition metal atom selected from Group 3 of the periodic table.

10. The olefin polymerization catalyst as claimed in claim 1, wherein M in the transition metal compound is a transition metal atom selected from Group 4 of the periodic table.

11. The olefin polymerization catalyst as claimed in claim 1, wherein M in the transition metal compound is a transition metal atom selected from Group 5 of the periodic table.

12. The olefin polymerization catalyst as claimed in claim 1, wherein M in the transition metal compound is a transition metal atom selected from Group 6 of the periodic table.

13. The olefin polymerization catalyst as claimed in claim 1, wherein M in the transition metal compound is a transition metal atom selected from Group 7 of the periodic table.

14. The olefin polymerization catalyst as claimed in claim 1, wherein M in the transition metal compound is a transition metal atom selected from Group 11 of the periodic table.

15. A method for polymerizing olefin, which comprises:

polymerizing a monomer with the olefin catalyst as claimed in any one of claims 1 to 14.

* * * * *